US00RE48318E

(19) United States
(12) Reissued Patent
Kwon

(10) Patent Number: US RE48,318 E
(45) Date of Reissued Patent: *Nov. 24, 2020

(54) TOOTH PREPARATION GUIDE DEVICE AND METHOD OF PREPARING TOOTH FOR DENTAL PROSTHESIS

(71) Applicant: DigiPrep Dental, Inc., Irvine, CA (US)

(72) Inventor: Oh-Dal Kwon, Yongin-si (KR)

(73) Assignee: DigiPrep Dental, Inc., Irvine, CA (US)

( * ) Notice: This patent is subject to a terminal disclaimer.

(21) Appl. No.: 15/916,177

(22) Filed: Mar. 8, 2018

Related U.S. Patent Documents

Reissue of:
(64) Patent No.: 8,651,860
Issued: Feb. 18, 2014
Appl. No.: 13/883,565
PCT Filed: Nov. 17, 2011
PCT No.: PCT/IB2011/003368
§ 371 (c)(1),
(2) Date: May 3, 2013
PCT Pub. No.: WO2012/110850
PCT Pub. Date: Aug. 23, 2012

U.S. Applications:
(63) Continuation of application No. 15/047,515, filed on Feb. 18, 2016, now Pat. No. Re. 46,813, which is an application for the reissue of Pat. No. 8,651,860.
(Continued)

(30) Foreign Application Priority Data

Nov. 17, 2010 (KR) ..... 10-2010-0114678
Jun. 30, 2011 (KR) ..... 10-2011-0065074
(Continued)

(51) Int. Cl.
*A61C 3/02* (2006.01)
*A61C 1/08* (2006.01)
(Continued)

(52) U.S. Cl.
CPC ..... *A61C 13/12* (2013.01); *A61C 1/082* (2013.01); *A61C 3/02* (2013.01); *A61C 5/70* (2017.02);
(Continued)

(58) Field of Classification Search
CPC ..... A61C 1/082; A61C 1/088
(Continued)

(56) References Cited

U.S. PATENT DOCUMENTS 472,004 A * 3/1892 Sweet ..... 433/75
4,144,645 A 3/1979 Marshall
(Continued)

FOREIGN PATENT DOCUMENTS

DE 4012327 A1 10/1991
DE 4013828 A1 1/1992
(Continued)

OTHER PUBLICATIONS

International Searching Authority, International Search Report and Written Opinion, PCT Patent Application PCT/IB2011/003356, dated Oct. 16, 2012, 9 pages.
(Continued)

*Primary Examiner* — Cary E Wehner
(74) *Attorney, Agent, or Firm* — Perkins Coie LLP

(57) ABSTRACT

Dental preparation uses a tooth preparation guide custom-made liar fitting with teeth of a patient. The preparation guide includes one or more guide channels for guiding a cutting tool. The preparation guide enables modification of the teeth as planned with high level of precision. A dental prosthesis for installing onto prepared teeth of the patient is provided before preparation of the teeth. The prosthesis includes features that are complementary to the prepared teeth. The prosthesis can be installed immediately after preparing the teeth using the preparation guide. With the
(Continued)

high level of accuracy and precision in the preparation of teeth, no modification of the prosthesis would be needed for installation.

12 Claims, 182 Drawing Sheets

Related U.S. Application Data

(60) Provisional application No. 61/503,580, filed on Jun. 30, 2011, provisional application No. 61/503,572, filed on Jun. 30, 2011.

(30) Foreign Application Priority Data

Aug. 4, 2011 (KR) ..... 10-2011-0077930
Nov. 16, 2011 (WO) ..... PCT/US2011/061090

(51) Int. Cl.

| | |
|---|---|
| ***A61C 13/12*** | (2006.01) |
| ***A61C 5/70*** | (2017.01) |
| ***A61C 5/77*** | (2017.01) |
| ***A61C 13/00*** | (2006.01) |
| ***A61C 13/271*** | (2006.01) |
| *B33Y 80/00* | (2015.01) |
| *A61C 9/00* | (2006.01) |

(52) U.S. Cl.
CPC ..... *A61C 5/77* (2017.02); *A61C 13/0004* (2013.01); *A61C 13/26* (2013.01); *A61C 9/0046* (2013.01); *B33Y 80/00* (2014.12)

(58) Field of Classification Search
USPC ..... 433/72, 74, 75
See application file for complete search history.

(56) References Cited

U.S. PATENT DOCUMENTS

| | | | | |
|---|---|---|---|---|
| 4,255,140 | A | 3/1981 | Marshall | |
| 4,306,866 | A | 12/1981 | Weissman | |
| 4,483,675 | A | 11/1984 | Marshall | |
| 4,941,826 | A * | 7/1990 | Loran et al. | 435/51 |
| 5,128,870 | A | 7/1992 | Erdman et al. | |
| 5,133,660 | A | 7/1992 | Fenick | |
| 5,725,376 | A | 3/1998 | Poirier | |
| 5,833,693 | A | 11/1998 | Abrahami | |
| 6,511,323 | B1 | 1/2003 | Wilkinson | |
| 6,537,067 | B1 | 3/2003 | Wennemann | |
| 7,004,757 | B2 | 2/2006 | Wilkinson | |
| 7,097,451 | B2 | 8/2006 | Tang | |
| 7,322,821 | B1 | 1/2008 | Lin et al. | |
| 7,393,211 | B2 | 7/2008 | Wilkinson | |
| 7,845,942 | B2 | 12/2010 | Wilkinson | |
| 8,651,860 | B2 | 2/2014 | Kwon | |
| RE46,813 | E | 5/2018 | Kwon | |
| 2003/0064346 | A1 | 4/2003 | Wennemann | |
| 2005/0095554 | A1 | 5/2005 | Wilkinson | |
| 2009/0202959 | A1 | 8/2009 | Ajlouni et al. | |
| 2010/0192375 | A1 | 8/2010 | Jacquemyns | A61C 3/02 29/896.1 |
| 2010/0196842 | A1 | 8/2010 | Jacquemyns | A61C 1/082 433/75 |
| 2010/0297574 | A1 | 11/2010 | Llop et al. | |
| 2012/0143364 | A1 | 6/2012 | Mcleod et al. | |
| 2014/0205968 | A1 | 7/2014 | Jung et al. | |
| 2014/0242541 | A1 | 8/2014 | Jung et al. | |
| 2014/0248577 | A1 | 9/2014 | Tahmasebi et al. | |
| 2014/0316750 | A1 | 10/2014 | Jung et al. | |
| 2015/0111172 | A1 | 4/2015 | Jung et al. | |
| 2016/0143717 | A1 | 5/2016 | Samrano | |

FOREIGN PATENT DOCUMENTS

| | | | |
|---|---|---|---|
| EP | 2072018 | A1 | 6/2009 |
| JP | 2009285358 | A | 12/2009 |
| SI | 23494 | A | 4/2012 |
| WO | 2012110850 | A2 | 8/2012 |

OTHER PUBLICATIONS

International Searching Authority, International Search Report and Written Opinion, PCT Patent Application PCT/IB2011/003368, dated Oct. 19, 2012, 21 pages.
Miyazaki, et al., A review of dental CAD/CAM: current status and future perspectives from 20 years of experience, Dental Materials Journal 2009; vol. 28, Issue 1, pp. 44-56.
International Search Report dated Oct. 16, 2012 of PCT Application No. PCT/IB2011/003356 which is the parent application—6 pages.
International Search Report dated Oct. 19, 2012 of PCT/IB2011/003368 which is the parent application—6 pages.

* cited by examiner

AMENDED

FIG. 48A
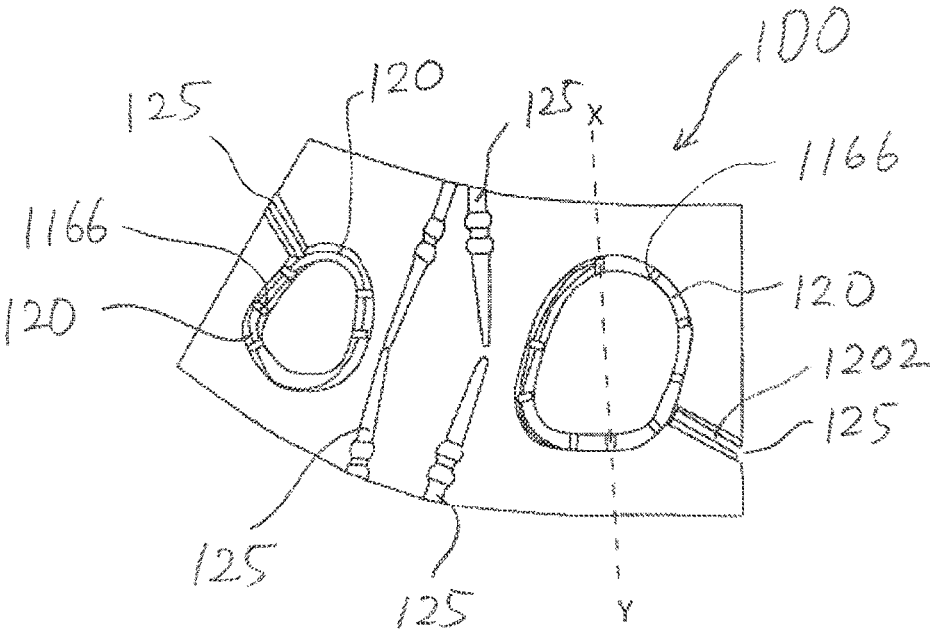
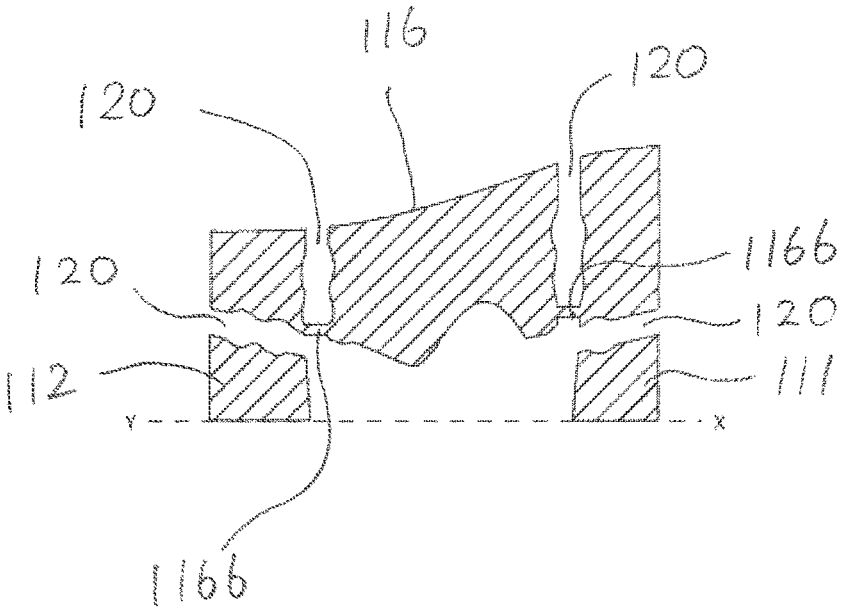
FIG. 48B

FIG. 50A
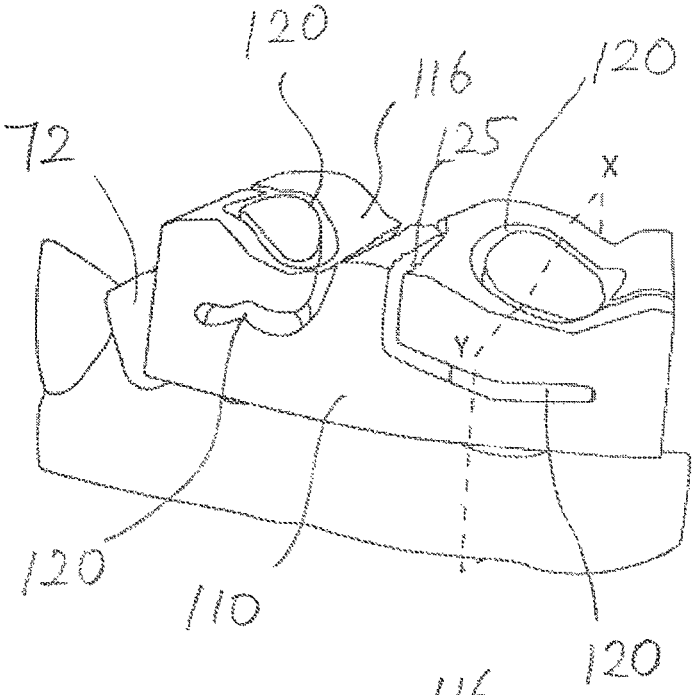
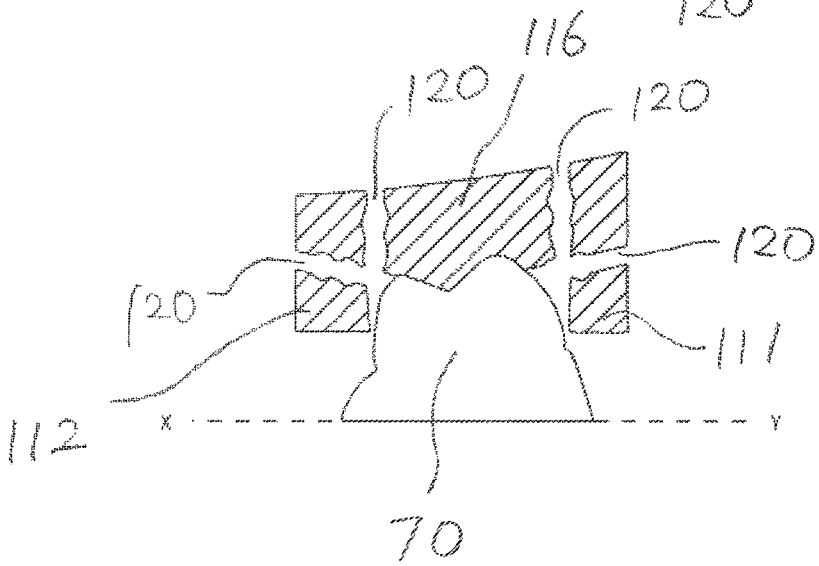
FIG. 50B

FIG. 51A
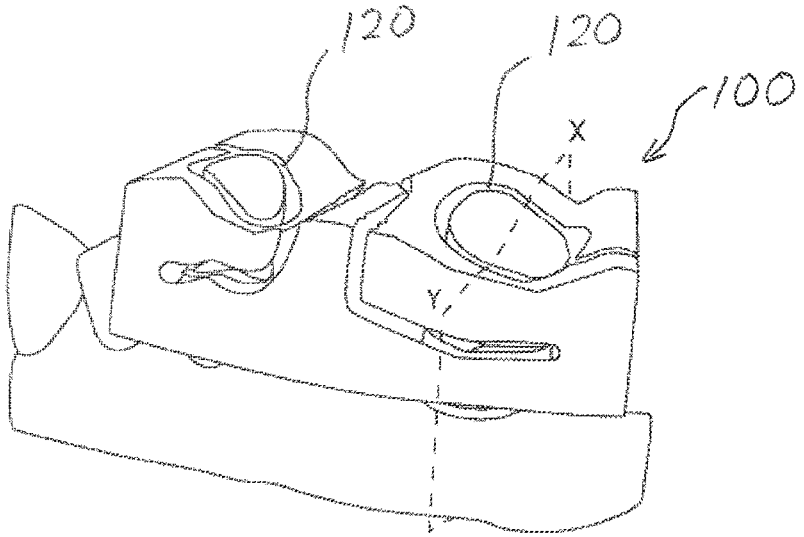
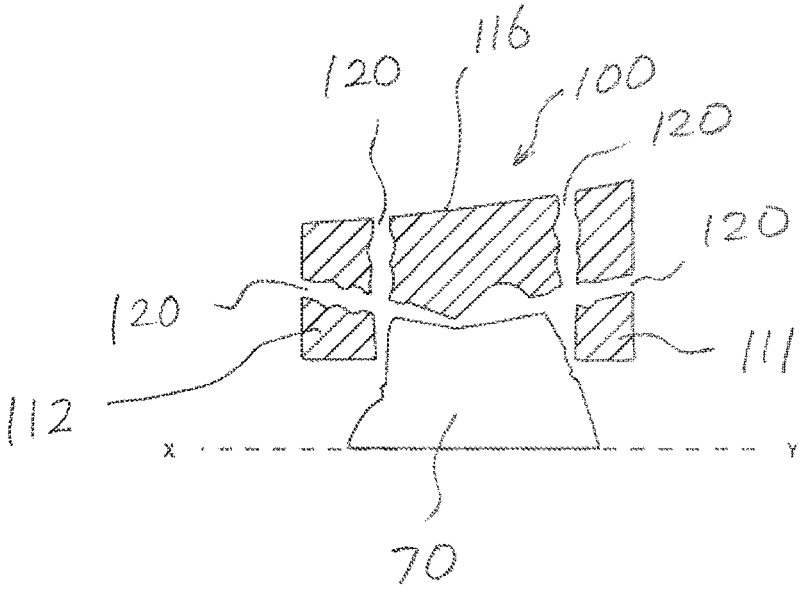
FIG. 51B

FIG. 55A
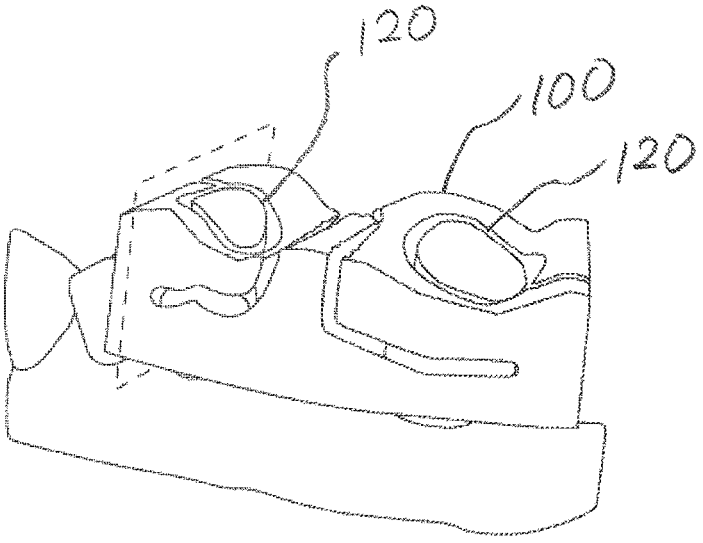
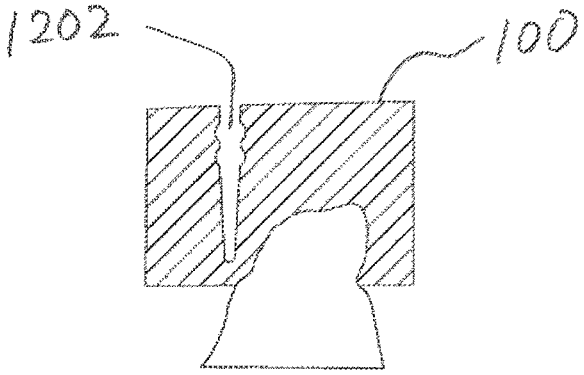
FIG. 55B

FIG. 60
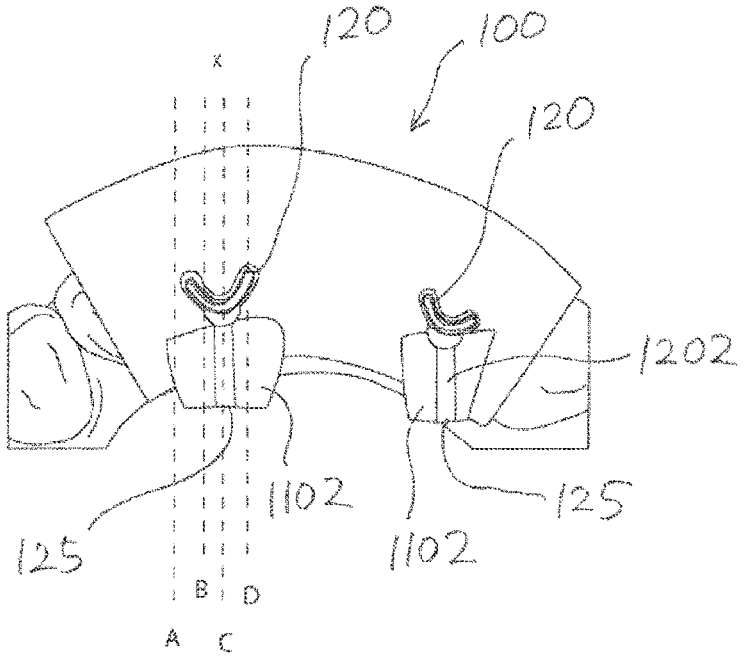
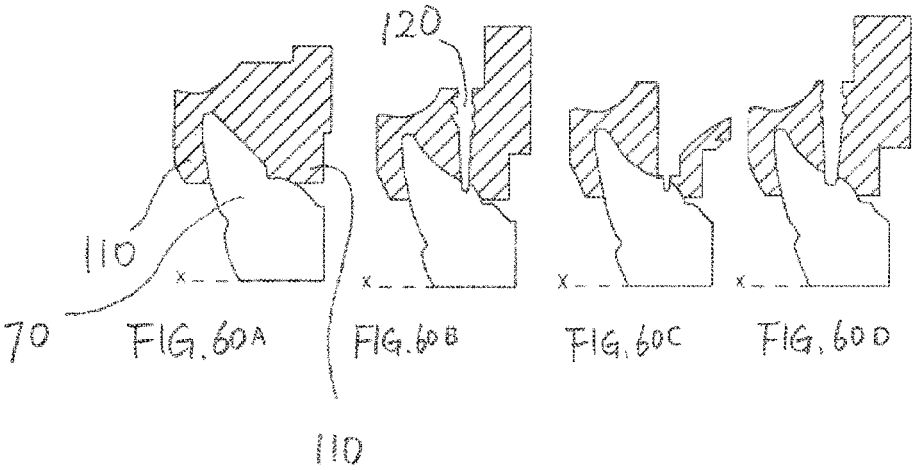

FIG. 69
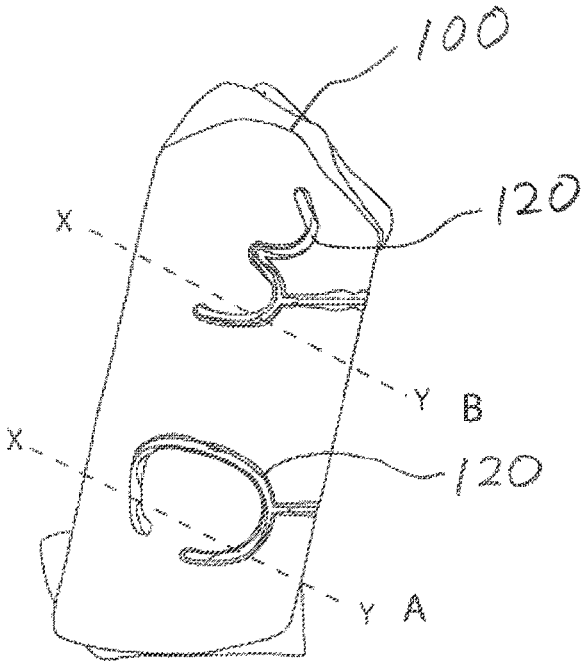
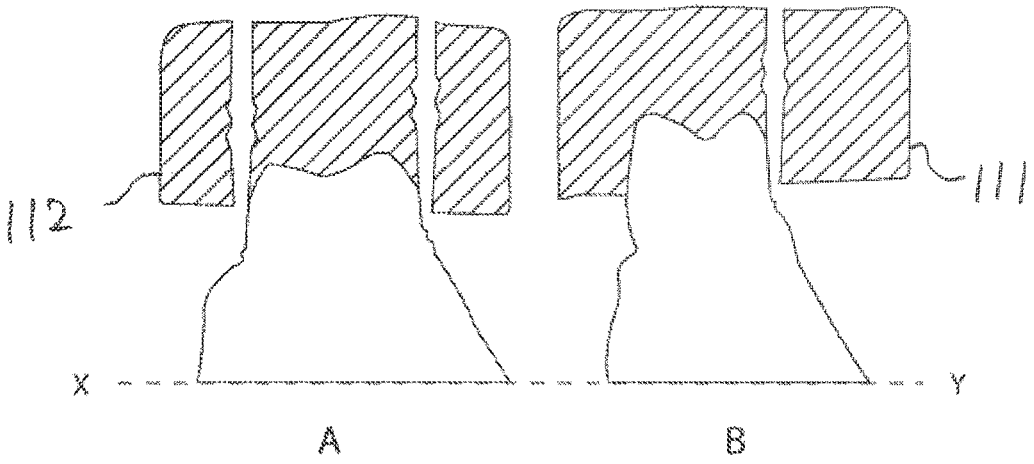

FIG. 76A
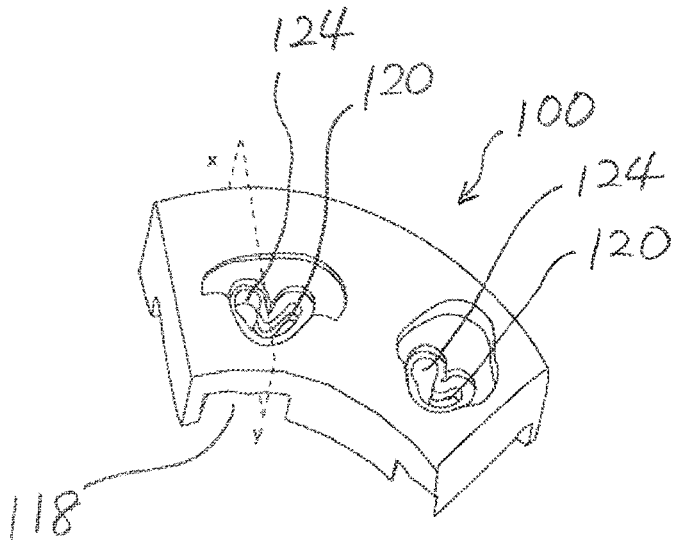
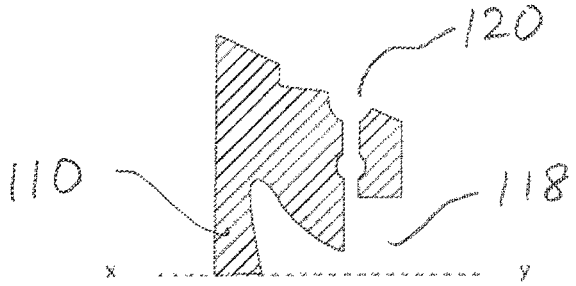
FIG. 76B

FIG. 77A
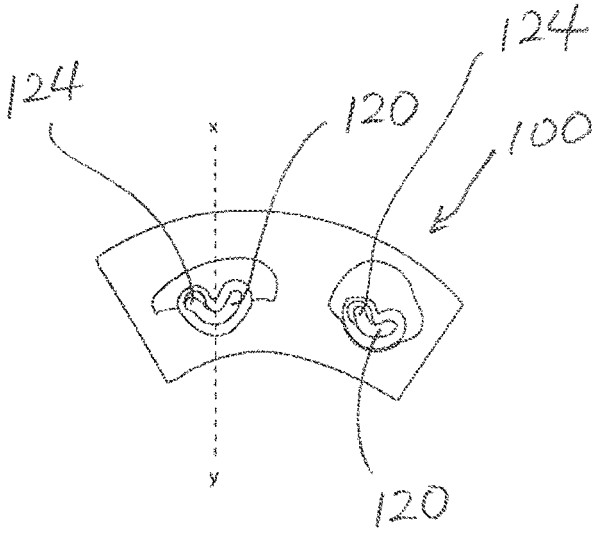
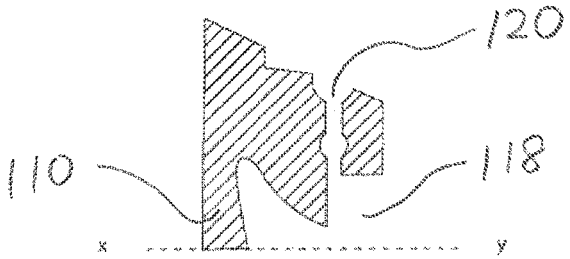
FIG. 77B

AMENDED

FIG. 79A
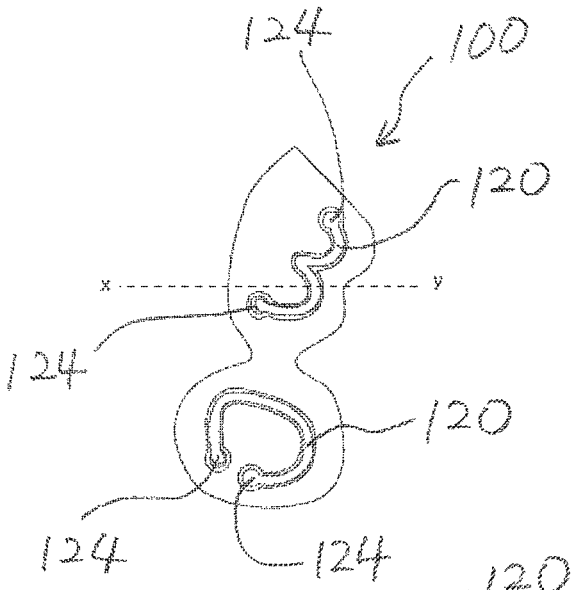
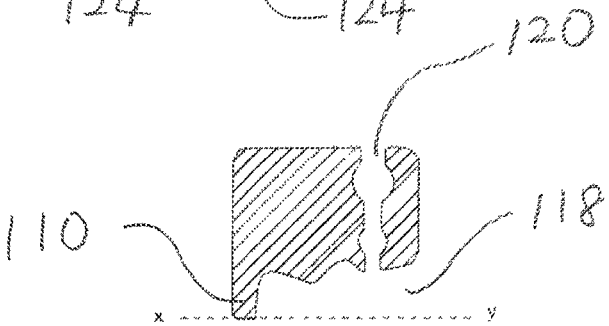
FIG. 79B

AMENDED

FIG. 81A
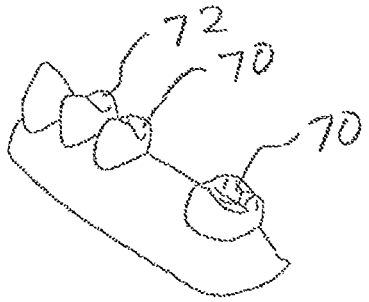
FIG. 81B
AMENDED
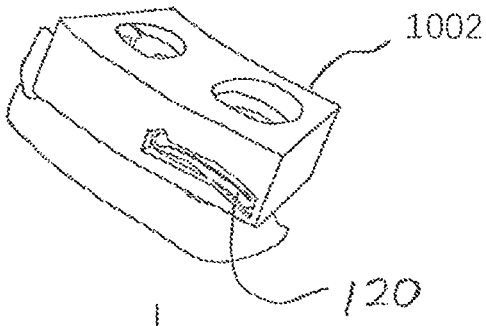
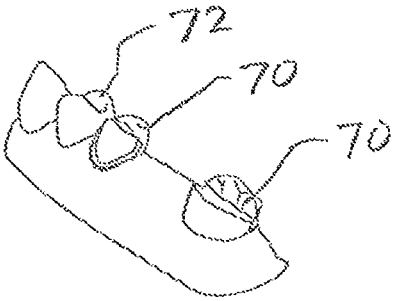
FIG. 81C

FIG. 82A
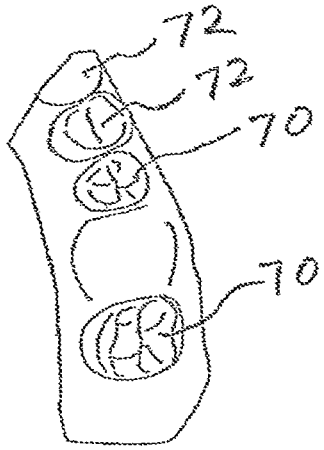
FIG. 82C
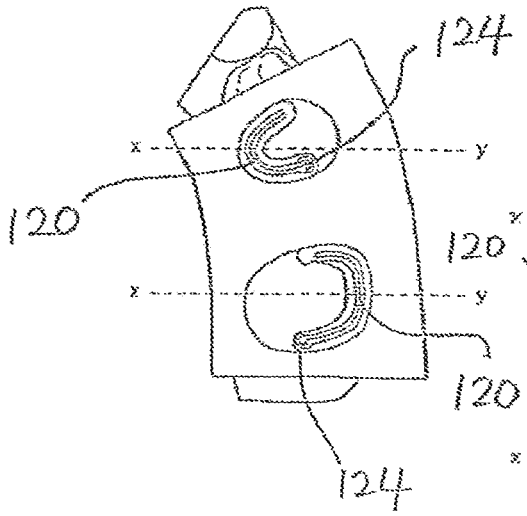
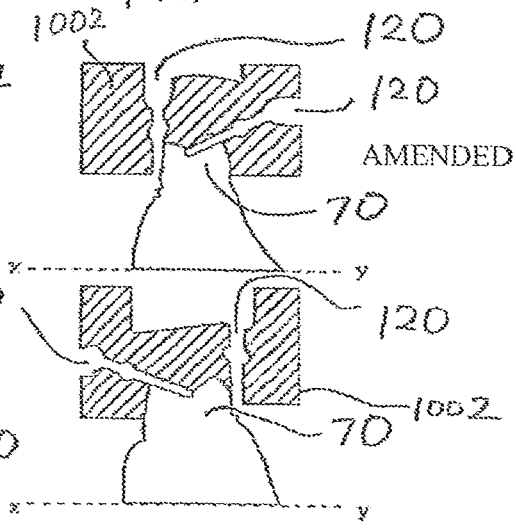
FIG. 82B
FIG. 82D AMENDED

FIG. 83A
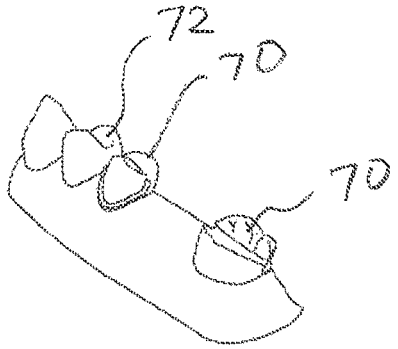
FIG. 83B
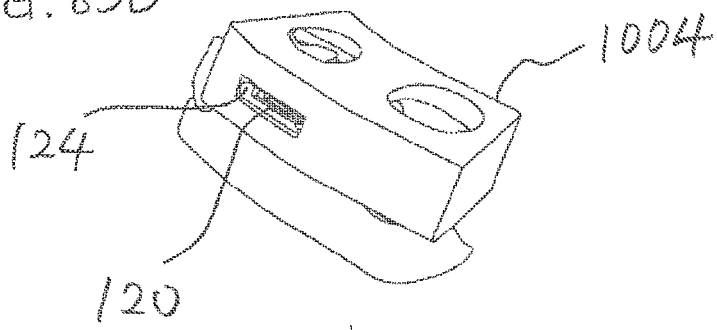
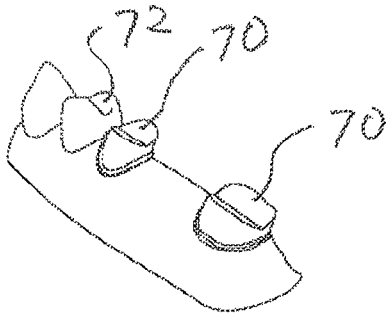
FIG. 83C

FIG. 84A
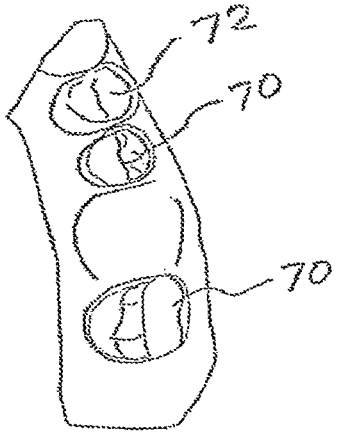
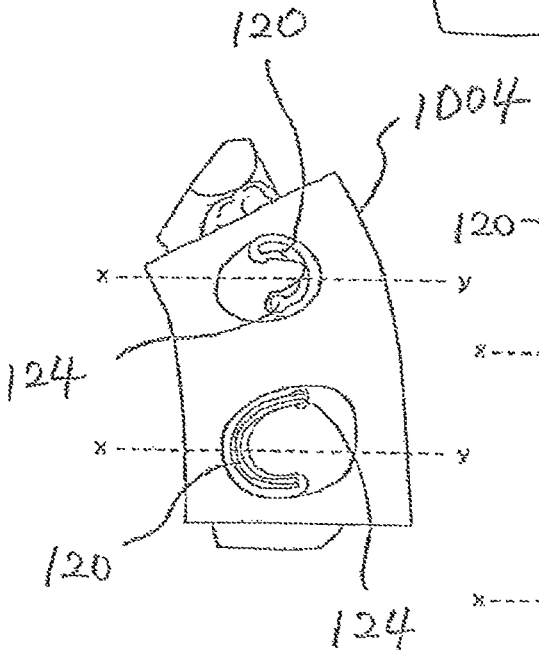
FIG. 84B
FIG. 84C
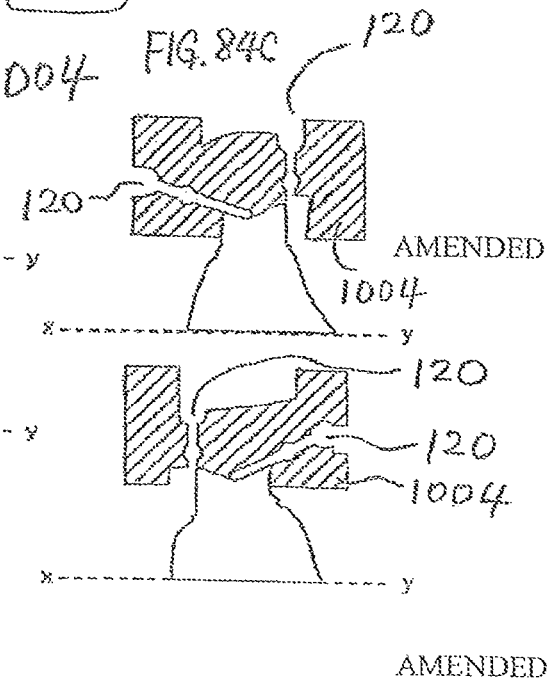
AMENDED
FIG. 84D

FIG. 86A
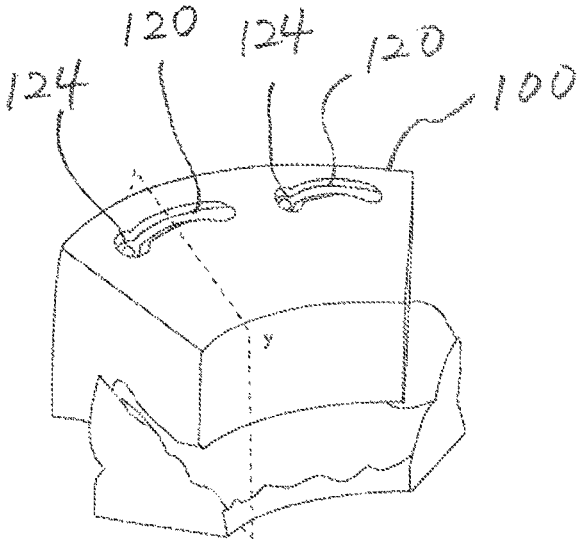
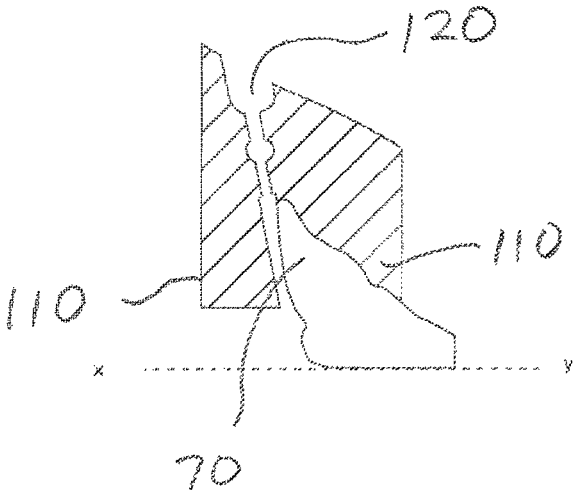
FIG. 86B

AMENDED

FIG. 93A
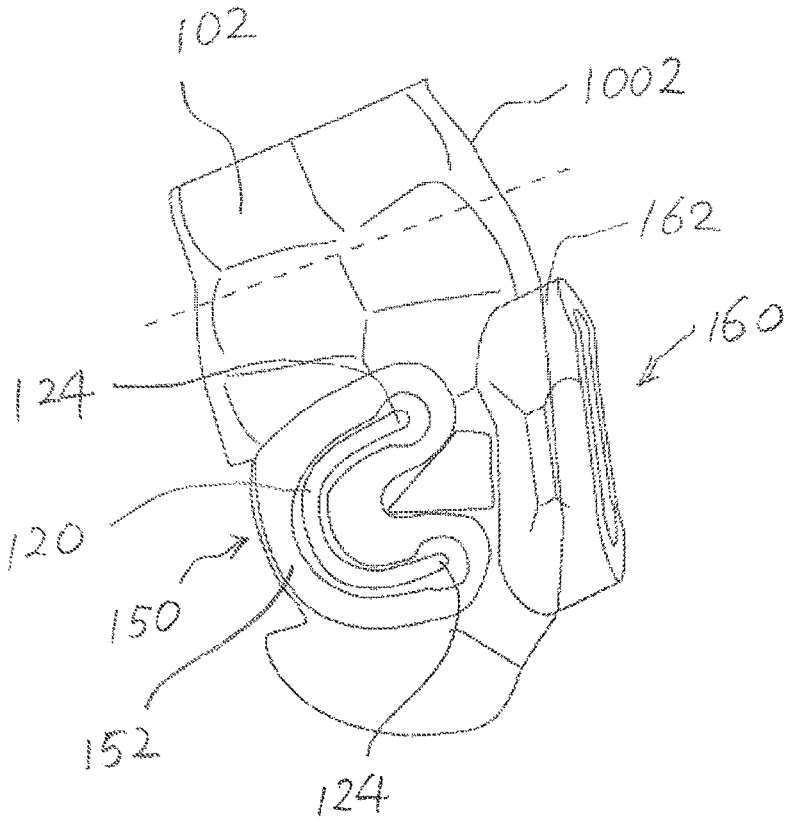
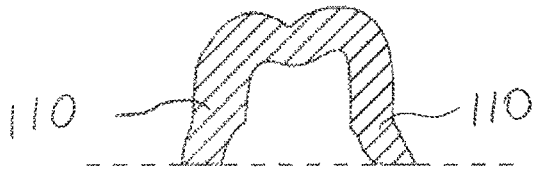
FIG. 93B

FIG. 94A
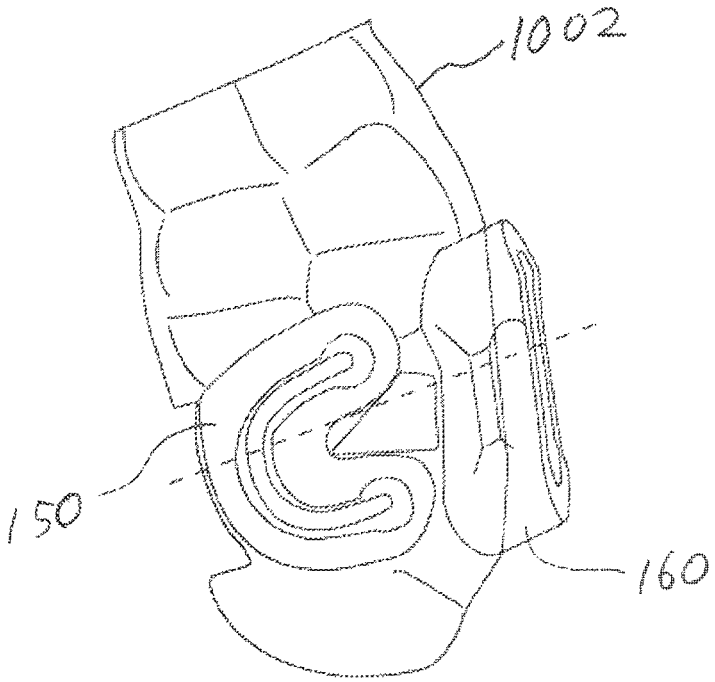
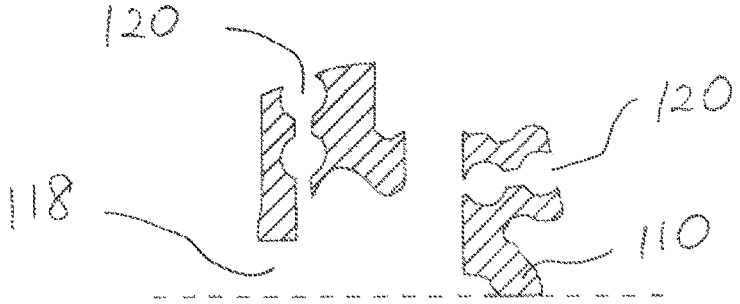
FIG. 94B

FIG. 95A
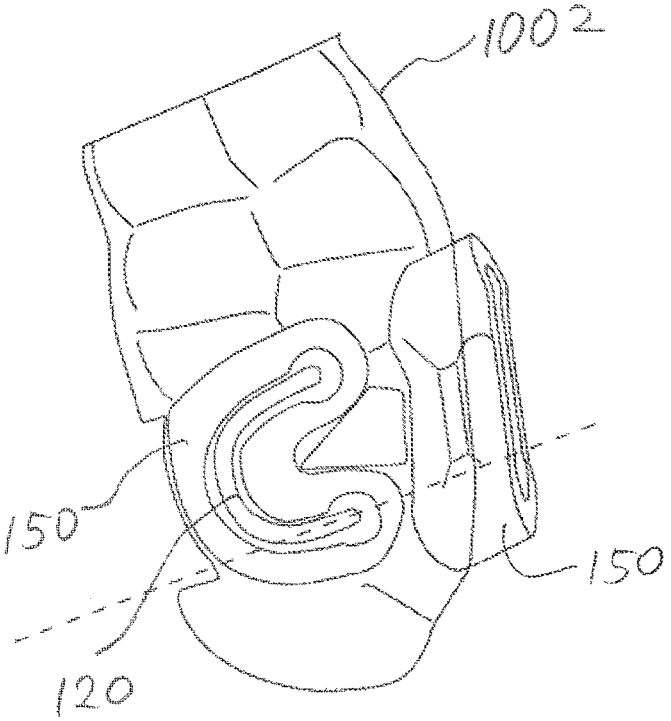
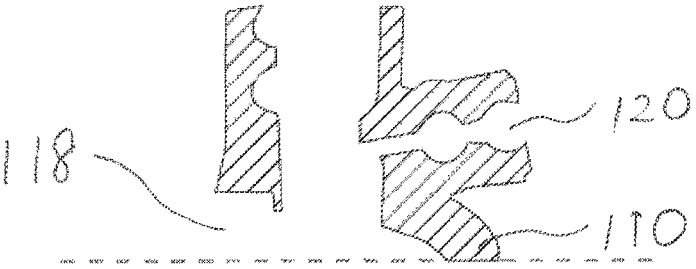
FIG. 95B

FIG. 98A
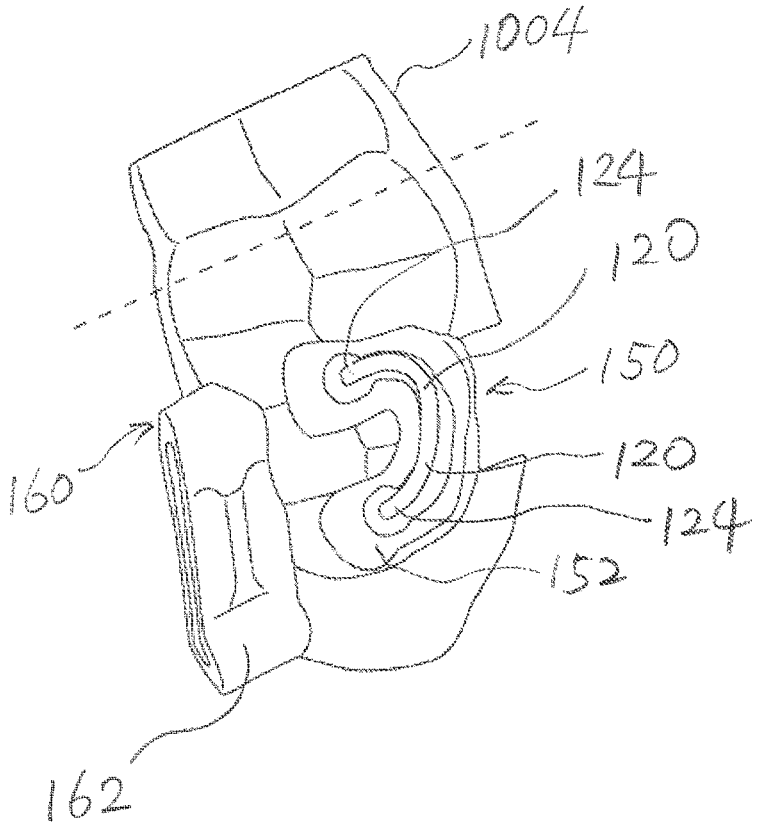
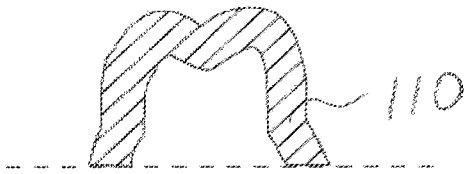
FIG. 98B

FIG. 99A
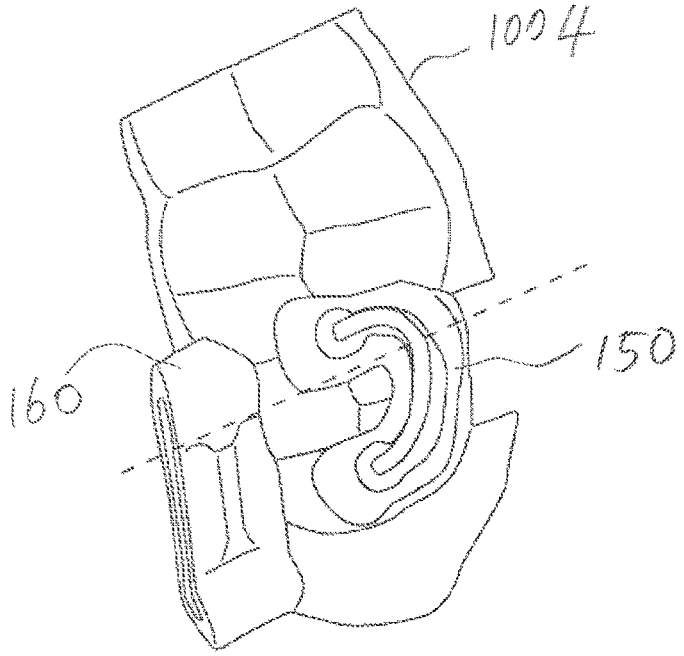
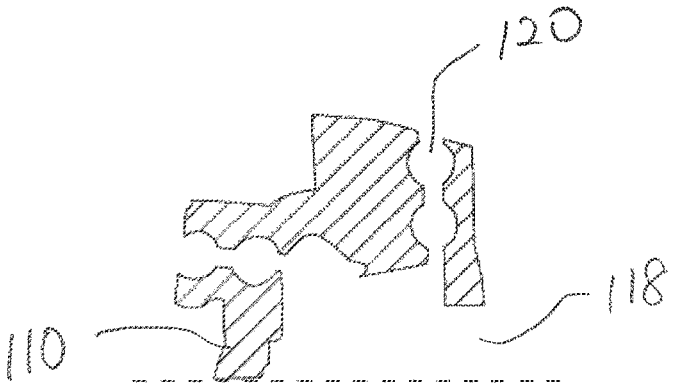
FIG. 99B

FIG. 100A
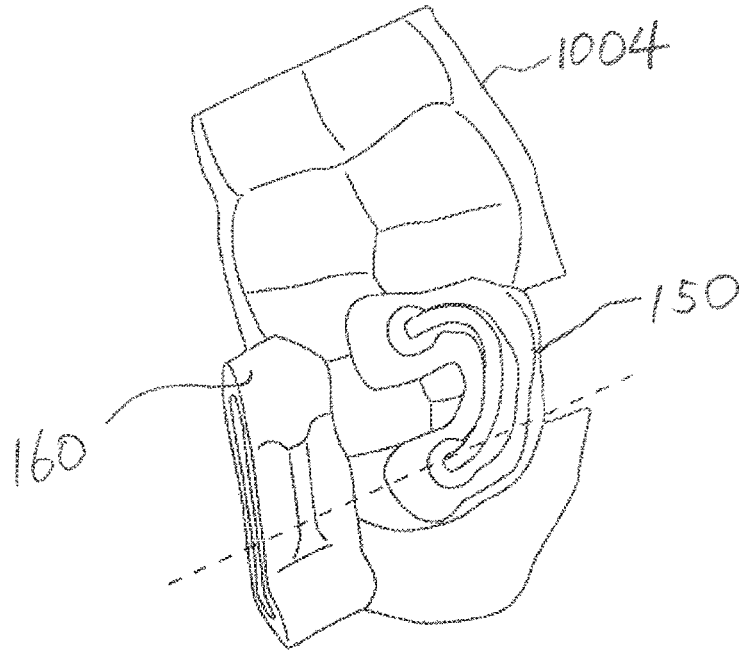
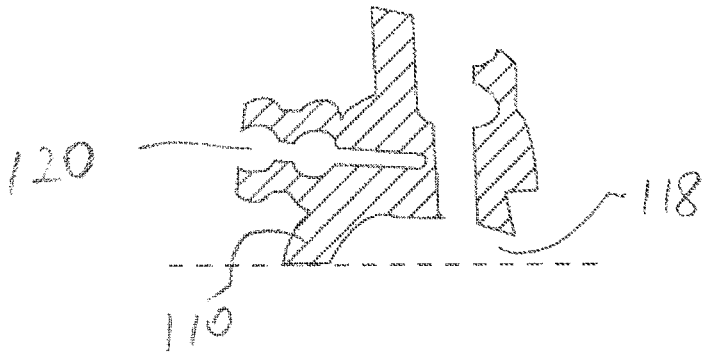
FIG. 100B

TOOTH PREPARATION GUIDE DEVICE AND METHOD OF PREPARING TOOTH FOR DENTAL PROSTHESIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[The present application] *Note: More than one reissue application has been filed for the reissue of U.S. Pat. No. 8,651,860. The reissue applications are application Ser. Nos. 15/916,177 (the present application) and 15/047,515. Application Ser. No. 15/916,117 is a continuation reissue of Ser. No. 15/047,515. Application Ser. No. 15/047,515 is a reissue of U.S. Pat. No. 8,651,860.*

*The present application is a reissue continuation of U.S. patent application Ser. No. 15/047,515, filed Feb. 18, 2016, which is a reissue of U.S. patent application Ser. No. 13/883,565, filed May 3, 2018, now issued as U.S. Pat. No. 8,651,860, which claims priority to International Patent Application No. PCT/IB2011/003368, filed Nov. 17, 2011, which claims priority to and the benefit of U.S. Provisional Application No. 61/503,572, filed Jun. 30, 2011 and U.S. Provisional Application No. 61/503,572, filed Jun. 30, 2011. U.S. patent application Ser. No. 13/883,565 also* claims [the] priority to Korean Patent Application No. 10-2010-0114678, filed Nov. 17, 2010, Korean Patent Application No. 10-2011-0065074, filed Jun. 30, 2011, Korean Patent Application No. 10-2011-0077930, filed Aug. 4, 2011, [U.S. Patent Application No. 61/503,572, filed Jun. 30, 2011, U.S. Patent Application No. 61/503,580, filed Jun. 30, 2011,] *and* International Patent Application No. PCT/US11/61090, filed Nov. 16, 2011, contents of which are hereby incorporated herein by reference in their entirety.

BACKGROUND

1. Field

The present application relates to dental restorations, and more particularly to systems, devices, and procedures for dental restorations.

2. Related Technology

A crown and bridge is a main example of dental restorations for restoring a missing or damaged tooth. When a crown and bridge prosthesis is chosen for restoring a missing tooth, the two adjacent teeth of the missing tooth are modified (cut) and prepared. Then, a copy of the tooth preparation is made by taking an impression of the oral configuration including the missing tooth and modified teeth. The copy is sent to a dental lab for the construction of a desired prosthesis. The preparation of the adjacent teeth typically exposes internal structures of the teeth including dentin and/or pulp tissues. Since fabricating the prosthesis takes some time, e.g., a period of one to three weeks, in order to cover and protect the exposed portions, typically a temporary prosthesis can be made and installed. Once the desired prosthesis is received from the dental lab, the temporary prosthesis is removed, and the prosthesis is placed over and cemented to the abutments, i.e., the prepared adjacent teeth.

In modifying and preparing teeth, once cutting is done in natural teeth, it is not reversible. When cutting is excessive, dentin and pulp tissues can be damaged. The preparation of teeth, particularly the amount cut or precision of cut, heavily depends on the hand skills and experience of the dentist. Presently there appears no technology that practically replaces hand skills and experience of dentists. Also, there appears no technology that significantly improves hand skills of dentists and significantly reduces the risk of possible inaccuracies of dentists.

The foregoing discussion is to provide background information of the invention and does not constitute an admission of prior art.

SUMMARY

Among many others, the present invention provides the following features and characteristics.

In one aspect of the invention, a dental preparation guide device includes a guide channel that guides a cutting tool to cut two or more teeth in one traveling of the guide channel.

In one aspect of the invention, a dental preparation guide device includes a guide channel for making a horse shoe shaped or similarly shaped groove into a lingual side of an anterior tooth. A dental prosthesis having a horse shoe shaped or similarly shaped protrusion that is fitting into the groove of the anterior tooth. The surfaces of the groove and protrusion are shaped and aligned with an axis at high precision so that the prosthesis and prepared tooth are engaged only when the prosthesis approaches the anterior tooth in the particular axis (of insertion) at substantially high accuracy.

In one aspect of the invention, a dental preparation guide device includes a guide channel with two or more sections, each of which is configured to fit only with a predetermined and specially shaped cutting tool.

In one aspect of the invention, a method of dental preparation includes cutting one or more teeth using a single preparation guide device with a guide channel, in which one cutting tool is used in a portion of the guide channel and another cutting tool is used in another portion of the guide channel.

In one aspect of the invention, a dental preparation guide device includes multiple guide channels, each of which is designed to cut one or more teeth.

In one aspect of the invention, a method of dental preparation includes cutting multiple teeth using a single preparation guide device.

In one aspect of the invention, a method of digital dentistry procedure includes determining an axis of insertion of a dental prosthesis to insert into or engage with a prepared tooth. The method includes tilting a 3D image of a tooth to check the size, magnitude and/or amount of undercut portions or areas and identifying a particular axis of orientation of the 3D image, in which the size, magnitude and/or amount of the undercut portions or areas are minimized or acceptable for a dental prosthesis. A computer program includes algorithms and process steps to conduct this method.

In one aspect of the invention, a dental preparation guide device includes a single body with a cutting-tool guide channel and a lump projecting or protruding from the single body like a peninsula, in which a cutting tool entrance is provided.

In one aspect of the invention, a dental preparation guide device includes a guide channel for guiding a cutting tool and an entrance of the guide channel through which the cutting tool enters into the guide channel, wherein the device includes a stopper or stopping feature, which stops the cutting tool at a proper level for sliding into the guide channel.

In one aspect of the invention, dental preparation guide device includes a guide channel for guiding a cutting tool and an entrance of the guide charnel through which the cutting tool enters into the guide channel, wherein the guide channel includes a non-cutting section from the entrance to a point in the guide channel where cutting of a tooth begins, wherein in the non-cutting section the cutting tool is only to travel along the section without cutting the tooth.

In one aspect of the invention, a dental preparation guide device includes a guide channel for guiding a cutting tool and an entrance of the guide channel through which the cutting tool enters into the guide channel, wherein the entrance is located very close to a point in the guide channel where cutting of a tooth begins, whereby no non-cutting section is not needed, wherein in the non-cutting section the cutting tool is only to travel along the section without cutting the tooth.

In one aspect of the invention, a dental preparation guide device includes a marking indicative of directions for using the preparation guide device.

In one aspect of the invention, an elongated dental cutting tool includes a cutting portion in the elongated body and a non-cutting tip stepped from the cutting portion.

In one aspect of the invention, a method of dental preparation using a dental preparation guide and an elongated dental cutting tool, which includes a cutting portion in the elongated body and a non-cutting tip stepped from the cutting portion. The method includes running the cutting tool to cut a tooth while the cutting tool is engaged with the dental preparation guide, wherein the cutting portion cuts the tooth and the non-cutting tip contacts and abuts un-cut surface of the tooth, which prevents the cutting tool (non-cutting tip) from tilting in a direction toward the un-cut surface of the tooth.

In one aspect of the invention, an elongated cutting tool includes configurations, features or structures for engaging with a guide channel of a dental preparation guide device. The dental preparation guide device also includes complementary or counter-part configurations, features and structures to accommodate those of the cutting tool. The engagement of the tool with the preparation guide device prevents or minimizes tilting of the cutting tool while the tool is engaged with the guide channel.

In one aspect of the invention, a dental preparation guide device includes a guide channel for cutting an occlusal surface of a tooth and also another guide channel for cutting a side surface of the same tooth.

In one aspect of the invention, a method of dental preparation includes preparing a tooth using a dental preparation guide device which includes a guide channel for cutting an occlusal surface of a tooth and also another guide channel for cutting a side surface of the same tooth.

In one aspect of the invention, a dental preparation guide device includes a single body configured to be placed over a group of teeth including an open space (missing tooth) interposed by a first tooth and a second tooth. The preparation guide device includes a first guide channel for cutting the first tooth and a second guide channel for cutting the second tooth.

In one aspect of the invention, a dental preparation guide device includes a single body configured to be placed over a group of teeth that do not include a missing tooth. The preparation guide device includes multiple guide channels, each of which is for cutting one tooth of the group.

A method of dental restoration includes: identifying a group of teeth that are in need of splinting and do not include a missing tooth; providing a dental preparation guide device that is custom-designed for the group of teeth; placing the dental preparation guide device over the group of teeth and engaging the same with the teeth; preparing (cutting) each of the group of teeth using the preparation guide device; providing a dental prosthesis having features configured to fit each of the prepared teeth; fixing the dental prosthesis to the group of teeth.

In one aspect of the invention, patients are allowed to view images of prospective prostheses and choose a desired one even before the preparation of a tooth for the prosthesis.

In one aspect of the invention, a dental preparation guide device includes a guide channel (guide way) that guides a cutting tool to cut three or more side surfaces of a tooth in one traveling of the guide channel.

In one aspect of the invention, a method of dental preparation includes cutting three or more side surfaces of a tooth using a single guide channel of a dental preparation guide device.

In one aspect of the invention, a method of dental preparation includes cutting two or more teeth using a single guide channel of a dental preparation guide device.

In one aspect of the invention, a dental restoration kit includes a dental preparation guide device configured to fit at least one tooth and to cut the at least one tooth. The dental restoration kit further includes a dental prosthesis custom-made in view of a desired preparation of the at least one tooth using the dental preparation guide device. The dental restoration kit further includes at least one cutting tool that is designed to engage with a guide channel of the dental preparation guide and to travel along the guide channel. The dental restoration kit may further includes a cement for bonding the dental prosthesis onto the at least one tooth after the desired preparation.

One aspect of the present invention provides a method of providing a dental restoration kit, the method comprising: providing, a first 3D image data representing one or more teeth of a patient before a desired preparation of the one or more teeth for installing a desired dental prosthesis; before the desired preparation and before making the desired dental prosthesis, determining an axis of insertion along which the desired dental prosthesis should approach the one or more teeth for engaging the desired dental prosthesis with the one or more teeth after the desired preparation, wherein the axis of insertion is determined relative to the one or more teeth; generating a second 3D image data representing the one or more teeth after the desired preparation; producing a preparation guide device based on the first 3D image data and the second 3D image data, wherein the preparation guide device is produced as a single piece device that comprises an interior space configured to receive the one or more teeth for engagement therewith and further comprises at least one guide channel configured to guide a burr for cutting at least part of the one or more teeth for the desired preparation; and producing the desired prosthesis based on the first 3D image data and the second 3D image data.

In the foregoing method, determining the axis of insertion may comprise: processing the first 3D image data to orient a 3D image of the one or more teeth in multiple directions; providing information of undercuts in multiple directions of orientation of the 3D image; and choosing a direction of orientation of the 3D image as the axis of insertion based on the information of the undercuts. Generating the second 3D image data may comprise processing the first 3D image data with the input of an area of cutting and depth of cutting.

Generating the second 3D image data may comprise processing the first 3D image data with the input of one or more selected from the group consisting of an orientation of the burr, a diameter of the burr, a length of the burr, tapered shape information of the burr, a position of the burr relative to the one or more teeth, a distance between a rotational axis of the burr and an exterior surface of the one or more teeth, and a level of the burr relative to the one or more teeth. Producing as the desired prosthesis may comprise: generating a fourth 3D image data of the desired prosthesis; and making the desired prosthesis using the fourth 3D image data. The method may further comprise providing the burr.

Another aspect of the invention provides a method of making devices for dental procedure, comprising: providing a first 3D image data representing one or more teeth of a patient before a desired preparation at the one or more teeth for installing a desired dental prosthesis; before the desired preparation, generating a first image illustrating a first prospective shape of the one or more teeth that would exist after installation of a first dental prosthesis; before the desired preparation, providing the first image for the patient's review of the first image; subsequent to the patient's approval of the first image and before the desired preparation, making the first dental prosthesis based on the first image; and subsequent to the patient's approval of the image, making a preparation guide device based on the fast 3D image data, wherein the preparation guide device is custom-made to fit at least part of the one or more teeth and comprises at least one guide channel configured to guide a burr to cut the one or more teeth for fitting the first dental prosthesis without the need of additional substantial cutting of the one or more teeth.

In the foregoing method, the method may further comprise: before the desired preparation, generating a second 3D image data representing a prospective, prepared shape of the one or more teeth that would exist after the desired preparation thereof. The method may further comprise: before the desired preparation, generating a second image illustrating a second prospective shape of the one or more teeth that would exist after installation of a second dental prosthesis; before the desired preparation, providing a plurality of images comprising the first and second images for the patient's review; and receiving the patient's approval of the first image rather than the second image, wherein the first and second prospective shapes differ in at least one selected from the group consisting of length, width, surface curvature, embrasure and shading.

Still in the foregoing method, the method may further comprise: subsequent to providing the first image and prior to the patient's approval, receiving the patient's request to modify the first image; changing the first prospective shape based n the patient's request to modify the first image; and providing an modified first image illustrating the changed first prospective shape for the patient's approval.

Still another aspect of the invention provides a method of dental procedure, comprising: making a first dental prosthesis and a preparation guide device in accordance with the foregoing method; and providing the first dental prosthesis and the preparation guide device to a dental practitioner for preparing the one or more teeth and installing the first dental prosthesis onto the one or more teeth after preparation.

In the foregoing method, the method may further comprising providing the burr along with the first dental prosthesis and the preparation guide device, wherein the preparation guide device further comprises a guide groove formed along the at least one guide channel, wherein the burr comprises an elongated body with a bump between two ends thereof, wherein the elongated body is configured to fit in the at least one guide channel of the preparation guide device and the bump is configured to fit the guide groove such that the guide channel and the guide groove in combination position and orient the burr relative to the one or more teeth in a predetermined manner.

Yet another aspect of the invention provides a method of dental procedure, comprising: providing, a dental prosthesis for installing onto one or more teeth of a patient, the one or more teeth comprising a first tooth comprising an occlusal surface and buccal, a lingual, distal and mesial sides; providing a preparation guide device in a single piece for use in preparing the one or more teeth of the patient for installing the dental prosthesis, wherein the preparation guide device is custom-made to fit at least part of the one or more teeth and comprises at least one guide channel configured to guide a cutting tool, wherein the at least one guide channel comprises a first single channel that the cutting tool can travel through without having to remove the cutting tool from the preparation guide device; mounting the preparation guide device over the one or more teeth such that the preparation guide device fit the at least part of the one or more teeth; and cutting the first tooth with use of a burr as the cutting tool by moving the burr through the first single channel configured to cut the first tooth on three or four of the buccal, lingual, distal and mesial sides without having to remove the burr from the preparation guide device, which completes preparation of the first tooth for installing the dental prosthesis onto the first tooth without the need of an additional preparation guide for preparing the first tooth and without the need of an additional substantial cutting of the first tooth; and installing the dental prosthesis onto the first tooth so as to surround the three or four of the buccal, lingual, distal and mesial sides of the first tooth.

In the foregoing method, cutting of the three or four sides may leave at least a portion of the four sides uncut, wherein the uncut portion comprises a contact point of the first tooth that contacts a neighboring tooth. The first single channel may be configured to cut the four of the buccal, lingual, distal and mesial sides, wherein cutting of the four sides entirely encircles the first tooth when viewing in a direction toward the occlusal surface, wherein the dental prosthesis comprises a ring structure contacting the four sides of the first tooth that are cut using the first single channel. The first single channel may be configured to cut the four of the buccal, lingual, distal and mesial sides, wherein cutting of the four sides does not entirely encircle the first tooth and leaves at least part of one of the four sides uncut when viewing in a direction toward the occlusal surface, wherein the dental prosthesis comprises a C-shaped structure contacting the four sides of the first tooth that are cut using the first single channel.

Still in the foregoing method, the one or more teeth may comprise a first tooth and a second tooth, wherein cutting the one or more teeth comprises cutting the first tooth and then cutting the second tooth, wherein the preparation guide device is not disconnected from the one or more teeth between cutting the first tooth and cutting the second tooth, and wherein the first single channel is further configured to cut the second tooth in addition to cutting the first tooth without having to remove the burr from the first single channel. The one or, more teeth may comprise a first tooth and a second tooth, wherein cutting the one or more teeth comprises cutting the first tooth and then cutting the second tooth, wherein the preparation guide device is not disconnected from the one or more teeth between cutting the first tooth and cutting the second tooth, and wherein the at least one channel comprises a second single channel that is distinct from the first single channel and configured to cut the second tooth. Providing the dental prosthesis may comprise receiving the dental prosthesis from a third party or making the dental prosthesis in-house, wherein providing the preparation guide device comprises receiving the preparation guide device from a third party or making the preparation guide device in-house.

Yet in the foregoing method, the method may further comprise: causing to provide a 3D image data representing the one or more teeth of the patient before preparation sufficient to install the dental prosthesis, wherein causing to provide the 3D image data comprises at least one selected from the group consisting of: scanning of the patient's oral features using a 3D scanning device; taking an impression of the patient's oral features; producing a 3D model of the patient's oral features from the impression; and scanning the 3D model using a 3D scanning device.

A further aspect of the invention provides a dental preparation guide apparatus in a single body, the single body apparatus comprising a lingual sidewall, a buccal sidewall opposing the lingual sidewall, and an occlusal wail interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, and the occlusal surface faces the occlusal wall, wherein the single body comprises a guide channel formed in the occlusal wall and shaped to receive with a cutting tool to guide the cutting tool to travel along a trajectory; wherein the guide channel comprises a buccal section, a lingual section, and an interconnecting section interconnecting the buccal and lingual sections to provide the guide channel as a single integrated channel that allows the cutting tool to travel through the guide channel without being removed therefrom; and wherein when viewing in a direction toward the occlusal wall, the buccal section extends generally along the buccal sidewall, and the lingual section extends generally along the lingual sidewall.

In the foregoing apparatus, the buccal section may be configured to have a portion of the cutting tool enter into the interior space and between the buccal sidewall and the tooth such that the portion of the cutting tool cuts at least part of the buccal surface while traveling in the buccal section; wherein the lingual section is configured to have the portion of the cutting tool enter into the interior space and between the lingual sidewall and the tooth such that the portion of the cutting tool cut at least part of the lingual surface while traveling in the lingual section; and wherein the interconnecting section is configured to have the portion of the cutting tool enter into the interior space and between the tooth and an immediately neighboring tooth such that the portion of the cutting tool cut at least part of the mesial or distal surface while traveling in the interconnecting section. When viewing in the direction toward the occlusal wall, a tangential line of the buccal section at a point thereof may be parallel to a tangential line of the lingual section at a point thereof. The guide channel further may comprise a second interconnecting section that further interconnects the buccal and lingual sections to provide the guide channel in the form of a closed loop when viewing in the direction toward the occlusal wall. The guide channel may further comprise another section extending from either the buccal section or the lingual section, wherein when viewing in the direction toward the occlusal wall, a tangential line of the other section at a point thereof is parallel to a tangential line of the interconnecting section at a point thereof.

Still in the foregoing apparatus, the guide channel may further comprise another section extending from either the buccal section or the lingual section, wherein when viewing in the direction toward the occlusal wall, a tangential hue of the other section at a point thereof is parallel to a tangential line of the interconnecting section at a point thereof, wherein the other section does not interconnect between the buccal and lingual sections to make the guide channel in the form of a closed loop. The guide channel may be configured to have the cutting tool pass through the occlusal wall such that the cutting tool extends into the interior space, such that the cutting tool cuts the buccal surface when the cutting tool travels in the buccal section and such that the cutting tool cuts one of the mesial and distal surfaces when the cutting tool travels in the interconnecting section. The interior space defined by the lingual sidewall, the buccal sidewall and the occlusal wall may be configured to receive one or more additional teeth.

One aspect of the invention provides a method of preparing, a tooth for dental restoration, the method comprising: providing the foregoing apparatus for preparation of a tooth comprising a buccal surface, a lingual surface, a mesial surface, a distal surface and an occlusal surface; engaging the apparatus with the tooth such that the tooth is received in the interior space and such that the lingual surface faces the lingual sidewall, the buccal surface faces the buccal sidewall, and the occlusal surface faces the occlusal wall; inserting a burr as the cutting tool into the guide channel via an insertion hole; traveling the burr along the trajectory of the guide channel comprising the buccal section, lingual section and interconnecting section, by which the burr cuts side surface of the tooth comprising at least part of the lingual surface, at least part of the buccal surface and at least part of the mesial or distal surface; and wherein during traveling of the burr along the trajectory, the burr is not removed from the guide channel until completion of the cutting side surfaces of the tooth. In the foregoing method, when viewing in the direction toward the occlusal wall, a tangential line of the buccal section at a point thereof may be parallel to a tangential line of the lingual section at a point thereof.

Another aspect of the invention provides a dental preparation guide apparatus in a single body, the single body apparatus comprising a lingual sidewall, a buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, and the occlusal surface faces the occlusal wall, wherein the single body comprising a first guide channel formed in the occlusal wall and shaped to engage with a first cutting tool to guide the first cutting tool to travel along a first trajectory; wherein when viewing in a direction toward the occlusal wall, the first guide channel comprising a section that extends generally along at least part of the buccal sidewall; wherein the single body comprising a second guide channel formed in at least one of the buccal and lingual sidewalls and shaped to engage with a second cutting tool to guide the second cutting tool to travel along a second trajectory; and wherein when viewing in a direction toward the buccal sidewall, the second guide channel extends generally along at least part of the occlusal wall.

In the foregoing apparatus, the occlusal wall may comprise an interior surface facing the occlusal surface of the tooth when the tooth is received in the interior space, wherein the second guide channel extends generally along the interior surface of the occlusal wall When viewing in the direction toward the buccal sidewall; and wherein the buccal side wail comprises art interior surface facing the buccal surface of the tooth when the tooth is received in the interior space, wherein the first guide channel extends generally along the interior surface of the buccal wall when viewing in the direction toward the occlusal wall. The first guide channel may further comprise another section, which is configured to have the cutting tool pass through the occlusal wall such that the cutting tool extends into the interior space, and further such that the cutting tool cuts one of the mesial and distal surfaces when the cutting tool travels in the other section.

A further aspect of the invention provides a method of preparing a tooth for dental restoration, the method comprising: providing the apparatus for preparation of a tooth comprising a buccal surface, a lingual surface, a mesial surface, a distal surface and an occlusal surface; engaging the apparatus with the tooth such that the tooth is received in the interior space and such that the lingual surface faces the lingual sidewall, the buccal surface faces the buccal sidewall, and the occlusal surface faces the occlusal wall; inserting a burr as the cutting, device into the first guide channel of the apparatus, whereby a cutting portion of the burr enters into the interior space and between the buccal sidewall and the tooth; cutting at least part of the buccal surface of the tooth while traveling the burr along the first guide channel; inserting the same burr or another burr into the second guide channel, whereby a cutting portion of the burr enters into the interior space and. between the occlusal wall and the tooth, wherein inserting the same or other burr can occur either before or after cutting the buccal surface; and cutting at least part of the buccal surface of the tooth while traveling the same burr or the other burr along the second guide channel.

One aspect of the invention provides a dental preparation guide apparatus in a single body, the single body apparatus comprising a lingual sidewall, a buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, and the occlusal surface faces the occlusal wall, wherein the single body comprising a guide channel formed in at least one of the lingual and buccal sidewalls and shaped to engage with a cutting tool to guide the cutting tool along a trajectory; and wherein the guide channel is configured to have [the] a portion of the cutting tool enter into the interior space and between the occlusal wall and the tooth such that the portion of the cutting tool cuts at least part of the occlusal surface while traveling in the guide channel.

In the foregoing apparatus, the guide channel may comprises a port configured to permit the entry of the cutting tool into the guide channel, wherein the port of the guide channel is formed through the occlusal wall such that the cutting tool enters into the guide channel formed din the at least one of the lingual and buccal sidewalls via the port through the occlusal wall.

Another aspect of the invention provides a method of preparing a tooth for dental restoration, the method comprising: providing the apparatus for preparation of a tooth comprising, a buccal surface, a lingual surface, a mesial surface, a distal surface and an occlusal surface; integrating the apparatus with the tooth such that the tooth is received in the interior space and such that the lingual surface faces the lingual sidewall, the buccal surface faces the buccal sidewall, and the occlusal surface faces the occlusal wail; engaging the guide channel of the apparatus with a burr as the cutting tool, whereby a cutting portion of the burr enters into the interior space and between the occlusal wall and the tooth; and traveling the burr along the guide channel while running the burr, thereby cutting at least part of the occlusal surface of the tooth.

A further aspect of the invention provides a dental preparation guide apparatus in a single body, the single body apparatus comprising, a lingual sidewall, a buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive two or more teeth comprising a first tooth and a second tooth, wherein the lingual sidewall comprises a first lingual sidewall and a second lingual sidewall, the buccal sidewall comprises a first buccal sidewall and a second buccal sidewall, the occlusal wall comprises a first occlusal wall and a second occlusal wall; wherein the first lingual sidewall and the first sidewall oppose each other and are configured to sandwich the first tooth when the first and second teeth are received in the interior space; wherein the second lingual sidewall and the second buccal sidewall oppose each other and are configured to sandwich the second tooth when the first and second teeth are received in the interior space; wherein the first occlusal wall is interposed between the first lingual sidewall and the first buccal sidewall and is configured to overlap the first tooth when the first and second teeth are received in the interior space; wherein the second occlusal wall is interposed between the second lingual sidewall and the second buccal sidewall and is configured to overlap the second tooth when the first and second teeth are received in the interior space; wherein the single body comprises a first guide channel formed in the first occlusal wall and shaped to receive a cutting tool to guide the cutting tool along the first guide channel; and wherein the single body comprises a second guide channel formed in the second occlusal wall and shaped to receive the cutting tool or another cutting tool to guide the stone along the second guide channel.

In the foregoing apparatus, the first and second teeth may be adjacent with each other with no tooth therebetween and with no missing tooth therebetween, wherein the first guide channel and the second guide channel are connected together and form a single connected channel such that the cutting tool received in the first guide channel can travel to the second guide channel without having to be removed from the first guide channel. The first and second teeth may be immediately next to each other with each other with no tooth therebetween and with no missing tooth therebetween, wherein the first guide channel and the second guide channel are separate from each other and a portion of the single piece body blocks between the first and second channels such that the cutting tool received in the first guide channel must be removed from the first guide channel in order to be received in the second guide channel.

Still in the foregoing apparatus, a missing tooth exist between the first and second teeth, wherein the lingual sidewall further may comprise a third lingual sidewall located between the first lingual sidewall and the second lingual sidewall; wherein the buccal sidewall further comprises a third buccal sidewall located between the first buccal sidewall and the second buccal sidewall; wherein the occlusal wall further comprises a third occlusal wall located between the first occlusal wall and the second occlusal wall; wherein the third lingual sidewall, the third buccal sidewall and the third occlusal wall at least partially surrounds a space of the missing tooth when the first and second teeth are received in the interior space. The single body may comprise a third guide channel formed in the third occlusal wall and shaped to receive the cutting tool or another cutting tool to guide the same along the third guide channel, wherein the first guide channel and the second guide channel are connected together via the third guide channel and form a single connected channel such that the cutting tool received in the first guide channel can travel to the second guide channel without having to be removed from the first guide channel. The single body does not comprises a guide channel in the third occlusal wall, wherein the first guide channel and the second guide channel are separate from each other and a portion of the third occlusal wall blocks between the first and second channels such that the cutting tool received in the first guide channel must be removed from the first guide channel in order to be received in the second guide channel.

Yet in the foregoing apparatus, a third tooth exist between the first and second teeth, wherein the lingual sidewall further comprises a third lingual sidewall located between the first lingual sidewall and the second lingual sidewall; wherein the buccal sidewall further comprises a third buccal sidewall located between the first buccal sidewall and the second buccal sidewall; wherein the occlusal wall further comprises a third occlusal wail located between the first occlusal wall and the second occlusal wall; wherein the third lingual sidewall, the third buccal sidewall and the third occlusal wall at least partially surrounds the third tooth when the first, second and third teeth are received in the interior space. The single body may comprise a third guide channel formed in the third occlusal wall and shaped to receive the cutting tool or another cutting tool to guide the same along the third guide channel, wherein the first guide channel and the second guide channel are connected together via the third guide channel and form a single connected channel such that the cutting tool received in the first guide channel can travel to the second guide channel without having to be removed from the first guide channel.

Further in the foregoing apparatus, the first guide channel may comprise a first buccal section, a first lingual section, and a first interconnecting section interconnecting the first buccal and first lingual sections to provide the first guide channel as a single integrated channel that allows the cutting tool to travel between the first lingual section and the first buccal section without having to remove the cutting tool therefrom, wherein when viewing in a direction toward the occlusal wall, the first buccal section extends generally along the first buccal sidewall, and the first lingual section extends generally along the first lingual sidewall. The first buccal section may be configured to have a portion of the cutting tool enter into the interior space and between the first buccal sidewall and the first tooth for cutting at least part of a buccal surface of the first tooth while traveling in the first buccal section when the first and second teeth are received in the interior space; wherein the first lingual section is configured to have the portion of the cutting tool enter into the interior space and between the first lingual sidewall and the tooth for cutting at least part of a lingual surface of the first tooth while traveling in the first lingual section when the first and second teeth are received in the interior space; and wherein the first interconnecting section is configured to have the portion of the cutting tool enter into the interior space for cutting at least part of a mesial or distal surface of the first tooth while traveling in the first interconnecting section when the first and second teeth are received in the interior space.

In the foregoing apparatus, when viewing in the direction toward the occlusal wall, a tangential line of the first buccal section at a point thereof may be parallel to a tangential line of the first lingual section at a point thereof. The first guide channel may further comprise a second interconnecting section that further interconnects the first buccal section and the first lingual section to provide the first guide channel in the form of a closed loop when viewing in the direction toward the occlusal wall. The first guide channel may further comprise another section extending from either the first buccal section or the first lingual section, wherein when viewing in the direction toward the occlusal wall, a tangential line of the other section at a point thereof is parallel to a tangential line of the first interconnecting section at a point thereof. The first guide channel may further comprise another section extending from either the first buccal section or the first lingual section, wherein when viewing in the direction toward the occlusal wall, a tangential line of the other section at a point thereof is parallel to a tangential line of the first interconnecting section at a point thereof, wherein the other section does not interconnect between the first buccal section and the first lingual section to make the guide channel in the form of an open loop.

BRIEF DESCRIPTION OF THE DRAWINGS

FIG. 48A is a plan view of the preparation guide device shown in FIG. 44.

FIG. 48B is a cross-sectional view taken along a line X-Y shown in FIG. 48A.

FIG. 50A is another perspective view of the preparation guide device shown in FIG. 44 as mounted on teeth.

FIG. 50B is a cross-sectional view taken along a line X-Y shown in FIG. 50A.

FIG. 51A is a further perspective view of the preparation guide device shown in FIG. 44 as mounted on teeth.

FIG. 51B is a cross-sectional view of the preparation guide device mounted on teeth taken along a line X-Y shown in FIG. 51A.

FIG. 55A is a further perspective view of a preparation guide device in accordance with one embodiment as mounted on teeth.

FIG. 55B is a cross-sectional view taken along a plane shown in FIG. 51A.

FIG. 60 is a plan view of the preparation guide device shown in FIG. 57 as mounted on teeth.

FIG. 60A is a cross-sectional view taken along line A shown in FIG. 60.

FIG. 60B is a cross-sectional view taken along line B shown in FIG. 60.

FIG. 60C is a cross-sectional view taken along line C shown in FIG. 60.

FIG. 60D is a cross-sectional view taken along line D shown in FIG. 60.

FIG. 69 is a plan view of the preparation guide device shown in FIG. 66 as mounted on teeth.

FIG. 69A is a cross-sectional view taken along line X-YA shown in FIG. 69.

FIG. 69B is a cross-sectional view taken along line X-YB shown in FIG. 69.

FIG. 76A is a perspective view of a preparation guide device in accordance with one embodiment.

FIG. 76B is a cross-sectional view taken along a line X-Y shown in FIG. 76A.

FIG. 77A is a plan view of the preparation guide device shown in FIG. 76A.

FIG. 77B is a cross-sectional view taken along a line X-Y shown in FIG. 77A.

FIG. 79A is a plan view of a preparation guide device in accordance with one embodiment.

FIG. 79B is a cross-sectional view taken along a line X-Y shown in FIG. 79A.

FIG. 81A is a perspective view of teeth before preparation.

FIG. 81B is a perspective view of a first preparation guide device shown in FIG. 80 as mounted on teeth.

FIG. 81C is a perspective view of prepared teeth.

FIG. 82A is a plan view of teeth before preparation.

FIG. 82B is a plan view of the first preparation guide device shown in FIG. 80 as mounted on teeth.

FIG. 82C a cross-sectional view taken along an upper line X-Y shown in FIG. 82B.

FIG. 82D is a cross-sectional view taken along an lower line X-Y shown in FIG. 82B.

FIG. 83A is a perspective view of partially prepared teeth.

FIG. 83B is a perspective view of a second preparation guide device shown in FIG. 80 as mounted on teeth.

FIG. 83C is a perspective view of fully prepared teeth.

FIG. 84A is a plan view of partially prepared teeth.

FIG. 84B is a plan view of the second preparation guide device shown in FIG. 80 as mounted on teeth.

FIG. 84C a cross-sectional view taken along an upper line X-Y shown in FIG. 84B.

FIG. 84D a cross-sectional view taken along an lower line X-Y shown in FIG. 84B.

Figure 85:
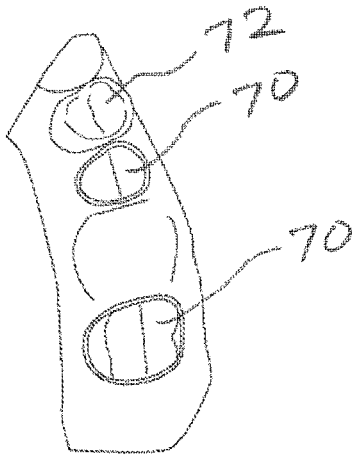

FIG. 85 is a plan view of fully prepared teeth.

FIG. 86A is a plan view of a preparation guide device in accordance with one embodiment as mounted on teeth.

FIG. 86B is a cross-sectional view taken along a line X-Y shown in FIG. 86A.

Figures 87A, 87B, 87C:
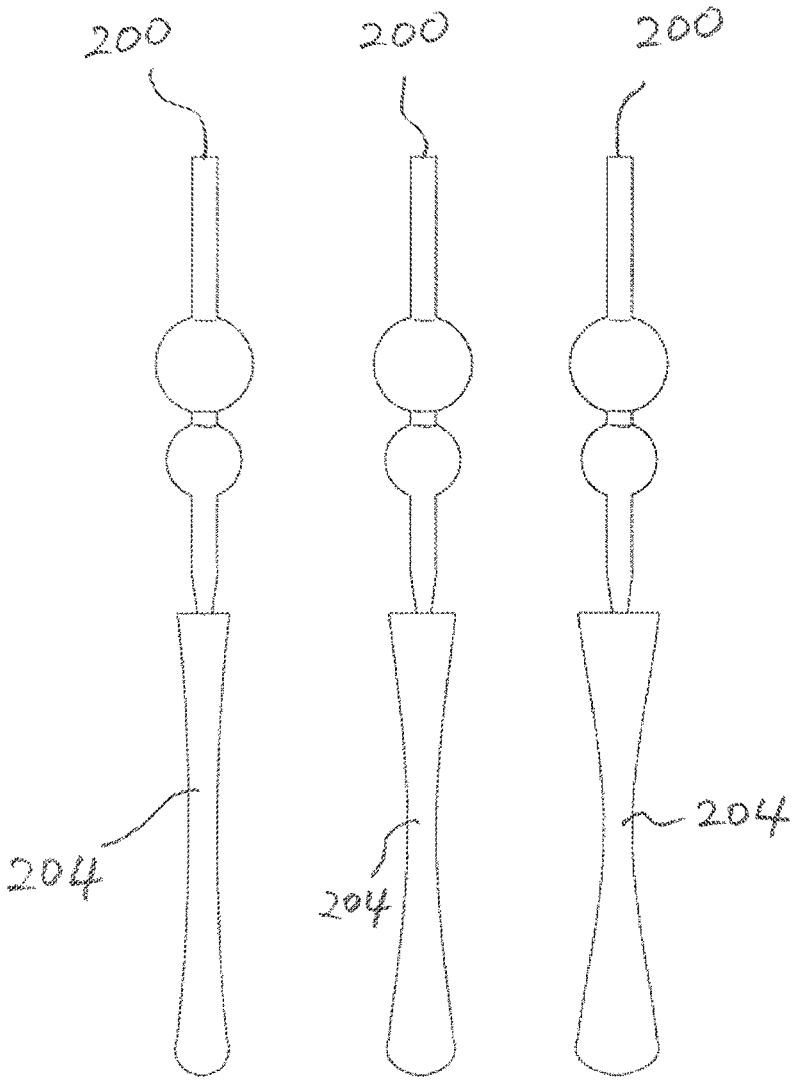

FIGS. 87A, 87B and 87C are side views of various burrs in accordance with embodiments.

Figure 88A:
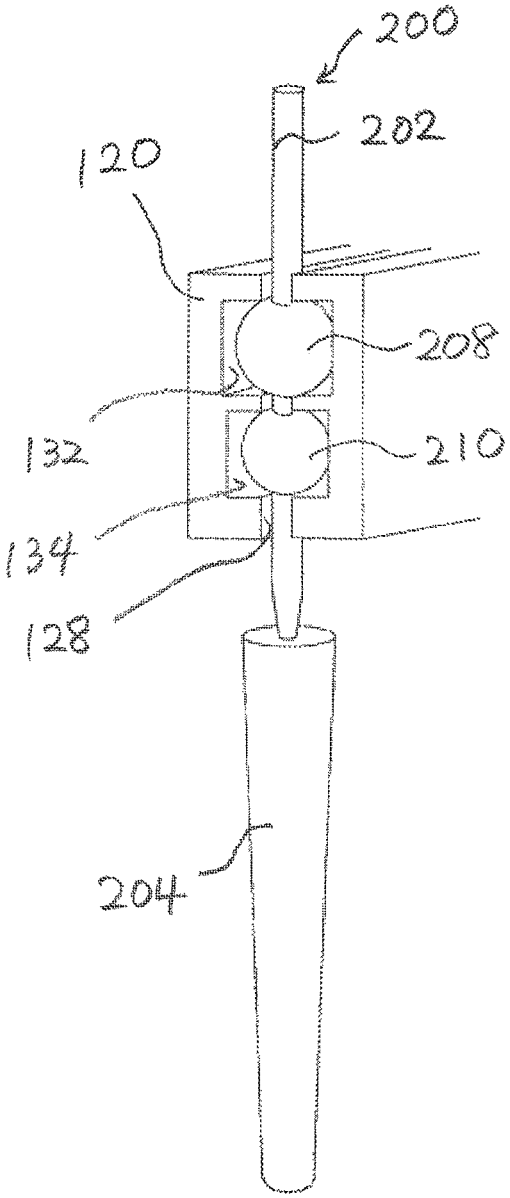
Figure 88B:
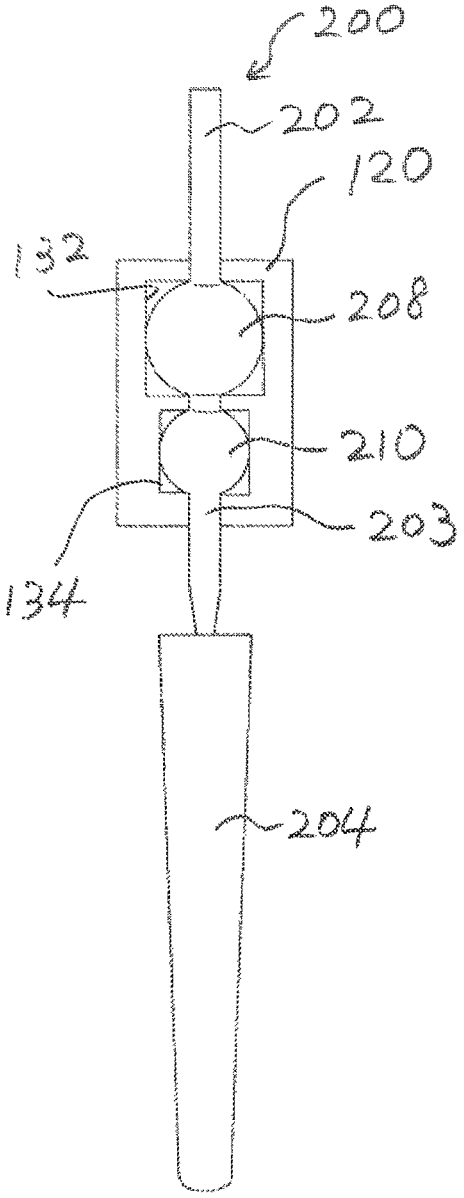

FIGS. 88A and 88B are perspective and cross-sectional views of a tool guide way and a burr in accordance with one embodiment, respectively.

Figure 89:
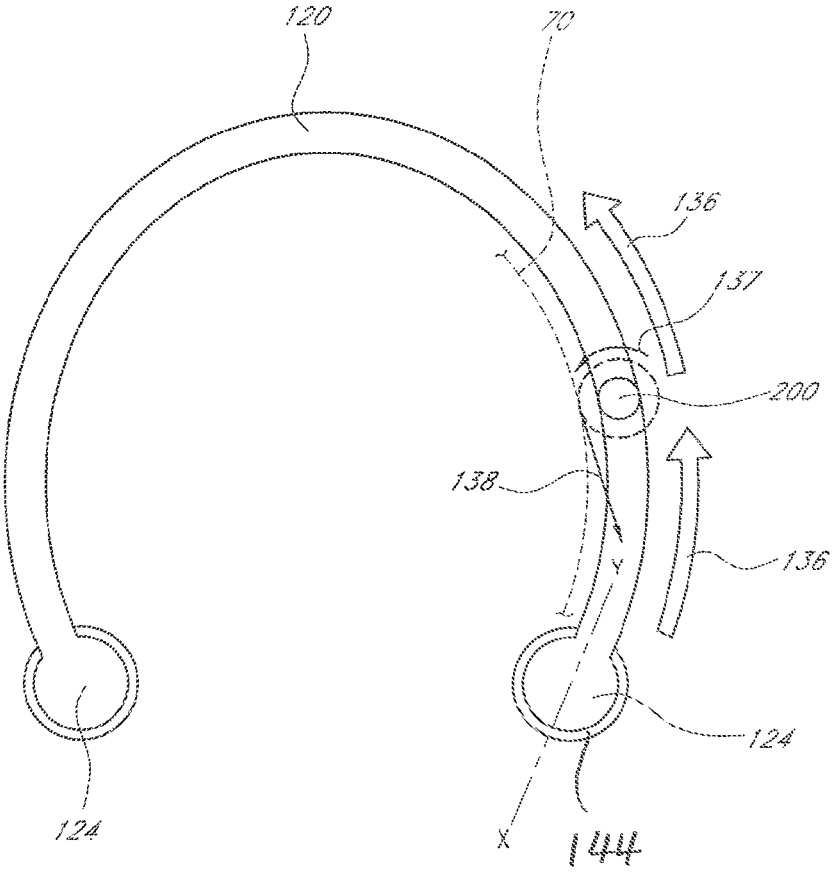

FIG. 89 is a plan view of a tool guide way in accordance with one embodiment.

Figure 90:
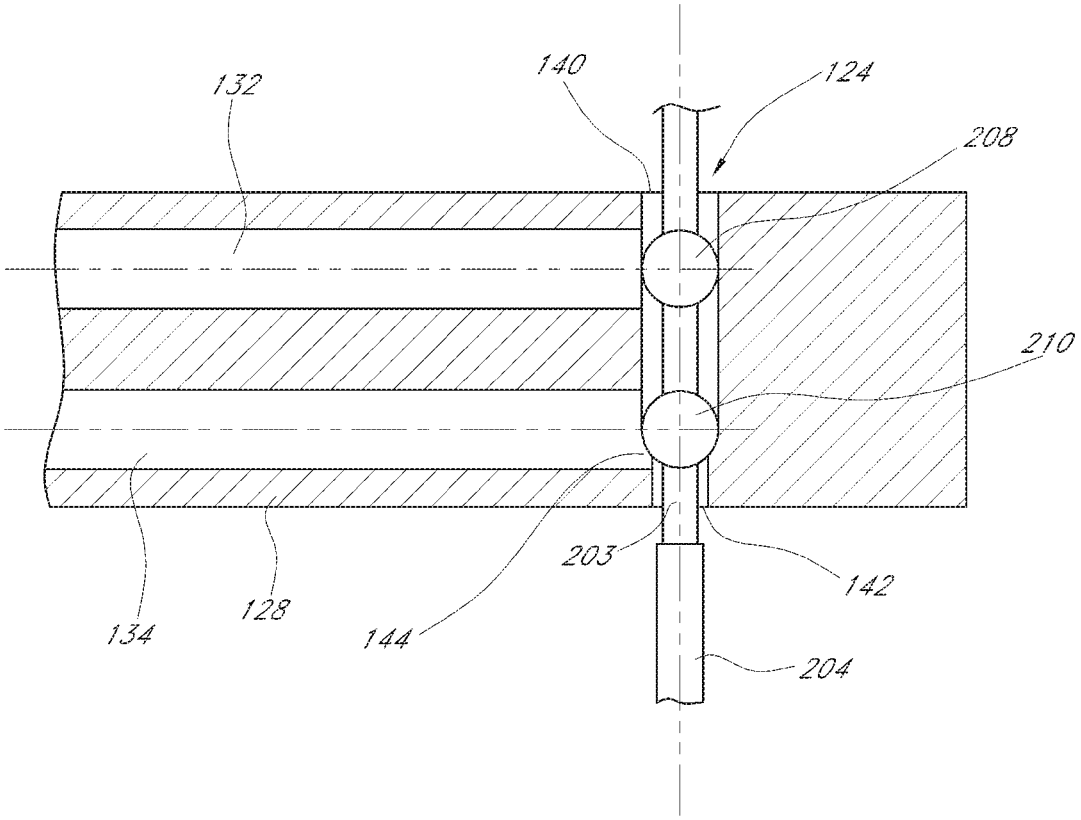

FIG. 90 is a cross-sectional view taken along a line X-Y shown in FIG. 89.

Figure 91:
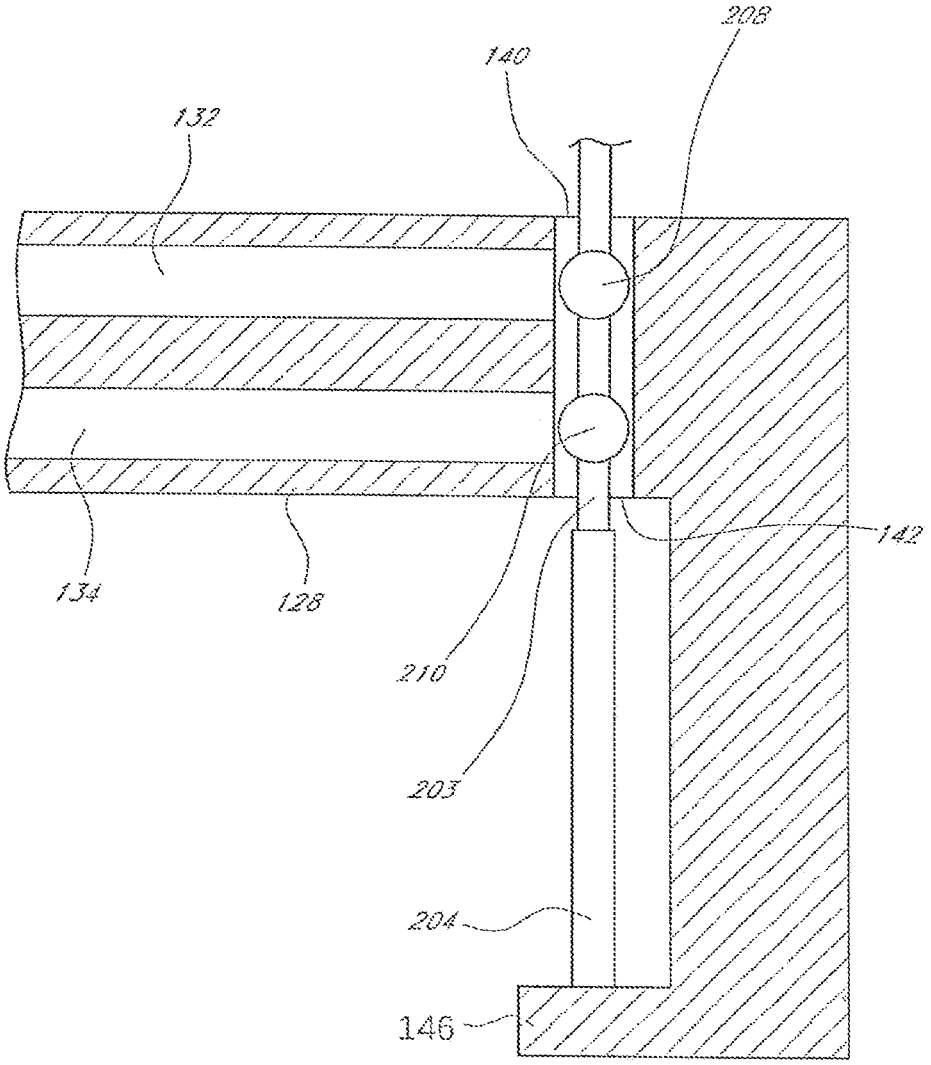

FIG. 91 is a cross-sectional view of a tool guide way in accordance with one embodiment.

Figure 92A:
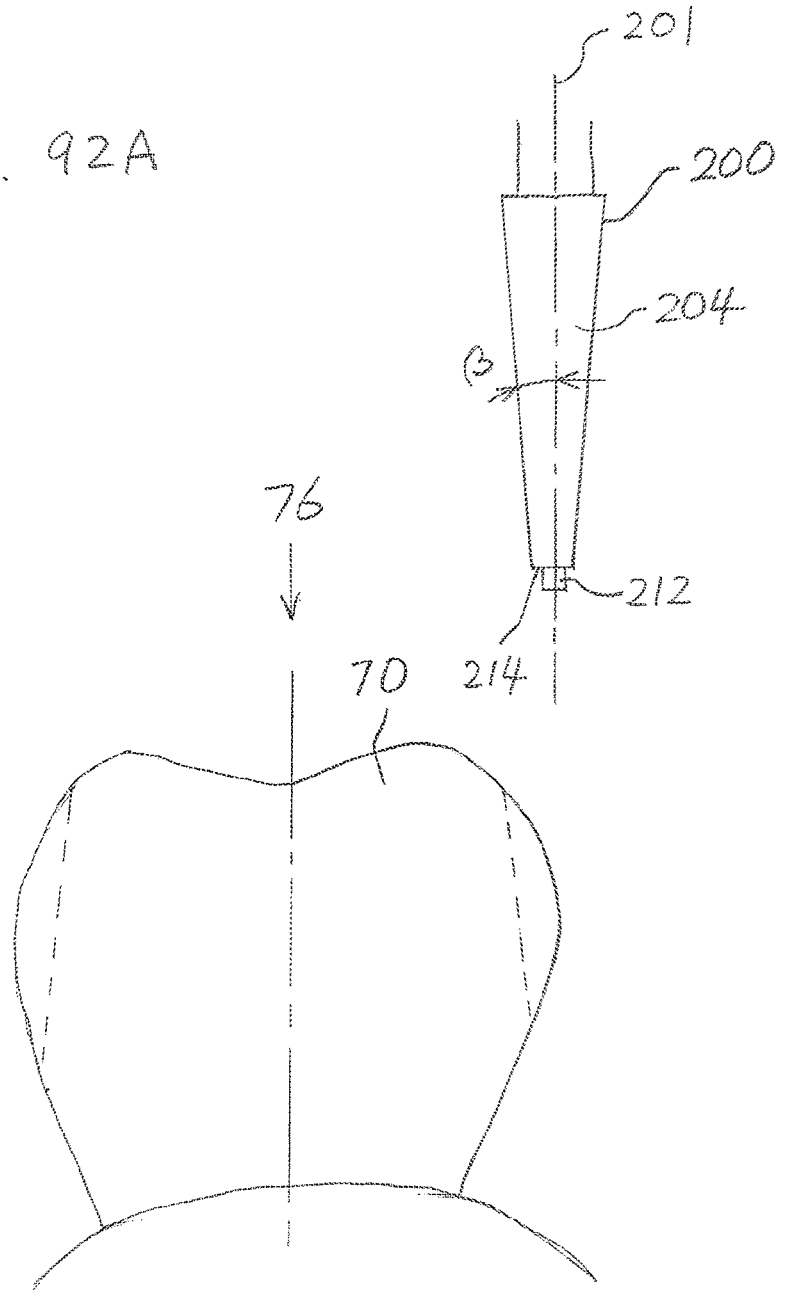

FIG. 92A is a side view of a tooth and a burr in accordance with one embodiment.

Figure 92B:
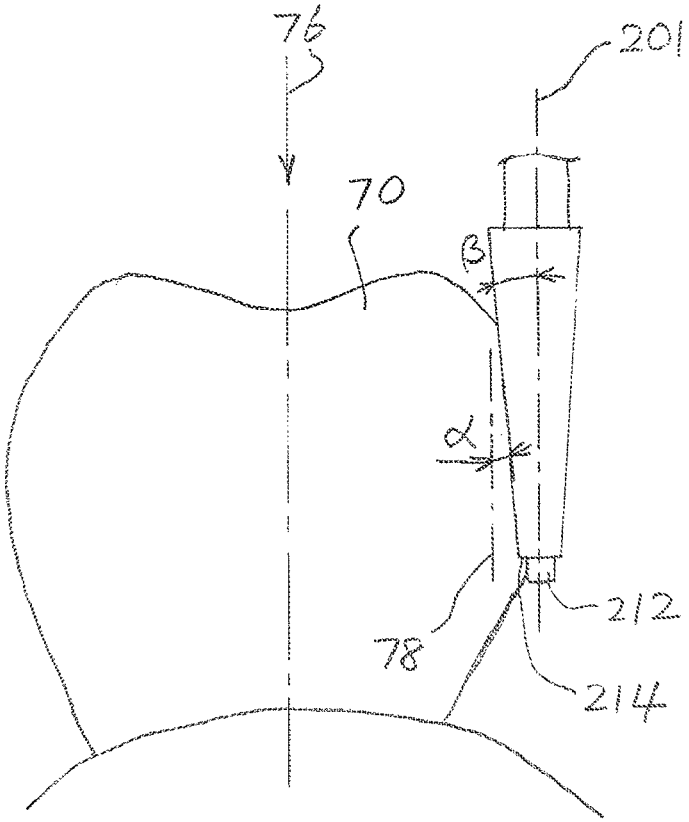

FIG. 92B is another side view of a tooth and a burr cutting the tooth in accordance with one embodiment.

Figure 92C:
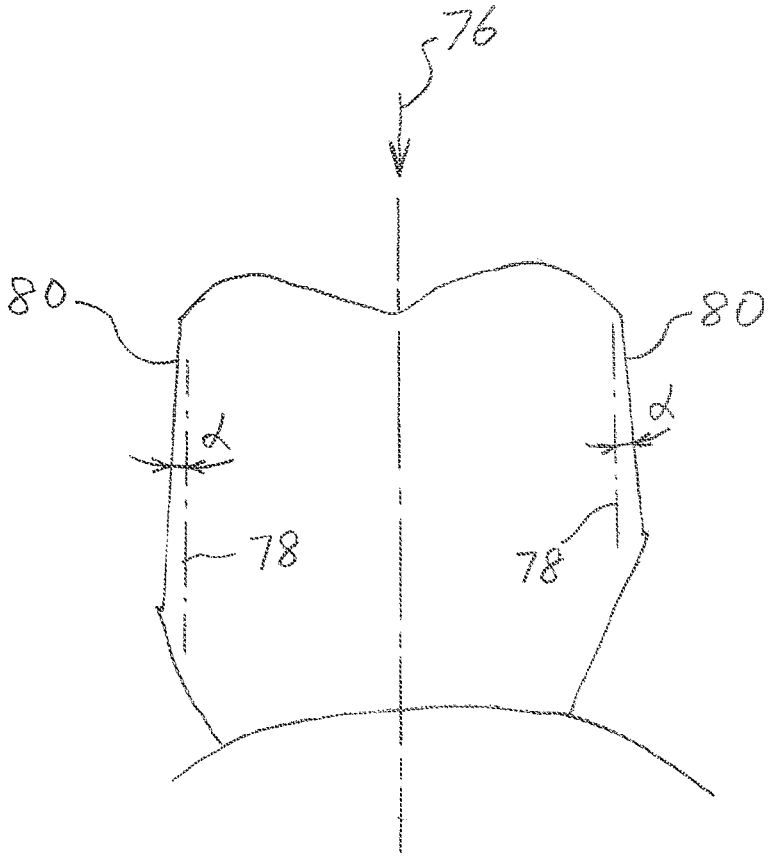

FIG. 92C is a side view of a prepared tooth in accordance with one embodiment.

Figure 92D:
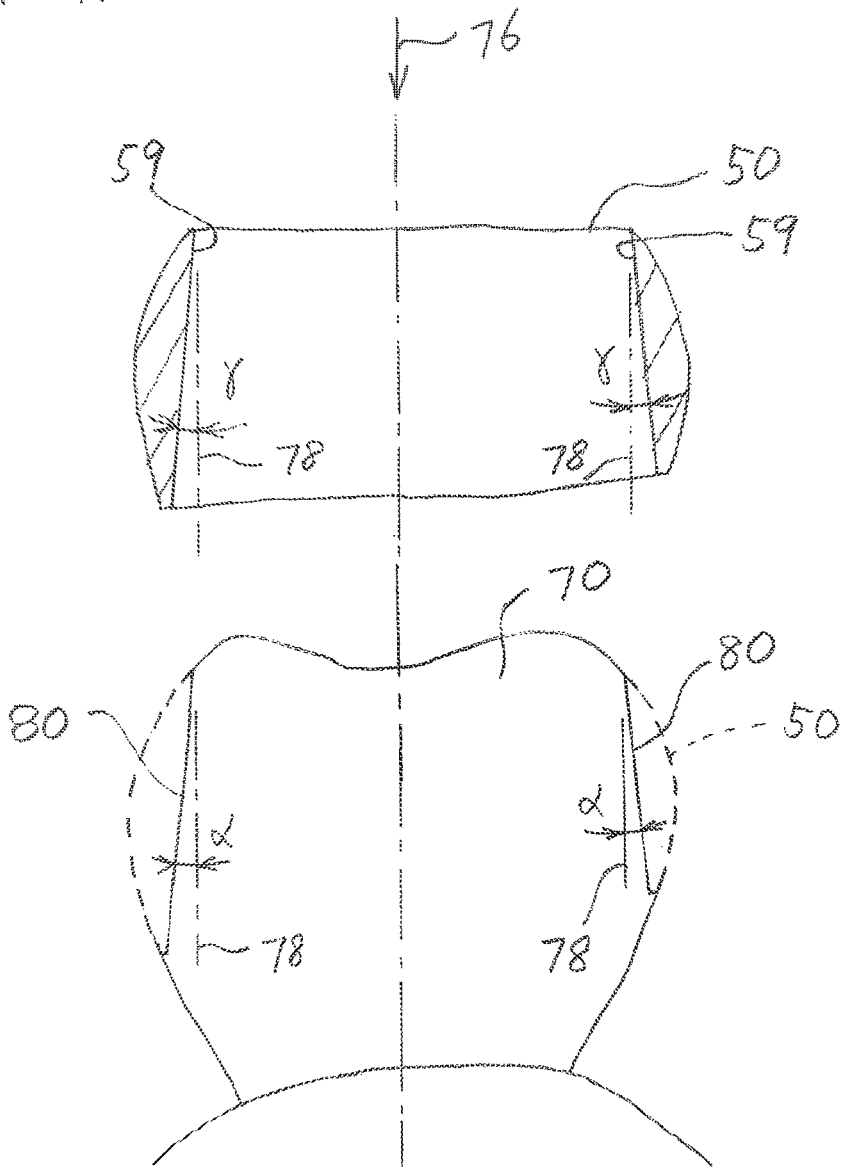

FIG. 92D is a view of a prepared tooth and a prosthesis in accordance with one embodiment.

Figure 92E:
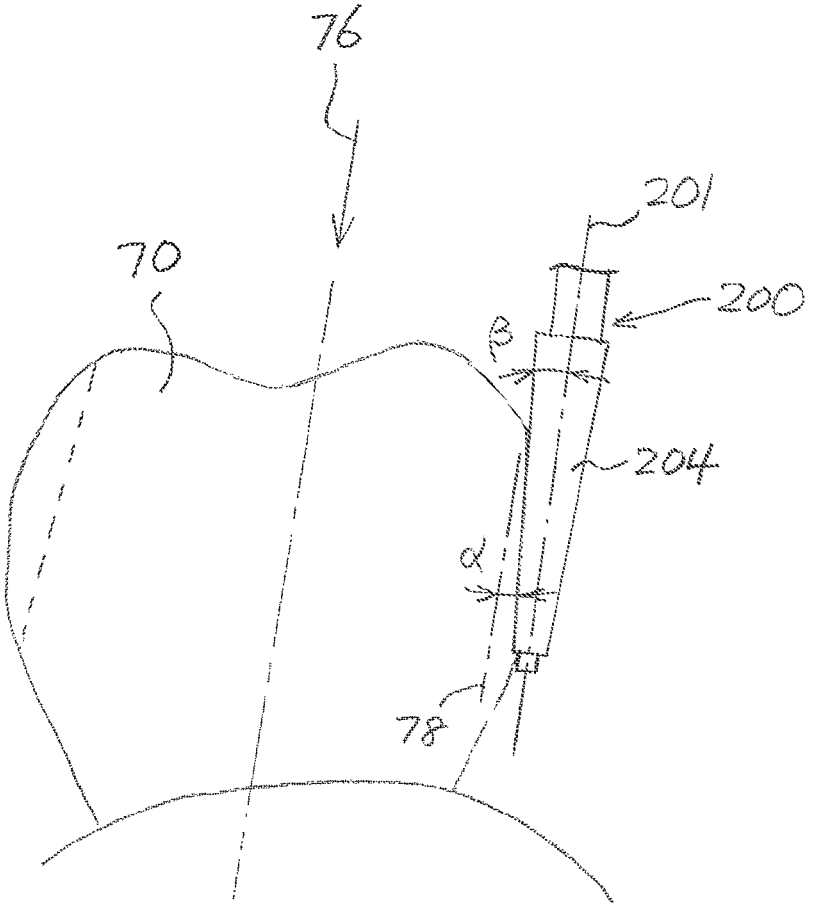

FIG. 92E is a side view of a tooth and a burr cutting the tooth in accordance with another embodiment.

FIG. 93A is a plan view of a first one of a pair of preparation guide devices in accordance with one embodiment.

FIG. 93B is a cross-sectional view taken along a broken line shown in FIG. 93A.

FIG. 94A is a plan view of the first preparation guide device shown in FIG. 93A.

FIG. 94B is a cross-sectional view taken along a broken line shown in FIG. 94A.

FIG. 95A is a plan view of the first preparation guide device shown in FIG. 93A.

FIG. 95B is a cross-sectional view taken along a broken line shown in FIG. 95A.

Figure 96:
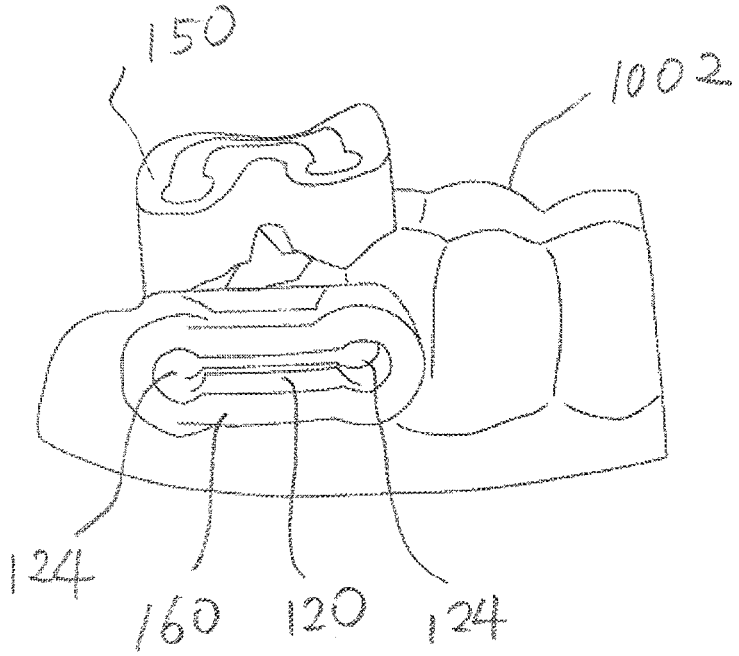

FIG. 96 is a side view of the first preparation guide device shown in FIG. 93A.

Figure 97:
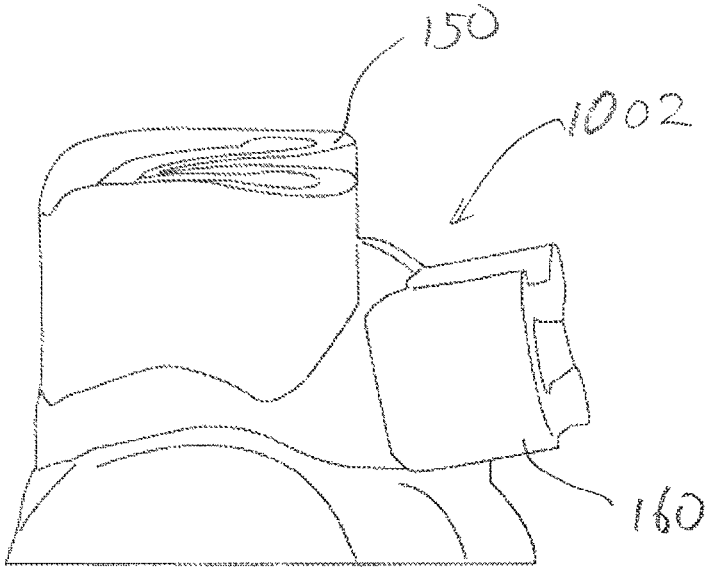

FIG. 97 is another side view of the first preparation guide device shown in FIG. 93A.

FIG. 98A is a plan view of a second one of a pair of preparation guide devices which pairs with the first preparation guide device shown in FIG. 93A.

FIG. 98B is a cross-sectional view taken along a broken line shown in FIG. 98A.

FIG. 99A is a plan view of the second preparation guide device shown in FIG. 98A.

FIG. 99B is a cross-sectional view taken along a broken line shown in FIG. 99A.

FIG. 100A is a plan view of the second preparation guide device shown in FIG. 98A.

FIG. 100B is a cross-sectional view taken along a broken line shown in FIG. 100A.

Figure 101:
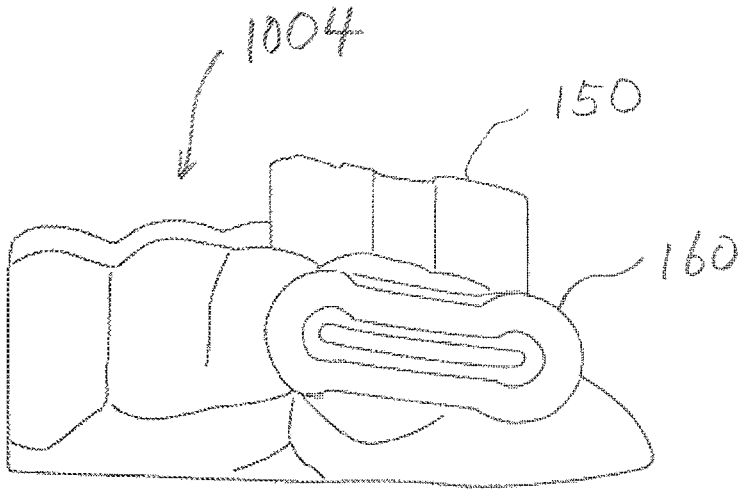

FIG. 101 is a side view of the second preparation guide device shown in FIG. 98A.

Figure 102:
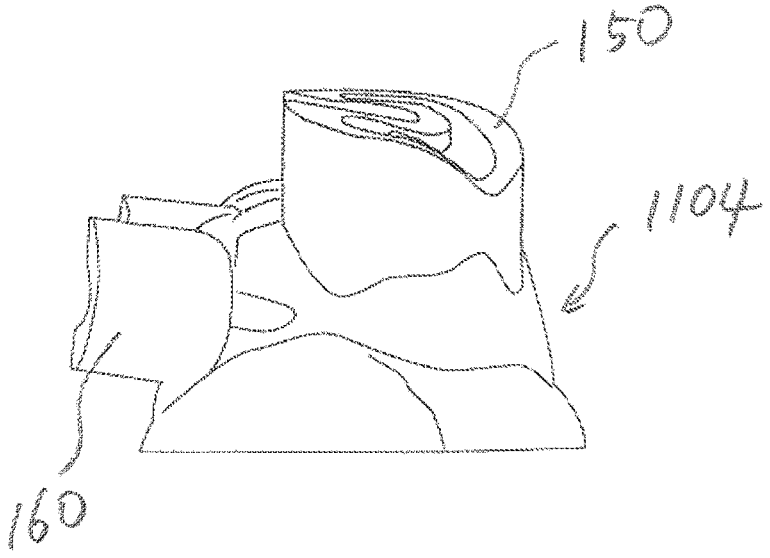

FIG. 102 is another side view of the second preparation guide device shown in FIG. 98A.

Figure 103:
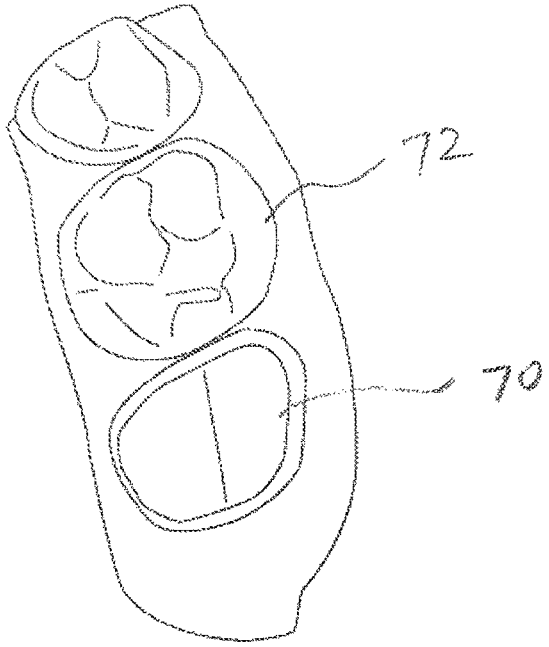
Figure 104:
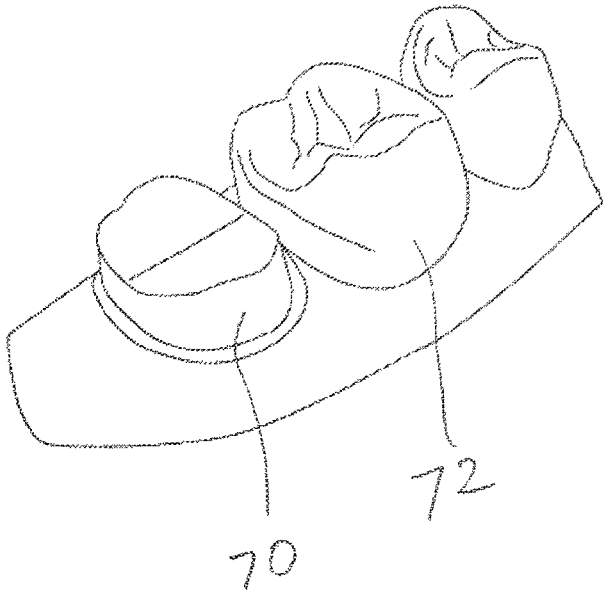

FIGS. 103 and 104 are plan and perspective views of teeth prepared using the preparation guide devices shown in FIGS. 93A and 98A, respectively.

Figure 105:
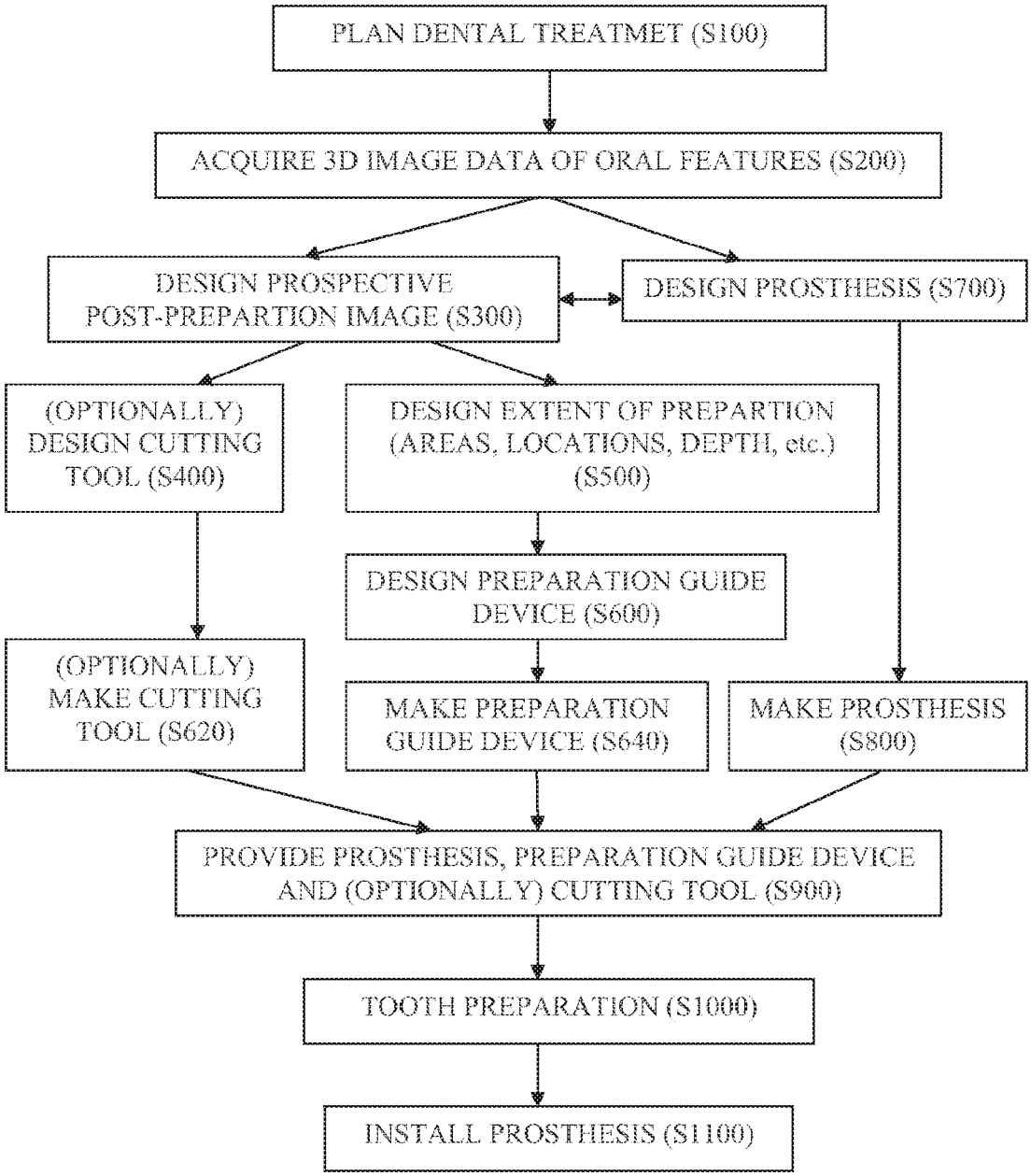
Figure 106:
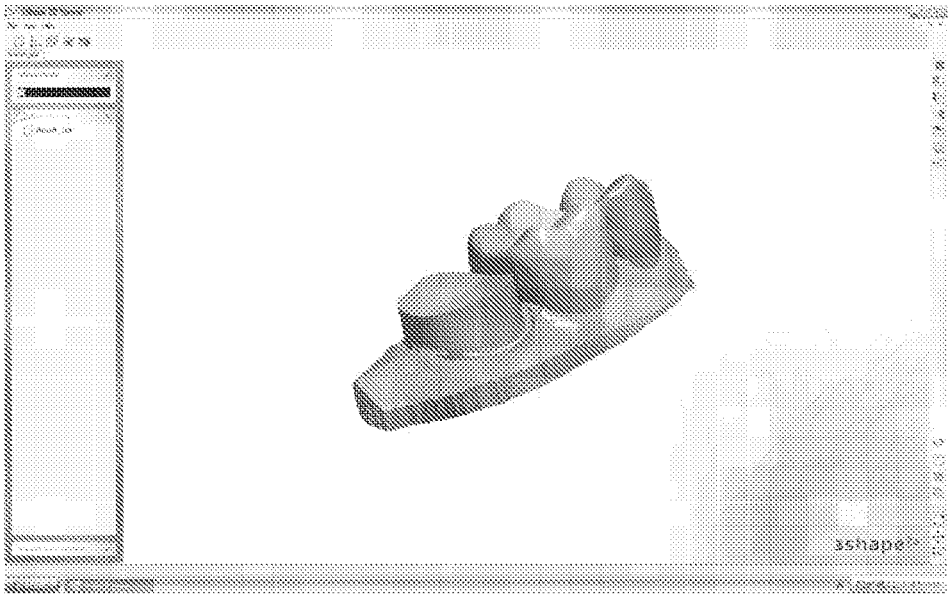
Figure 107:
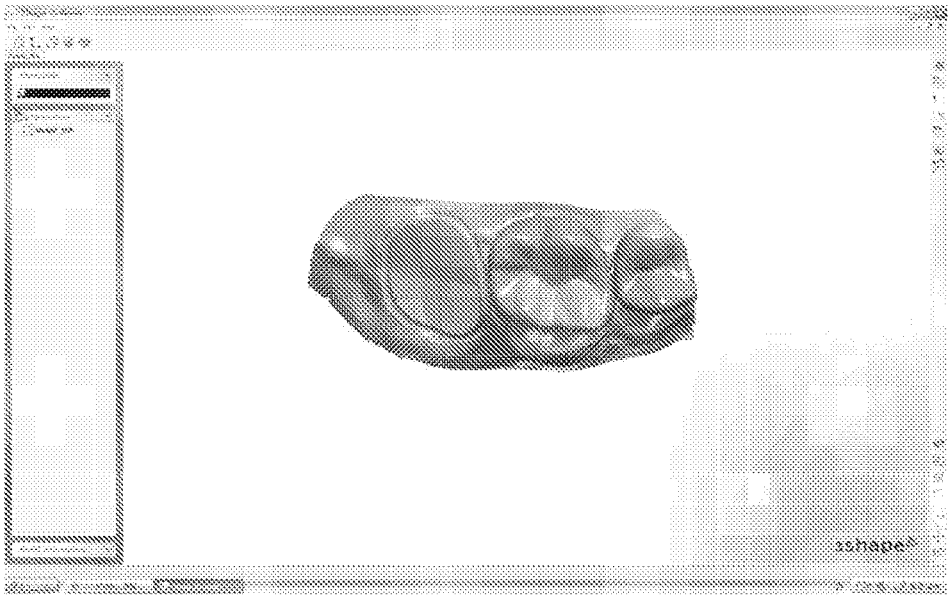
Figure 108:
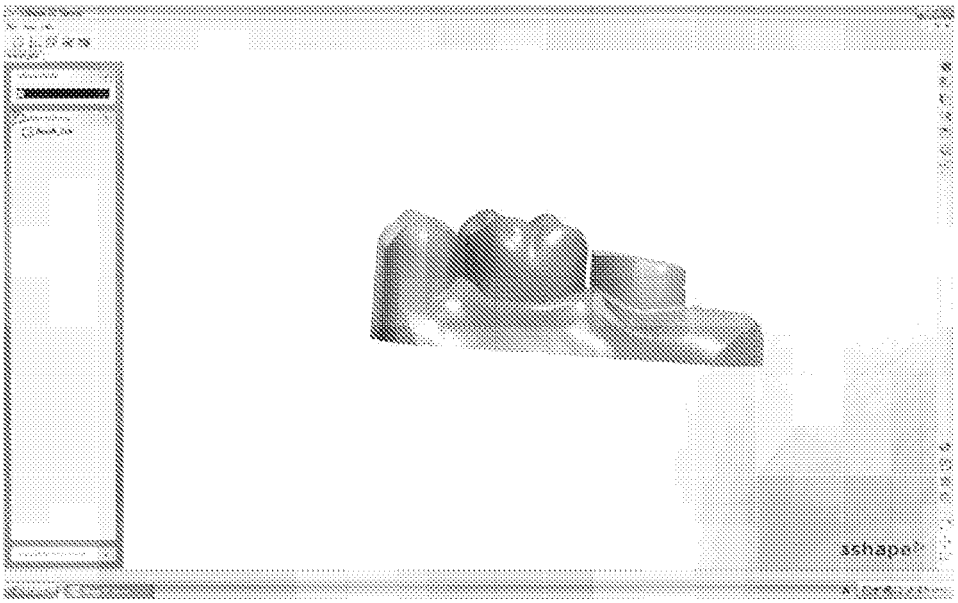
Figure 109:
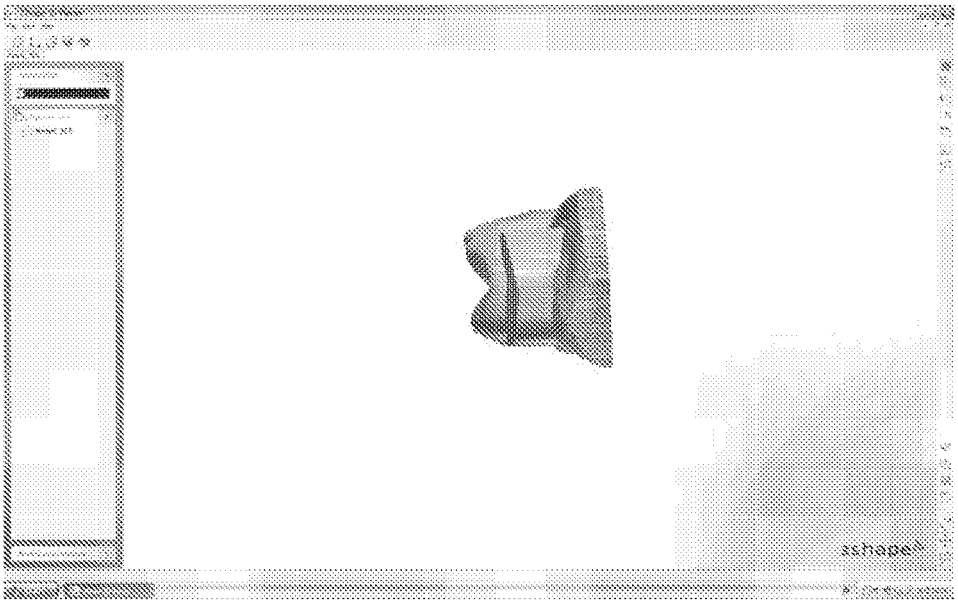
Figure 110:
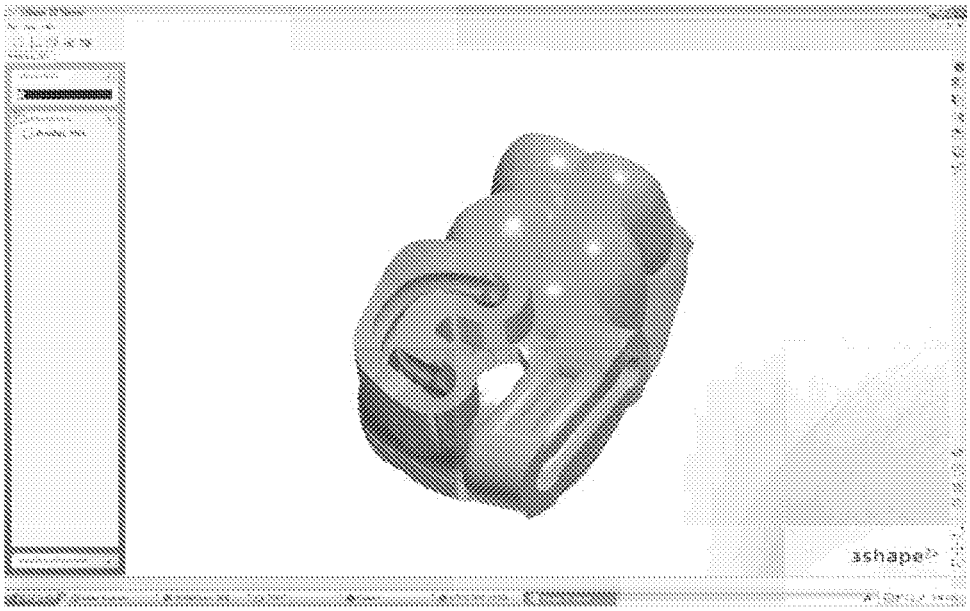
Figure 111:
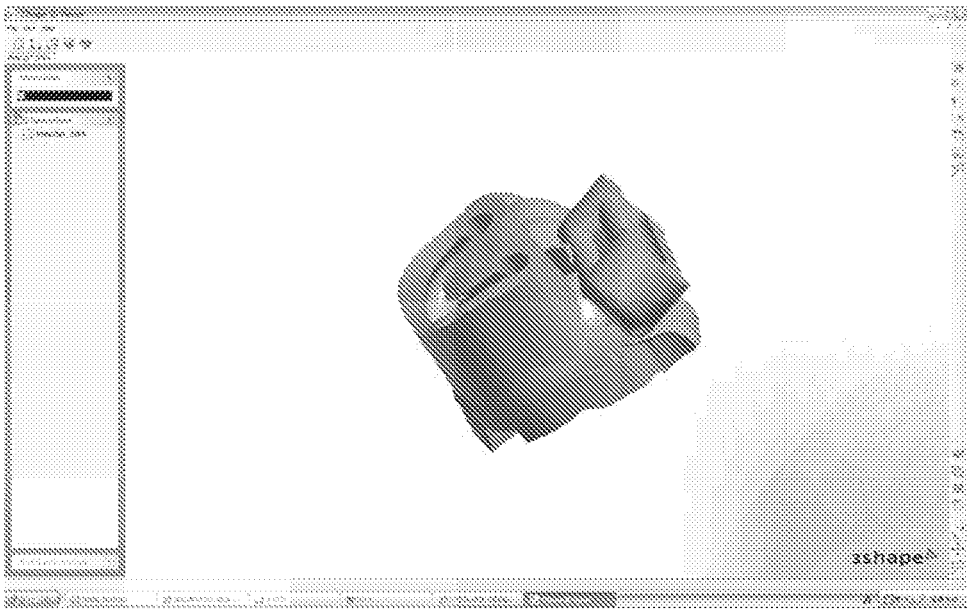
Figure 112:
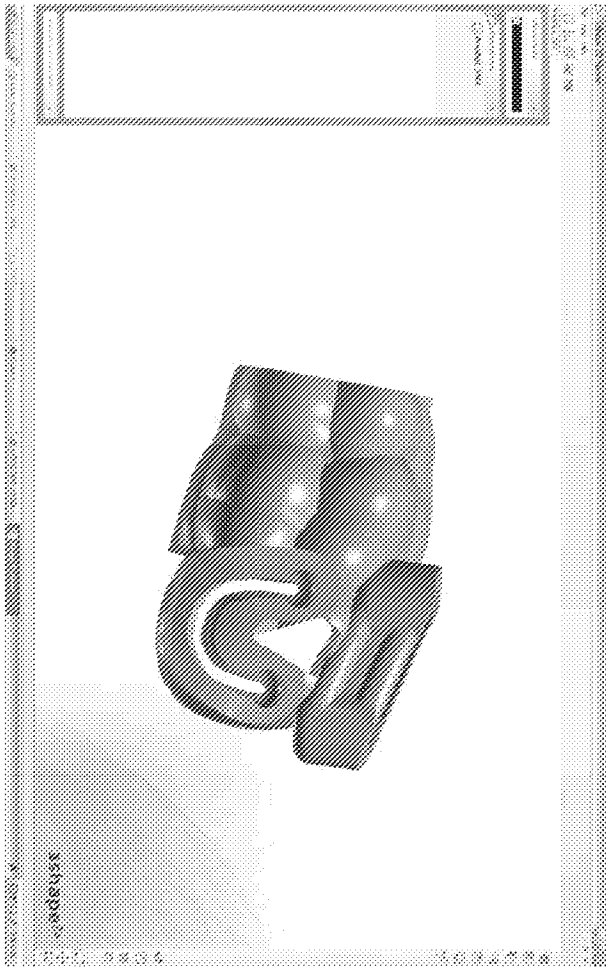
Figure 113:
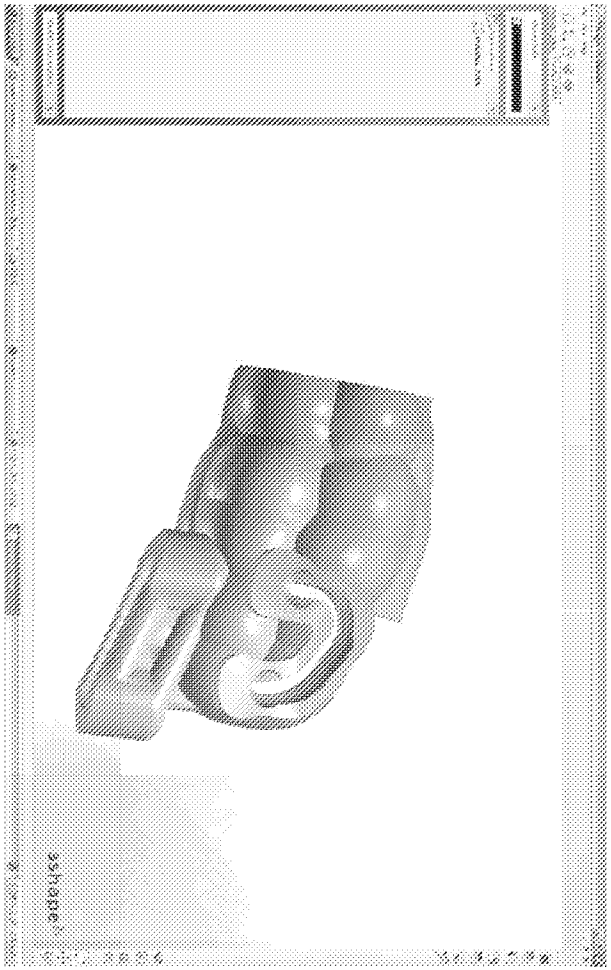
Figure 114:
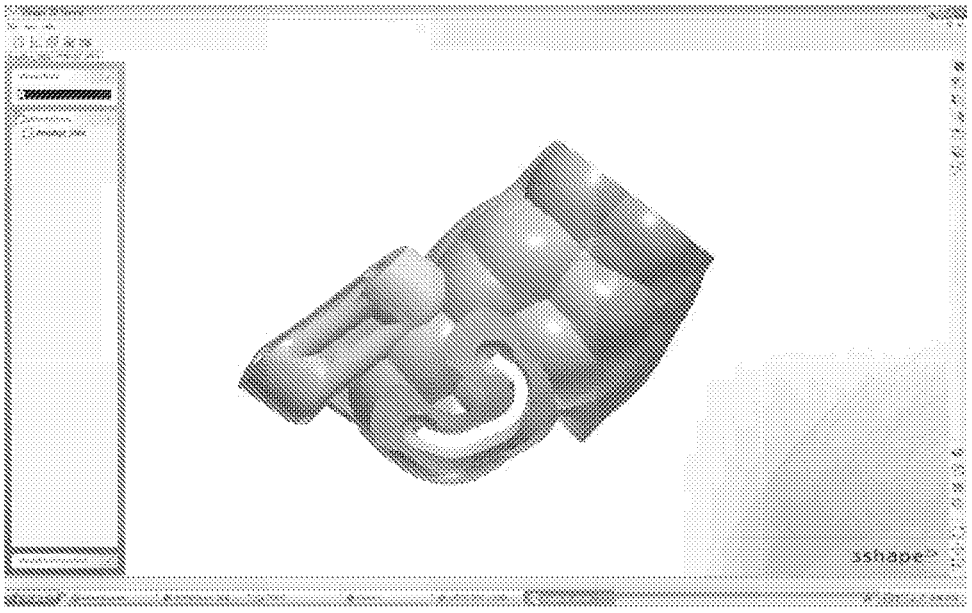
Figure 115:
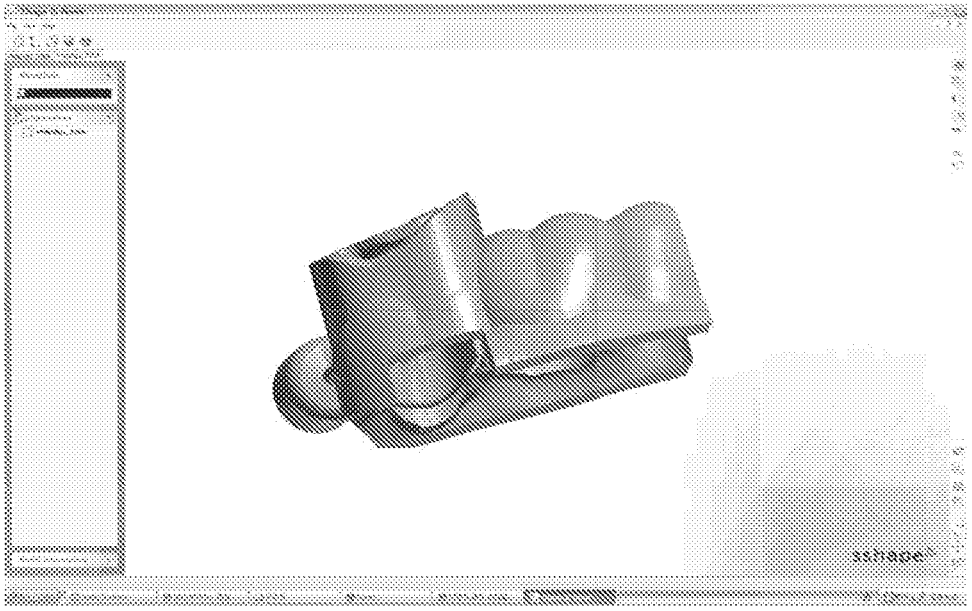

FIG. 105 is a flowchart of the dental procedure in accordance with one embodiment.

FIGS. 106-109 are screenshots of prospective prepared teeth.

FIGS. 110-115 are screenshots of preparation guide devices designed using a CAD/CAM system in accordance with one embodiment.

Figure 116:
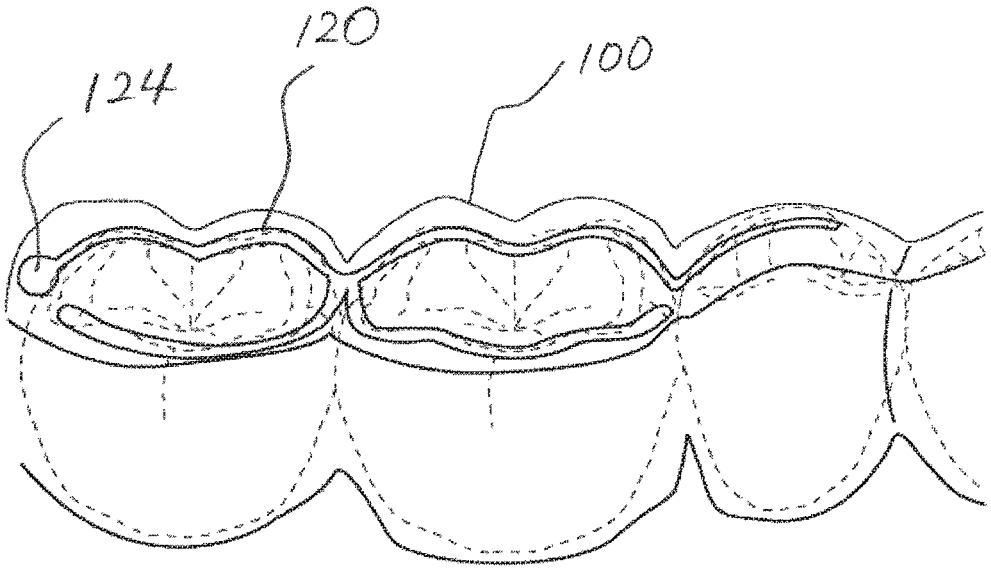

FIG. 116 is a perspective view of a preparation guide device in accordance with one embodiment as mounted on posterior teeth.

Figure 117:
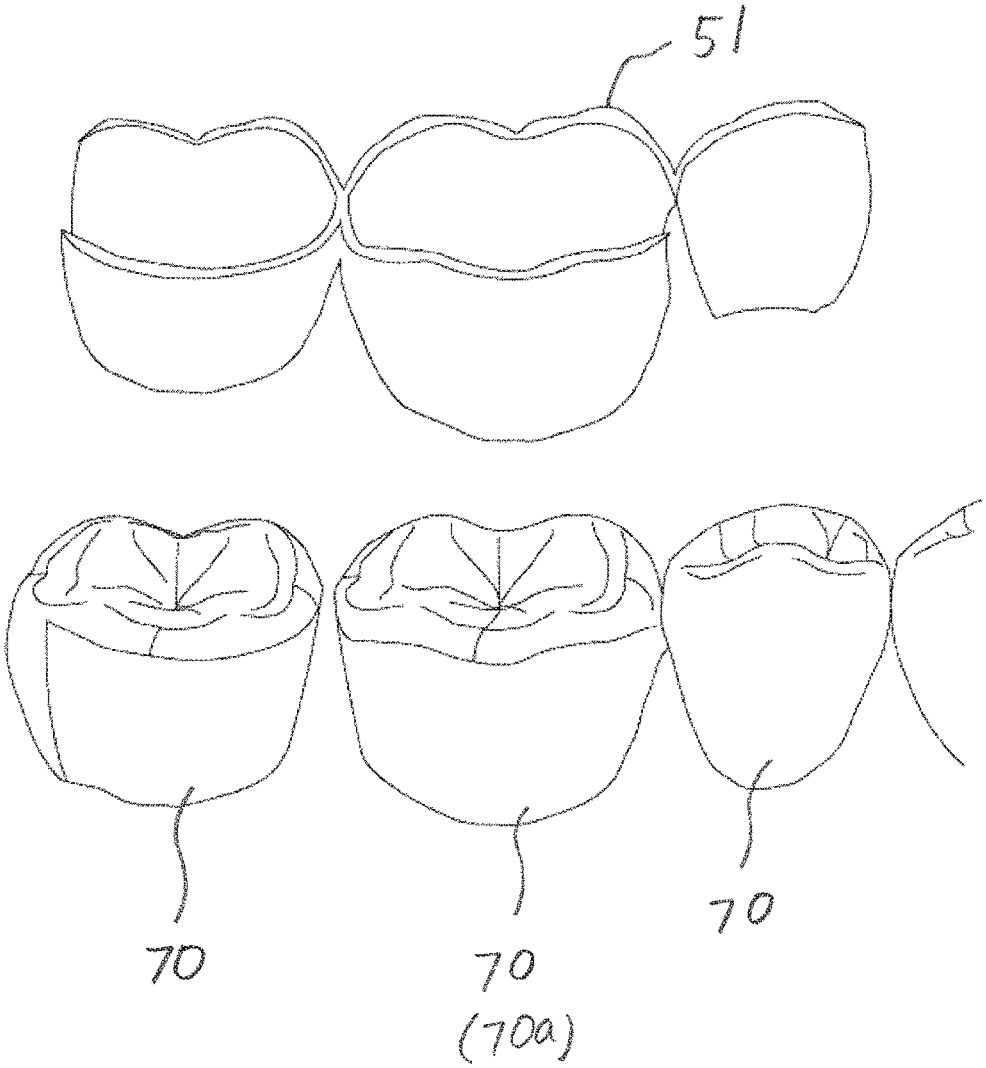

FIG. 117 is a perspective view of prepared posterior teeth and a splint prosthesis to be installed on the prepared posterior teeth.

Figure 118:
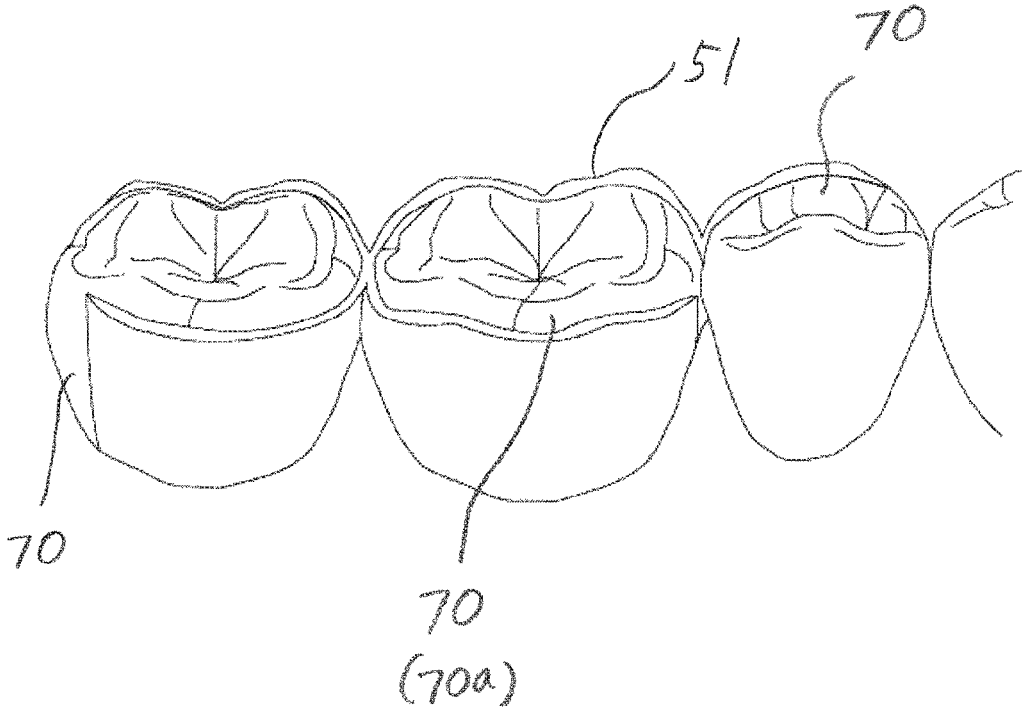

FIG. 118 is a perspective view of the prepared posterior teeth and the splint prosthesis shown in FIG. 117 as installed on the posterior teeth.

Figure 119:
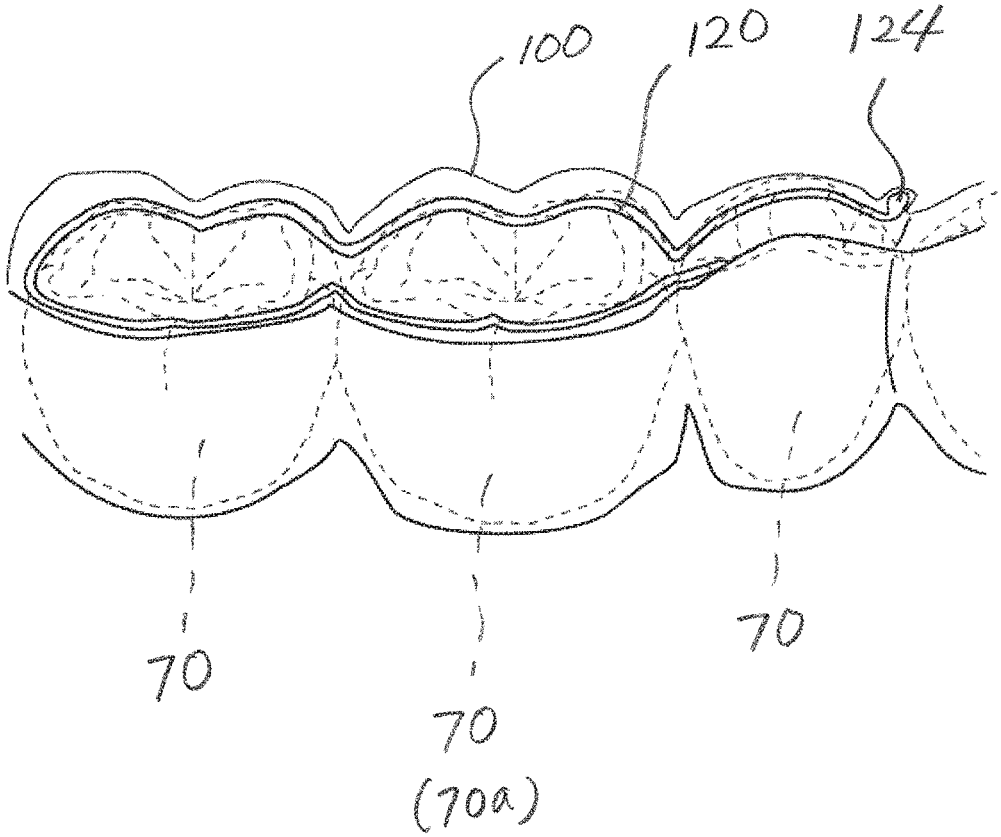

FIG. 119 is a perspective view of a preparation guide device in accordance with another embodiment as mounted on posterior teeth.

Figure 120:
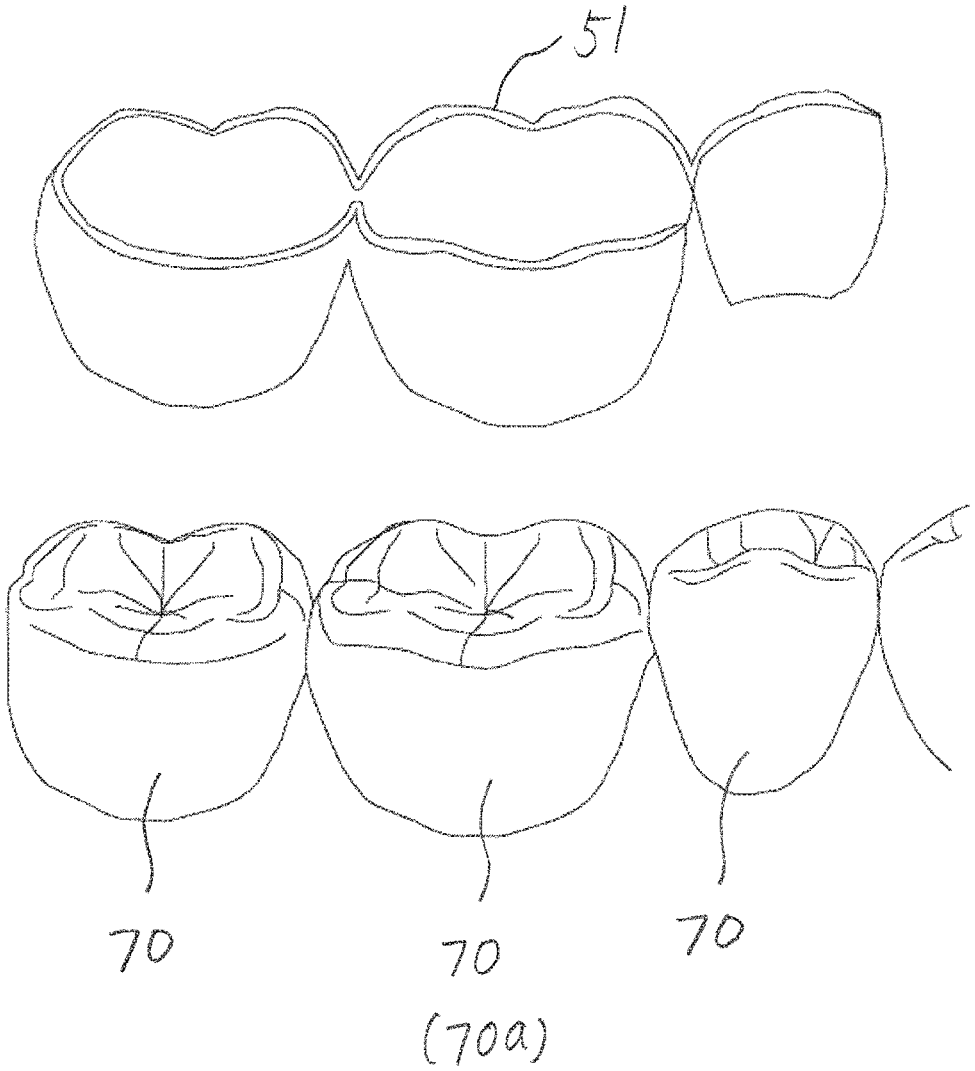

FIG. 120 is a perspective view of prepared posterior teeth and a splint prosthesis to be installed on the prepared posterior teeth.

Figure 121:
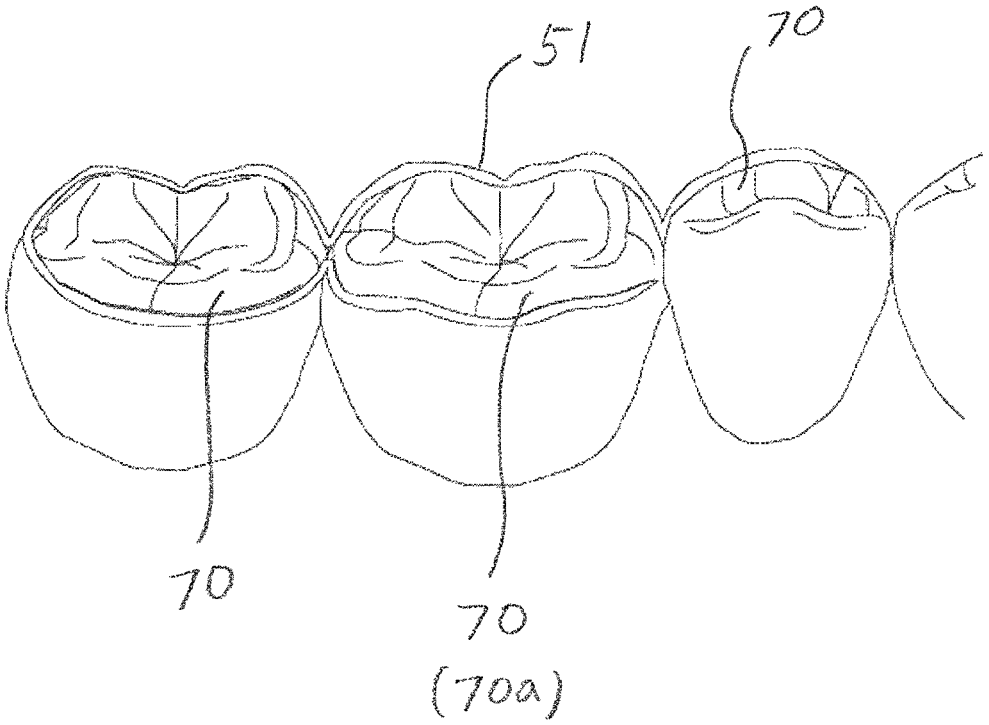

FIG. 121 is a perspective view of the prepared posterior teeth and the splint prosthesis shown in FIG. 120 as installed on the posterior teeth.

Figure 122:
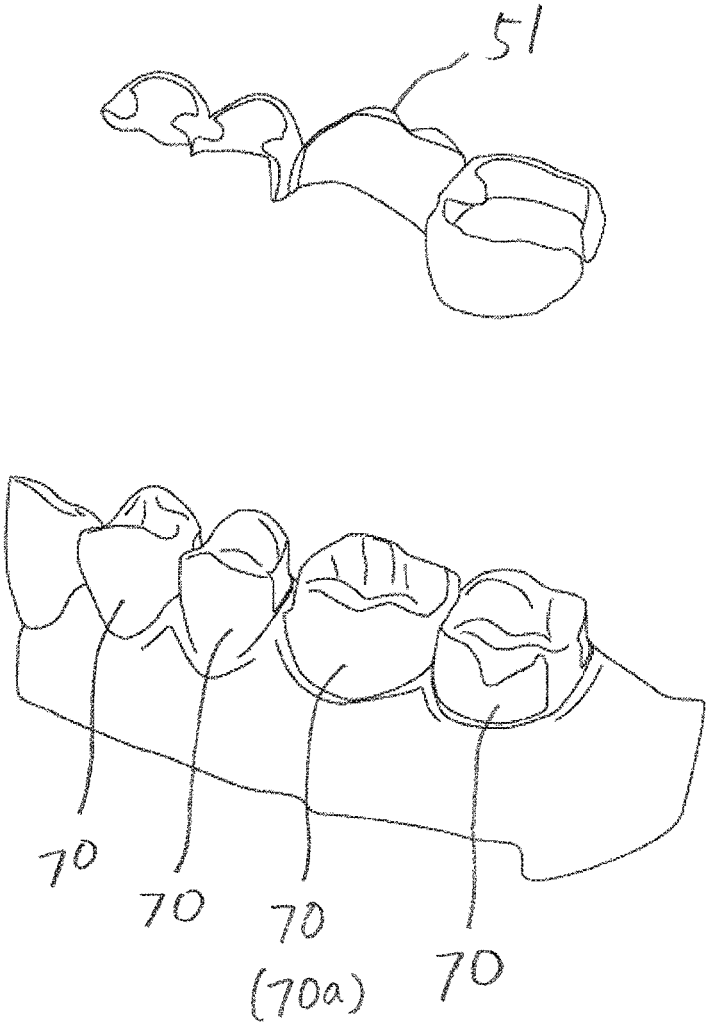

FIG. 122 is a perspective view of prepared posterior teeth and a splint prosthesis in accordance with one embodiment.

Figure 123:
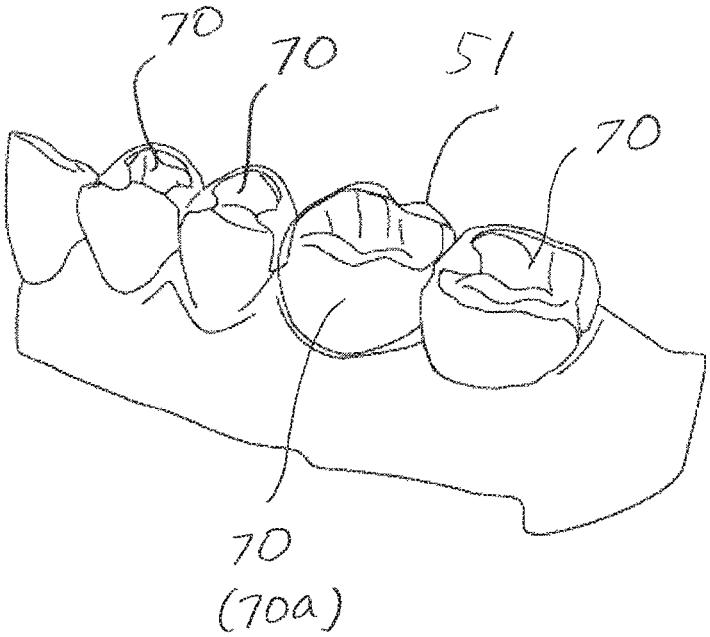

FIG. 123 is a perspective view of the prepared posterior teeth and the splint prosthesis shown in FIG. 122 as installed on the posterior teeth.

Figure 124:
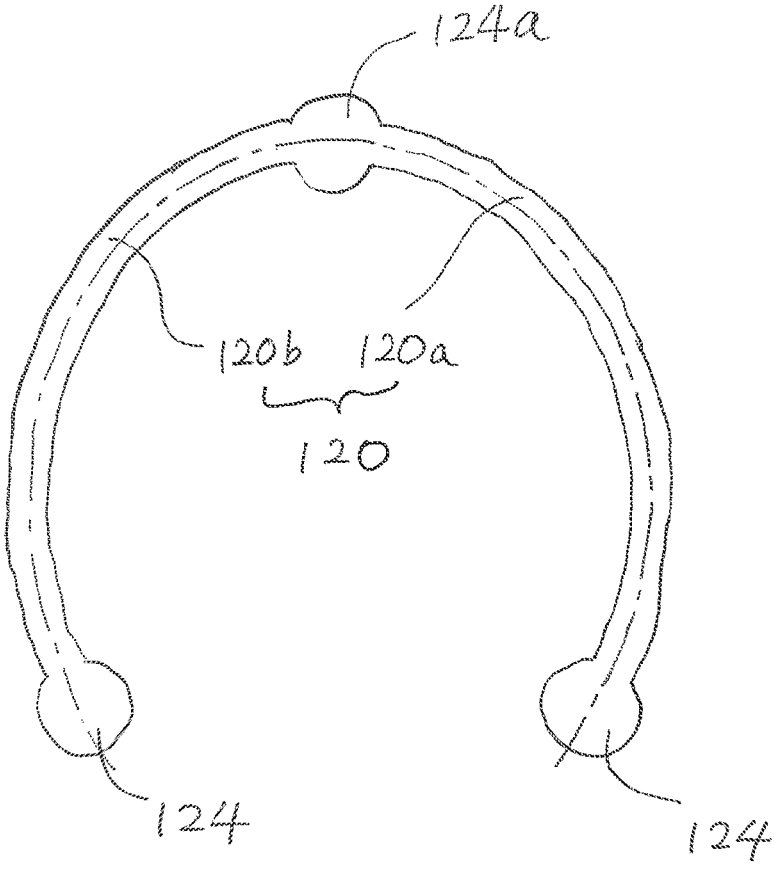

FIG. 124 is a plan view of a tool guide way in accordance with one embodiment.

Figure 125:
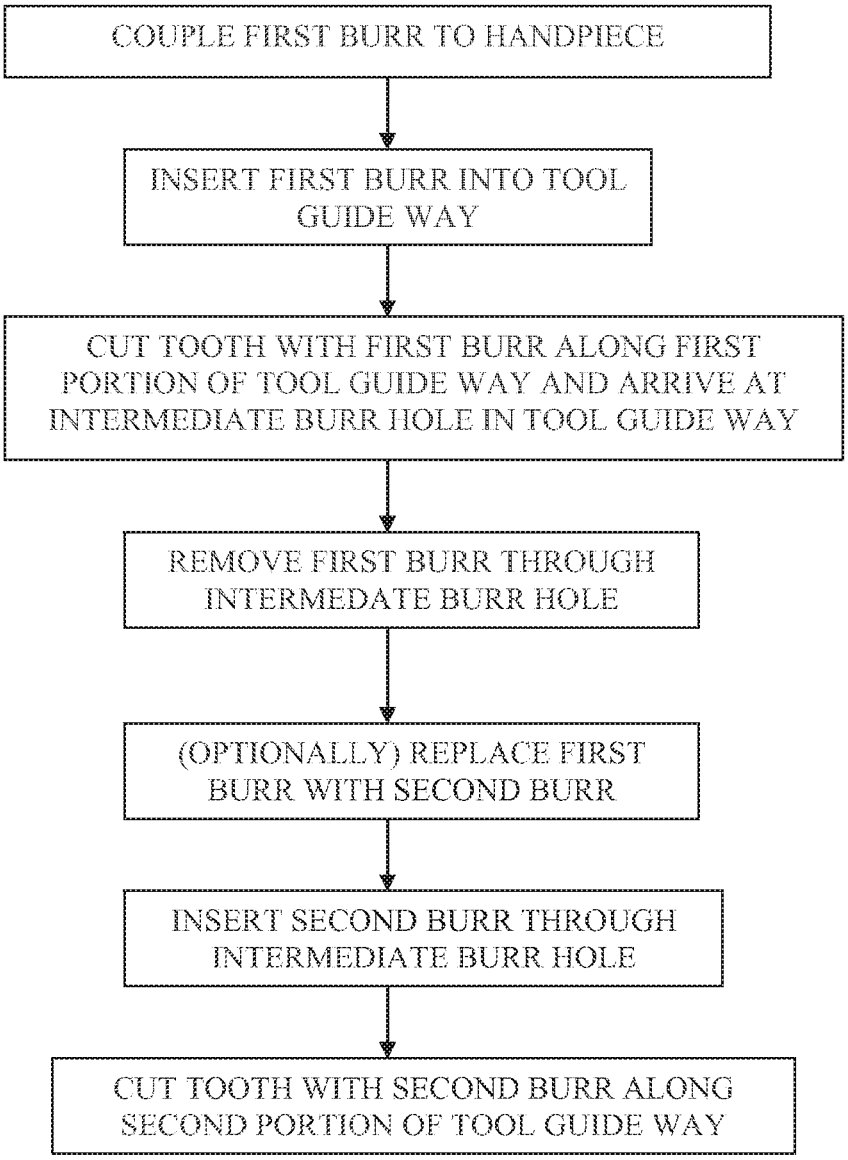

FIG. 125 is a flowchart of changing tools during a cutting process in accordance with one embodiment.

Figure 126:
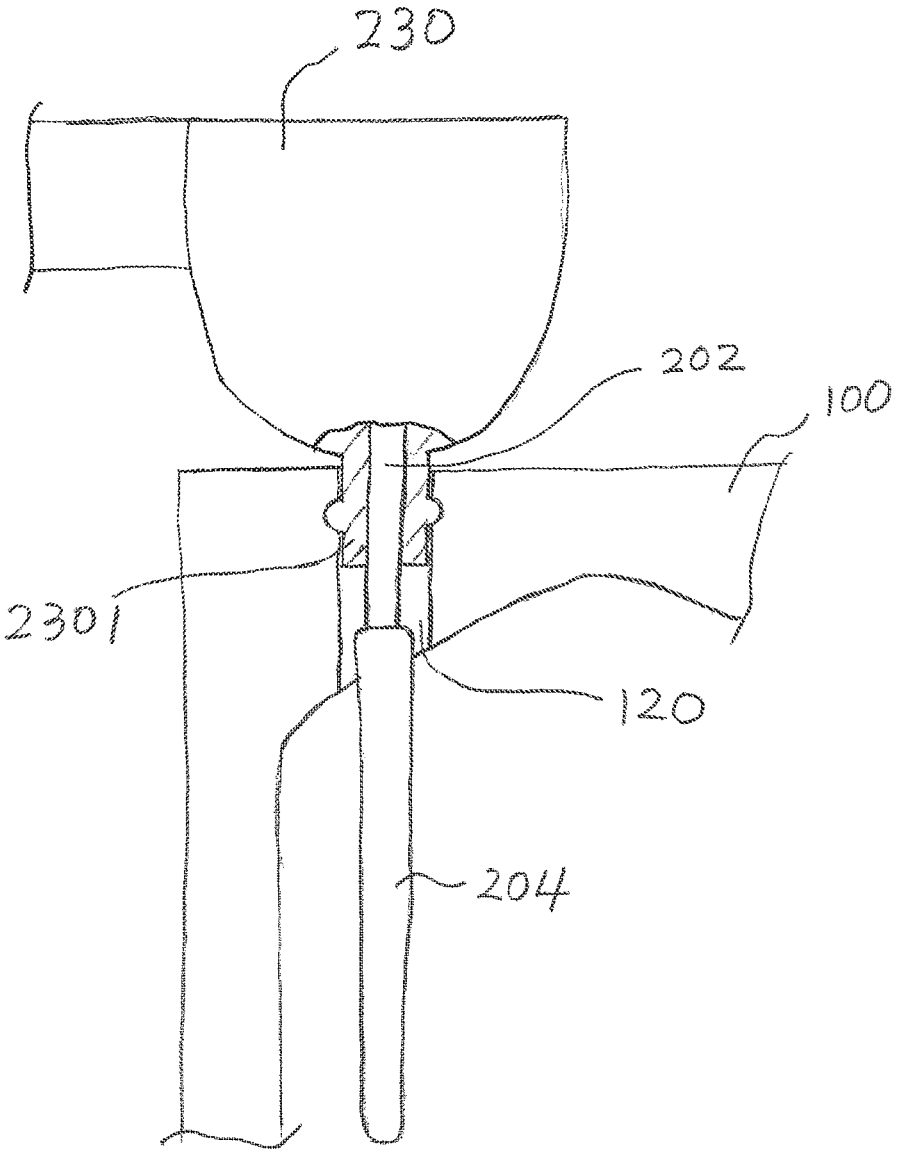

FIG. 126 is a side view of a hand piece and a tool guide way in accordance with one embodiment.

FIG. 127-172 are screen shots of a process of designing a preparation guide device in accordance with one embodiment.

DETAILED DESCRIPTION OF EMBODIMENTS

Various embodiments of the present invention will now he described in more detail with reference to the accompanying drawings. In the drawings, similar symbols typically identify similar components, unless context dictates otherwise. The illustrative embodiments described in the detailed description, drawings, and claims are not meant to be limiting. Other embodiments may be utilized, and other changes may he made, without departing from the spirit or scope of the subject matter presented here. It will be readily understood that the aspects of the present disclosure, as generally described herein, and illustrated in the drawings, can be arranged, substituted, combined, and designed in a wide variety of different configurations, all of which are explicitly contemplated and make part of this disclosure.

Definitions

Here are definitions of some terms and expressions used in this disclosure. These terms and other terms appealing in other locations of the disclosure are used consistently throughout the disclosure including the claims unless expressly stated otherwise.

"Abutment" or "abutment tooth" refers to a tooth, to which a prosthesis or a portion thereof is fixed. For example, a tooth adjunct to a missing (lost) tooth is used as an abutment to fix a prosthesis that includes an artificial tooth filling the space of missing tooth.

"Adjacent tooth" refers to a tooth located immediately next to or neighboring a subject tooth. For example.

"Lingual surface" is a side surface of a tooth that faces the tongue. "Buccal surface" is a side surface that faces the cheek and generally faces away from lingual surface. "Labial surface" is a side surface of an anterior tooth that faces the lips and generally faces away from the lingual surface of the anterior tooth. "Proximal surfaces" refer to the two side surfaces of a tooth that face adjacent teeth. "Mesial surface" is one of the proximal surfaces and generally faces the center of the dental arch. "Distal surface" is the other of the proximal surfaces and faces away from the center of the dental arch.

The term "preparation" of a tooth refers to cutting, reducing, modifying, ablating, and/or grinding of the tooth to remove or delete a portion or portions of the tooth such that the prepared tooth is ready for installing a dental prosthesis. "Before preparation" or "without preparation" refers to a state in which the tooth subject to preparation has not been prepared at all or sufficient to ready for installing the dental prosthesis. Thus, even if the tooth has been somewhat cut, reduced, modified ablated, and/or ground, it is still in the state of "before preparation" or "without preparation" if it is not yet readily engageable with the particular prosthesis fabricated nor installing with the prepared tooth, with no additional cutting, reducing, modifying, ablating or grinding of the particular tooth. When the preparation of the tooth is complete or finished, i.e., "after completion," the prepared tooth can be engaged with a particular portion of the prosthesis that is designed to be engaged with the prepared tooth, without additional cutting, reducing, ablating, or grinding of the prepared tooth.

The terms indicating directions or relative positions, such as up, down, top, bottom, side are used only to identify certain features more easily or to make such features more easily understood. The terms themselves do not limit the present invention to particular directions or positions in their literal meaning. For example, many embodiments disclosed in this application are illustrated and described in terms of lower teeth, i.e., teeth in the lower jaw. However, the embodiments or any claimed inventions are not limited to lower teeth. Also, for example, sometimes the terms "top" may be used to indicate that it is away from the guru, gingival or root, as opposed to limit its absolute location. One of ordinary skill in the art will understand the relative nature of these terms and will be able to appreciate their meaning in the context.

Dental Preparation for Restorations

Figure 1:
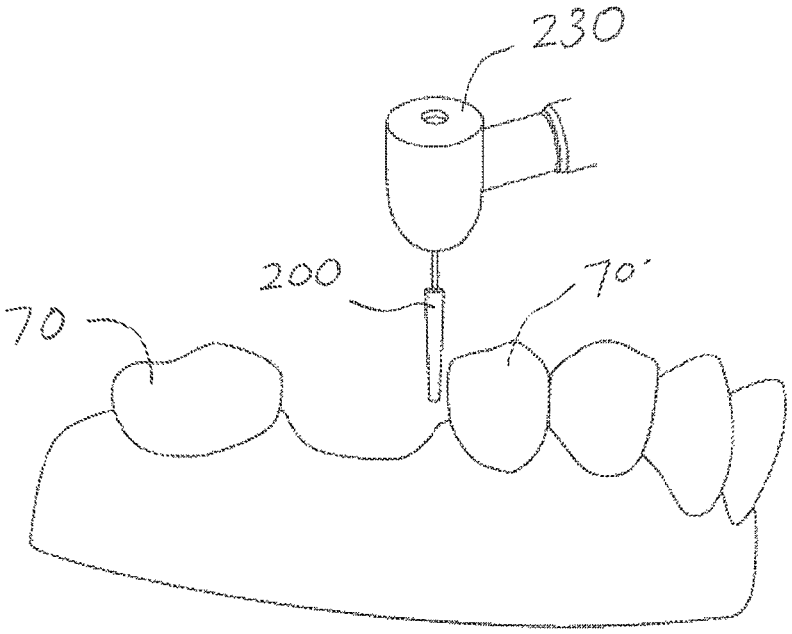
FIG. 1 is a perspective view of typical tooth cutting.
Figure 2:
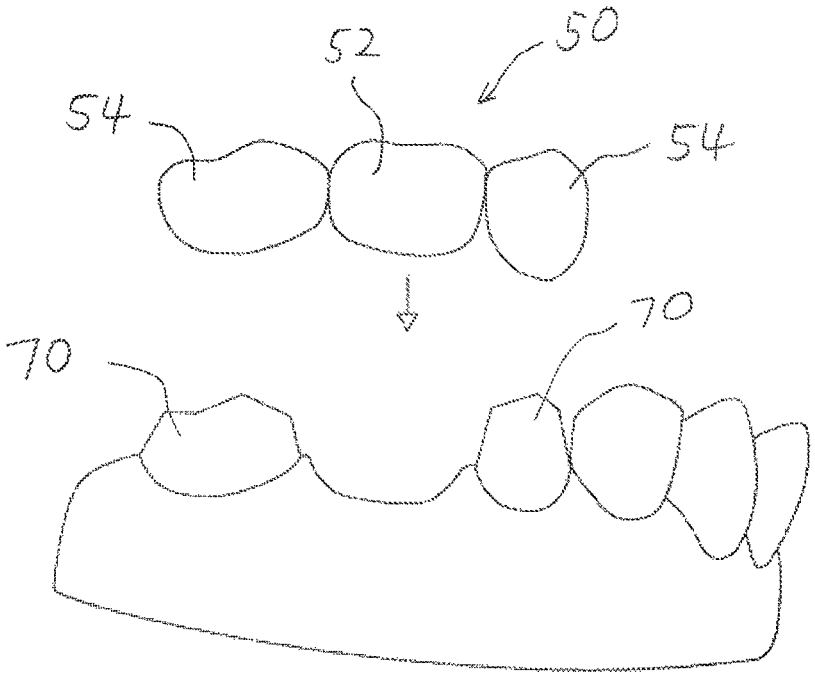
FIG. 2 is a perspective view of tooth shape alter typical tooth cutting.

In the conventional dental procedure for restorations, the patient's teeth are first prepared before making an appropriate restoration. More specifically, the dentist and/or dental practitioner prepare the patient's teeth first, make an impression of the prepared teeth, fabricate a prosthesis based on the impression, and install the prosthesis on the patient's teeth. FIG. 1 illustrates preparing teeth. The dentist (not shown) grinds or cuts teeth 70 using hand piece 230 and associated burr 200. The amount of deletion of the teeth or the level of precision largely depends on the hand skills and experience of the dentist. FIG. 2 depicts the prepared teeth 70 (the teeth after preparation) and a prosthesis 50 to be installed on the teeth 70. The teeth 70 of FIG. 2 represents that they are modified excessively, and that the cut is rough or not smooth. This result may not be uncommon when the dentist did not have good hand skills. Even dentists with very good hand skills and experience, the preparation for dental restorations typically cut into the dentin inside the enamel, which can lead to a risk of damaging pulp tissues or nerve cells.

Manufacturing Prosthesis Prior to Preparing a Tooth

In embodiments, a dental prosthesis is provided prior to tooth preparation, and the prosthesis can be installed immediately after the preparation. In embodiments, the dental prosthesis can be installed over the prepared tooth without modifying the provided prosthesis to fit it with the prepared tooth. In embodiments, the prepared tooth will need to have shapes and configurations that are substantially exactly complementary and counterpart of the shapes and configurations of to the pre-made prosthesis with high level of precision. If the preparation is not well complementing or corresponding to the configurations of the pre-made prosthesis, it would be likely that the prosthesis would not fit the prepared tooth without further modification, cutting or grinding.

Preparing a tooth to fit the pre-made prosthesis without further modification would be difficult to accomplish when relying only on the hand skills and experience of the dentist. In embodiments, a dental preparation guide device is introduced. in embodiments, this preparation guide device guides the movement of a cutting tool such as a burr (hence the hand piece) along a predetermined path or trajectory so that the tooth can be cut as planned without much relying on hand skills of the dentist. In embodiment, the preparation guide device and the pre-made prosthesis are related such that preparing a tooth using the preparation guide device will result in a prepared tooth that fits well the pre-made prosthesis without further modifications of the prepared tooth or prosthesis.

Dental Procedure

In embodiments, new dental procedures can be developed using the technology of providing a dental prosthesis before preparing a tooth. Now an embodiment of dental procedure is discussed referring to FIG. 105. When a dentist or dental practitioner examines teeth of patient and identifies a need for dental restoration. The dentist develops a plan for dental restoration. S100. Upon the patient's approval of the plan, three-dimensional (3D) image data of the patient's oral features including a subject tooth is acquired. S200. The 3D image data is then used to design a prospective post-preparation image, which is a prospective image of the subject tooth after a proposed preparation. S300. Optionally, a cutting tool is designed for the proposed preparation. S400. Then, the extent of preparation is considered and determined for arriving at the prospective post-preparation image in actual tooth. S500. With the determined extent of preparation, now the structures of a preparation guide device are designed. S600. Further, based on the prospective post-preparation image, a dental prosthesis is designed. S700. Using the designs made thus-far, the cutting tool, preparation guide device and prosthesis are manufactured. S620, S640 and S800. Subsequently, these manufactured devices are provided to the dentist. S900. The dentist prepares the subject tooth using the preparation guide device and cutting tool. S1000. Immediately after the preparation, the dentist installs the prosthesis onto the prepared tooth. S1100.

Impression before Preparing a Tooth

In embodiments, 3-dimensional (3D) image data of the patient's teeth or oral configurations and features is obtained before preparing a tooth subject to restoration. Then, the 3D image data is processed to produce a dental prosthesis and a preparation guide for preparing the tooth to fit the particular prosthesis. In one embodiment, the 3D image data is conveniently obtained using a 3D scanner when it is available. In another embodiment when a 3D scanner is not available, the 3D image data is obtained by first taking a copy (impression) of patient's oral features and the 3D image data is taken from the copy where a 3D scanner is available.

When the patient visits the dentist's office or a clinic, the dentist or dental practitioner examines the patient's teeth and proposes, for example, a dental restoration or prosthesis for one tooth. Once the patient approves the dental prosthesis, 3D image information/data of the subject tooth and features of neighboring teeth is collected using a 3D scanner or the impression technique. The dentist does not cut or prepare the subject tooth before obtaining the 3D image data. In embodiments, scanning the patient's oral features can be done at the dentist's office, a clinic, a dental lab, or some other place. Alternatively, taking an impression of the patient's oral features can be done at the dentist's office, a clinic, a dental lab, or some other place. Converting the impression to 3D image data can be done at any appropriate location and by any appropriate persons.

Prospective Post-Preparation Shape

In embodiments, a CAD/CAM system is used to process the 3D image data to provide a prospective post-preparation shape, which is a computer-modeled prospective shape or image of the tooth after a preparation. The prospective post-preparation image illustrates a resulting shape of the tooth (with or without neighboring tooth or teeth) that would be obtained when an imaginary preparation has been conducted on the tooth. In one embodiment, a prospective post-preparation shape or image is obtained based on the 3D image data and using parameters for a proposed preparation. In embodiments, multiple prospective post-preparation shapes or images can be obtained using different parameters for preparation. In one embodiment, one desired prospective post-preparation shape can be chosen. Alternatively, by selecting certain appropriate parameters for preparation, a prospective post-preparation shape may be automatically generated. In embodiments, the prospective post-preparation shape is provided in a 3D image data and can be displayed on a display screen.

Axis of Insertion

According to embodiments, when designing preparation guide device, a CAD/CAM system is used to process the 3D image data (of the patient's oral features) to determine a path of insertion (or approach) of prosthesis toward the prepared tooth for installing. In one embodiment, in designing, a prospective post-preparation shape, the 3D image data is processed to determine a preferred or optimum path of insertion of the prosthesis for installing. In one embodiment, the preferred or optimum path of insertion has an axis of insertion or approach, in which direction the prosthesis is suggested to move for most convenient engagement between the prosthesis and the prepared tooth.

In one embodiment, the path and axis of insertion is chosen or determined such that when viewing the prospective post-preparation shape along the axis of insertion, no substantial undercuts can be found on the cut or modified side surfaces of the prospective post-preparation shape. In one embodiment, the path and axis of insertion is chosen or determined such that cutting or modifying of the tooth can be minimized to make that when viewing the prospective post-preparation shape along the axis of insertion, there are no substantial undercuts on the cut or modified side surfaces of the prospective post-preparation shape. In one embodiment, the path and axis of insertion is chosen or determined such that cutting or modifying of the tooth can be balanced (no heavy cutting on one surface) between two or more surfaces that are to be cut for making that when viewing the prospective post-preparation shape along the axis of insertion, there are no substantial undercuts on the cut or modified side surfaces of the prospective post-preparation shape.

High Level of Precision

In embodiments, there are no substantial undercuts on the side surfaces of the prospective post-preparation shape when viewing in the direction of the determined axis (path) of insertion. This can be accomplished by utilizing a preparation guide device that is designed in view of the determined axis of insertion. When relying on hand skills of a dentist, it would be difficult to prepare a tooth without significant undercuts on the side surfaces of a tooth. In order to avoid significant undercuts, cutting of a side surface should result in a significant slope angle of the side surface against the axis of insertion like over 6°.

In one embodiment, the preparation guide device allows a level of precision that would not be possible when relying on the dentist's skills only. Accordingly, side surfaces of a tooth can be prepared without significant undercuts even if the side surface is modified to have only a minimum slope (the slope against the axis of insertion). In one embodiment, the small slope is possible because the preparation guide device includes a tool guide channel that includes configurations for keeping the axis of rotation of the burr against the axis of insertion constant. The orientation can be maintained even while the tool is moving during cutting. For example, the axis of rotation of the burr and the axis of insertion can be parallel while cutting. By cutting as explained above, precise cut surface can be obtained.

In one embodiment, the slope angle of the side surface against the axis of insertion is about 0° to about 3°, although not limited thereto. In one embodiment, a sloping surface can have an angle greater than this, e.g., about 3° to about 6° and also about 6° to about 15°.

Design of Preparation Guide Device

In embodiments, a CAD/CAM system is used to process the 3D image data for designing a preparation guide device. In one embodiment, the preparation guide device is designed based on the 3D image data of the patient's oral features prior to preparation and the 3D image data of the prospective post-preparation shape or image. In embodiments, the preparation guide device is designed to fit the subject tooth (or teeth) for preparation and/or its neighboring teeth. In embodiments, the preparation guide device is designed to include features to assist, facilitate and/or guide cutting, modifying, grinding, ablating of a subject tooth (or teeth) for fitting a desired prosthesis.

Design of Preparation Guide Device—Fitting with Tooth

In embodiments, the preparation guide device is designed to have two or more sidewalls and a top wall interconnecting the two or more sidewalls. In embodiments, the preparation guide device includes an interior space or a recess defined by the top wall and two or more sidewalls. In embodiments, the interior space or recess is configured to receive one or more teeth. In one embodiment, the interior space or recess is configured to tightly fit one or more teeth. In one embodiment, inner surfaces of interior space or recess are configured to engage with portions of one or more teeth. In one embodiment, the inner surfaces of the interior space or recess include features that are at least partly complementary to the exterior configurations of the one or more teeth so that the tooth is well fit in the recess.

In one embodiment, the top wall is to cover, correspond to and/or face the occlusal surface of a posterior tooth. In one embodiment, the top wall is to cover, correspond to and/or face the occlusal surfaces of two or more teeth. In one embodiment, the top wall is to cover, correspond to and/or face the incisal edge of an anterior tooth. In one embodiment, the top wall is to cover, correspond to and/or face the occlusal surface of one posterior tooth and the incisal edge of an anterior tooth.

In one embodiment, the preparation guide device includes two sidewalls: one sidewall covers, corresponds to and/or faces the lingual surface of a tooth, and the other sidewall covers, corresponds to and/or the buccal surface of the tooth. In one embodiment, one sidewall covers, corresponds to and/or faces the lingual surfaces of two or more teeth. In one embodiment, one sidewall covers, corresponds to and/or faces the buccal surfaces of two or more teeth. In one embodiment, the preparation guide device includes another sidewall that covers, corresponds to and/or a mesial surface of the tooth.

Design of Preparation Guide Device—Tool Guide Channel

In embodiments, the preparation guide device is designed to include a tool guide way or tool guide channel, which is to guide a cutting tool to stay in its trajectory. In one embodiment, the tool guide way is a three-dimensional structure formed in the body of the preparation guide device that is to engage with a cutting tool or burr and to permit movement of the cutting tool along its trajectory.

In one embodiment, the preparation guide device includes an engagement feature configured to engage with an engagement feature of the cutting tool or burr. In one embodiment, the engagement feature of the preparation guide device is generally structurally complementary to the engagement feature of the burr. In one embodiment, the engagement feature of the preparation guide device is sized to accommodate the engagement feature of the burr while being shaped and sized to prevent disengagement of the burr except moving in directions along the trajectory. In one embodiment, the engagement feature of the preparation guide device includes a groove extending along the trajectory. In one embodiment, the size and shape of the groove is substantially maintained throughout the trajectory or at least part of the trajectory.

In one embodiment, the engagement feature of the burr may not be disengaged until the burr reaches a disengaging feature formed in the trajectory of the tool guide channel. In one embodiment, the disengaging feature of the tool guide channel includes lacking of the particular engagement feature that maintains the engagement feature of the burr. In one embodiment, one or more disengagement features are located in the middle of the trajectory. In one embodiment, at least one disengagement feature is located at an end of the trajectory.

In one embodiment, the engagement feature of the preparation guide device extends in the body of the preparation guide device, which defines the trajectory of the tool guide channel. In embodiments, the extension of the engagement feature (and the trajectory) may be straight and/or curved. In embodiments, the extension of the engagement feature (i.e., the trajectory) may be made in any directions in the three-dimensional space or body the preparation guide device.

In embodiments, once engaged with the tool guide channel, the burr's distal (tip) portion is buried in the body of the preparation guide device or enters the interior space or recess defined by the walls of the preparation guide device, while the burr's proximal portion is coupled to a hand piece gripped by the dentist. Once the burr's tip portion has entered the interior space, the burr's cutting head may contact a tooth surface and cut it as the burr rotates. As the burr moves along the trajectory of the tool guide way, the burr's cutting head cuts the tooth only along the trajectory as designed or planned.

Design of Preparation Guide Device—Anti-Tilting Features

In one embodiment, the preparation guide device is designed to include anti-tilting structures and/or configurations of the tool guide way that prevents or reduces the possible tilting of the burr in certain directions while the burr is engaged in the tool guide way. In one embodiment, the anti-tilting feature is configured to prevent or reduce tilting in a direction of burr's movement at a point in the trajectory of the tool guide channel. In one embodiment, the anti-tilting feature is configured to prevent or reduce tilting in a plane perpendicular to the direction of burr's movement at a point in the trajectory of the tool guide channel. In one embodiment, the anti-tilting structures are incorporated or integrated in the engagement feature of the tool guide channel.

In one embodiment, the anti-tilting structures include two or more engagement features arranged in the body of the preparation guide device, in which each of the two or more engagement features can individually function as an engagement feature with the counterpart feature of the burr without the other(s). In one embodiment, the anti-tilting feature of the preparation guide device includes two or more grooves that are extending substantially parallel to each other. In one embodiment, the two or more grooves are about the same shape and size. In another embodiment, the two or more grooves are of substantially different shapes and sizes. In embodiments where the preparation guide device includes an ant-tilting feature, the cutting tool (burr) also includes a complementary or counterpart feature that cooperates with the anti-tilting feature of the preparation guide device.

Design of Prosthesis

In embodiments, a CAD/CAM system is used to process the 3D image data for designing a desired prosthesis to install onto a tooth (or teeth) prepared using the preparation guide device. In one embodiment, the prosthesis is designed to have features to engage with and fixed to the prepared tooth. In one embodiment, the prosthesis is designed to include one or more surfaces for cementing to the prepared tooth. In one embodiment, the prosthesis is designed to include two surfaces that are opposing such that the two surfaces interpose the prepared tooth therebetween. In one embodiment, the prosthesis is designed to include at least one anchoring feature such as inlays. In one embodiment, the prosthesis is designed to include one or more bridging portions, each of which is configured to fix to the prepared tooth. In one embodiment, the prosthesis is designed to include a closed loop portion configured to encircle or surround the prepared tooth, in which the closed loop portion does not include a top covering and therefore is nota crown. In one embodiment, the prosthesis is designed based on the 3D image data of the prospective post-preparation shape or image. In one embodiment, the prosthesis is designed based on a desired appearance of the tooth and the 3D image data of the prospective post-preparation shape or image. In embodiments, the prosthesis is in the form of a crown, a crown and bridge, crownlay, laminate, veneer, inlay, onlay, splinting prosthesis, etc. although not limited thereto.

Designing Burrs

In one embodiment, a cutting tool such as a burr is designed along with the preparation guide device. In one embodiment, design parameters for a burr includes the length of the burr, the length of cutting portion (cutting head) of the burr, the length of abrasive portion of the burr, the radius or diameter of the burr, the tapering angle of the burr, the height of the cutting portion from the tip of the burr, etc. In one embodiment, one or more parameters for the burr are used in designing of the preparation guide device. In one embodiment, the burr is designed to include engagement structures that enable specific engagement with engagement structures of the tool guide way or toot guide channel. In one embodiment, the burr is designed to include engagement structures that are complementary to the engagement structures of the tool guide way or tool guide channel with a slight gap therebetween, which permits movement of the burr along the trajectory or path of the tool guide way. In one embodiment, the burr is designed to include one or more features that reduce tilting of the burr in the tool guide channel while traveling along the tool guide channel. In one embodiment, two or more burrs are designed for use with one preparation guide device.

In the alternative, the cutting tool can be selected from pre-made burrs. In such embodiments, the pre-made burrs include features that are configured to engage with engagement features of preparation guide devices. In such embodiments, parameters of the pre-made burrs are already considered in the development of the preparation guide device. In one embodiment, a particularly shaped burr is already preselected for use with dental preparation guides.

Time and Location for Designing and Manufacturing

In one embodiment, designing the preparation guide device can occur prior to, subsequently to, or simultaneously as designing the prospective post-preparation shape or image. In one embodiment, designing the prosthesis can occur prior to, subsequently to, or simultaneously as designing the prospective post-preparation shape or image. In one embodiment, designing the preparation guide can occur prior to, subsequently to, or simultaneously as designing the prosthesis. In one embodiment, this series of processes occurs at the dentist's office, a dental lab, or some other location. These processes can occur during the patient's initial visit for diagnosis or afterwards.

When designing is completed, the devices are manufactured based on their design, In one embodiment, the preparation guide device is manufactured using various technologies including 3D printing. In embodiments, the preparation guide device is manufactured at the dentist's office, dental lab or another location. In embodiments, the prosthesis device is manufactured at the dentist's office, dental lab or another location.

Minimally Invasive Preparation Technique

In embodiments, the prospective post-preparation shape or image is obtained using parameters for a minimally invasive preparation, although not limited thereto. In one embodiment, the minimally invasive preparation involves cutting of the tooth only within its enamel layer. In one embodiment, the minimally invasive preparation involves cutting of the tooth substantially within its enamel layer, in which cutting into the dentin tissues is permitted as long as cutting into the dentin tissues is maintained as less than about 30%, about 25%, about 20%, about 15% about 10%, about 5% of the total cut surface areas of the tooth. In one embodiment, the preparation guide device is designed to enable the minimally invasive dental preparation. Accordingly, the prosthesis is designed to fit the minimally prepared tooth.

Tooth Preparation

Once the prosthesis and preparation guide device are custom-made, they are provided to the demist. In one embodiment, the prosthesis and preparation guide device are provided to the dentist as a kit. In one embodiment, the kit of prosthesis and preparation guide device further includes one or more appropriate burrs for use with the preparation guide device. Subsequent to the receipt of preparation guide device, the dentist conducts dental preparation of the subject tooth using the preparation guide device. In embodiments, the dentist connect an appropriate burr to a hand piece, engages the burr with the tool guide channel of the preparation guide device, and then moves the burr along the trajectory or path of the tool guide channel while running the burr.

As the burr moves along the path of the tool guide channel, the burr cuts the subject tooth as prescribed in accordance with the tool guide channel. In embodiments, the preparation guide device prevents free movement of the burr and permits the movement of the burr only along the trajectory of the tool guide channel. In embodiments, the preparation guide device substantially prevents tilting of the burr while engaged with the tool guide channel. As such, in embodiments, the subject tooth is prepared as planned and as prescribed in the preparation guide device, in terms of the locations and areas of cutting, the depth of cutting, the accuracy and precision of cutting, etc. In embodiments, once prepared the subject tooth does not include undercuts on the prepared surfaces.

Installing Prosthesis

In embodiments, once the tooth preparation is finished, the prosthesis is installed onto or over the prepared tooth. In embodiments, the prosthesis is engaged with the prepared tooth and cemented to be fixed to the prepared tooth. In one embodiment, the prosthesis is cemented or installed to the prepared tooth without modifying the prosthesis after completion of preparation using the preparation guide device or after removing the preparation guide device from the patient's mouth. In one embodiment, the prosthesis is cemented or installed, to the prepared tooth without modifying the prepared tooth after completion of preparation using the preparation guide device or after removing the preparation guide device front the patient's mouth. In one embodiment, the prosthesis is cemented or installed to the prepared tooth without modifying the prosthesis and further without modifying the prepared tooth after completion of preparation using the preparation guide device or after removing the preparation guide device from the patient's mouth.

Time Frame

In one embodiment, the following steps occur on the same day: selecting a dental treatment using a prosthesis: obtaining 3D image data of the subject tooth; designing the prosthesis; designing the preparation guide device; installing the preparation guide device within the patient's mouth; preparing the subject tooth using the preparation guide device; and installing the prosthesis to the prepared tooth. In one embodiment, all of the foregoing steps are completed during the patient's visit to the dentist's office or clinic without leaving the location.

In one embodiment, selecting a dental treatment occurs during the patient's initial visit to the dentist's office or clinic; and preparing the subject tooth using the preparation guide device, and installing the prosthesis to the prepared tooth occur during the next visit. The steps of obtaining 3D image data of the subject tooth, designing the prosthesis, and designing the preparation guide device occur on the same day as the day of selecting the dental treatment or on any subsequent day.

Prospective Post-Installation image

In one embodiment, the CAD/CAM system processes the 3D image data of the patient's tooth to generate a prospective post-installation shape or image, which is a computer-modeled shape or image of the tooth after installation of a proposed prosthesis. The prospective post-installation image illustrates a resulting shape of the tooth (with or without neighboring tooth or teeth) that would be obtained once an imaginary (proposed) prosthesis has been installed. In one embodiment, the prospective post-installation image includes the proposed prosthesis and one or more adjacent teeth. In one embodiment, various prospective post-installation shape or image are provided for the same prosthesis. In one embodiment, various prospective post-installation shapes or images are provided with more than one prostheses having different appearance. In one embodiment, one or more prospective post-installation shapes are provided in the form of still images and/or videos (collectively "images.")

Accommodating Patient's Input on the Design

In one embodiment, one or more images representing/illustrating the prospective shape(s) are provided to the patient and/or guardian (collectively "patient") for review. In one embodiment, the patient is provided the opportunity to submit comments about the images or to approve the proposed prosthesis. In one embodiment, the preparation guide device is designed after receiving or in response to the patient's acceptance or approval of the proposed prosthesis. In one embodiment, the preparation guide device is fabricated after receiving or in response to the patient's acceptance or approval of the proposed prosthesis. In one embodiment, if the patient does not approve the proposed prosthesis, designing and manufacturing a preparation guide device is delayed.

In one embodiment, the patient provides a comment or request for changes, the proposed prosthesis is modified in view of the comment or request, and one or more images representing/illustrating prospective shape(s) of the tooth after installation of the modified proposed prosthesis are provided to the patient. in one embodiment, the patient is provided with two or more images representing or illustrating the prospective shapes that are of two or more proposed prostheses, and in response the patient is provided with the opportunity to select or choose one of the two or more proposed prostheses with or without the opportunity to provide a comment or request to modify. In one embodiment, the preparation guide device is designed after receiving or in response to the patient's selection of one of the proposed prostheses. In one embodiment, the preparation guide device is fabricated after receiving or in response to the patient's selection of one of the proposed prostheses. In one embodiment, if the patient does not make a selection, designing and manufacturing a preparation guide device is delayed.

In embodiments, the images of the prospective shape(s) are provided to the patient in various ways. In embodiments, the patient's input (a comment, request, approval and/or selection) can be provided in various ways. In one embodiment, the patient's input can be made and received during consultation with the dentist, dental practitioner or person in charge either at the dentist's office or another place or during a telephonic, video or web conference. In one embodiment, the patient's input can be made and received in its entirety, in part, or individually by email as contents of an email or attachment, by mail, or on a website that allows the patient to take the above steps.

Preparation Guide Device—Surfaces/Portions to Cut

In the configurations of a tooth, there are no sharp boundaries between adjacent surfaces of a single tooth. Many times, people can easily agree that a point on a tooth belongs to one of the five surfaces of the tooth, i.e., the lingual surface, mesial surface, buccal surface, distal surface and occlusal surface (incisal edge). Many other times, however, people may not easily that a point on a tooth belongs to one of the five surfaces of the tooth. Thus, in this disclosure and application, cutting or modifying a first surface (one of the five, e.g., lingual surface) of a tooth means cutting or modifying at least a portion that is clearly belonging to the first surface (here, e.g., the lingual surface) with no or little disagreement. On the other hand, when cutting or modifying a portion that is not clearly belonging to one surface and therefore there could be some disagreement about which surface it belongs to between two (or three) surfaces, it is considered and determined as cutting or modifying of one of the two (or three) surfaces, if that portion is isolated like an island in the uncut area and if that portion is not integrated as a single large cut area with another cut portion that is clearly belonging to one of the five surfaces with no or little disagreement. When a boundary area between two adjacent surfaces is wide, and therefore a cut portion within the boundary area looks extending into the two adjacent surfaces, it is considered and determined that the two surfaces are cut as opposed to one. One of ordinary skill in the art such as a dentist should be able to appreciate the criteria for consideration and determination provided herein and determine which surface(s) a cut portion belongs to.

In embodiments, a preparation guide device is used to cut or modified one or more surfaces of a tooth, i.e., the lingual surface, mesial surface, buccal surface, distal surface and occlusal surface (incisal edge). Here, cutting or modifying a surface means that the whole surface or at least a portion of the surface is cut or modified. In one embodiment, a preparation guide device is used to cut only one surface of a tooth. In other embodiments, a preparation guide device is used to cut only two surfaces of a tooth, in which the two surfaces are opposing or neighboring, and in which the cut portions of the two surfaces are connected together or disconnected by an intervening uncut portion therebetween. In other embodiments, a preparation guide device is used to cut only three surfaces of a tooth. In other embodiments, a preparation guide device is used to cut only four surfaces of a tooth. In other embodiments, a preparation guide device is used to cut five surfaces of a tooth.

Preparation Guide Device—Two or More Separate Tool Guide Ways

In one embodiment, a single preparation guide device includes two or more separate tool guide ways that are separate from each other in a way that there is a blockage between the two or more tool guide ways where a burr cannot pass through. In this embodiment, once the burr is engaged with one of the tool guide ways, the burr must be first removed, from the tool guide way in order for the particular burr to be inserted in the other tool guide way(s).

In one embodiment, the preparation guide device includes one tool guide way configured for preparing one tooth and another tool guide way configured for preparing another tooth. Referring to FIGS. 66-74, for example, the preparation guide device has one tool guide way for the first molar and another tool guide way for the first and second premolars. In one embodiment, the preparation guide device includes two or more tool guide ways configured for preparing a single abutment tooth.

Preparation Guide Device—Preparing Three or Four Side Surfaces of a Single Tooth In embodiments, the preparation guide device is configured to cut or modify three or four side surfaces of a single tooth, i.e., lingual, mesial, buccal, and distal surfaces of the tooth. In one embodiment, no additional preparation guide devices are used to cut or modify the three or four surfaces. Here, cutting or modifying a side surface refers to cutting or modifying at least a portion of the whole area of the side surface. In one embodiment, the preparation guide device includes a single tool guide channel or way that is configured to cut or modify three or four side surfaces of a single tooth, i.e., lingual, mesial, buccal, and distal surfaces. In one embodiment, the preparation guide device is configured to cut or modify four side surfaces to form a closed loop of cut areas when viewing in a direction toward the occlusal surface or incisal edge of the tooth. In one embodiment, the preparation guide device includes a tool guide channel forming a closed loop, ring shape or annular configuration when viewing in a direction toward the occlusal surface or incisal edge of the tooth.

In one embodiment, the preparation guide device is configured to cut or modify four side surfaces of a single tooth without forming a closed loop of cut surfaces when viewing in a direction toward the occlusal surface or incisal edge of the tooth. In this embodiment, at least [par] *part* of one side surface is not cut or modified when viewing in a direction toward the occlusal surface or incisal edge of the tooth. The portion that is not modified or cut includes a contact point of that tooth [wit] *with* an adjacent tooth. In one embodiment, the preparation guide device includes a single tool guide channel that is configured to cut or modify all four side surfaces of a single tooth, in which the single tool guide channel does not have a closed loop trajectory when viewing in a direction toward the occlusal surface or incisal edge of the tooth. In this embodiment, once a burr is engaged with the single tool guide channel, traveling through the tool guide channel may accomplish cutting or modifying of the four surfaces without having to remove the burr from the tool guide channel, although not limited thereto.

Preparation Guide Device—Preparing for a Crown

In one embodiment, one or more preparation guide devices are used to prepare a tooth for a crown prosthesis, in which the lingual, mesial, buccal, distal, and occlusal surfaces of the tooth are cut. In one embodiment, a single preparation guide device includes one or more tool guide ways that are configured to cut all of these surfaces without the need of additional preparation guide device and further without cutting any surfaces of the tooth in the absence of a preparation guide device. In one embodiment, a single preparation guide device includes one tool guide way formed in the occlusal surface that form a closed loop that is used to cut all four side surfaces. This single preparation guide device includes one or more tool guide way formed the buccal sidewall and/or lingual sidewall that is/are configured to cut the occlusal surface of the tooth.

In one embodiment, two preparation guide devices are used to prepare a tooth for a crown prosthesis without the need of additional preparation guide device and further without cutting any surfaces of the tooth in the absence of a preparation guide device. In this embodiment, one preparation guide device includes one tool guide way formed in the occlusal wall for cutting, the buccal or lingual surface of the tooth and the other tool guide way formed in the buccal or lingual sidewall for cutting at least part of the occlusal surface of the tooth. Further, the other preparation guide device includes one tool guide way formed in the occlusal wall for cutting the lingual or buccal surface of the tooth and the other tool guide way formed in the lingual or buccal sidewall for cutting the remainder of the occlusal surface of the tooth. In another embodiment, more than two preparation guide devices are used to prepare a tooth for a crown prosthesis.

Restoring Missing Teeth

Referring, to embodiments of FIGS. 53, 63, 65, 71, 72, and 78, a bridge prosthesis 50 that includes an artificial tooth 52 is used to restore a missing tooth. In an embodiment, a bridge prosthesis 50 includes fixing portions 54 and an artificial tooth 52 to be placed in the location of a missing tooth. The fixing portions 54 are cemented with abutment teeth 70. Abutment teeth 70 are prepared to tightly fit the fixing portions 54. In an embodiment for a crown and bridge prosthesis 50, fixing portions 54 are of a crown shape. Such fixing portions 54 bond with abutment teeth 70, thereby fixing the prosthesis 50.

In embodiments, artificial tooth 52 can be made of various materials, including ceramic, metallic, and polymer materials. Examples of metallic materials that can be used include gold, platinum, gold alloys, platinum alloys, titanium, titanium alloys, tantalum, and tantalum alloys. Examples of ceramic materials that can be used include zirconia, alumina, hydroxyapatite, tricalcium phosphate ceramic, glass, and crystallized glass. In fact, any material used for dental purposes can be employed as long as it is not harmful to the human body, is biocompatible, can be formed into artificial teeth, and can endure physical force exerted on teeth.

Elastic deformation of a fixing portion 54 may or may not be required depending on the circumstances, and so it is important to select an appropriate material for each case. Metallic materials are generally flexible, and ceramic materials generally are not. In various embodiments of the invention, prosthesis 50 can be installed by moving it linearly according to a predetermined axis of insertion from above the occlusal surface of the teeth towards the gum 68. In such embodiments, because neither the cut portion of tooth nor the fixing portion 54 of the prosthesis 50 has any undercut, no elastic deformation of the fixing portion 54 is required while the prosthesis 50 is installed. Therefore, according to such embodiments, materials with almost no flexibility can be used in nearly all cases.

Preparation Guide Device

Figure 71:
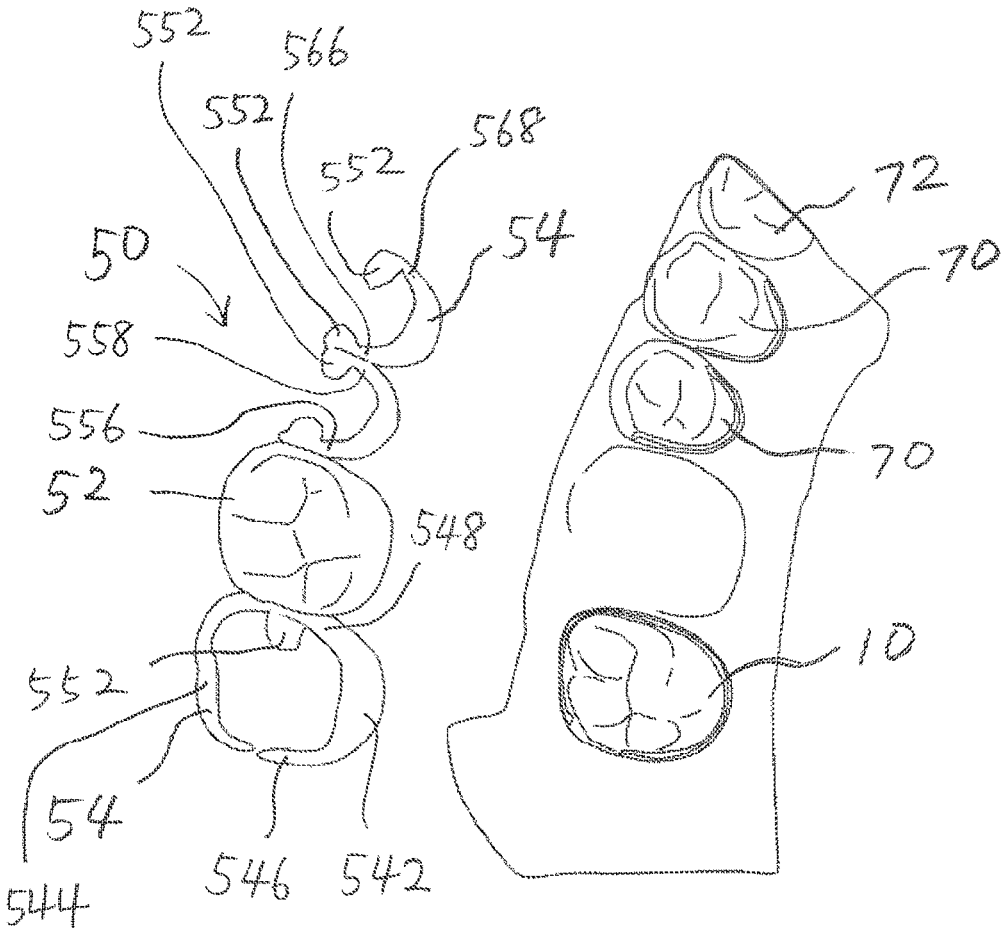
FIG. 71 is a plan view of prepared teeth and prosthesis to be installed on the prepared teeth.

Referring to FIGS. 66-74, a preparation guide device 100 is used to cut a second molar and first and second premolars as abutments such that a prosthesis 50 can be installed in cases where a first molar is missing. The preparation guide device 100 includes a tool guide way or channel 120 for cutting a second molar's side surface, except for a portion of the distal surface. In addition, the preparation guide device 100 has a single tool guide way 120 for cutting a first premolar's lingual surface, a second premolar's lingual surface, and a portion of a first molar's proximal surface. The single tool guide way 120 for premolars allows for cutting of two premolars at once. As shown in FIG. 71, the prosthesis 50 exposes the premolar's buccal surface as is without any cutting thereof such that the prosthesis is not easily visible. The prosthesis 50, nonetheless, obtains sufficient retention force by being installed on two premolars. Although one preparation guide device 100 is configured to cut three teeth in the embodiment, other embodiments can have a separate guide device for cutting each tooth.

In an embodiment, the preparation guide device 100 is engaged such that it does not move within a patient's mouth, and guides the cutting of an abutment's 70 side surfaces. In an embodiment, a preparation guide device 100 is placed over the location of a missing tooth and abutments 70 on each side thereof. In other embodiments, a preparation guide device covers not only abutment teeth 70, but also teeth adjacent to the abutments 72 and/or the gum or even alveolar bone.

Mounting of Preparation Guide Device

In an embodiment, a preparation guide device 100 has a sidewall 110 that extends along the side surface of teeth. The sidewall has a lingual sidewall 111 that extends along the lingual surface and a buccal sidewall 112 that extends along the buccal surface. The interior of these sidewalls 110 correspond to the shapes of the lingual and buccal surfaces of teeth. However, in certain embodiments, the interior surface of the sidewall beneath the survey line 84 is configured to not have any undercut (see FIGS. 6 and 9) to prevent problems that can arise while installing the preparation guide device 100 inside a mouth. In embodiments shown in FIGS. 6 and 9, the top part 1104 of the interior sidewalls 110 comes into contact with a tooth's side surfaces. Accordingly, the interior shape of that top part is formed as the shape of the tooth. In contrast, the bottom part 1106 does not come into contact with the tooth's side surfaces. In embodiments where the preparation guide device is made of a flexible material, however, undercut can be present on surfaces beneath the survey line 84 (see FIG. 55B). Such guide devices can well retain their original state of installation.

Figure 66:
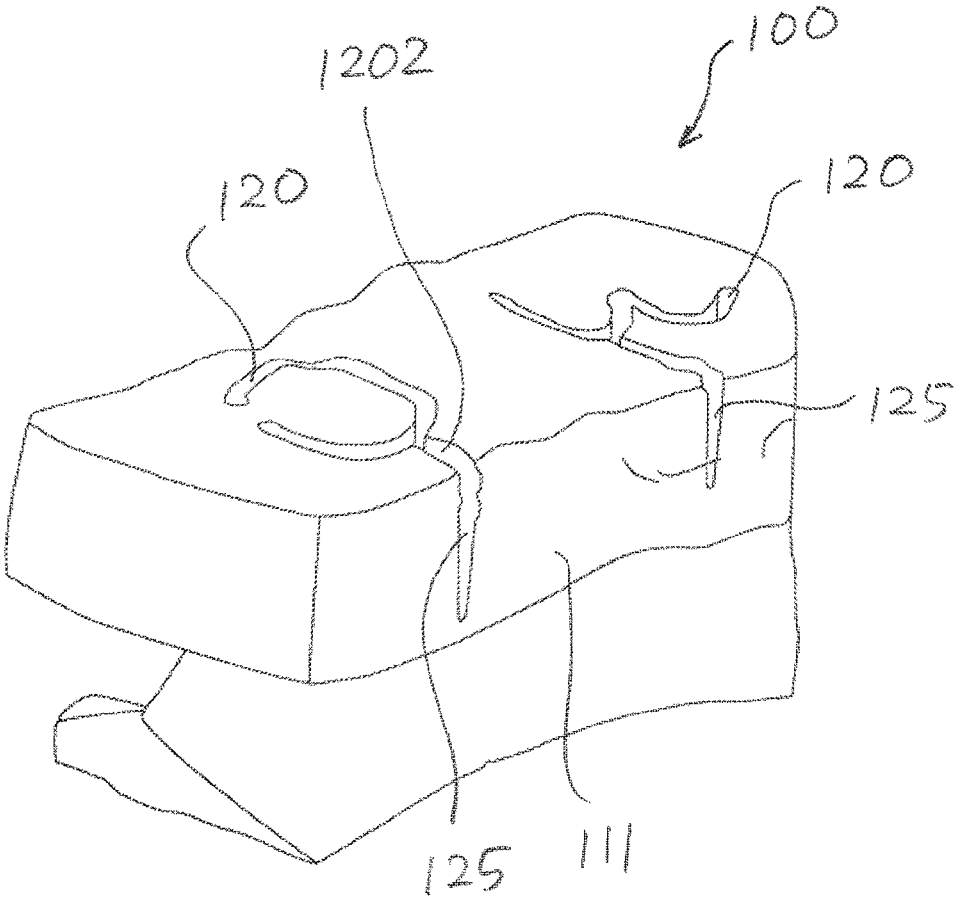
FIG. 66 is a perspective view of a preparation guide device in accordance with one embodiment as mounted on posterior teeth.

In an embodiment, a preparation guide device 100 has a top wall [114] that covers teeth by connecting a lingual sidewall 111 and a buccal sidewall 112. The interior of the top wall [114] is configured to be of a shape that corresponds to the occlusal surface of a tooth to be accommodated. As shown in FIG. 66, in an embodiment where a second molar is to be accommodated, a preparation guide device 100 has a proximal sidewall 113 that connects the lingual sidewall 110 and the buccal sidewall 112.

Burr

Referring to FIGS. 7-10, 12, 13, 24-43, and 88, a burr 200 has a shank 202, a neck 203, and a cutting head 204. The shank 202 is the portion that is fixed to the hand piece 230. The cutting head 204 is the portion that contacts teeth for cutting. The neck 203 connects the cutting head 204 and the shank 202 and is the portion that is guided by a guide slot of a preparation guide device 100, as discussed below.

In an embodiment, a burr 200 is made of tungsten carbide or stainless steel, and abrasives are attached at the cutting head 204. For example, a diamond abrasive can be used. In another embodiment of the invention, the cutting head can include multiple cutting edges instead of abrasives.

In an embodiment, the neck 203 fits within and moves along the tool guide way 120, which comprises the shape of a guide slot as discussed below. For such purposes, referring to FIGS. 38, 39, and 88, in an embodiment, the neck 203 has two sphere-shaped guide projections 208, 210. As the burr 200 rotates and moves along the tool guide way 120, the guide projections 208, 210 move along grooves formed on the wall of the tool guide way 120 as discussed below. In some embodiments, the guide projections 208, 210 can be disc-shaped. In other embodiments, the guide projections 208, 210 can be in the shape of an oval, a cone, or a trapezoid. In some embodiments, the guide projections 208, 210 are configured as parts of the neck 203, but in other embodiments, the guide projections can be separate from the neck. For example, a rotatable ring can be separately installed on the neck 203 as a guide projection.

Hand Piece

In an embodiment, a hand piece 230 is a device that installs and rotates a burr 200 (see FIGS. 7-10, 12, and 13). Generally, dental practitioners hold a burr with their hands. The hand piece 230 has a chuck to which the shank 202 of a burr 200 is connected. The hand piece 230 has a motor that can rotate the burr 200 at high speeds. In some embodiments, a hand piece 230 can be configured for high speed rotations (about 300,000 RPM to about 400,000 RPM) or for low speed rotations (about 3,000 RPM to about 30,000 RPM).

Tool Guide Way or Channel

In an embodiment, a tool guide way 120 is provided to guide a burr 200 such that it follows a predetermined path or trajectory. After the burr 200 is properly inserted into the tool guide way 120 through an entrance hole, the burr 200 can only move along the predetermined path. The burr 200 moves along the tool guide way 120 and removes or cuts teeth. In an embodiment, as shown in FIG. 66, a tool guide way includes a non-cutting access way 1202. The non-cutting access way 1202 is a portion of the tool guide way 120 to guide a burr 200 to a location at which cutting is to begin. In some embodiments, the burr 200 does not cut teeth while it is traveling along the non-cutting access way. In embodiments in which a tool hole is located near the point within the tool guide way at which cutting is to start, a separate non-cutting access way may not be necessary.

Cutting Tooth along a Tool Guide Way

In an embodiment, a burr 200 may not cut teeth at every location along a tool guide way 120. Whether or nota burr 200 cuts teeth at a given location is determined by the radius of the burr 200 (size of a cross section) and the distance between the tool guide way 120 and surface of teeth. Because the radius of a burr 200 can change depending on the burr's lengthwise shape, the shape of the burr also affects the cutting of teeth.

Figure 6:
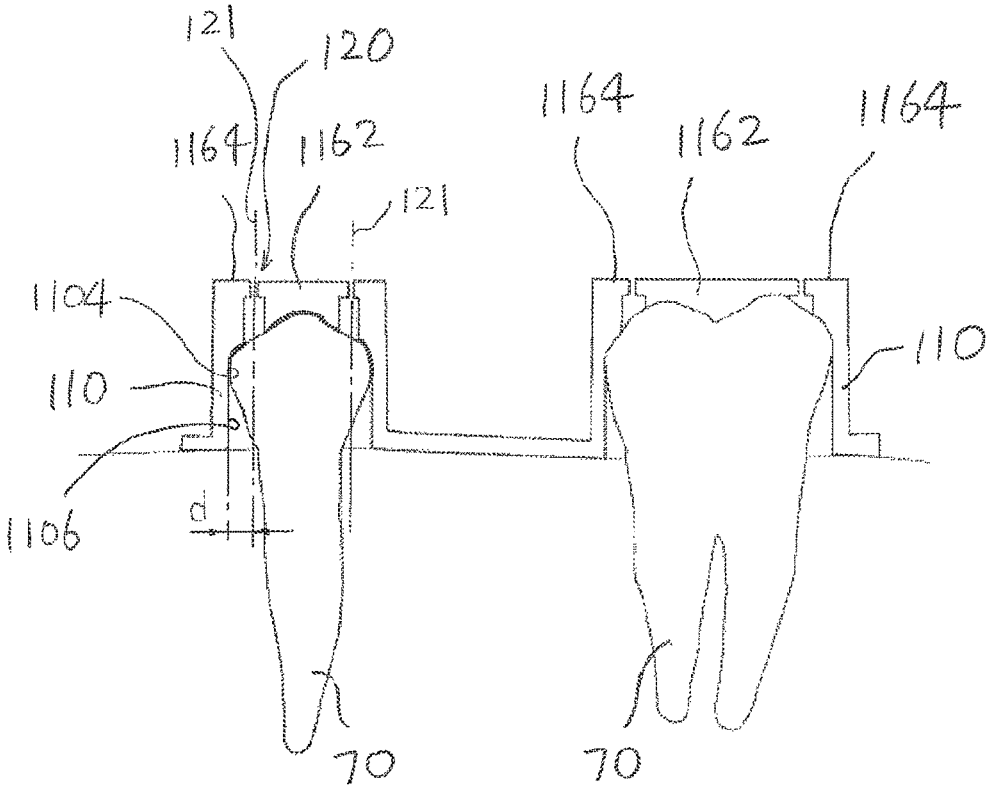
FIG. 6 is a cross-sectional view of a preparation guide device mounted on teeth.
Figure 7:
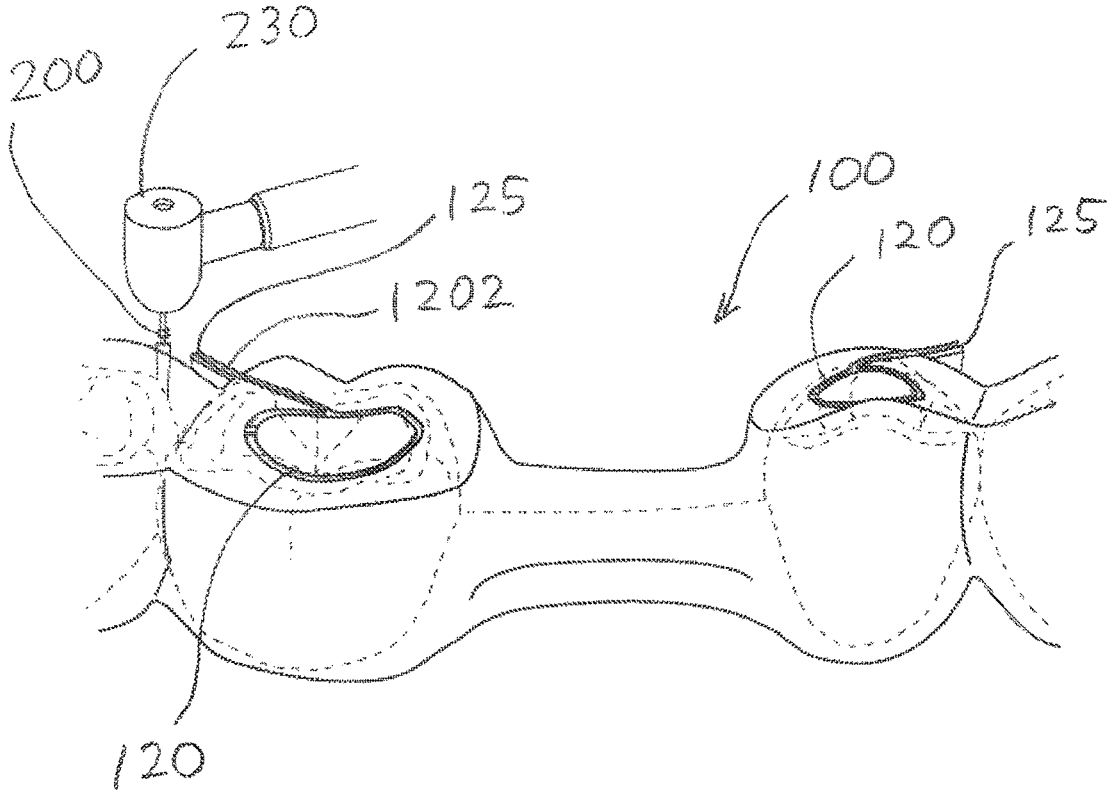
FIG. 7 is a perspective view of a hand piece and a preparation guide device mounted on teeth.
Figure 8:
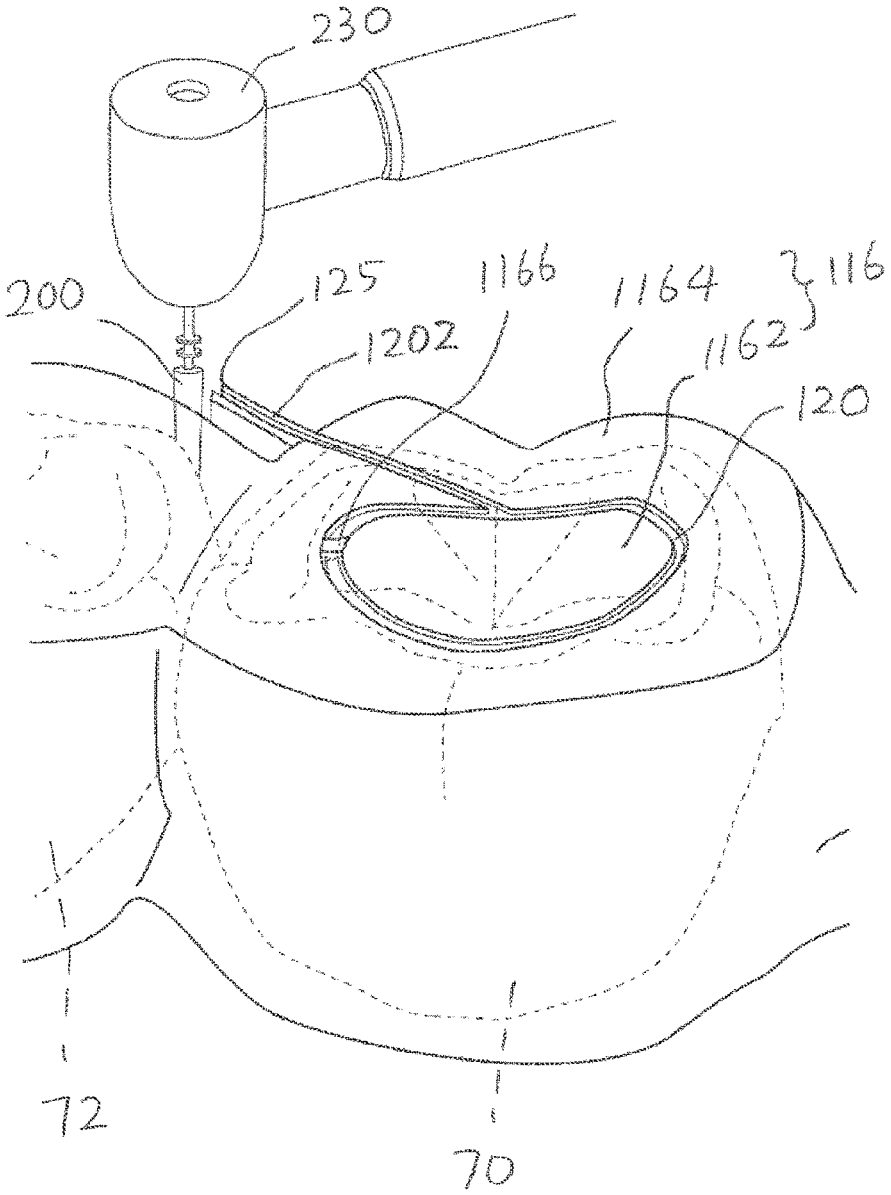
FIG. 8 is an enlarged view of a portion of the cutting tool and the preparation guide device shown in FIG. 7.
Figure 9:
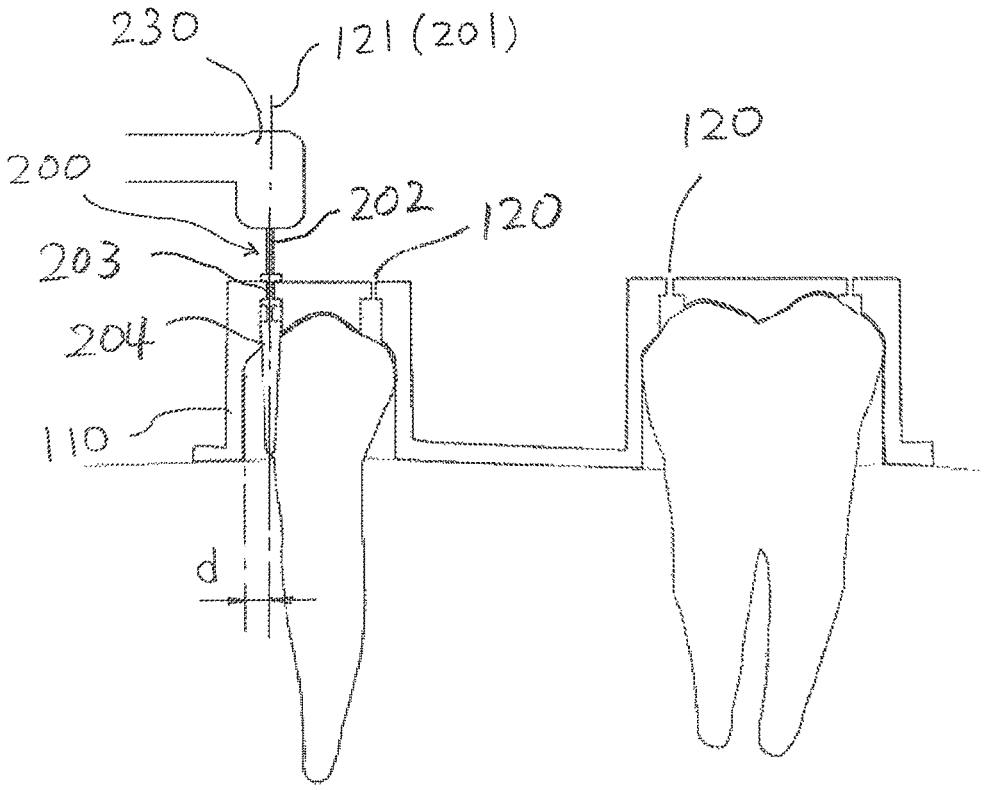
FIG. 9 is a cross-sectional view of a cutting tool and a preparation guide device in accordance with one embodiment as mounted on teeth.

In an embodiment, the distance between a tool guide way 120 and surface of teeth can be defined as a distance d between the vertical centerline of the tool guide way 120 and the surface of teeth, as shown in FIG. 6. In an embodiment, ideally, the vertical centerline of the tool guide way 120 coincides with the axis of rotation 201 of the burr 200, as illustrated in FIG. 9. In some embodiments, the distance d between the axis of rotation 121, 201 of the burr 200 and the surface of teeth can change depending on the path of the tool guide way 120. Assuming a burr 200 with a predetermined radius and shape is used, the depth of cutting can vary according to changes in the distance d changes, and there can be sections where teeth are not cut at all. For example, although not shown in FIG. 6, in an embodiment, teeth are not cut along locations where the burr's 200 axis of rotation 121, 201 is farther out away from teeth than the radius of the burr 200.

In one embodiment, a preparation guide device 100 is designed so that a burr 200 cuts teeth along all points on a path of a tool guide way 120. In an embodiment, the depth of cutting can be configured to be almost constant at all points along a path or to vary greatly. In another embodiment, a preparation guide device 100 is designed so that a burr 200 cuts teeth while moving along certain sections of the tool guide way 120, but not along other sections. In an embodiment, a preparation guide device 100 is designed so that a section where the burr 200 moves without cutting teeth is followed by a connected section where the burr moves while cutting teeth. In some embodiments, a preparation guide device 100 is designed so that a section where a burr 200 moves while cutting teeth is located between, or intervenes, sections where the burr moves without cutting teeth. In some other embodiments, a preparation guide device 100 is designed so that a section where the burr 200 moves without cutting teeth is located between, or intervenes, sections where the burr moves while cutting teeth. The various types of embodiments discussed in this paragraph all assume using a burr with a predetermined radius and shape.

No Cutting of Occlusal Surface

Referring to FIGS. 66-74, in an embodiment, a preparation guide device 100 has two tool guide ways 120 for cutting side surfaces of teeth and a non-cutting access way. A first one of the two tool guide ways 120 is for cutting a first molar, and the other is for cutting first and second premolars. Bridge prostheses 50 used in the illustrated embodiments do not require cutting occlusal surfaces. Since occlusal surfaces are not cut, a tool guide way for cutting occlusal surface is not necessary.

Restriction of Burr within Tool Guide Way

Referring to FIGS. 39A, 39B, 69A, and 69B, which show cross sections of tool guide ways 120, in an embodiment, a tool guide way 120 has two guide side surfaces 128 that face each other. The two guide side surfaces 128 form a guide slot. When a burr 200 enters the guide slot, movement of the burr 200 is constrained and the burr 200 is guided along the tool guide way 120. The distance between the guide side surfaces 128, that is, the width of the guide slot, is limited to reduce tilting when a neck 203 of a burr 200 is inserted, but is large enough for the neck 203 to overcome friction and rotate. In an embodiment of the invention, the tool guide way 120 is shaped as a guide slot, but the present invention is not limited to such embodiments.

In some embodiments, a portion of a burr 200 enters a guide slot and becomes constrained in its movement, but other embodiments have structures wherein a hand piece 230 is inserted into and constrained by a guide slot of a tool guide way 120. For example, in an embodiment as shown in FIG. 126, a structure 2301 of a hand piece 230 is inserted into and constrained by a guide slot. In contrast, a burr 200 is not directly constrained by the guide slot. Alternatively, although not shown, other embodiments can include configurations where both a structure of a hand piece 230 and a portion of a burr 200 are inserted into and constrained by a tool guide way.

Using Two or More Burrs in One Tool Guide Way

While in some embodiments, a single burr is used for cutting tooth, in other embodiments two or more burrs can be used inclining tooth. For example, in embodiments with thick portions to cut, a first burr can cut some layers of the portion to be cut by moving along a tool guide way 120, and a second burr can subsequently move along, the same tool guide way 120 to cut the remaining layers in order to obtain a final cut shape. In another embodiment of the invention, a first burr can perform a rough cut, and a second burr can subsequently perform a precise cut.

In one embodiment using two or more burrs, the two or more burrs enter a tool guide way 120 through the same entrance. In another embodiment, referring to FIG. 124, burrs can be substituted in the middle of a tool guide way 120. To allow for such substitutions, an embodiment has a middle tool hole 124a, or intermediate tool hole, formed in the middle of the tool guide way 120. Although not illustrated, some embodiments can have two or more middle tool holes in a tool guide way 120 so that it is possible to replace a burr two or more times. In an embodiment, first, a preselected first burr enters a tool guide way and cuts along a first part 120a. Then, the first burr is removed through a middle tool hole 124a located on a terminal end of the first part 120a. Next, a preselected second burr enters the tool guide way through the middle tool hole 124a and cuts teeth following the second part 120b of the tool guide way 120. Here, the first 120a and second parts 120b of the tool guide way 120 are not separated and are connected to each other, constituting a single tool guide way 120. FIG. 125 is a flowchart of such embodiment.

In one embodiment, a first part 120a and a second part 120b have different internal structures, so a first burr cannot move past the first part 120a to move along the second part 120b. More specifically, the internal structure of the first part 120a of a tool guide way 120 complements the shape of the first burr, and the internal structure of the second part 120b of the tool guide way complements the shape of the second burr. Moreover, the first burr and the second burr differ with respect to one or more of the following: length of a neck 203, thickness of a neck 203, number of guide projections 208, 210, shape of guide projections 208, 210, size of guide projections 208, 210, and other considerations. The first 120a and second parts 120b can also have various structures that correspond to those of their respective burrs. Accordingly, in an embodiment, the first part 102a can accommodate the first burr, but the second part 1206 cannot accommodate the first burr, and only the second burr can enter and move along the second part 120b. In other embodiments, first 120a and second parts 120b of a tool guide way 120 can have the same internal structure so that a first burr can pass through a middle or intermediate tool hole 124a and move along the second part 120b as well.

Guide grooves

Referring to FIGS. 39, 44, 69A, and 69B, in an embodiment of the invention, each tool guide way 120 has guide grooves 132, 134 to guide a burr 200. Guide projections 208, 210 of a burr are inserted into and move along their corresponding guide grooves 132, 134. In some embodiments, the distance between guide grooves 132, 134 is constant throughout a tool guide way. Therefore, in an embodiment with a preparation guide device 100 that has two guide grooves 132, 134, the thickness of a top wall 116 near the tool guide way need not be uniform. However, in other embodiments as shown in FIGS. 27-30, the thickness of a top wall 116, that is, the distance between a top supporting surface 129 and the bottom supporting surface 130 is kept uniform.

Sidewall Entrance for Burrs

Figure 67:
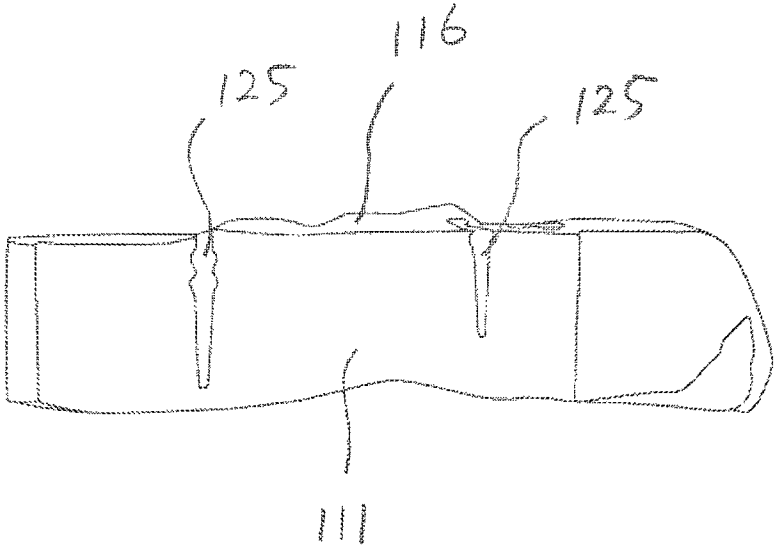
FIG. 67 is a side view of the preparation guide device shown in FIG. 66.
Figure 68:
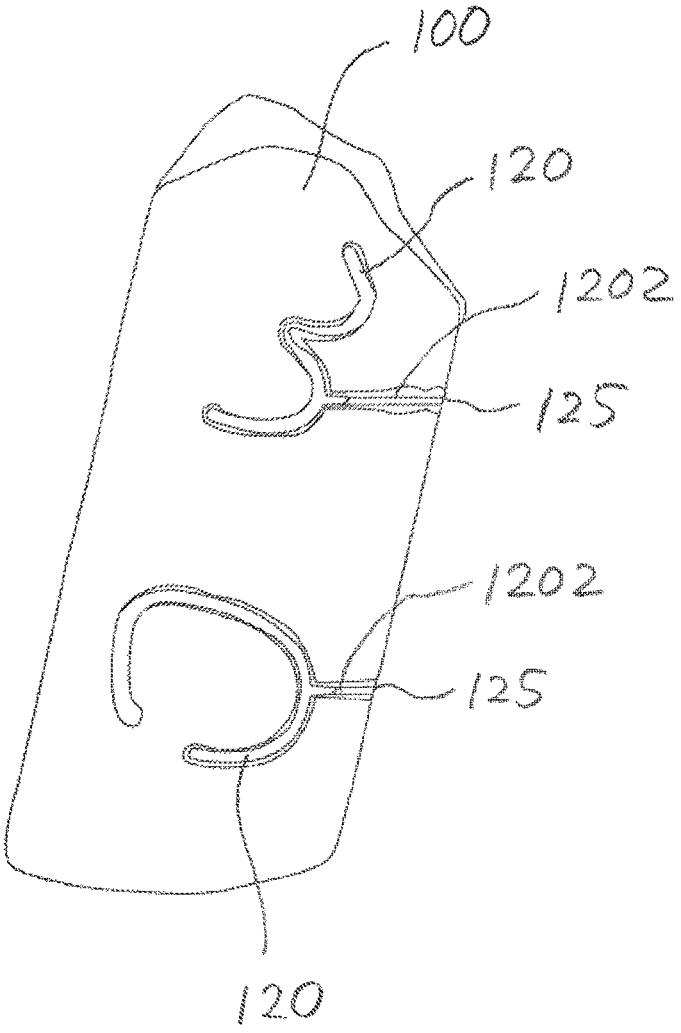
FIG. 68 is a plan view of the preparation guide device shown in FIG. 66.
Figure 70:
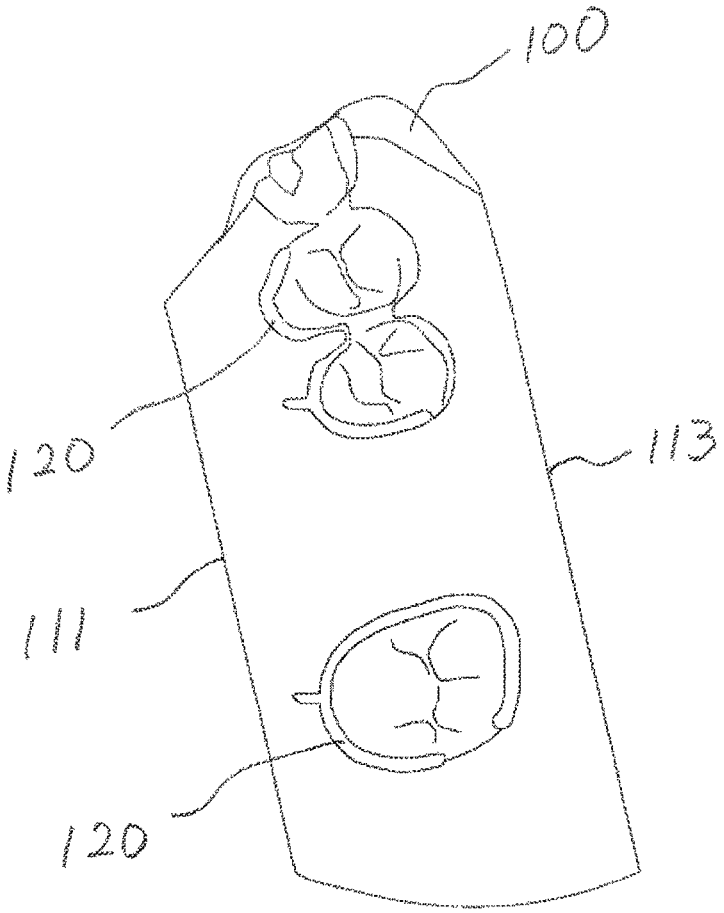
FIG. 70 is a bottom view of the preparation guide device shown in FIG. 66.

In an embodiment as shown in FIGS. 66 and 67, a sidewall has an entrance 125 for burrs. The entrance 125 and tool guide way 120, where cutting of teeth occurs, are connected by a non-cutting access way 1202. A burr 200 enters through the entrance (125), is guided by the non-cutting access way 1202, and after cutting teeth, exits through the same entrance 125 by passing back through the non-cutting access way 1202.

Cutting Three or More Side Surfaces using a Single Tool Guide Way

Referring to FIGS. 66-74, in an embodiment, a preparation guide 100 has a single tool guide way for cutting three or more side surfaces of a single tooth. In addition, such preparation guide device 100 has an additional single tool guide way that is configured to cut four side surfaces of a single tooth. A first tool guide way 120 is formed on a top wail 116 to be placed over a second molar. The first tool guide way 120 is configured to guide a burr to cut the following surfaces of a second molar: the buccal surface, the entire proximal surface closest to the missing tooth, a portion of the proximal surface farther from the missing tooth, and the lingual surface. In some embodiments, the burr 200 enters through an entrance 125, travels through the non-cutting access way 1202, and is inserted into the tool guide way 120. The burr moves along the tool guide way 120 and cuts the buccal surface, entire proximal surface closest to the missing tooth, a portion of the proximal surface farther from the missing tooth, and the lingual surface. After all the cutting is completed, the burr travels back through the non-cutting access way 1202 and exits through the entrance 125.

Still referring to FIGS. 66-74, in an embodiment, the preparation guide device 100 has a tool guide way configured to cut three or more side surfaces of two or more teeth. A second tool guide way 120 is formed on the top wall 116 to be placed over the first and second premolars. The second tool guide way 120 is configured to guide a burr to cut side surfaces of the first and second premolars. Although buccal surfaces can also be cut to engage a prosthesis, the amount of buccal surfaces cut can be reduced for aesthetic reasons if the proximal surface, lingual surface, and a portion of the opposite proximal surface provide sufficient retention force.

Vertical Tool Entrance Hole

Figure 75A:
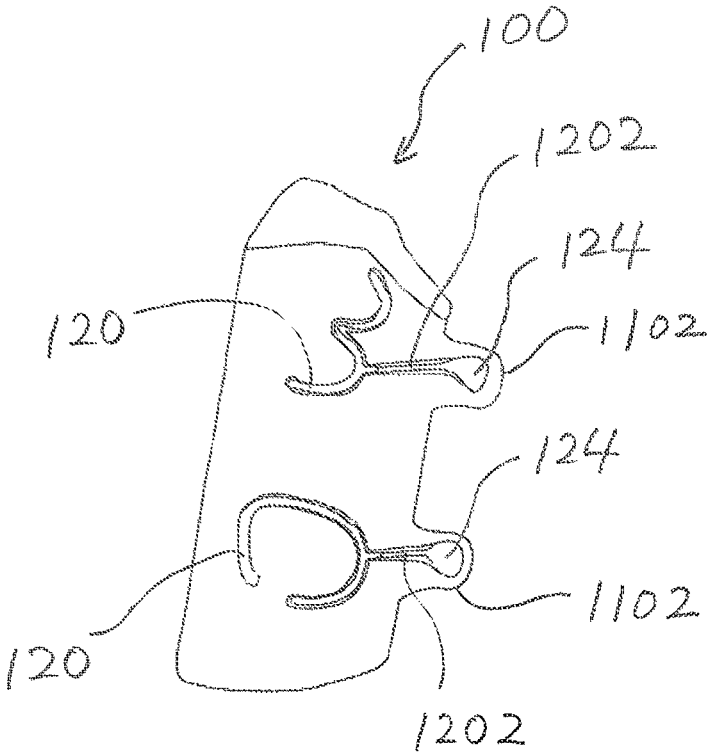
FIG. 75A is a plan view of a preparation guide device in accordance with one embodiment.

In an embodiment as shown in FIG. 75A, a preparation guide device 100 has a tool hole 124 that allows a projected structure 1102 to be inserted in a top-down direction. If a burr entrance is designed in such manner, a sidewall 110 need not have a gap, and thus the preparation guide device 100 can become more stable, and can well maintain the burr in position during cutting.

Figure 75B:
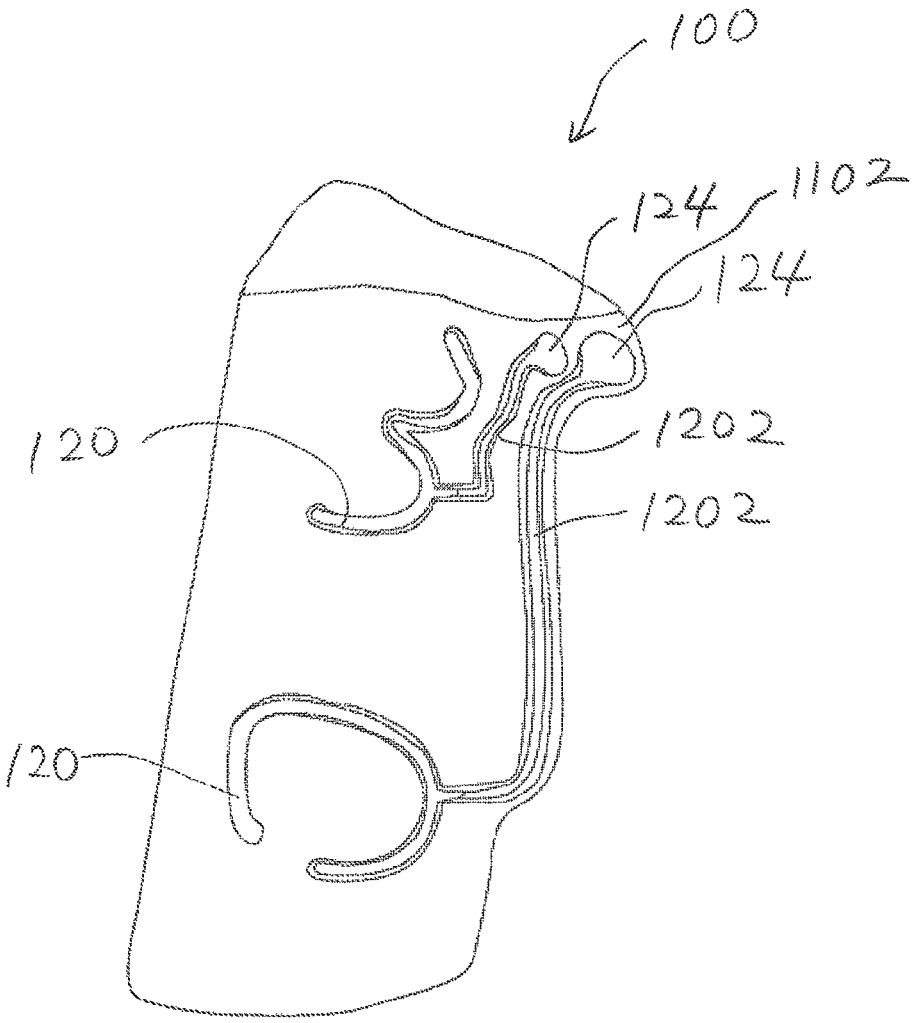
FIG. 75B is a plan view of a preparation guide device in accordance with one embodiment.

In an embodiment as shown in FIG. 75B, a preparation guide device 100 has tool holes 124 located on one side of a preparation guide device. A non-cutting access way 1202 front each tool guide way 120 extends to one end of the preparation guide device, and tool holes 124 are formed at this end. The tool holes 124 are located on the end of the preparation guide device closer to the front of the mouth when the preparation guide device is installed, that is, the end by the incisors. Some patients are not able to open their mouths widely, but even for such patients, the front of the mouth opens more than the rest. Placing tool holes 124 near the front of the mouth, as in the embodiment, allows a burr to be inserted at the front of the mouth and can then move along the tool guide way 120, thus not requiring patients to open their mouths as wide.

Figure 75C:
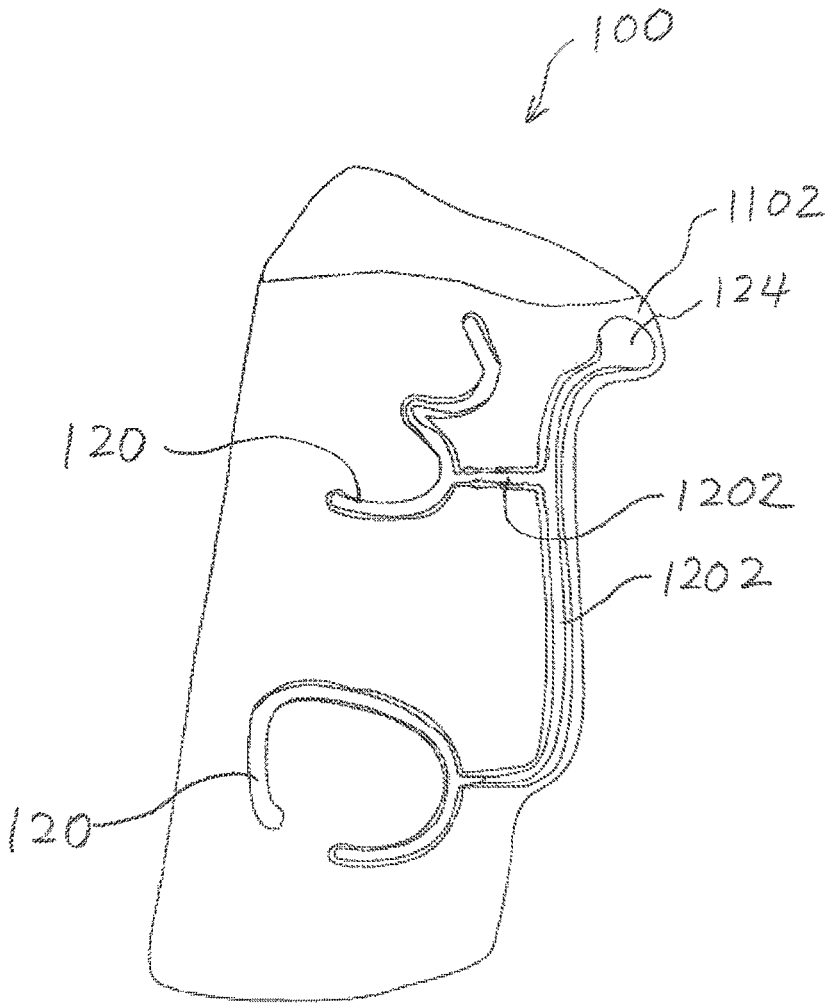
FIG. 75C is a plant view of a preparation guide device in accordance with one embodiment.

Although each tool guide way 120 of an embodiment as shown in FIG. 75B has a separate non-cutting access way with separate tool holes 124, in other embodiments, as shown in FIG. 75C, non-cutting access ways 1202 of different tool guide ways 120 can converge and share a single tool entrance hole 124.

Another Embodiment of a Vertical fool Entrance Hole

An embodiment of the invention as shown in FIG. 79 has a similar shape as the embodiments shown in FIGS. 66-74 and is for cutting a second molar, a first premolar, and a second premolar. The main difference between the preparation guide devices 100 of these embodiments is that the tool guide way 120 shown in FIG. 79 has tool holes 124 at both ends. Such embodiment does not include a separate non-cutting access way 1202 or non-cutting guide section that guides the burr to the start point for cutting after it is inserted into the tool hole 124. Such embodiments include cases where a non-cutting region is included between the tool hole 124 and the cutting start point in the tool guide way 120, but where the distance is so short (e.g., diameter of the cutting head of the burr) that the region cannot be called a separate non-cutting access way 1202 or non-cutting guide section. In such embodiments, the burr can start cutting teeth almost immediately after it is inserted through the tool hole 124 and enters the tool guide way.

Referring to FIGS. 79A and 89, in one embodiment of the invention, a tool guide way 120 for the second molar has two tool holes 124 at each end of the tool guide way for the burr 20 to enter. The tool holes 124 are located inside the sidewall 110. In some embodiments, the burr 200 is inserted into one tool hole 124 and moves along the tool guide way 120, cuts side surfaces, and exits from the tool guide way 120 through a different tool hole 124.

In the foregoing embodiments, the tool hole 124 On the buccal surface side is used as the entrance, and the tool hole 124 on the lingual surface side is used as the exit. In other embodiments, the tool hole 124 on the lingual surface side can he used as the entrance, and the tool hole 124 on the buccal surface side can be used as the exit. In yet other embodiments, a single tool hole 124 can be provided for the tool guide way 120 and he used as both an entrance and an exit.

Still referring to FIG. 79A, an in embodiment, the second tool guide way 120 is formed on the top wall [115] to be placed over first and second premolars. The second tool guide way 120 is formed to guide a portion of the side surface of the first and second premolars. In an embodiment, the second tool guide way 120 has tool holes 124 at both ends for the burr 200 to enter. These tool holes 124 are located inside the sidewalls 110. The burr 200 enters through one of these tool holes 124, moves following the tool guide way 120, and exits through a different tool hole 126.

Marking the Travel Direction of a Burr and Other Information

According to an embodiment of the present invention, the preparation guide device 100 can include signs or indications that provide information to dental practitioners. For example, referring to FIG. 89, the preparation guide device of an embodiment has signs 136 that indicate the direction in which a burr should travel. Although not illustrated, in some embodiments, signs indicating whether a tool hole 124 is an entrance or an exit can be included. In some embodiments, such signs 136 are placed where they are easily seen by a dental practitioner. For example, in some embodiments, signs are provided on the top. In some embodiments, signs can be raised or recessed and can be in color so that it stands out from the background. In some embodiments, signs 136 that indicate the travel direction of the burr 200 can include various types of icons, such as an arrow as shown. In an embodiment, the dental practitioner inserts the burr 200 into the tool hole 124 and cuts teeth by rotating and moving the burr 200 in the direction of the arrow 136.

In one embodiment, when a dentist moves a burr along a tool guide way While grasping a hand piece coupled to the burr, the dentist can push the hand piece away from his/her body to move the burr. The burr can be moved by way of pushing the hand piece through the entire portion of the tool guide way or a certain portion of the tool guide way. In another embodiment, the dentist can pull the hand piece toward his/her body to move the burr. In a certain embodiment, the dentist can apply a force to the hand piece from left to right to move the burr. In an alternative embodiment, the dentist can apply a force to the hand piece from right to left to move the burr.

Rotational Direction of a Burr

In an embodiment as shown in FIG. 89, a burr 200 rotates counterclockwise *137* as viewed from the shank 202 of the burr towards the cutting head 204. To be more precise, the burr 200 is rotated so that the tangential direction at the contact point between the cutting head 204 and teeth is opposite from the travel direction of the burr 200. In an embodiment, most particles of cut teeth pop out towards the tangential direction 138. This is to prevent particles from blocking the burr 200. However, the invention is not limited as such, and in other embodiments, the tangential direction and the travel direction at the contact point of the burr 200 and teeth can be the same.

Structure of Tool Holes for Burrs

Referring to FIGS. 89 and 90, in an embodiment, the tool hole 124 is located at the end of the tool guide way 120. The tool hole 124 has a top opening 140 and a bottom opening 142. In an embodiment, the size of the top opening 140 is large enough for the cutting head 204 of the burr 200 and the guide projections 208, 210 to pass through, in an embodiment, the size of the bottom opening 142 is large enough for the cutting head 204 of the burr 200 to pass through but not large enough for the lower guide projections 210 to pass through. In an embodiment, a stopper 144 is located near the bottom opening 142 to prevent the lower guide projections 210 from moving down further.

In some embodiments, When the stopper 144 stops the lower guide projection 210, the upper guide projection 208 is situated at the height of the upper guide groove 132, and the lower guide projection 210 is situated at the height of the lower guide groove 134. Therefore, when the burr 200 is stopped from moving down further due to the stopper 144, the burr 200 can be rotated and moved towards the tool guide way 120 as the guide projections 208, 210 are inserted into the groove to move along the tool guide way.

Referring to FIG. 91, in an embodiment, the top opening 140 and the bottom opening 142 of tool holes 124 are large enough to allow the burr 200, the cutting head 204, and the guide projections 208, 210 to pass through. The stopper 146 is located below the tool hole 124 and is configured such that a terminal end of the cutting head 204 is stopped. In sonic embodiments, the stopper 146 is located at a point where the guide projections 208, 210 and the guide groove are aligned, but the present invention is not limited to such.

[Anti-Titling] *Anti-tilting* Structures

As the burr 200 moves along the path provided by a tool guide way 120 and cuts teeth, the burr 200 can tilt from its ideal axis of rotation 201. Tilting can occur in various directions. Any such direction includes a first tilting component in the direction of the travel of the burr 200 along the tool guide way 120 and a second tilting component in the plane perpendicular to the direction. These tilting components can be substantially reduced by using complementary shapes and structures for the tool guide way 120 and the burr 200. Factors for reducing tilting can include the length of the burr's neck 203, diameter of the neck 203, number of guide projections 208, 210, shape of guide projections 208, 210, size of guide projections 208, 210, position of guide projections 208, 210, length of guide surfaces 128 facing each other in the tool guide way 120 that corresponds to the aforementioned configurations, width of guide surfaces 128, number of guide grooves, shape of guide grooves, size of guide grooves, and position of guide grooves.

One embodiment includes a tilting prevention structure located at the terminal portion 210 of the cutting head 204 of the burr 200. As shown in [FIG. 92] *FIGS. 92A-92B*, the burr 200 includes a cylindrical projection 212 that extends vertically from the terminal end of the cutting head 204. In this embodiment, the diameter of the cylindrical projection 212 is smaller than the diameter of the cutting head 204. Thus, an elevation 214 is formed between the cylindrical projection 212 and the cutting head 204. In this embodiment, no abrasives or cutting edges are formed around the exterior of the cylindrical projection 212. Therefore, the exterior of the cylindrical projection 212 moves while in contact with uncut surfaces of teeth, [and the burr does not move in the indicated direction 216 during cutting,] thus preventing tilting. During such process, teeth themselves become guide surfaces to guide the burr 200. In another embodiment, abrasives or cutting edges can be formed around the elevation 214.

Cutting Margin Line

Figure 24:
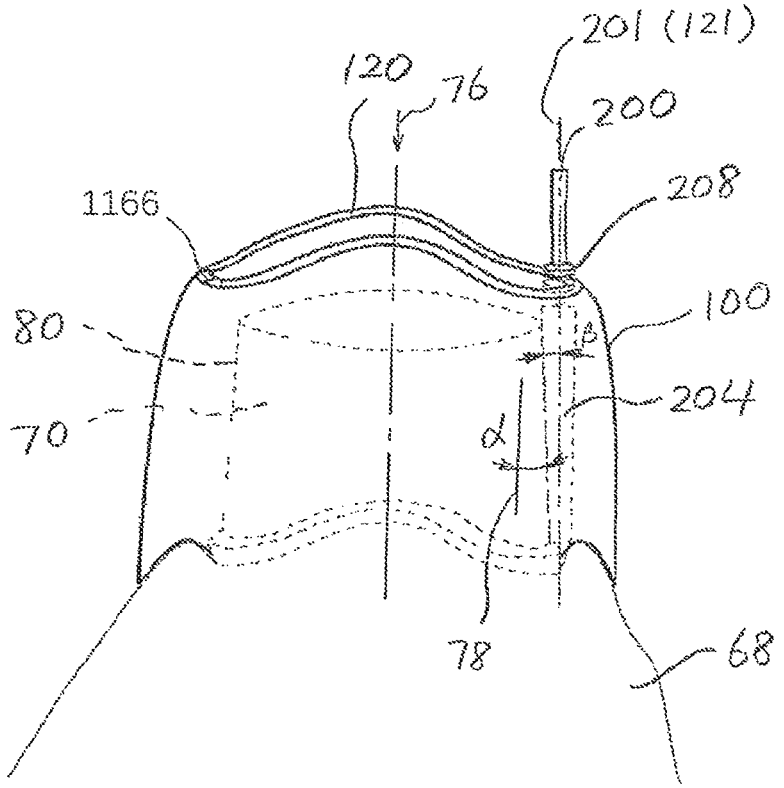
FIG. 24 is a schematic view of preparing a tooth using a preparation guide device and a cutting tool.

As the burr 200 moves along the tool guide way 120, a terminal cutting portion of the cutting head 204 cuts tooth as far as it can reach, forming a boundary line (cutting margin line) between cut portions and uncut portions. Prostheses are produced such that they can reach anti be engaged onto the cutting margin line. Referring to FIG. 24, one embodiment includes a preparation guide device 100 and burr 200 configured such that the terminal cutting, portion of the cutting head 204 moves along the gingival line. In such cases, the cutting margin line on tooth either coincides or nearly coincides with the gingival line. In contrast, in the embodiment illustrated in FIG. 92B, the end of the cutting head 204 moves along a line located between the survey line 84 (or cervical ridge line) and the gingival line. In such cases, the cutting margin line on tooth can easily be seen because it is not on the gingival line. In other embodiments, the preparation guide device 100 and the burr 200 can be configured such that the terminal cutting portion of the cutting head 204 moves above the survey line 84 along some portions of the tooth and below the survey line 84 along other portions. In addition, although not shown, a preparation guide 100 and burr 200 can be configured such that the terminal cutting portion of the cutting head 204 moves below the gingival line, In such cases, the cutting margin line of tooth can be hidden under portions of the gum.

Cut Portions without any Substantial Undercuts

If cutting is solely dependent on a dental practitioner's hand movement, an undercut can result from cutting. However, in one embodiment of the invention, there is no noticeable undercut on the cut portions of the teeth as viewed along the axis of insertion of the prosthesis. In other words, no undercut is present in the portion where the prosthesis is to be engaged, as viewed along the intended axis of insertion of the prosthesis. Referring to FIGS. 92A-92E, when viewed along the prosthesis's axis of insertion 76, the cut portion of teeth is either generally parallel to the axis of insertion 76 or is sloped such that it tapers slightly towards the occlusal surface.

Sloped Angle of a Cut Surface

In one embodiment of the invention, the angle $\alpha$between the cut surface of teeth and the axis of insertion 76, 78 of the prosthesis 50 ranges from about 0° to about 3°. In one embodiment, the angle $\alpha$can be about 0.1°, about 0.2°, about 0.3°, about 0.4°, about 0.5°, about 0.6°, about 0.7°, about 0.8°, about 0.9°, about 1°, about 1.1°, about 1.2°, about 1.3°, about 1.4°, about 1.5°, about 1.7°, about 1.9°, about 2°, about 2.3°, about 2.7°, about 3°, about 3.5°, or about 4°. In other embodiments, the angle can be within the range of any two of the aforementioned angles. The aforementioned angles are much less than the angle typically formed by cutting without a preparation guide device, which ranges from about 6° to about 10°. It is also possible to cut at an angle of about 4°, about 5°, about 6°, about 7°, about 8°, about 9°, about 10°, about 11°, about 12°, about 13°, about 14°, or about 15° using the preparation guide device. Here, the angle can also be within the range of any two of the aforementioned angles.

In one embodiment, the angle $\alpha$between the cut surface 80 and the (intended) axis of insertion 76 of the prosthesis 50 is either constant throughout all cut portions or is substantially the same. In other words, the angle $\alpha$is the same or substantially the same at any location within any cut surface of a single tooth. In this context, substantially similar means that although the angle $\alpha$is slightly different from location to location, distribution from the intended angle is about ±5%, about ±6%, about ±7%, about ±8%, about ±9%, about ±10%, about ±11%, about ±12%, about ±13%, about ±14%, about ±15%, about ±16%, about ±17%, about ±18%, about ±19%, about ±20%, about ±21%, about ±22%, about ±23%, about ±24%, about ±25%, or is within the range of any two of the aforementioned numbers.

Tapered Slope of the Cutting Head

In embodiments, the cutting head 204 of the burr 200 is tapered towards the terminal end. The tapered angle, or the angle $\beta$ between the burr's axis of rotation and the cut surface of teeth, is substantially similar to the angle $\alpha$. In other embodiments, the sloped angle $\alpha$of the cut surface 80 may not be constant throughout the cut surface 80. Even though the tapered angle β of the burr is constantly maintained along the exterior surface of the burr, the sloped angle α of the cut surface 80 may be of a different angle than β if the slope of the guide surface 128 of the guide slot of the tool guide way 120 is varied with reference to the prosthesis's axis of insertion.

Depth/Thickness of Cut Teeth

In various embodiments of the invention, cut surfaces can have sloped angles ranging from about 0° to about 3°. Accordingly, the depth or thickness of a cut may be smaller compared to traditional methods of cutting without a preparation guide device. The preparation guide device in one embodiment of the invention allows the prosthesis to be engaged after cutting only the enamel layer of teeth. When cutting just the enamel layer, even those procedures that require cutting substantial portions of teeth (e.g., for crowns or cutting three or four surfaces of a tooth) may be undertaken without anesthesia. In another embodiment, it is possible to cut a portion of the dentin layer as well, although it is preferable to cut only within the enamel layer.

According to one embodiment of the invention, the depth (thickness) of the cut in parts where the most amounts of teeth are cut is markedly less than cutting by other methods. More specifically, as viewed along, the intended axis of insertion of the prosthesis, the depth of cutting near the cervical ridge line or survey line is about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, or about 3.0 mm. Alternatively, the depth of cutting near the cervical ridge linear survey line can also be within the range of two of the aforementioned numbers. Preferably, the depth of cutting is about 0.5 mm, about 0.6 mm, about 0.7 mm, about 0.8 mm about 0.9 mm, about 1.0 mm, about 1.1 mm, about 1.2 mm, about 1.3 mm, about 1.4 mm, about 1.5 mm, about 1.6 mm, or within the range of two of the aforementioned numbers.

Thickness of Prosthesis Fixing Portions

Because the depth of cut is smaller, the thickness of the fixing portions 52 of the prosthesis 50 to be engaged on such locations can also be substantially smaller. When materials that allow thin fixing portions are used, the depth of cutting can be even smaller, The thickness of the prosthesis that is engaged over cut surfaces 80 is measured from the same location as for measuring the depth of the teeth cut, namely from the cervical ridge line or survey line. The thickness of the prosthesis can be about 0.1 mm, about 0.2 mm, about 0.3 mm, about 0.4 mm, about 0.5 mm, about 0.6 mm, about 0.7 mm, about 0.8 mm, about 0.9 mm about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, or about 3.0 mm or within the range of two of the aforementioned, numbers. Preferably, the thickness of the prosthesis is about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, or within the range of two of the aforementioned numbers.

Interior Side Surfaces of a Prosthesis Fixing Portion

The three-dimensional shape anti size of interior side surfaces 59 of the prosthesis 50 fixing portion 52 is precisely complementary to the three-dimensional shape and size of cut surfaces 80 formed on an abutment tooth. Referring to FIG. 92D, such interior surfaces 59 are angled with reference to an intended axis of insertion 76 of the prosthesis. Such sloped angle γ is substantially similar to the angle α. In other embodiments, the angle γ can be slightly larger than α.

Scope of Error

Errors are inevitable in manufacturing and cutting procedures. However, cutting teeth using a preparation guide device and burr according to embodiments of the invention lead to substantially similar results as the prospective cut surface images prepared by CAD/CAM systems during the design stages of the preparation guide device. Comparisons of data obtained, from three-dimensional digital scans of actually cut teeth with data of simulated prospective cut surface images using CAD/CAM systems show that the data obtained from actually cut teeth err on average by about 20μ, about 40μ, about 60μ, about 80μ,about 100μ, about 120μ, about 140μ, about 160μ, about 180μ, about 200μ, about 220μ, about 240μ, about 260μ, about 280μ, about 300μ, or within the range of two of the aforementioned numbers.

If an error occurs repeatedly under the same conditions (materials of the preparation guide device, manufacturing tools used for the preparation guide device, materials of the burr, etc.), such error can be greatly reduced by undergoing subsequent corrective measures. Whether or not subsequent correction measures have been taken, the average scope of error is preferably under about 100μ or, to be more specific, about 20μ, about 40 μ, about 60μ, about 80μ, or about 100μ. Also, this average scope of error can be within the range of any two of the aforementioned numbers. When obtaining data for actually cut teeth, the burr 200 must not be forced to tilt within the tool guide way 120, and the cutting process must be performed to minimize any error. Considering the fact that the shape of the actually cut teeth is obtained by cutting a minimal amount and by not excessively changing its original shape, the scope of error mentioned above is even more unexpected.

Shape of Prosthesis's Fixing Portion

Figure 72:
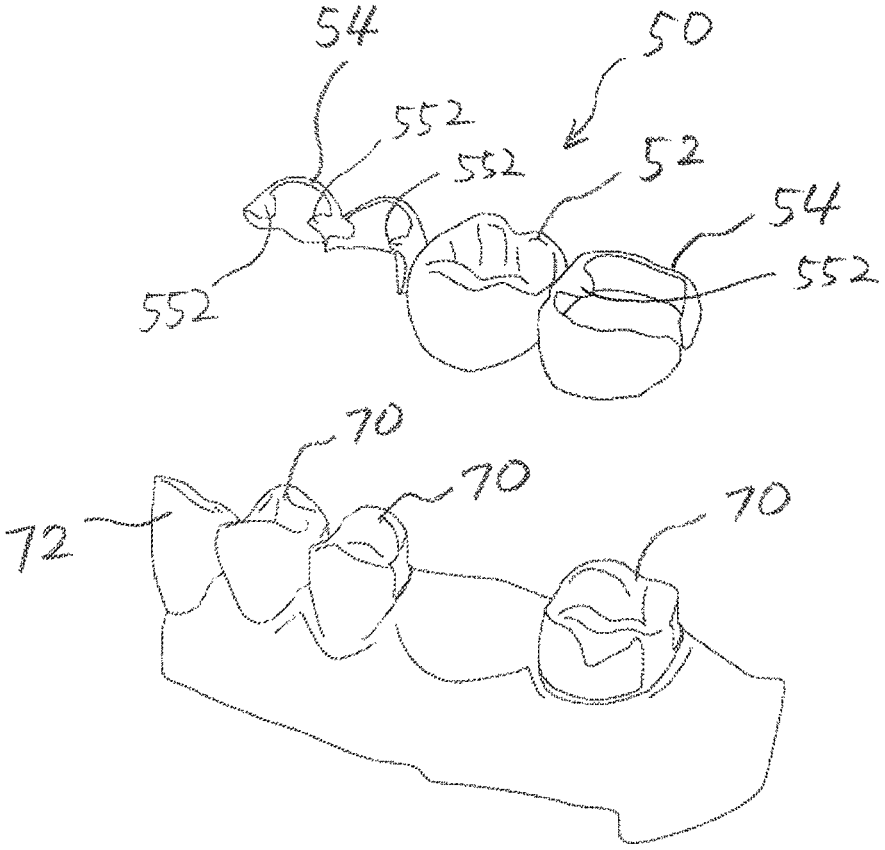
FIG. 72 is a perspective view of the prepared teeth and the prosthesis shown in FIG. 71.
Figure 73:
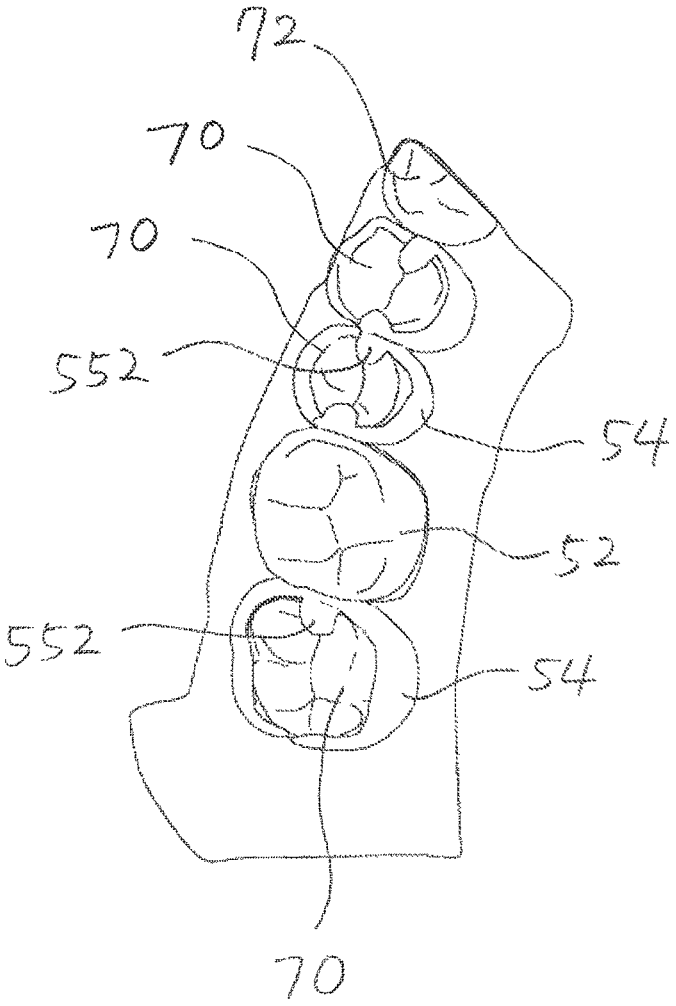
FIG. 73 is a plan view showing a prepared teeth and a prosthesis installed on the prepared teeth.
Figure 74:
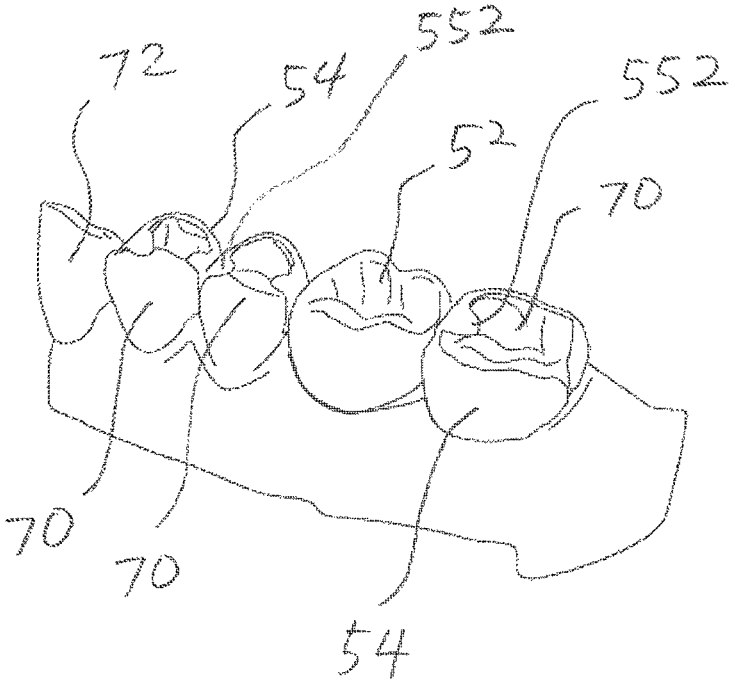
FIG. 74 is a perspective view of the prepared teeth and the prosthesis shown in FIG. 73.

In one embodiment of the present invention, the fixing portion 54 of the prosthesis 50 does not need to have a ring shape. As shown in FIGS. 71 and 72, the fixing portion 54 of the prosthesis to be engaged on a molar is open on one side. In the embodiment shown, the fixing portion 54 to be engaged on a molar includes a lingual portion 542 to engage the lingual surface and a buccal portion 544 to engage the buccal surface, wherein the two portions face each other. The lingual portion 542 and buccal portion 544 include interior surfaces that face each other. As the fixing portion 54 engages a molar, the molar fits within these two interior surfaces facing each other, creating retention force to fix the prosthesis. Moreover, the proximal portions 546, 548 engaged on the two proximal surfaces of a molar also face each other to keep the prosthesis in position.

On the other hand, as shown in FIGS. 71 and 72, the fixing portion [55] of a second premolar does not include a portion to be engaged on the buccal surface. Nonetheless, side portions 556, 558 are positioned to face each other in such case as well, and the interior surfaces of these side portions 556, 558 face each other. As described above, a second premolar is fit between these two interior surfaces facing each other, creating retention force to fix the prosthesis. The fixing portion [56] for a first premolar has a similar design wherein side portions 566, 568 face each other. The interior surfaces of these side portions 566, 568 face each other as well. As described above, a first premolar is inserted between these two interior surfaces that face each other, creating retention force to fix the prosthesis. In the illustrated embodiment, the retention force of the first premolar and the retention force of the second premolar in combination provide sufficient retention effects.

Preservation of Occlusal Surfaces

Dental procedures that employ a preparation guide device and a prosthesis as shown in FIGS. 66-74 can preserve the occlusal surfaces without cutting thereof. In one embodiment shown, the amount cut can be precisely controlled using a preparation guide device. By employing a preparation guide device as shown in one embodiment, sufficient retention force between the prosthesis and teeth can be maintained while cutting only a minimum amount of side surfaces. This allows the teeth to substantially maintain their original shape and strength.

On the other hand, traditional methods of cutting that cut large amounts result in smaller remains of teeth, requiring thicker crowns in order to increase tensile strength and endure the amount of force exerted from chewing. To accomplish this, cutting of occlusal surfaces is necessary. In addition, if the cut amount is so large as to cut into the dentin layer, cavities may spread along the boundary between the prosthesis and teeth even if covered with prosthesis. To minimize such risk, traditional dental procedures require cutting of occlusal surfaces and covering the whole occlusal surface with a crown.

However, if minimally invasive preparation (or cutting) is performed as shown in the embodiment, cutting of occlusal surfaces is not always necessary. In addition, because cutting is performed only within the enamel layer if possible, there is less risk of cavities spreading to the dentin through the boundary surface between the teeth and the prosthesis. Thus, occlusal surfaces are not cut in the illustrated embodiment. Moreover, the prosthesis does not need to cover the entire occlusal surface. However, other embodiments can include cutting portions of the occlusal surfaces to engage the prosthesis.

As shown in FIGS. 71-74, the prosthesis 50 includes an extended protruding portion (inlay portion) 552 that extends and protrudes from a proximal portion at the top of the fixing portion 54. Such extended protruding portion 552 fits tightly within a nonfunctional groove between the cusps of the occlusal surface of an abutment tooth 70 to increase retention force of the prosthesis. In such case, the nonfunctional groove can either be preexisting and natural or can be artificially farmed by using, for example, a preparation guide device. When a groove is artificially formed, it is called an inlay bridge.

Preservation of Contact Points

Prior to cutting, all abutment tooth 70 and a proximal tooth 72 come into contact at a contact point. In one embodiment of the invention, the abutment tooth is cut without damaging this contact point such that functions of the abutment tooth prior to cutting are not lost. In embodiments, the whole contact surface between an abutment tooth 70 and proximal tooth 72 or at least the contact point within the contact surface is not cut during the cutting process. As shown in FIGS. 71-74, although the fixing portion 54 of the prosthesis on a first premolar is in contact with a portion of the mesial surface from the lingual surface of the first premolar, the prosthesis does not cover the whole mesial surface, thus retaining the contact point between the first premolar and a canine.

In addition, in one embodiment as shown in FIGS. 71-74, the fixing portion 54 of the prosthesis 50 on a second molar includes a first wing that extends from an artificial tooth 52 and covers the second molar's mesial and buccal surfaces. The terminal end thereof extends to the distal surface or the transitional region between the buccal surface and distal surface. A second wing on the other side extends from the artificial tooth 52 and covers the second molar's mesial and lingual surfaces. The terminal end thereof extends to the distal surface or the transitional region between the lingual and distal surfaces. Thus, the fixing portion 54 may preserve the contact point between a second molar and a wisdom tooth (not shown). In the method, of cutting and configuration of prosthesis according to one embodiment of the present invention, such preservation of contact points is possible because sufficient retention force may be provided without covering the entirety of side surfaces.

Materials for and Manufacturing of Preparation Guide Devices

In one embodiment of the invention, the burr 200 spins at high speeds (for example, 3,000-400,000 rpm) while cutting teeth. Because the preparation guide device 100 is in contact with the neck 203 of the burr 200 rotating at high speeds, it should be made of a material that is not easily damaged by physical contact and is not easily transformed by frictional heat. The material must also be biocompatible. For example, plastic resin, ceramic, or metallic materials may be used. More specifically, materials such as gold, gold alloys, titanium, titanium alloys, glass, and high molecular compounds may be used. If the material of the preparation guide device is transparent or translucent, the installation status or cutting procedure may easily be observed.

A preparation guide device 100 can be manufactured by using precise manufacturing processes via a CNC Machining Center or by using additive manufacturing processes via three dimensional printing or stereolithography. Methods of manufacturing a preparation guide device 100 of the invention are not limited to such means. Although the preparation guide device 100 is made of a single material in the embodiment mentioned above, the preparation guide device 100 can be made of two or more materials as well. For example, portions of the preparation guide device 100 surrounding, the tool guide way 120 can be made of the above-described materials, and the rest can be made of other materials.

Embodiment as Shown in FIGS. 3, 4, 6-9, and 24

Referring to FIGS. 3, 4, 6-9, 12, and 24, a preparation guide device 100 according to one embodiment of the invention includes a tool guide way 120 within each of two guide portions 104 to allow for cutting of two teeth. The two guide portions 104 are connected to form a single piece. While the embodiment as shown illustrates a structure wherein the guide portion 104 is engaged directly on an abutment tooth 70, another embodiment may include a structure wherein an additional installation portion 102 engages a proximal tooth 72 adjacent to the abutment tooth.

The tool guide way 120 has a looped curve shape to allow for processing all side surfaces at once. The top wail 116 of the guide portion 104 includes a central section 1162 and a surrounding section 1164 divided by the tool guide way 120. The central section 1162 and surrounding section 1164 are connected by an appropriate number of rod-shaped connectors 1166 to prevent the central section 1162 from becoming separated. In the embodiment shown, the sidewall 110 extends below the survey line.

In one embodiment shown, a non-cutting access way 1202 of the looped tool guide way 120 extends beyond the sidewall 110. The end of this non-cutting access way 1202 becomes a tool entrance 125, which is located beyond the sidewall 110. A burr 200 enters through the entrance 125 and passes the non-cutting access way 1202 to reach the tool guide way 120. A burr 200 moves along the tool guide way 120 to cut side surfaces of teeth. A burr 200 may also cut the connector 1166 while cutting side surfaces to move further along the tool guide way 120. FIG. 24 shows an embodiment of cutting side surfaces using a preparation guide device 100. As shown in FIGS. 14, 19, 20, and 44, a tool entrance 125 may be located on the sidewall 110 itself without a non-cutting access way 1202.

Figure 5:
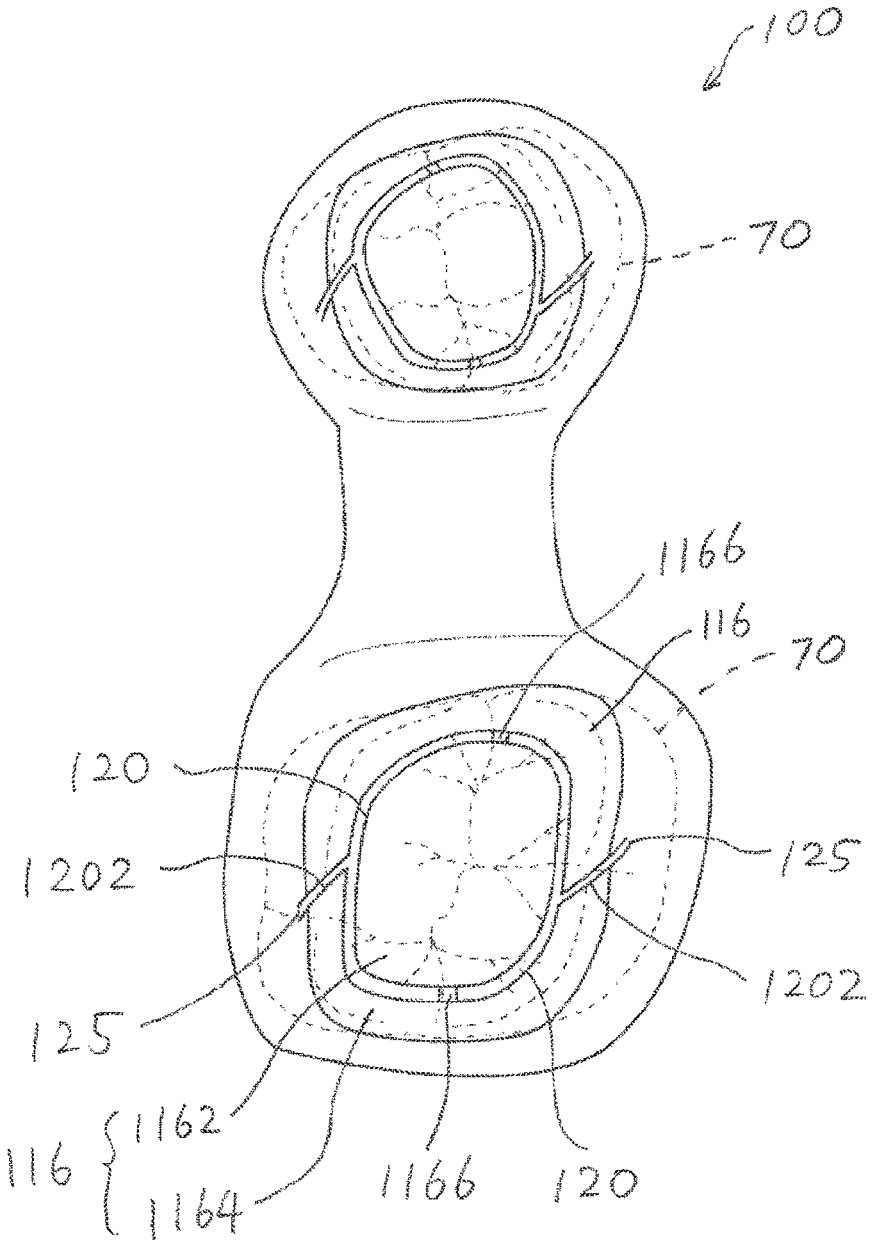
FIG. 5 is a plan view of a preparation guide device mounted on posterior teeth.

Embodiment as Shown in FIG. 5

The preparation guide device 100 according to one embodiment, as shown in Fla 5, includes two connectors 1166. A resulting, tool guide way 120 includes two sections divided by the connectors 1166. Each section has its own non-cutting access way 1202 in the tool guide way 120. In addition, each non-cutting access way 1202 has its own tool entrance 125. A preparation guide device 100 of such structure allows for cutting all side surfaces of teeth without having to cut the connector(s) 1166. The size, structure, location, and number of connector(s) 1166 can be varied according to the shapes of teeth and burr.

Connector(s)

The example in FIGS. 3-9 includes a rod-shaped connector 1166. When a connector 1166 extends across the guide slot, it is still possible to cut teeth surfaces below the connector 1166 without damaging the connector 1166 if the diameter of a cutting head 204 of a burr 200 is sufficiently large. In other words, if the diameter of the cutting head 204 of a burr 200 is larger than the width of the connector 1166 when cutting portions beneath the connector 1166, the cutting head 204 of the burr can reach surfaces of a tooth beneath the connector 1166. Thus, the connector 1166 does not obstruct the process of cutting. In such embodiments, the number of tool entrances 125 is equal to the number of sections in the tool guide way 120 formed by connectors 1166 mentioned above.

The width of the connector 1166 can vary according to the material used for the preparation guide device 100. If the material of a preparation guide device 100 is strong, the width of the connector 1166 can be relatively narrow compared to a preparation guide device 100 made from relatively weak material, A connector(s) 1166 is not necessary if the tool guide way 120 does not have a looped curve shape, for example, if it is linear or sectioned.

Figure 10:
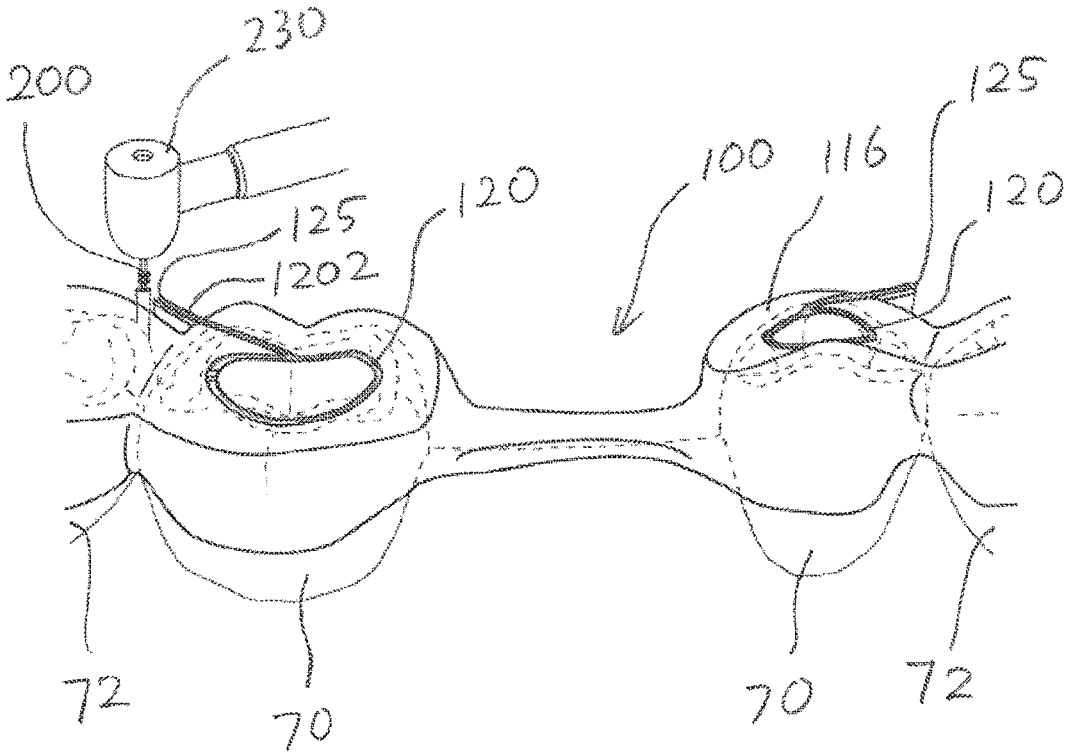
FIG. 10 is a perspective view of a preparation guide device in accordance with one embodiment as mounted on posterior teeth.
Figure 11:
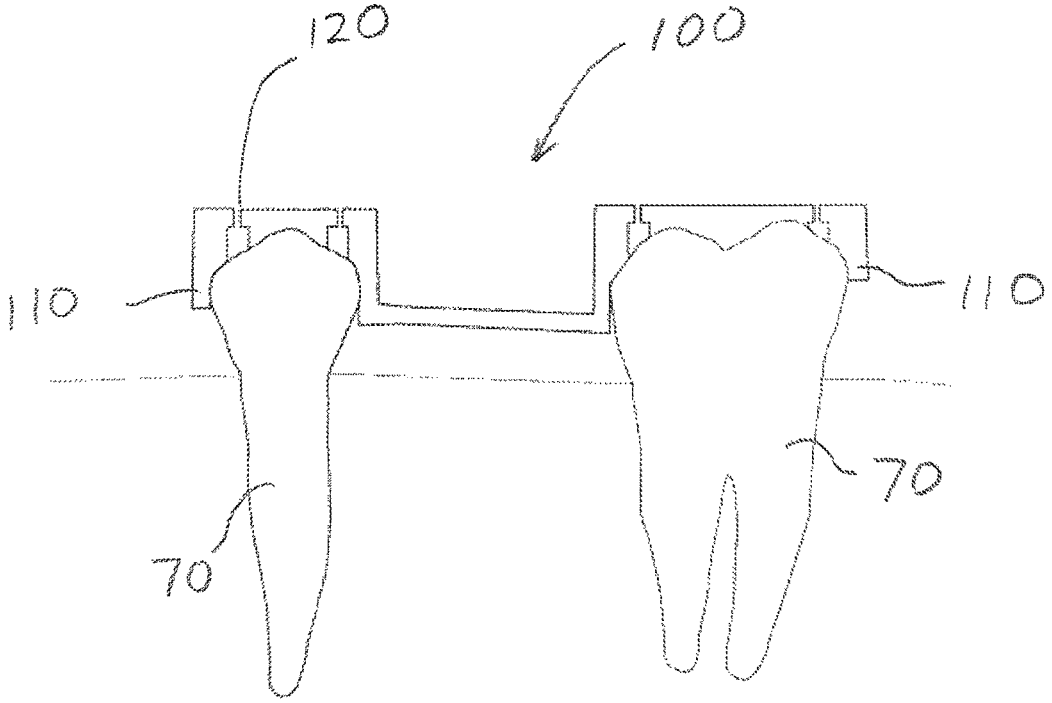
FIG. 11 is a cross-sectional view of a preparation guide device mounted on posterior teeth.

Embodiment as Shown in FIGS. 10 and 11

A preparation guide device 100 as shown in FIGS. 10 and 11 includes a sidewall 110 that either does not extend or extends only slightly below the survey line. In such an embodiment, whether the preparation guide device 100 is properly engaged on an abutment tooth 70 can easily be checked by observing the boundary of the survey line or by using a probe. Therefore, it is not necessary to have a separate blocked-out portion 118 that opens up a portion of the sidewall 110 to check whether the preparation guide device 100 has been properly engaged. In this embodiment, the cutting procedure can also be seen under the preparation guide 100.

Flow of Cooling Water

In one embodiment, cooling water can flow from the hand piece 230 through a guide slot and tool entrance 124 etc. of a tool guide way 120, for example, and through the interior of a guide portion 104 to exit through a blocked-out portion 118 below the survey line (see FIGS. 94B, 95B, 99B, and 100B). In other embodiments, cooling water can flow through an additional hole(s) or some other opening. The size of such opening(s) can be varied according to the amount of cooling water and rigidity of the preparation guide device 100.

Figure 12:
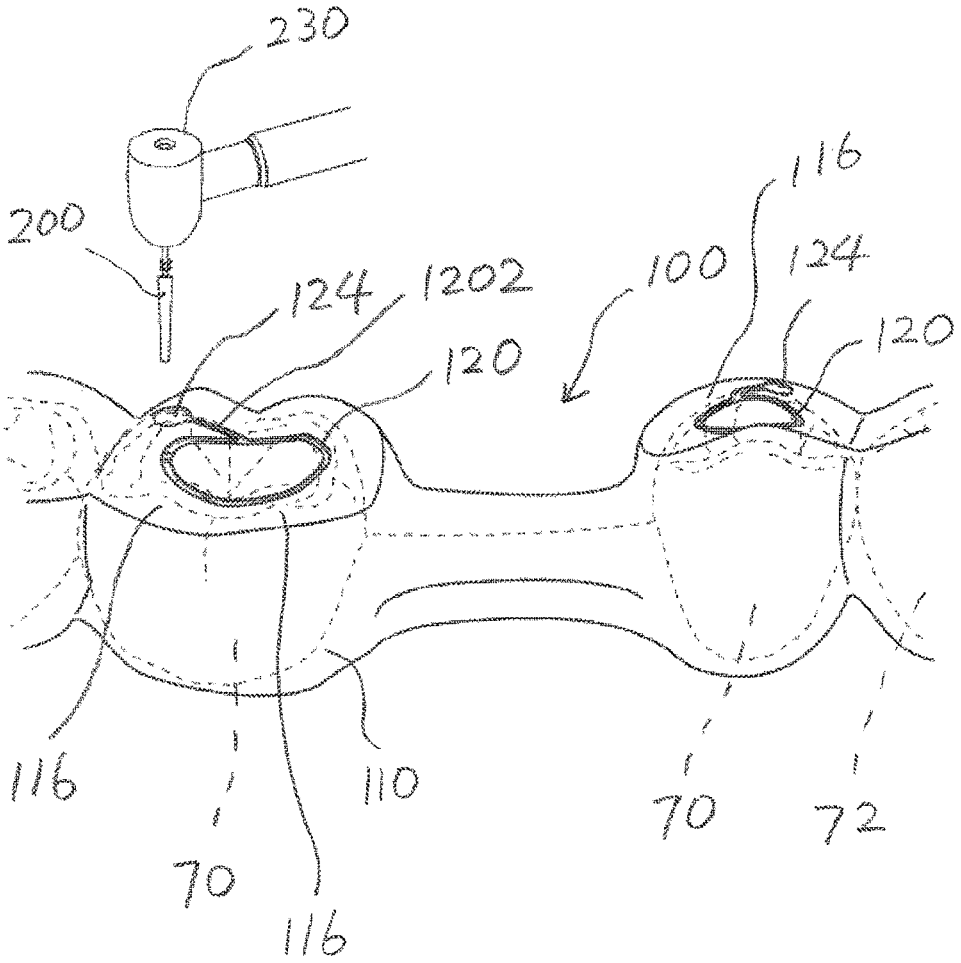
FIG. 12 is a perspective view of a preparation guide device in accordance with one embodiment as mounted on posterior teeth.
Figure 13:
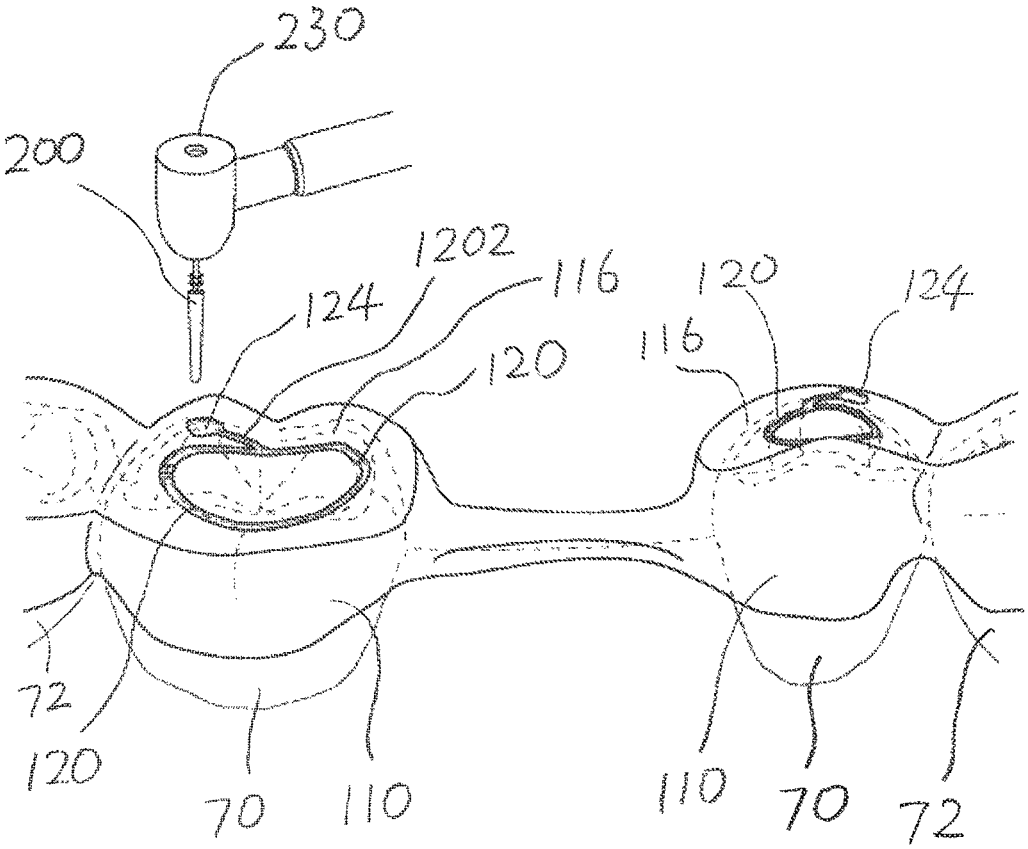
FIG. 13 is a perspective view of a preparation guide device in accordance with one embodiment as mounted on posterior teeth.

Embodiment as Shown in FIGS. 12 and 13

An entrance for a burr 200 is located on the interior of a sidewall 110, that is, as a hole 124 on the top wall 116. Because a notch is not formed on the sidewall 110 according to such configuration, transformation of the preparation guide device 100 is less likely.

Embodiment as Shown in FIGS. 14-17

Figure 14:
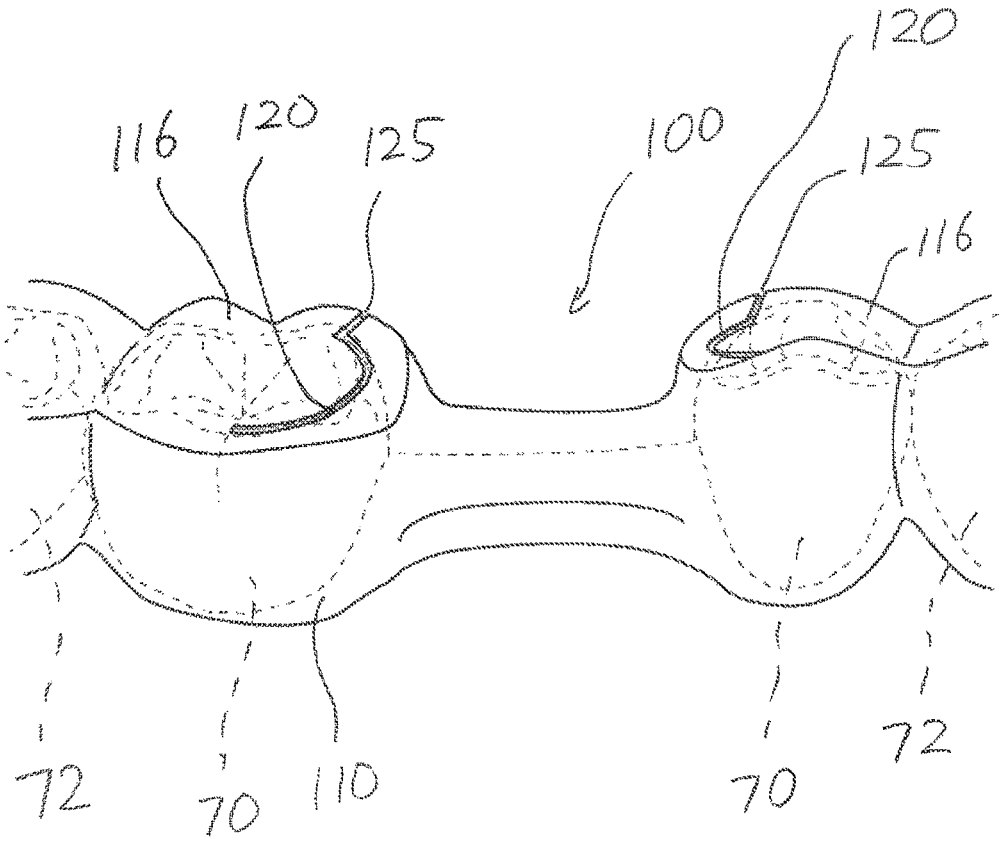
FIG. 14 is a perspective view of a preparation guide device in accordance with one embodiment as mounted on posterior teeth.
Figure 15:
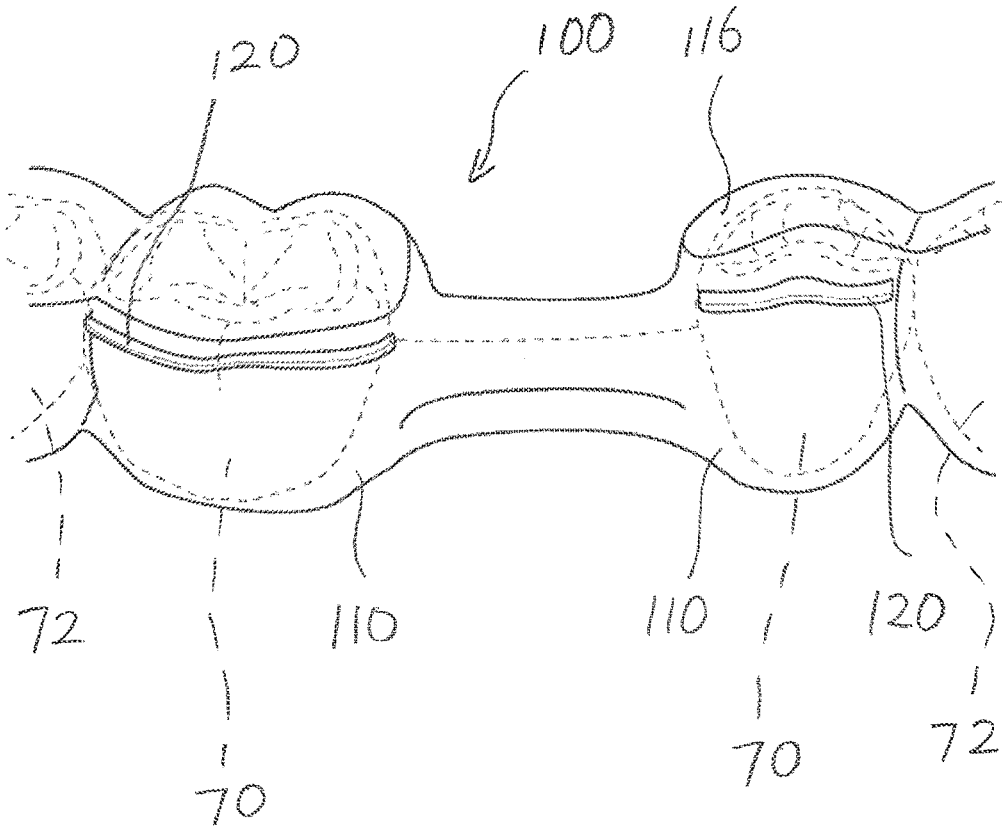
FIG. 15 is a perspective view of a preparation guide device in accordance with one embodiment as mounted on posterior teeth.
Figure 16:
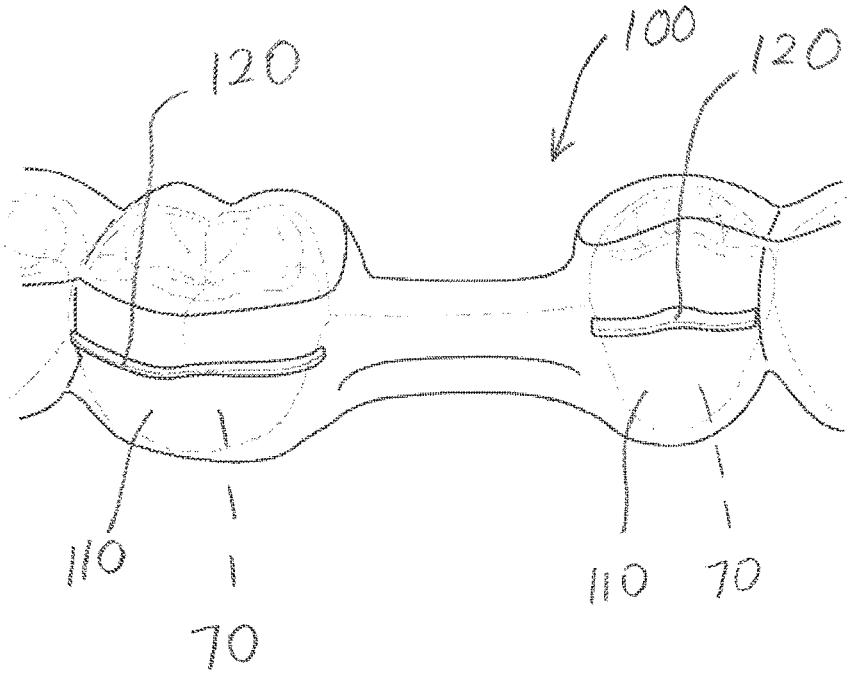
FIG. 16 is a perspective view of a preparation guide device in accordance with one embodiment as mounted on posterior teeth.
Figure 17:
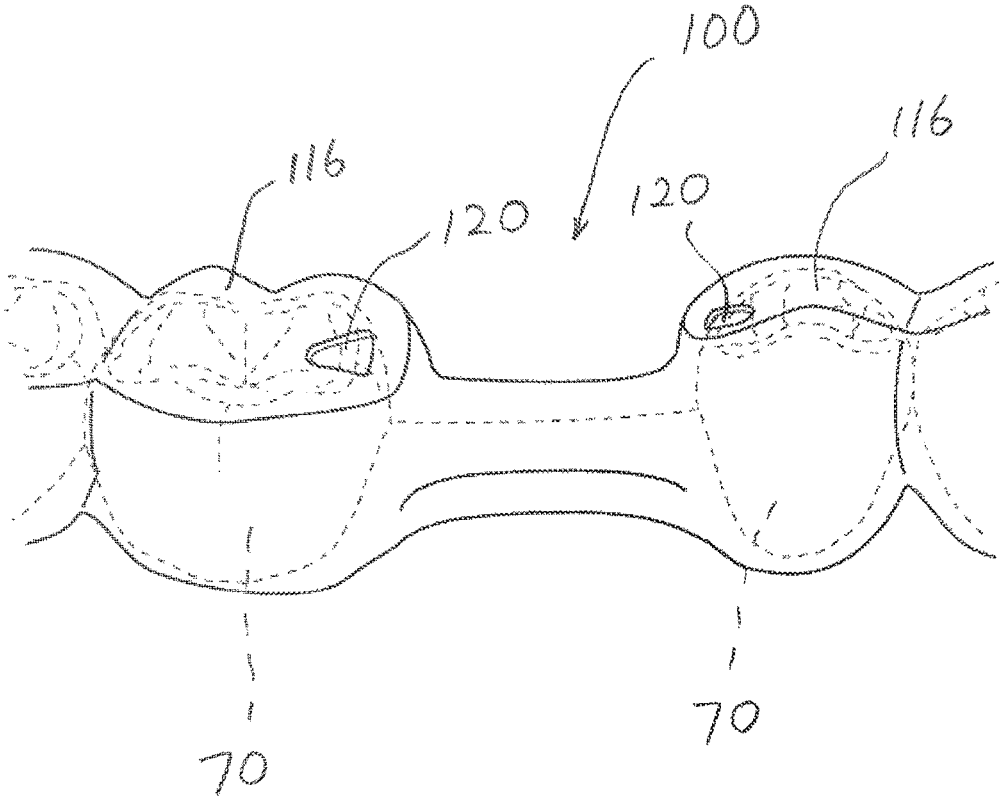
FIG. 17 is a perspective view of a preparation guide device in accordance with one embodiment as mounted on posterior teeth.

A preparation guide device 100 according to one embodiment as shown in FIG. 14 includes a burr 200 entrance located on a sidewall 110 and a tool guide way 120 formed along only a portion of a side surface of a tooth. The preparation guide device 100 of one embodiment as shown in. FIG. 15 includes a tool guide way 120 formed along a sidewall 110 to allow cutting of occlusal surfaces. The preparation guide device 100 of one embodiment as shown in FIG. 16 includes a tool guide way 120 formed on a sidewall 110 to allow installation of strip-shaped grooves on buccal or lingual surfaces. The preparation guide device 100 of one embodiment as shown in FIG. 17 includes a guide hole located on a top wall 116 to form a rest seat on occlusal surfaces.

Figure 18A:
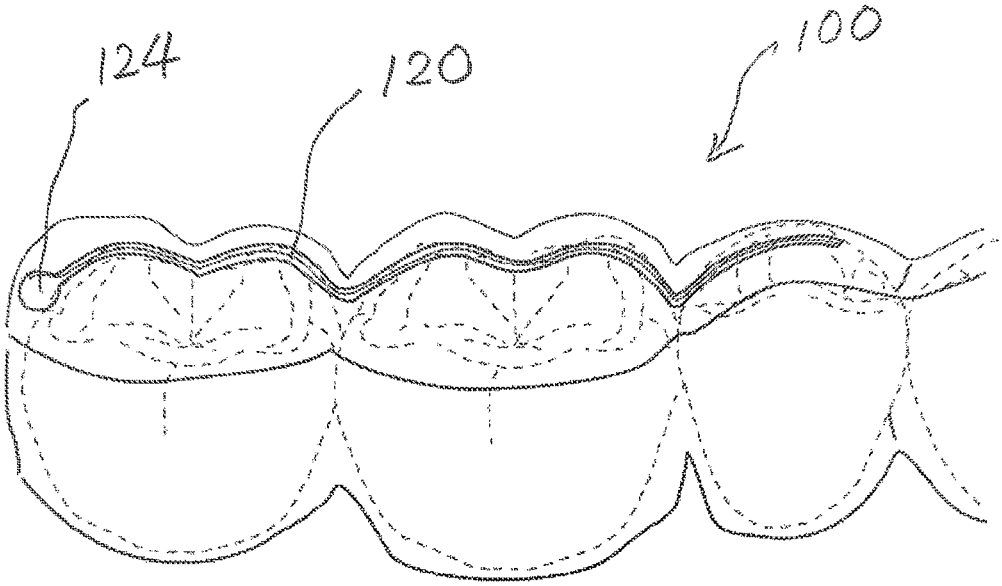
FIG. 18A is a perspective view of a preparation guide device in accordance with one embodiment as mounted on posterior teeth.
Figure 18B:
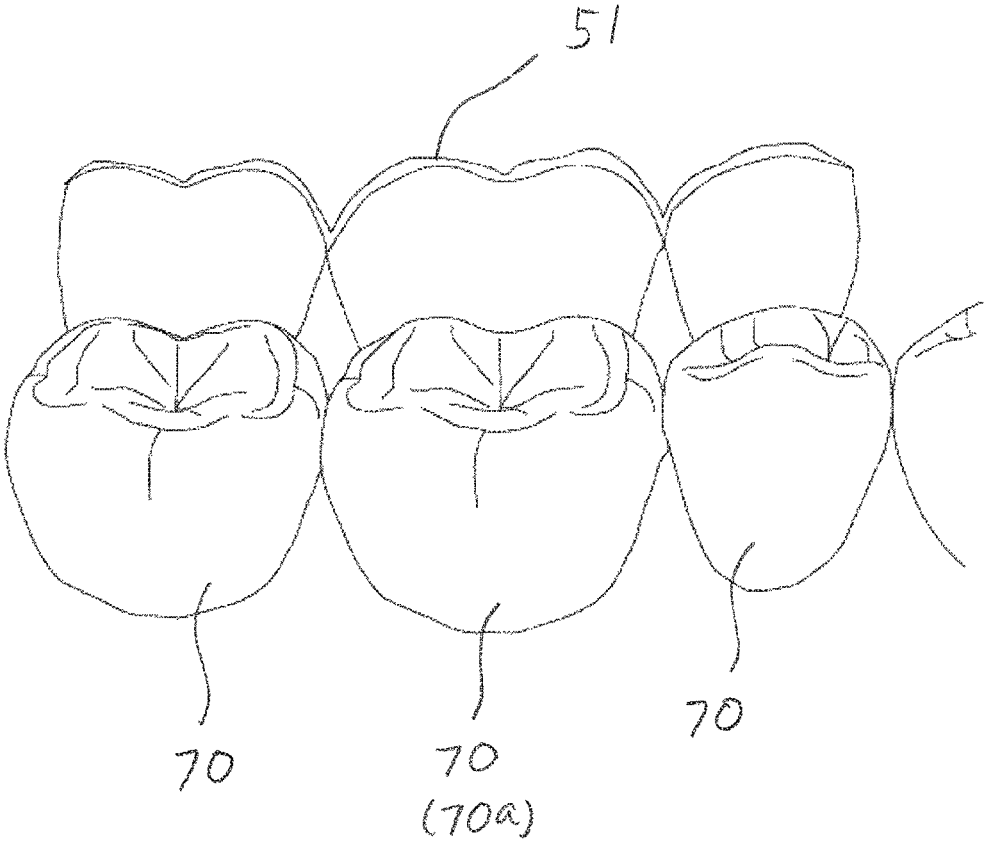
FIG. 18B is a perspective view of prepared posterior teeth and a splint prosthesis to be installed on the posterior teeth.
Figure 18C:
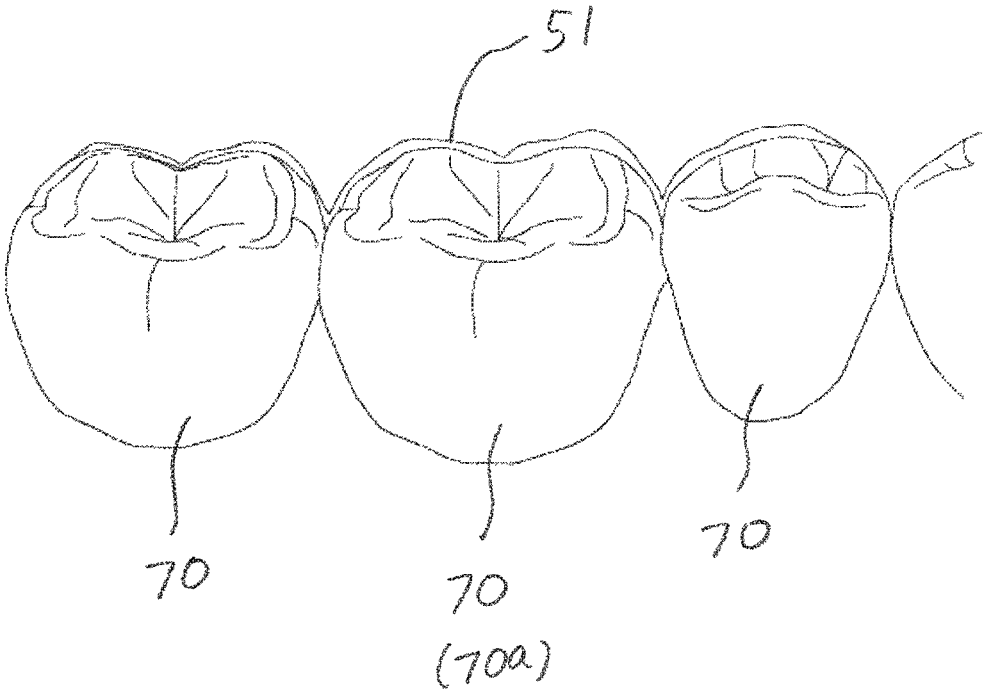
FIG. 18C is a perspective view of the prepared posterior teeth and the splint prosthesis shown in FIG. 18B as installed on the posterior teeth.

Embodiment as Shown in FIG. 18

The preparation guide device 100 of one embodiment as shown in FIG. 18 includes a tool guide way 120 that allows for continuous cutting of lingual or buccal surfaces of multiple teeth at once. By engaging a single-body prosthesis 50 on three teeth after such cutting, an unstable tooth (for example, the middle tooth) can be fixed in place.

Figure 19:
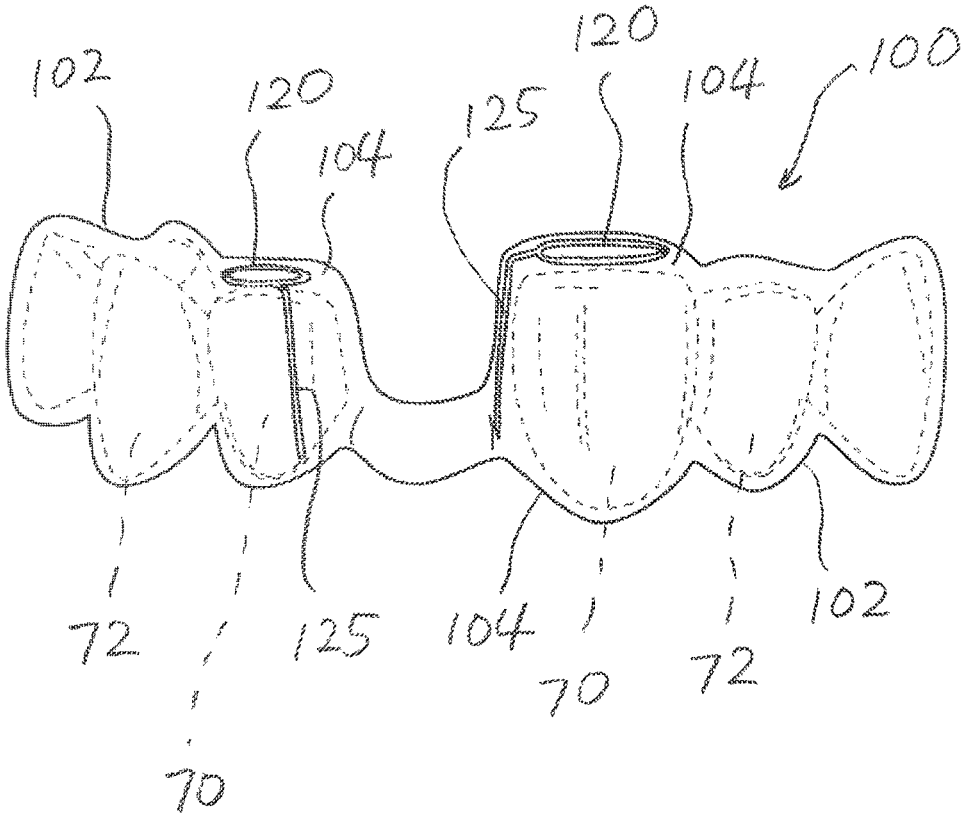
FIG. 19 is a perspective view of a preparation guide device in accordance with one embodiment as mounted on teeth.
Figure 20:
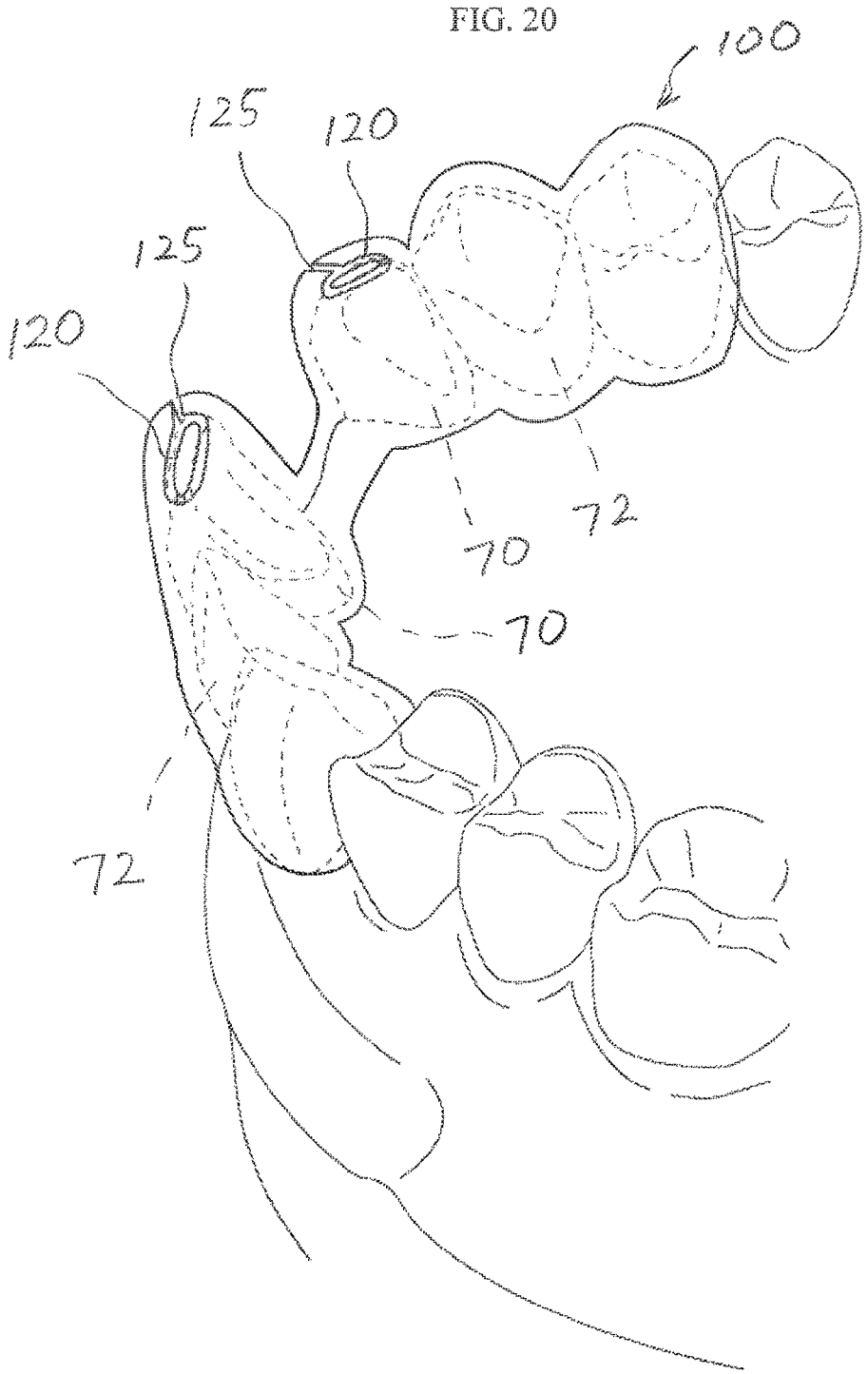
FIG. 20 is a perspective view of a preparation guide device mounted on teeth.
Figure 21:
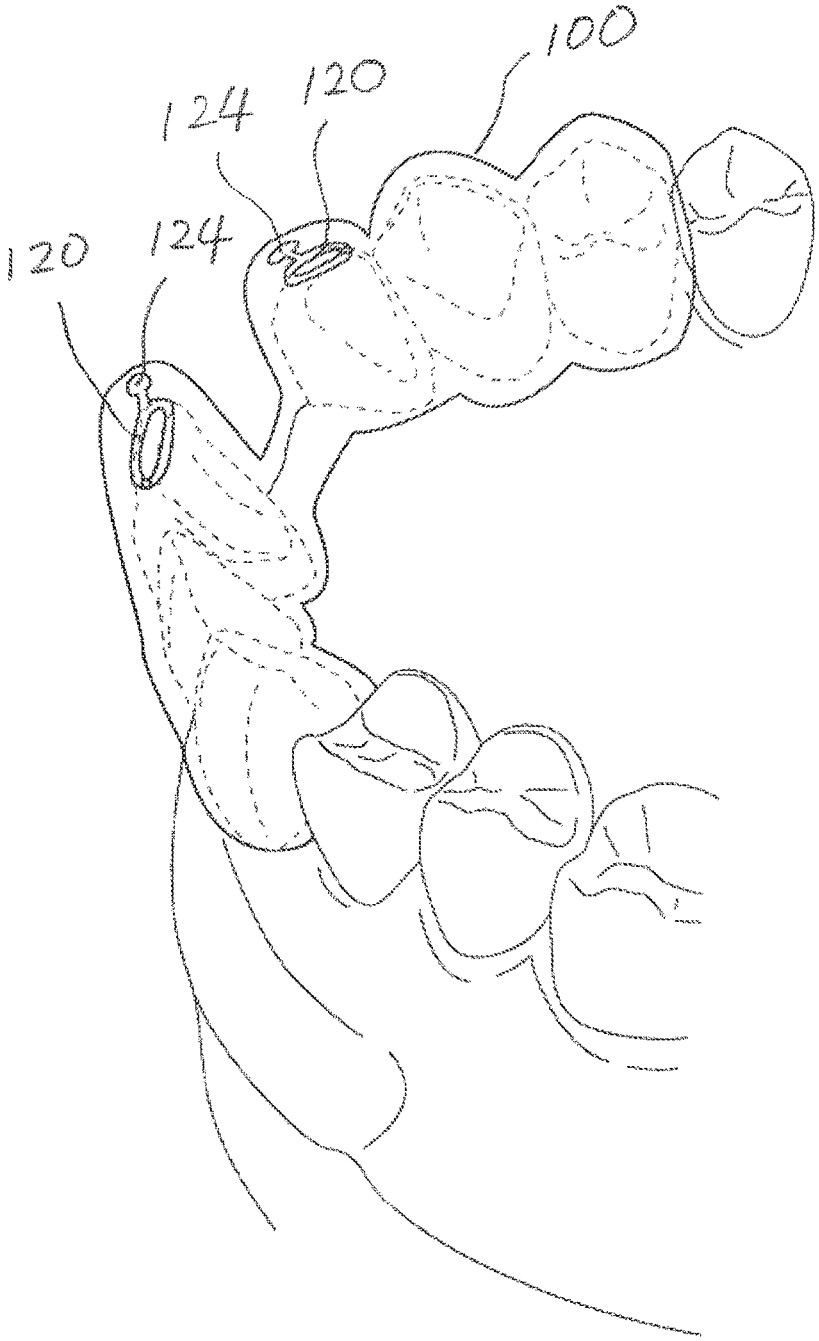
FIG. 21 is a perspective view of a preparation guide device in accordance with one embodiment as mounted on teeth.

Embodiment as Shown in FIGS. 19-21

The preparation guide device 100 according to one embodiment as shown in FIGS. 19-21 includes a tool guide way 120 that allows for cutting of side surfaces of multiple anterior teeth. A preparation guide device 100 as shown in FIG. 19 includes a tool entrance located on a sidewall 110. A preparation guide device 100 as shown in FIG. 21 includes a tool entrance located on a top wall 116.

Figure 22:
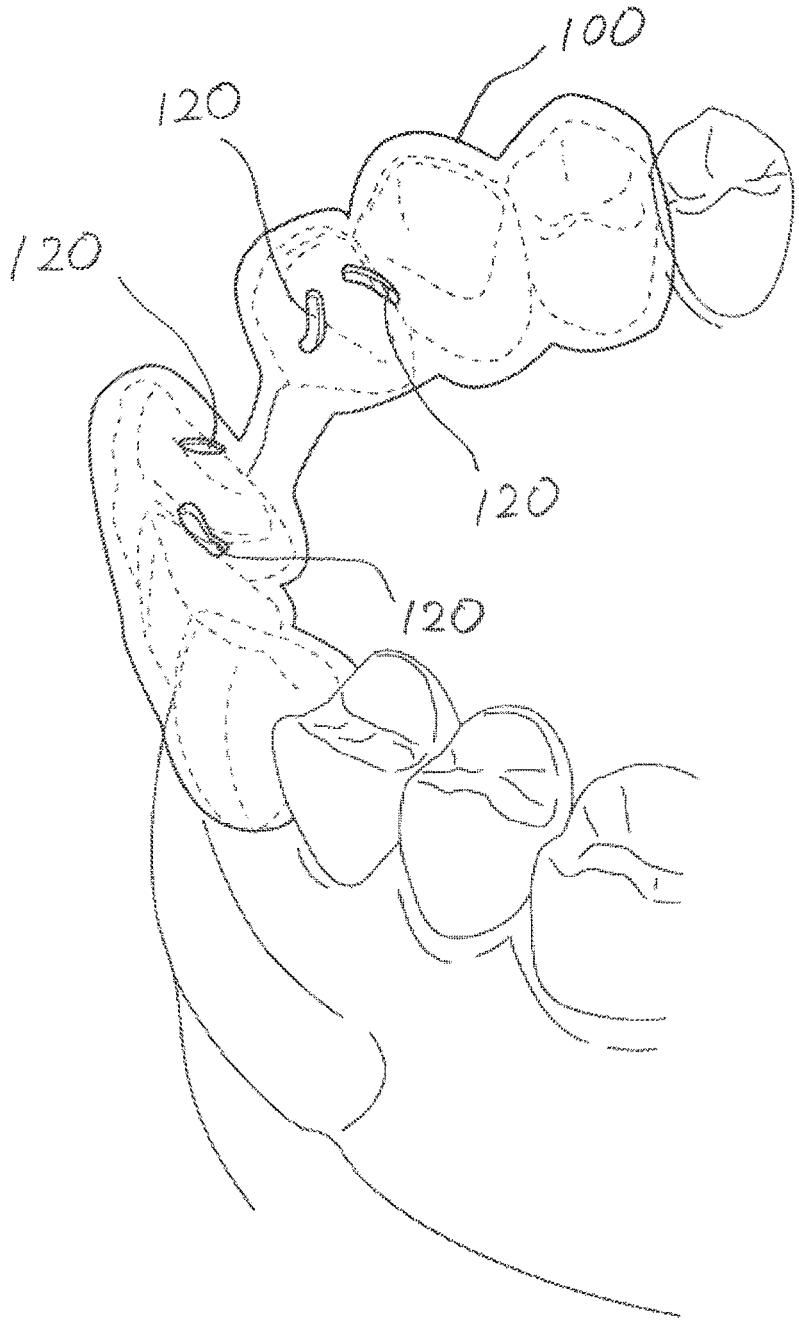
FIG. 22 is a perspective view of preparation guide device in accordance with one embodiment as mounted on teeth.

Embodiment as Shown in FIGS. 22 and 23

The preparation guide device 100 according to one embodiment as shown in FIGS. 22 and 23 includes a tool guide way 120 formed on a sidewall 110 of lingual surfaces to allow cutting of lingual surfaces of multiple anterior teeth. In one embodiment as shown in FIG. 23, the preparation guide device 100 includes two tool guide ways 120 per anterior tooth to form two cavities per anterior tooth. As such, two or more tool guide ways 120 may be engaged on a single tooth as needed. The preparation guide device 100 of one embodiment as shown in FIG. 23 includes one tool guide way 120 per anterior tooth to allow for cutting along the cingulum of each anterior tooth.

Embodiment as Shown in FIG. 24

Figure 25:
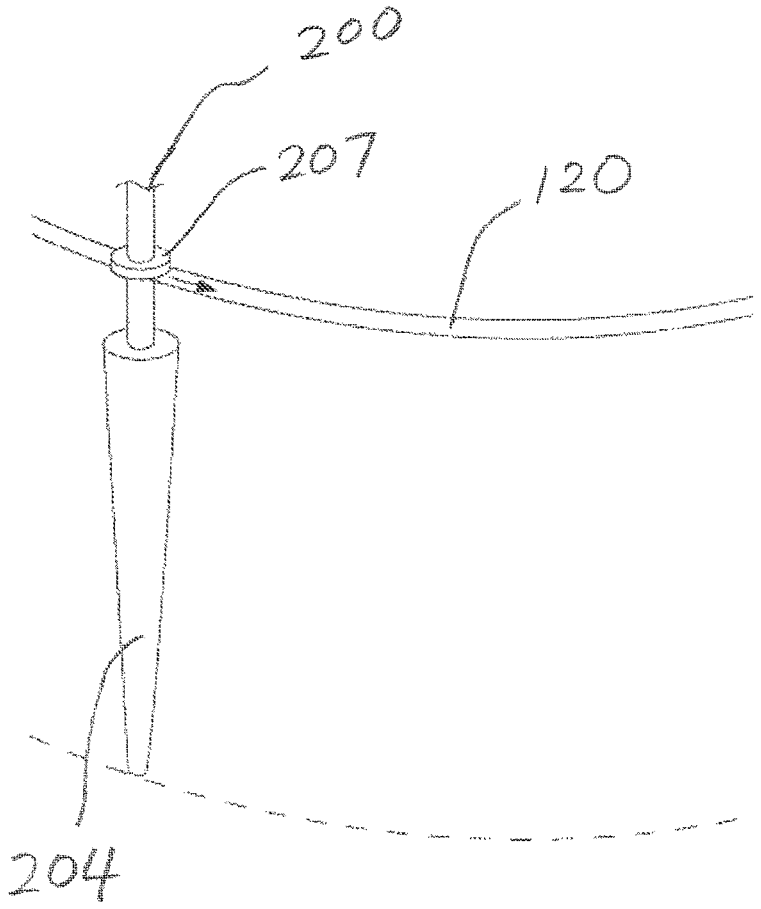
FIG. 25 is a schematic perspective view of a tool guide and a burr in accordance with one embodiment.
Figure 26:
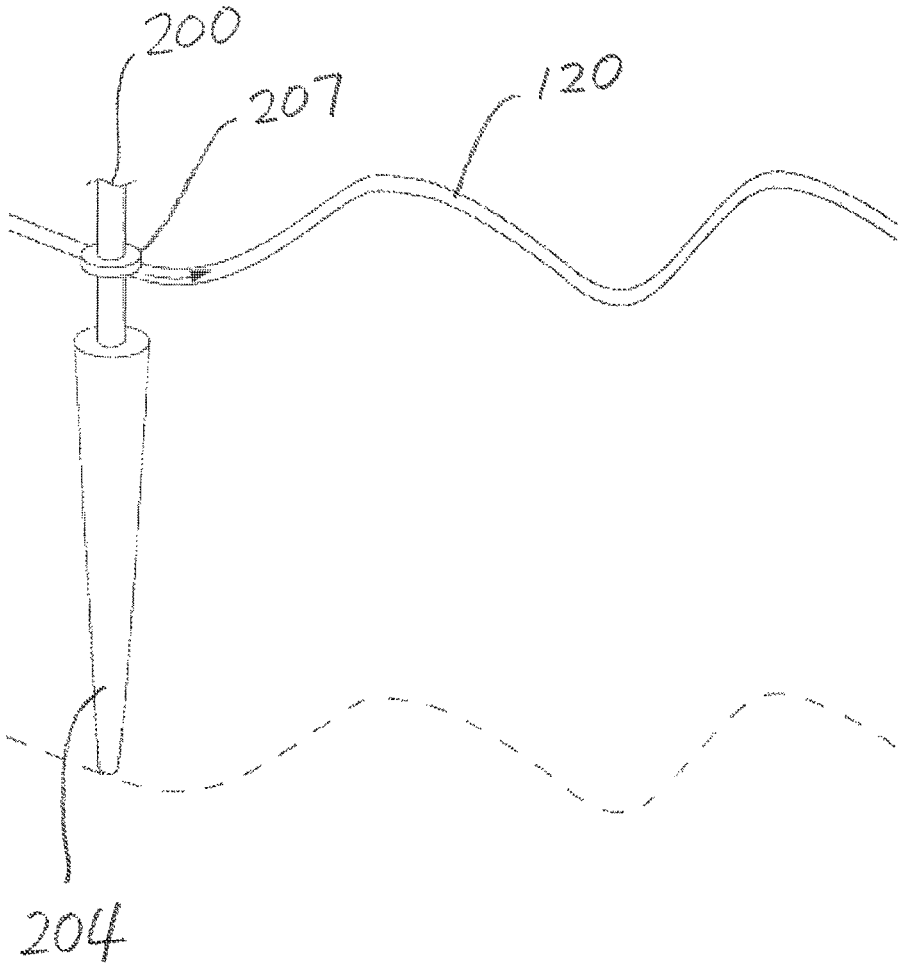
FIG. 26 is a schematic perspective view of a tool guide way and a burr in accordance with one embodiment.

Referring to FIG. 24, the preparation guide device 100 of one embodiment includes a tool guide way 120 with vertical curves. In cases where the bottommost section of teeth to be cut is vertically curved along the gum, a toot guide way 120 can also include vertical curves generally parallel to the curves of the portion to be cut. As shown in FIGS. 25 and 26, a tool guide way 120 is configured to follow in parallel the broken lines showing the path or trajectory of the bottommost point of the burr 200. In another embodiment as shown in FIG. 25, the tool guide way 120 is configured without any vertically undulating curves because there are no vertically undulating curves along the bottommost path of a burr. On the other hand, when vertically undulating curves exist along the bottommost path of the burr, as shown in FIG. 26, a tool guide way 120 is installed with vertically undulating curves substantially parallel to the vertically undulating curves of the bottommost path of the burr. Thus, in the illustrated embodiments, the tool guide way 200 is configured according to the shape of the bottommost path of the burr.

In the embodiments illustrated in FIGS. 24, 25, and 26, a guide projection 207 of the burr 200 moves along above the top support surface 129 of the tool guide way 120. Thus, if vertical curves exist at the bottommost path of the burr, the top support surface 129 also includes vertical curves that are substantially parallel, in embodiments where guide projections 208, 210 move along guide grooves 132, 134, as in embodiments as shown in FIGS. 38 and 39, the guide grooves 132, 134 also include vertical curves that are largely parallel if vertical curves exist at the bottommost path of the burr.

On the other hand, in one embodiment as shown in FIG. 24, the tool guide way 120 is configured such that the bottommost end of the burr 200 follows the gingival line. In other embodiments, the tool guide way 120 can be placed at a vertically higher point or the length of the cutting head 204 can be shorter to allow the bottommost end of the burr 200 to move along a path between the survey line and the gingival line (see FIG. 108). Thus, once a portion to be cut is determined, the path of the end of the cutting head 204 is determined, and the vertical curves of the tool guide way 120 are determined according to the vertical curves of that path.

As shown in FIG. 24, when the burr 200 cuts teeth 70 while moving along the tool guide way 120, the burr 200 moves up and down along the tool guide way's 120 top support surface above a guide projection (or guide grooves, see FIGS. 31, 32, 33, 38, and 39) following the vertical curves and cuts teeth. The cut portion of teeth thus formed includes a curved step 82 in its bottommost portion, and the shape of the prosthesis 50 is configured to accommodate such curved step. In other embodiments, a step in the bottommost portion may not be formed. Especially in cases where the bottommost end of the cutting head 204 is placed between the survey line and the gingival line, a clear boundary may not be visible depending on the angle and depth of the cutting.

Various Embodiments of Burrs and Tool Guide Ways

Tilting may occur as the burr 200 cuts teeth while moving along a tool guide way 120. If excessive tilting occurs, cutting of unexpected areas may result. Also, the amount cut may be ore or less than intended. When such errors in cutting occur, the binding of prosthesis 50 and tooth may not be proper or other complications may develop afterwards. Embodiments of the invention provide configurations to minimize such tilting.

Figure 27A:
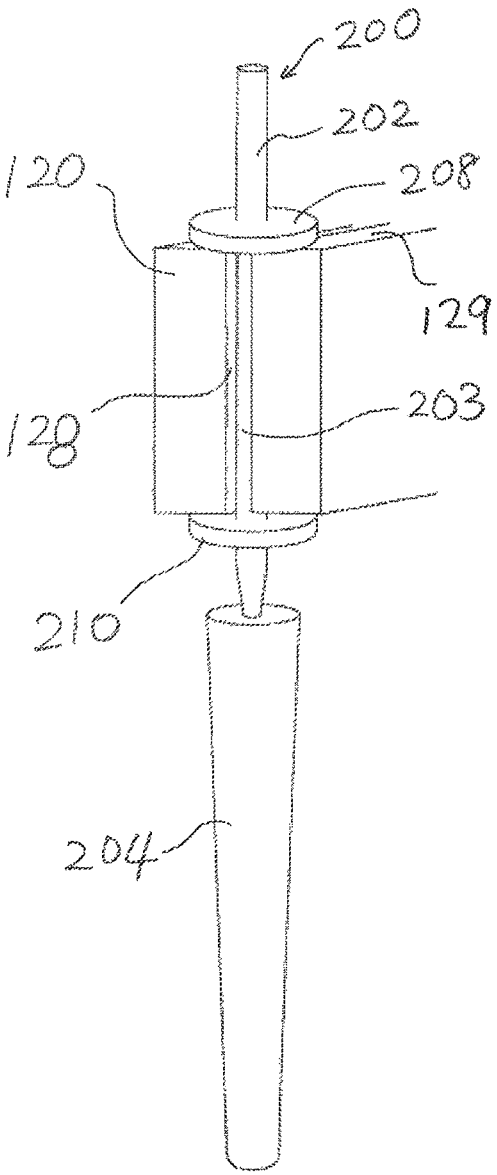
FIGS. 27A and 27B are perspective and cross-sectional views of a tool guide way and a burr in accordance with one embodiment, respectively.
Figure 27B:
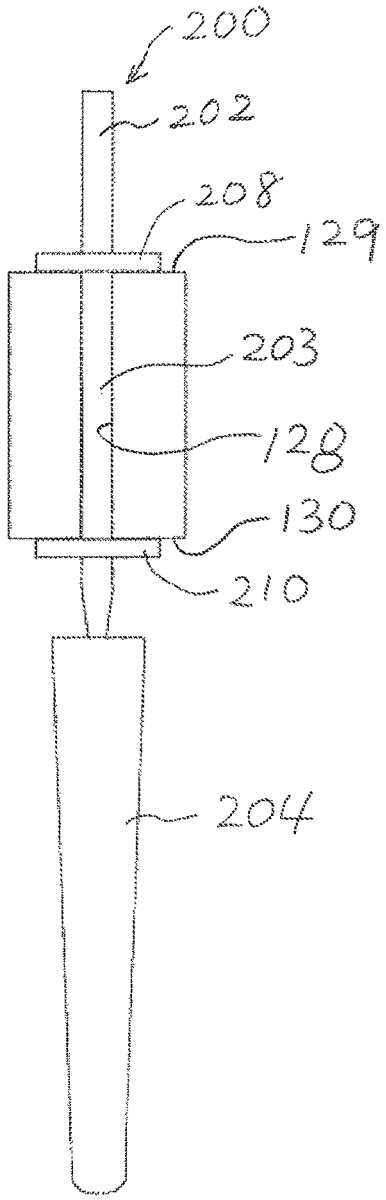
Figure 43:
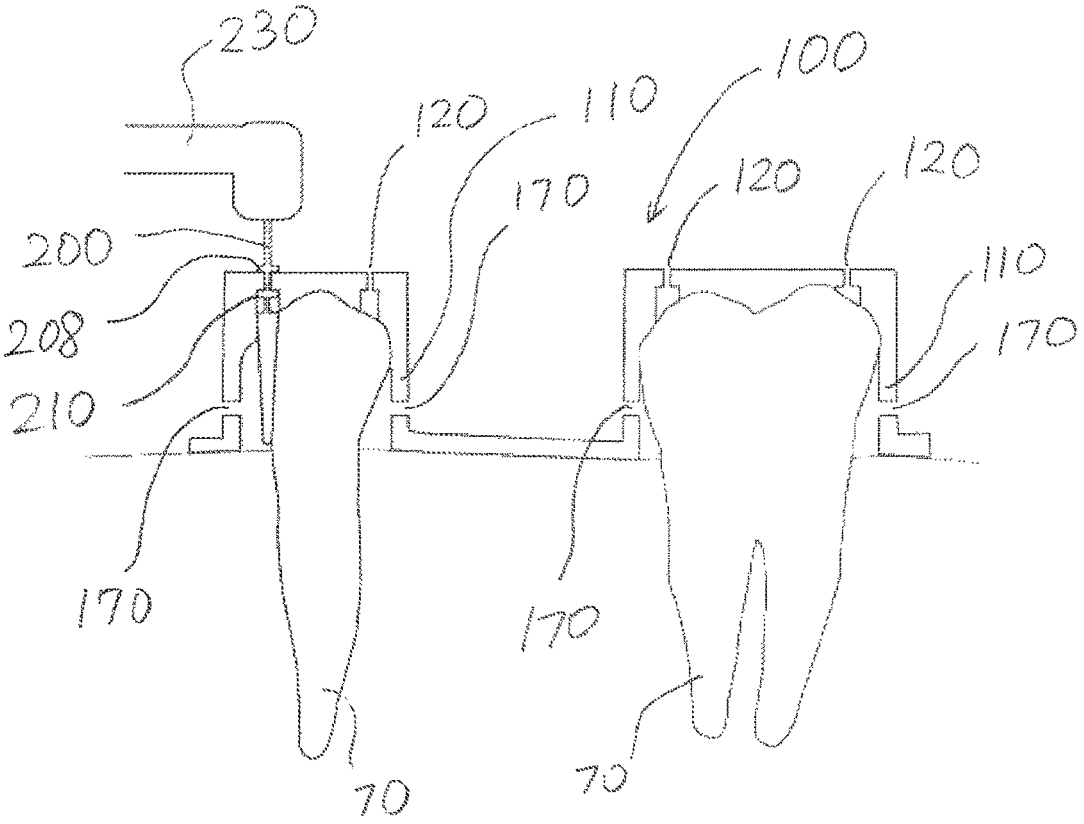
FIG. 43 is a cross-sectional view of a cutting tool and a preparation guide device in accordance with one embodiment as mounted on teeth.
Figure 44:
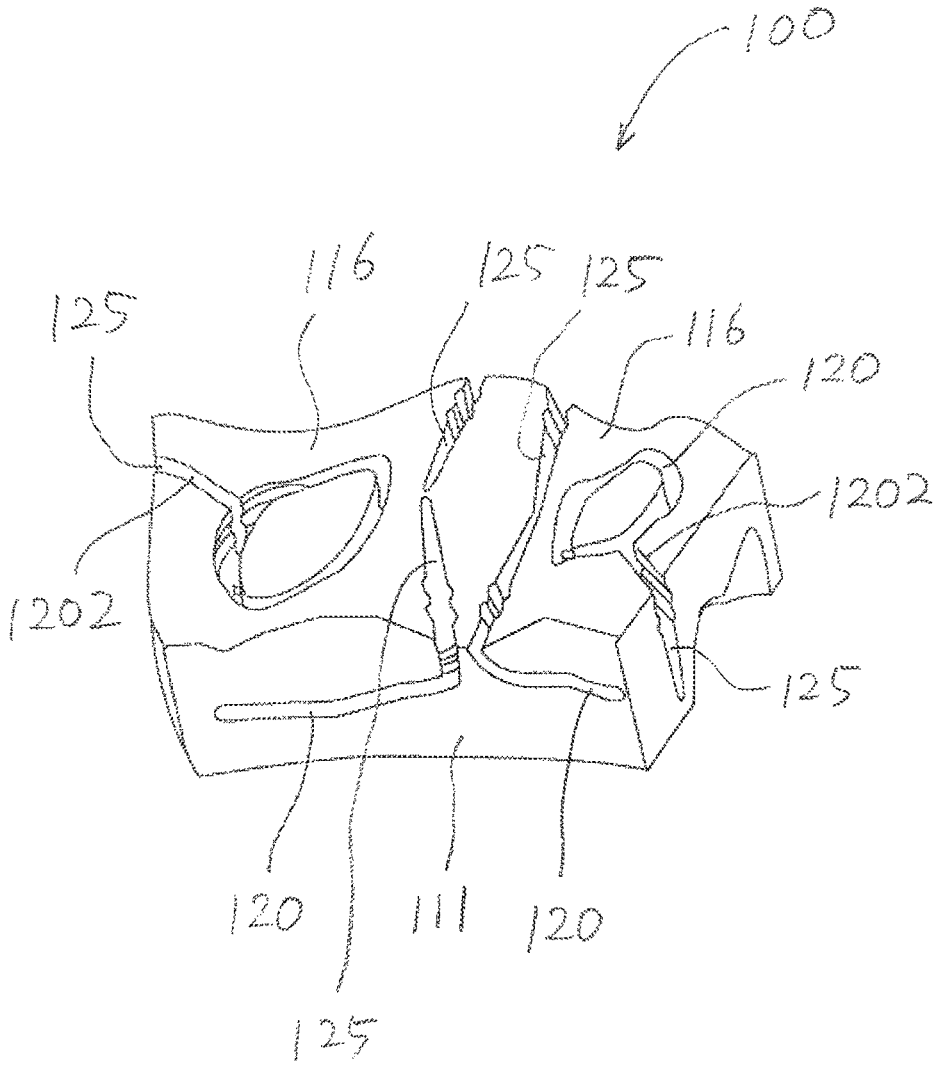
FIG. 44 is a perspective view of a preparation guide device in accordance with one embodiment.
Figure 45:
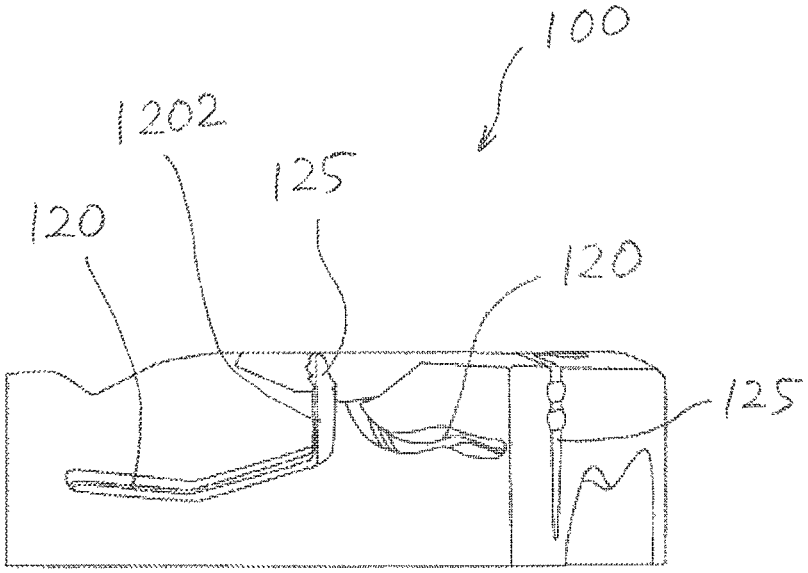
FIG. 45 is a side view of the preparation guide device shown in FIG. 44.
Figure 46:
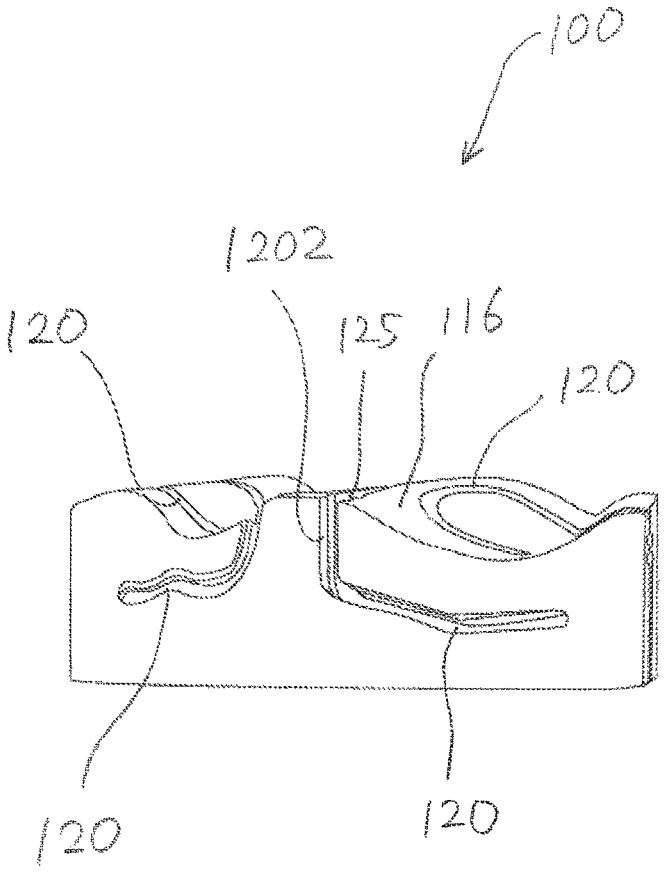
FIG. 46 is another side view of the preparation guide device shown in FIG. 44.
Figure 47:
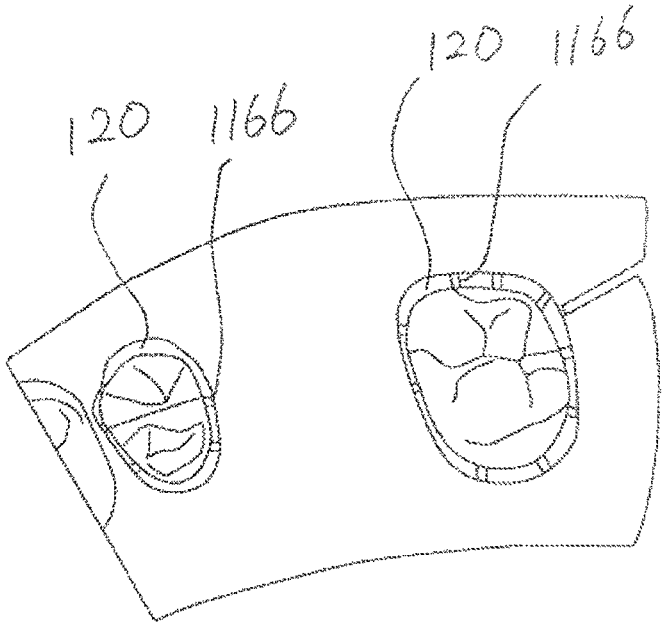
FIG. 47 is a bottom view of the preparation guide device shown in FIG. 44.

In one embodiment as shown in FIGS. 27A and 27B, the burr 200 includes two disc-shaped guide projections 208, 210, wherein one is positioned above the other. The top guide projection 208 of the burr 200 is supported by and moves along the top support surface 129 of the tool guide way 120. while the bottom guide projection 210 is supported by and moves along the bottom support surface 130, allowing the burr 200 to move. FIGS. 9 and 43 show a cutting procedure using such a burr 200.

Figure 28A:
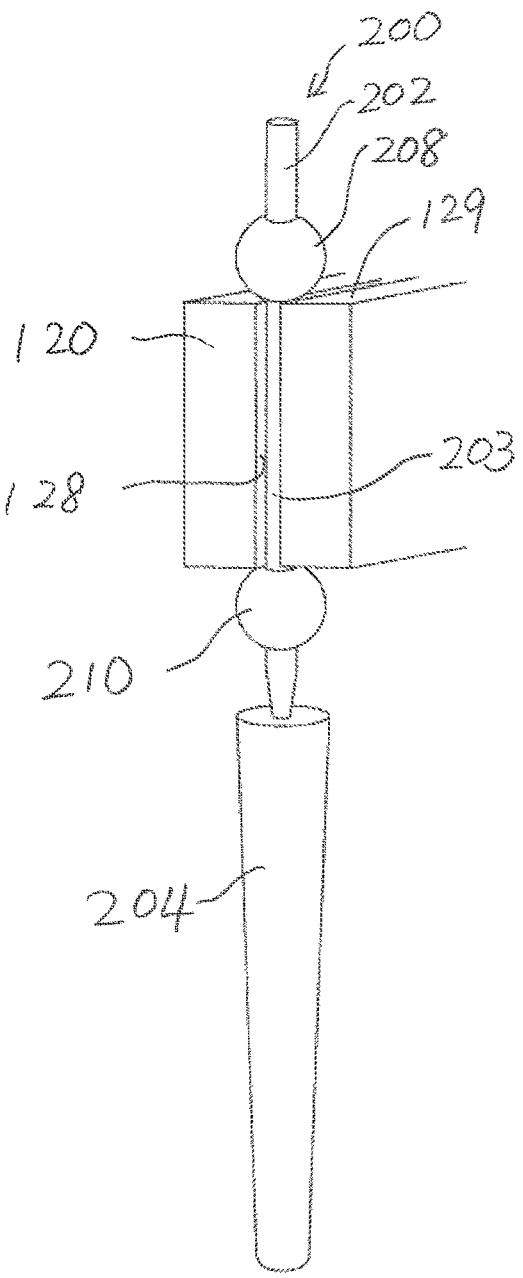
FIGS. 28A and 28B are perspective and cross-sectional views of a tool guide way and a burr in accordance with one embodiment, respectively.
Figure 28B:
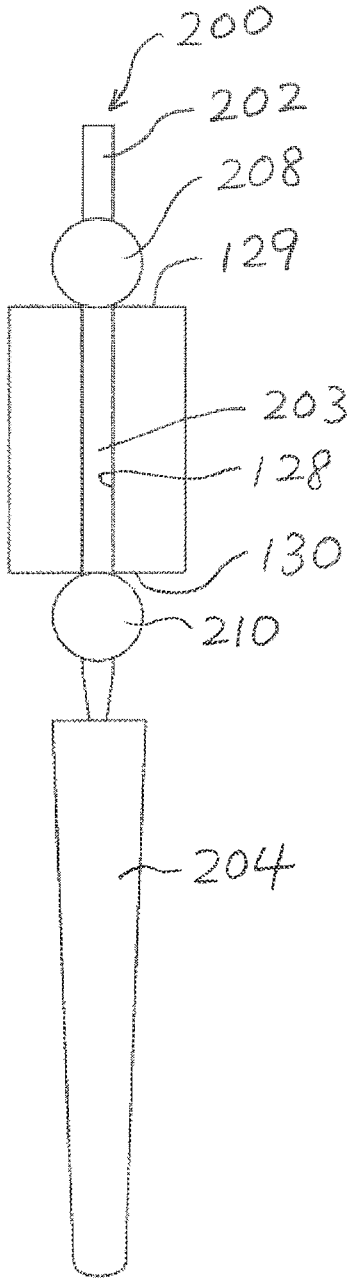
Figure 40:
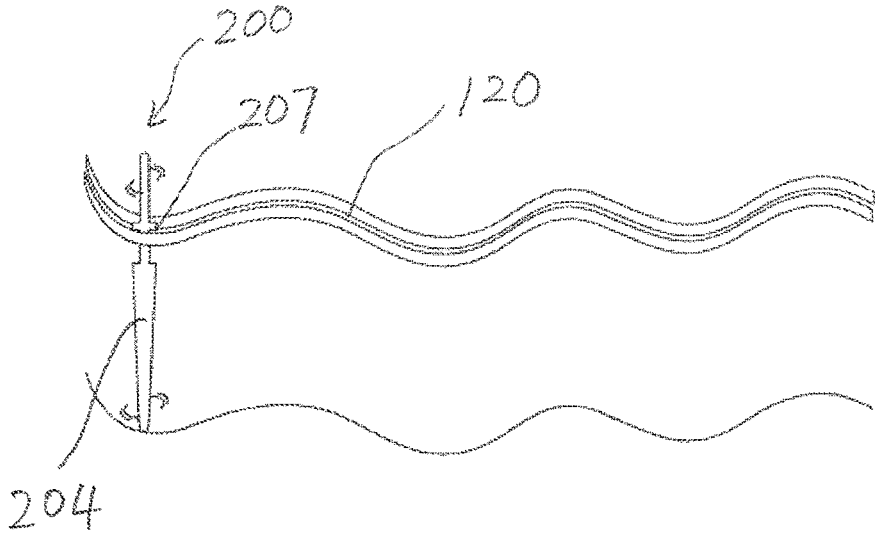
FIG. 40 is a schematic perspective view of a tool guide way and a burr in accordance with one embodiment.
Figure 41:
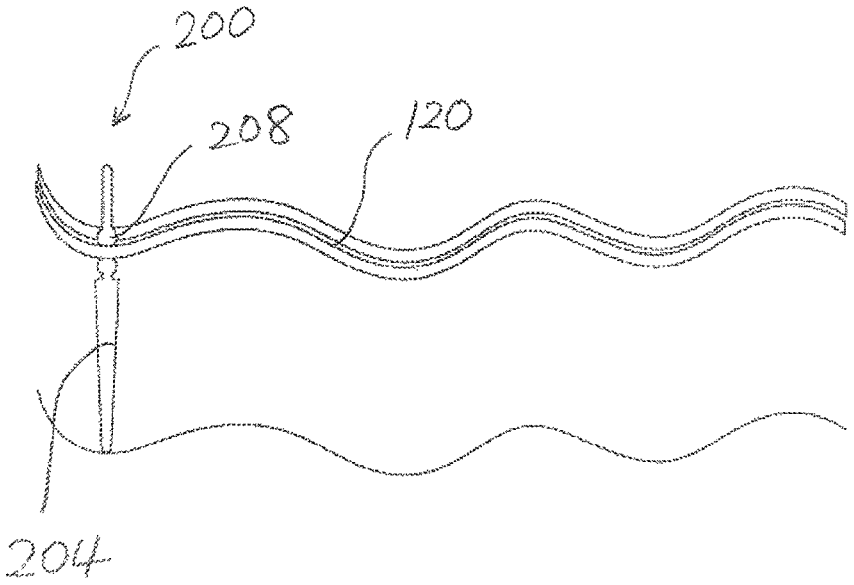
FIG. 41 is a schematic perspective view of a tool guide way and a burr in accordance with one embodiment.
Figure 42:
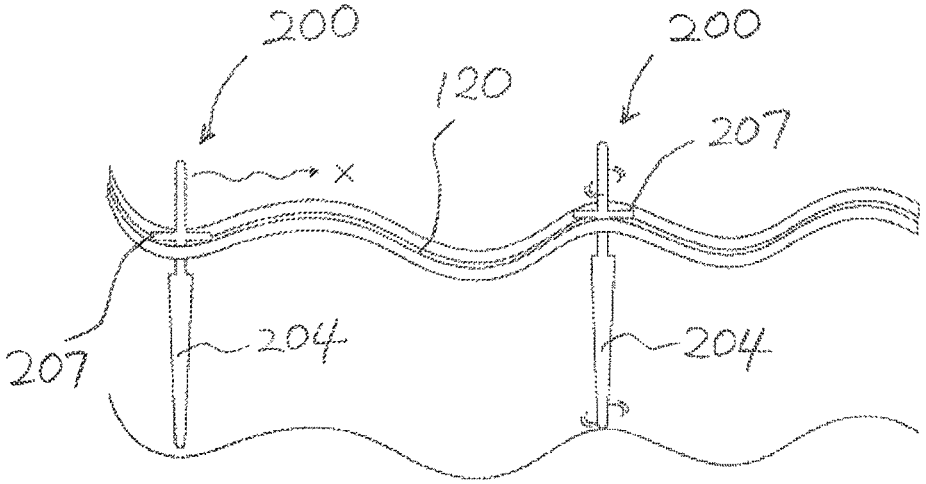
FIG. 42 is a schematic perspective view of a tool guide way and a burr in accordance with one embodiment.

In one embodiment as shown in FIGS. 28A and 28B, the burr 200 includes two sphere-shaped guide projections 208, 240, wherein one is positioned above the other. As illustrated in FIG. 41, sphere-shaped guide projections are preferred for moving along a tool guide way 120 with vertical curves. Because the contact area is small as the burr 200 spins and moves to cut teeth, tilting of the burr 200 as well as friction is reduced. As shown in FIG. 40, burrs 200 with disc-shaped guide projections 207 of relatively small diameters can move along smoothly even in the presence of slight vertical curves. However, as shown in FIG. 42, burrs 200 with disc-shaped guide projections 207 of larger diameters may not be able to properly follow a tool guide way 120 with vertical curves. Although such guide projections 207 with large diameters may be advantageous to prevent tilting while moving, movement along vertically curved portions may be restricted due to stronger friction with support surfaces of the tool guide way 120.

Figure 3:
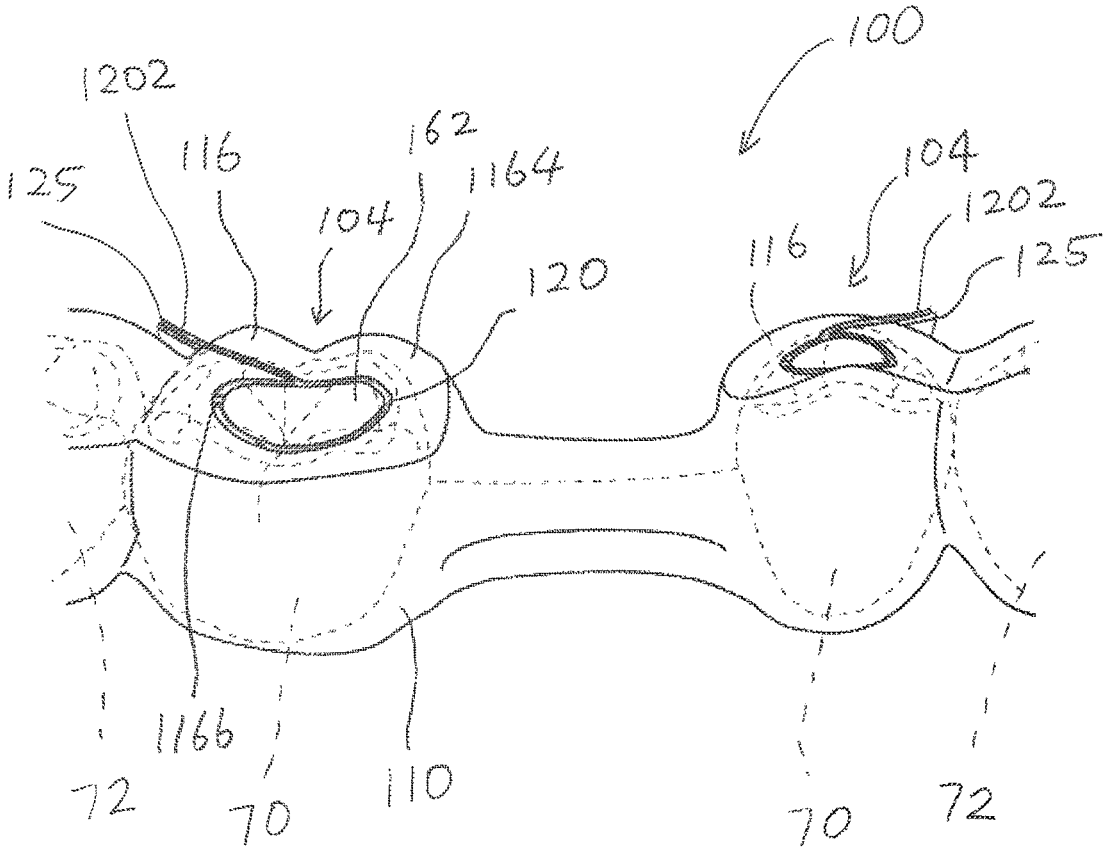
FIG. 3 is a perspective view of a preparation guide device in accordance with one embodiment as mounted on posterior teeth.
Figure 4:
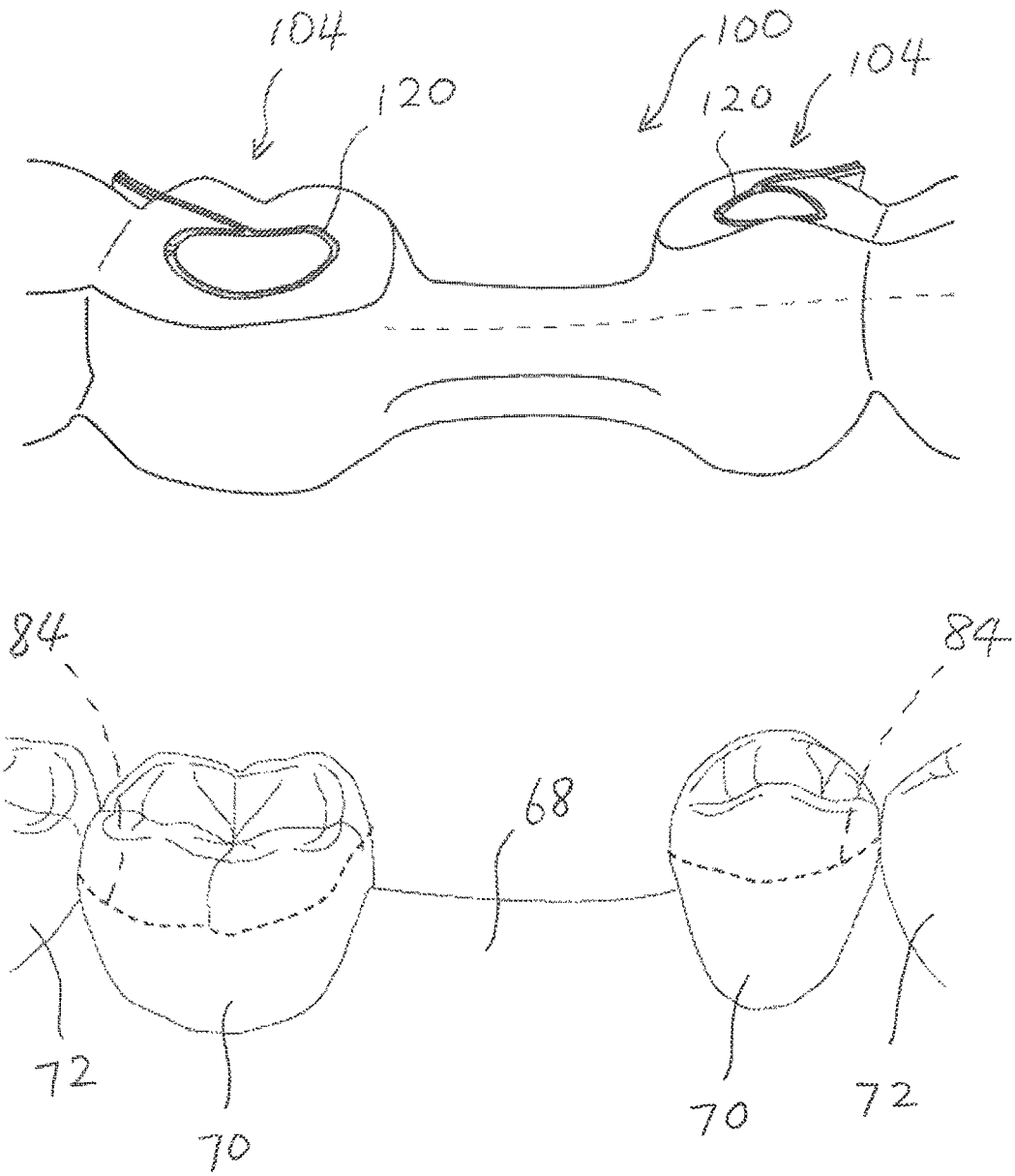
FIG. 4 is a perspective view of a preparation guide device and posterior teeth on which the preparation guide is mounted.
Figure 29A:
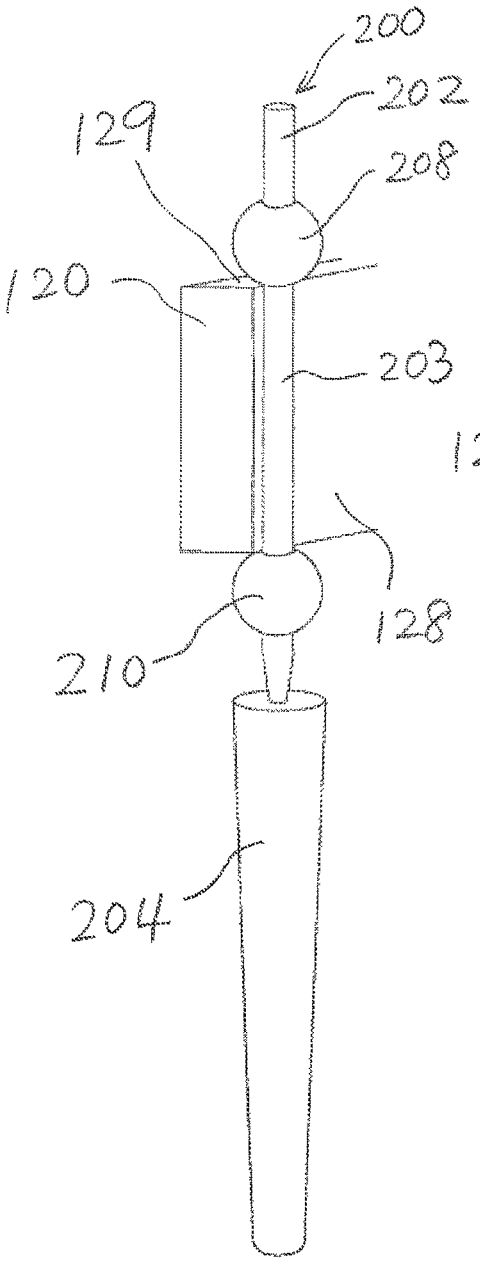
FIGS. 29A and 29B are perspective and cross-sectional views of a tool guide way and a burr in accordance with one embodiment, respectively.
Figure 29B:
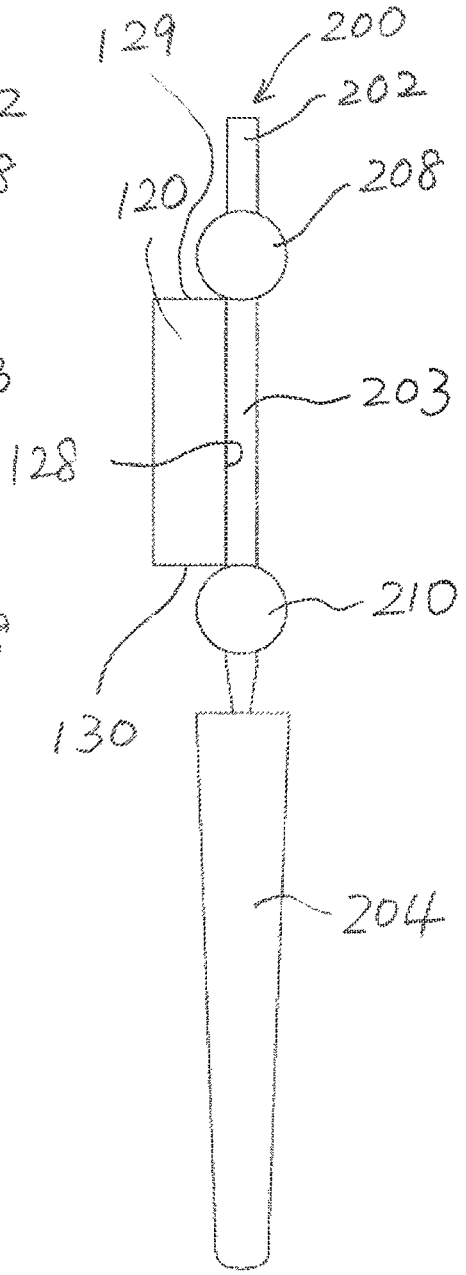
Figure 30A:
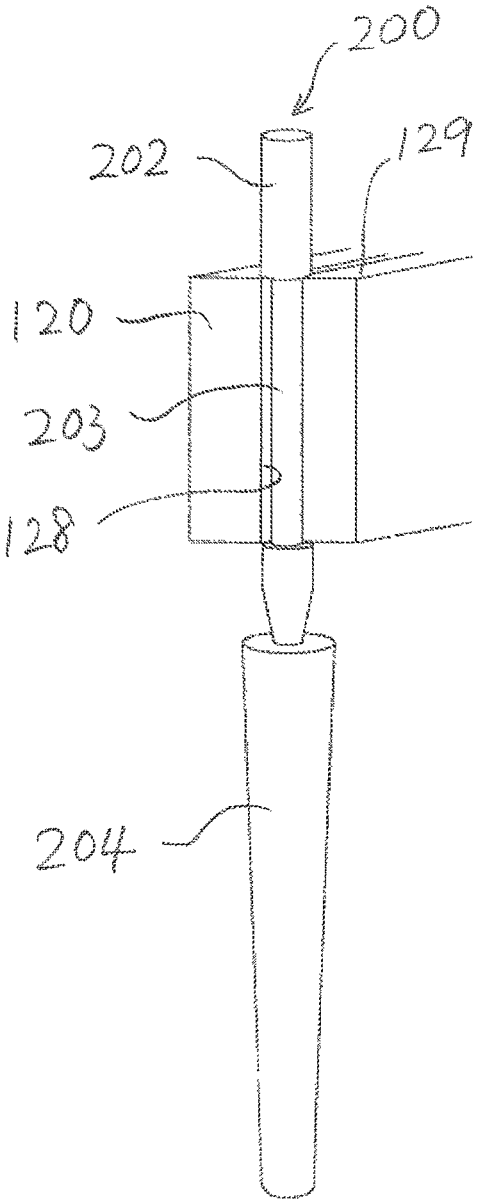
FIGS. 30A and 30B are perspective and cross-sectional views of a tool guide way and a burr in accordance with one embodiment, respectively.
Figure 30B:
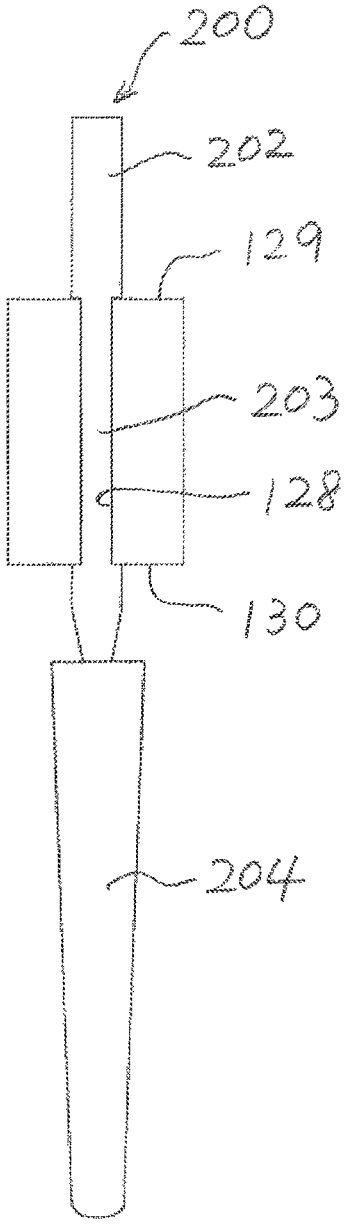

In one embodiment as shown in FIGS. 29A and 29B, a burr 200 moves along a tool guide way 120 that includes a guide surface 128 on only one side. In addition, the burr 200 moves along the tool guide way 120 via contacts between guide projections 208, 210 and the top and bottom corners of a guide surface 128. If the tool guide way configuration of such embodiment is employed, a central section 1162 or connector 1166 as shown in FIG. 3 is unnecessary. In one embodiment as shown in FIGS. 30A and 30B, the neck portion 203 of the burr 200 has a small diameter and fits within and moves along the tool guide way 120.

Figure 31A:
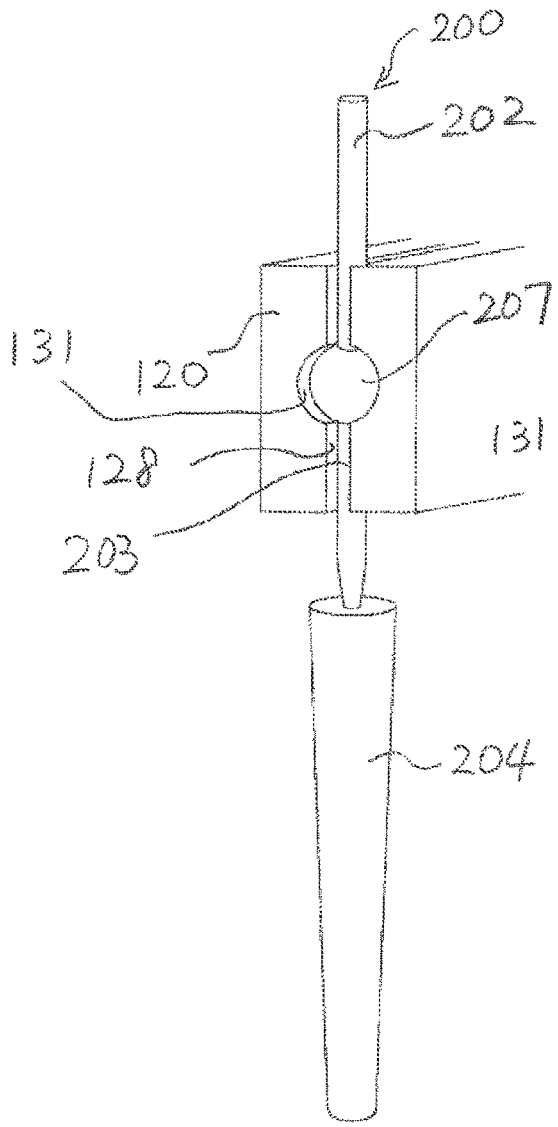
FIGS. 31A and 31B are perspective and cross-sectional views of a tool guide way and a burr in accordance with one embodiment, respectively.
Figure 31B:
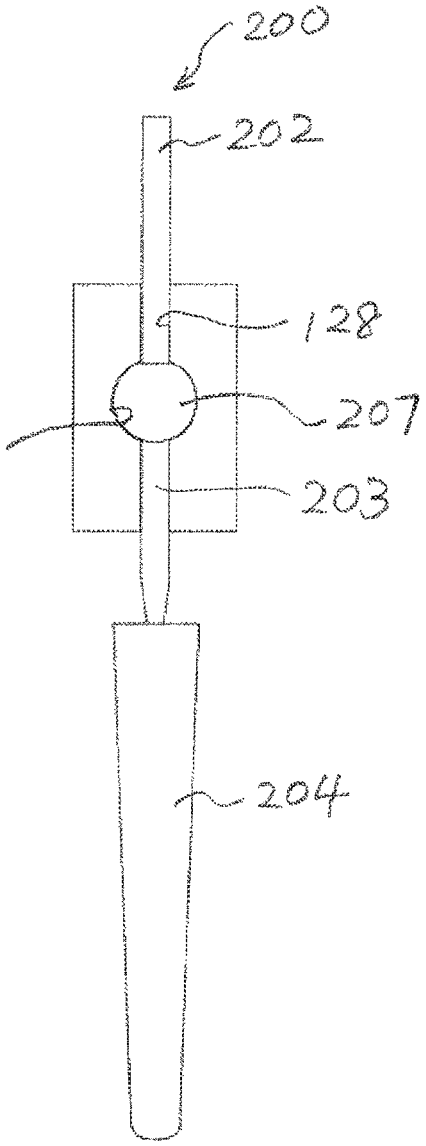
Figure 32A:
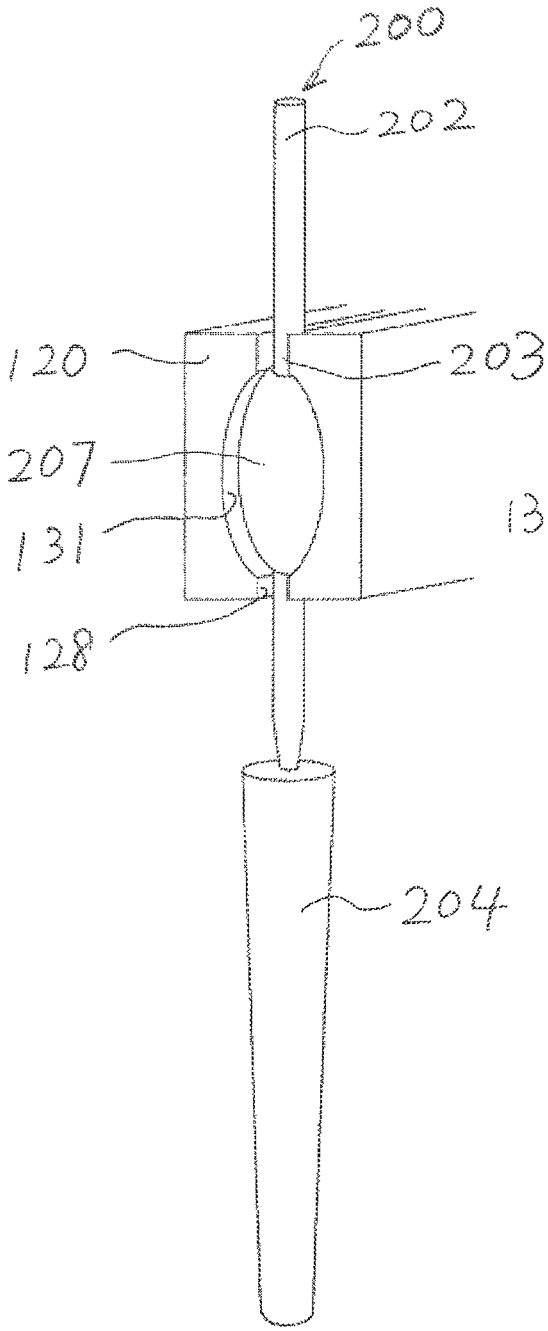
FIGS. 32A and 32B are perspective and cross-sectional views of a tool guide way and a burr in accordance with one embodiment, respectively.
Figure 32B:
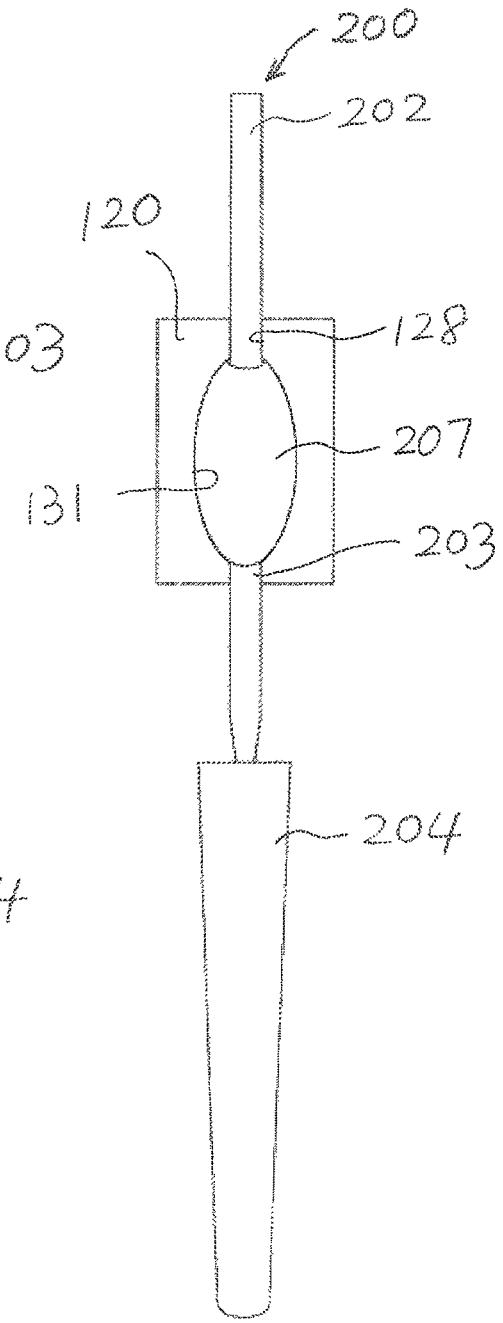

On the other hand, in one embodiment as shown in FIGS. 31A and 31B, the burr 200 includes a single sphere-shaped guide projection 207. Such guide projection 207 fits within a hemispheric groove of the guide surface in the tool guide way in order to guide the burr 200. In one embodiment as shown in FIGS. 32A and 32B, the burr 200 includes an elliptical guide projection 207. The elliptical guide projection 207 moves along within the groove of the tool guide way 120 as the burr 200 moves along the tool guide way 120.

Figure 33A:
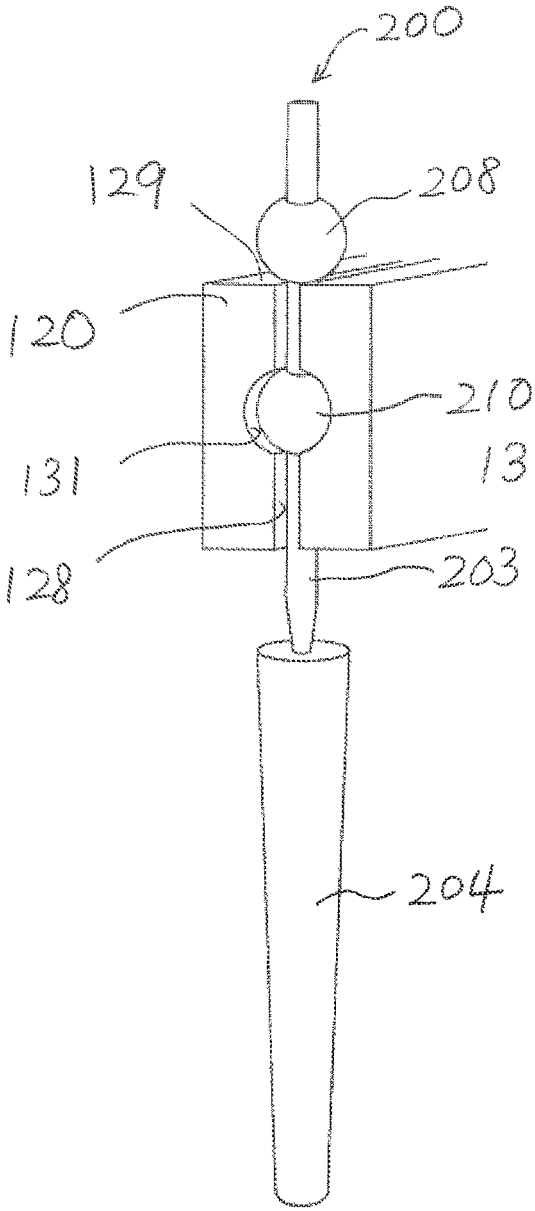
FIGS. 33A and 33B are perspective and cross-sectional views of a tool guide way and a burr in accordance with one embodiment, respectively.
Figure 33B:
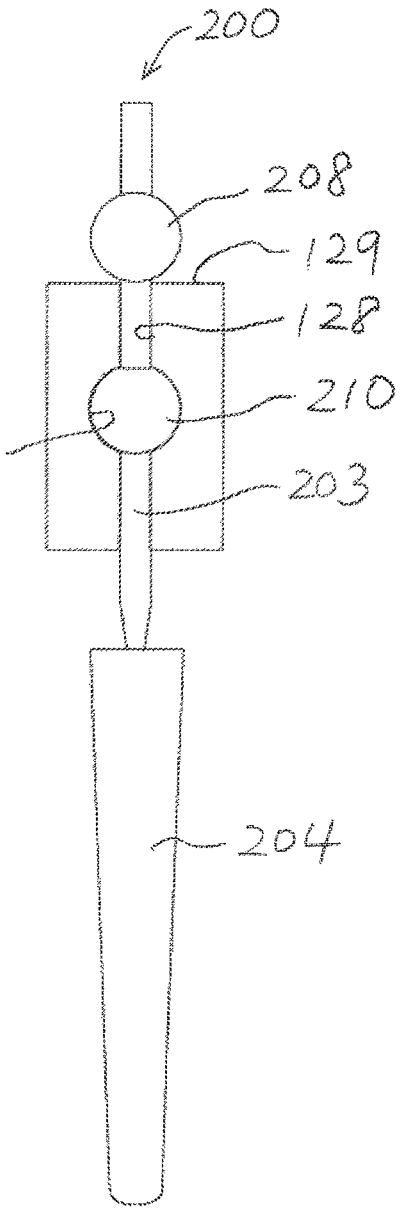

In one embodiment as shown in FIGS. 33A and 33B, the burr 200 includes two sphere-shaped guide projections 208, 210. Of the two, the bottom guide projection 210 fits within a groove 131 provided within a guide surface 128 of the tool guide way 120. The top guide projection 208 moves along while being in contact with the top support surface 129 of the tool guide way 120.

Figure 34A:
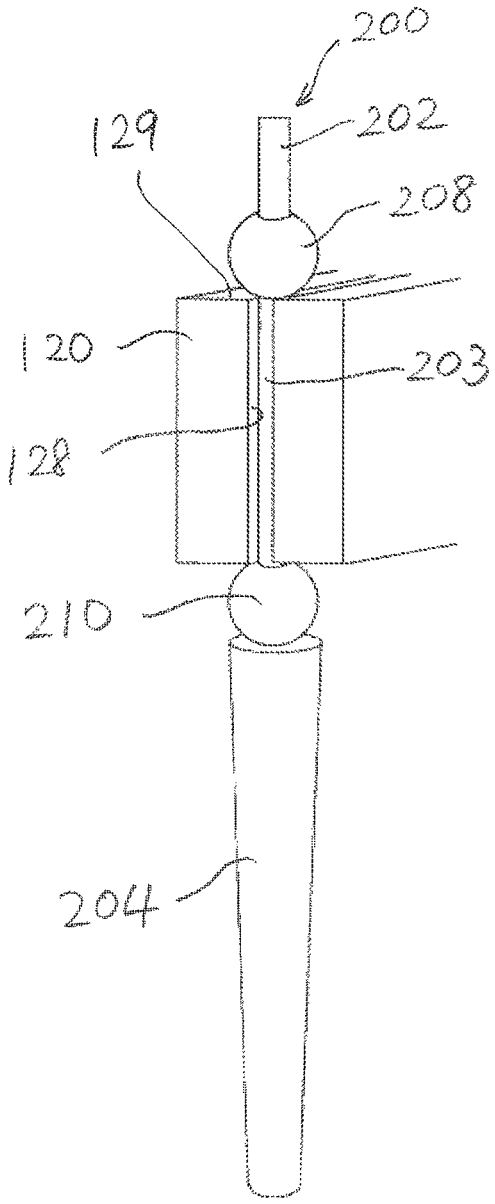
FIGS. 34A and 34B are perspective mid cross-sectional views of a tool guide way and a burr in accordance with one embodiment, respectively.
Figure 34B:
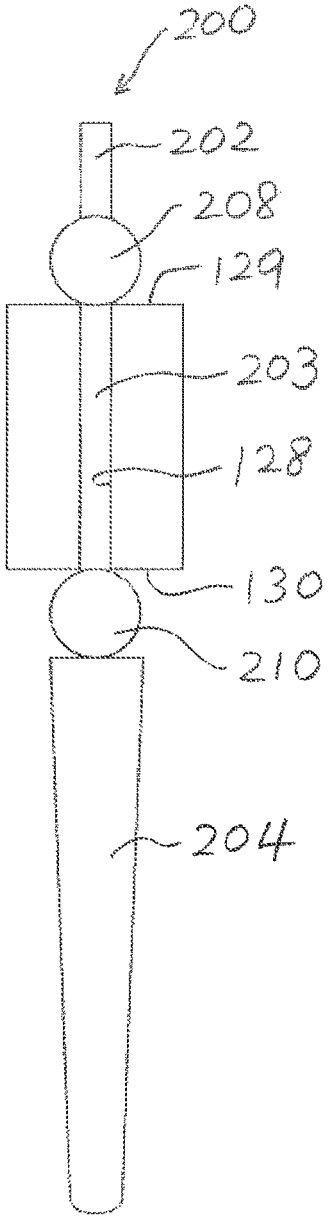

In one embodiment as shown in FIGS. 34A and 34B, the burr 200 includes two sphere-shaped guide projections 208, 210. As the burr 200 moves along a tool guide way 120, the bottom guide projection 210 moves along while in contact with the bottom support surface 130 of the toot guide way 120, and the top guide projection moves along while in contact with the top support surface 129.

Figure 35A:
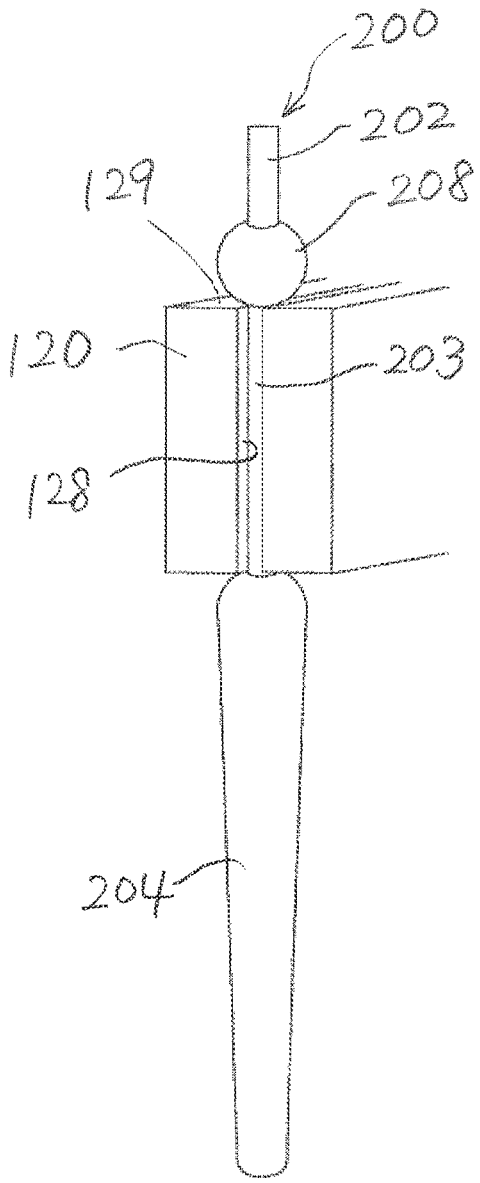
FIGS. 35A and 35B are perspective and cross-sectional views of a tool guide way and a burr in accordance with one embodiment, respectively.
Figure 35B:
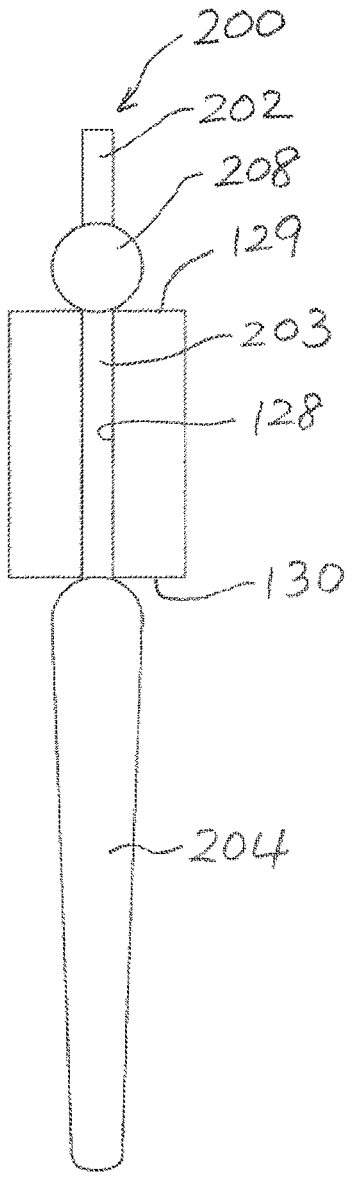

In one embodiment as shown in FIGS. 35A and 35B, the burr 200 includes a sphere-shaped guide projection 207 on the top. In addition, the top of the cutting head 204 includes a hemispheric shape to function as a guide projection. As the burr 200 moves along a tool guide way 120, the guide projection 207 moves along while in contact with the top support surface 129 of the tool guide way 120, and the top of the cutting head 204 moves along while in contact with the bottom support surface 130 of the tool guide way 120.

Figure 36A:
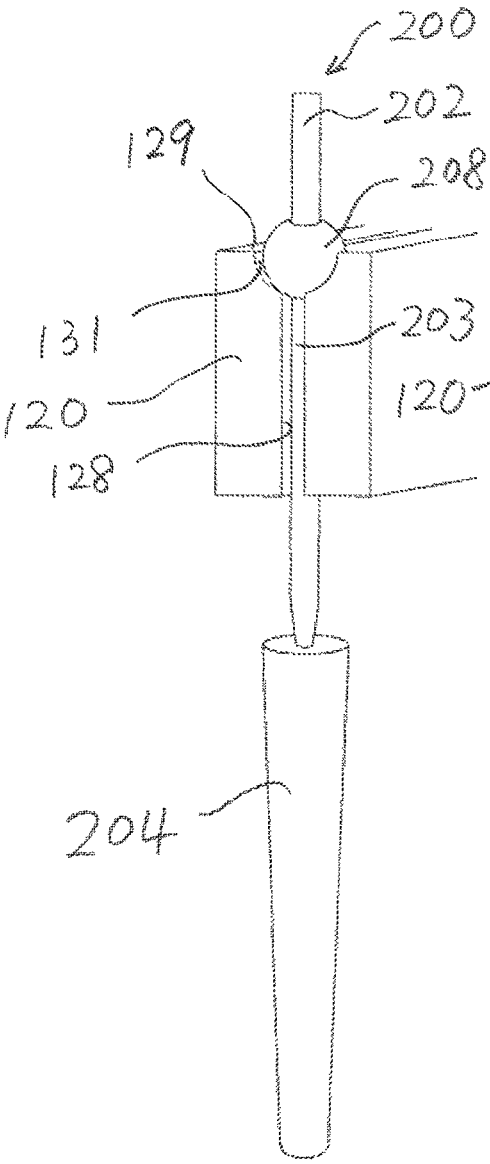
FIGS. 36A and 36B are perspective mid cross-sectional views of a tool guide way and a burr in accordance with one embodiment, respectively.
Figure 36B:
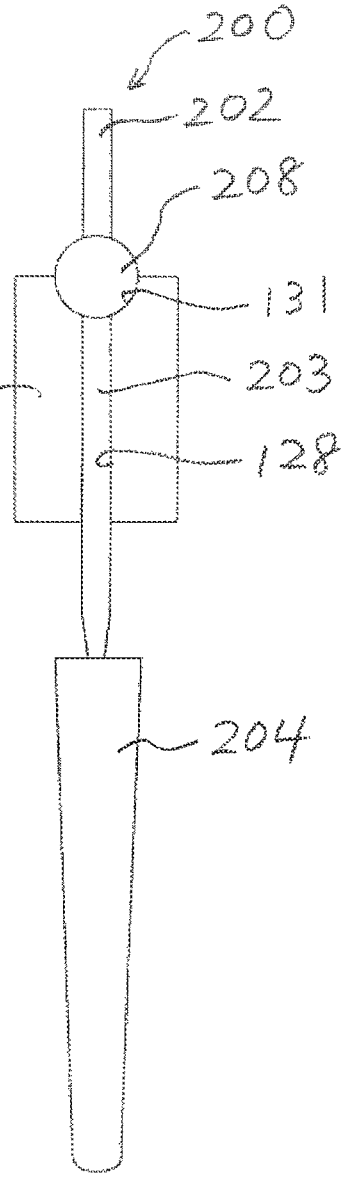
Figure 36C:
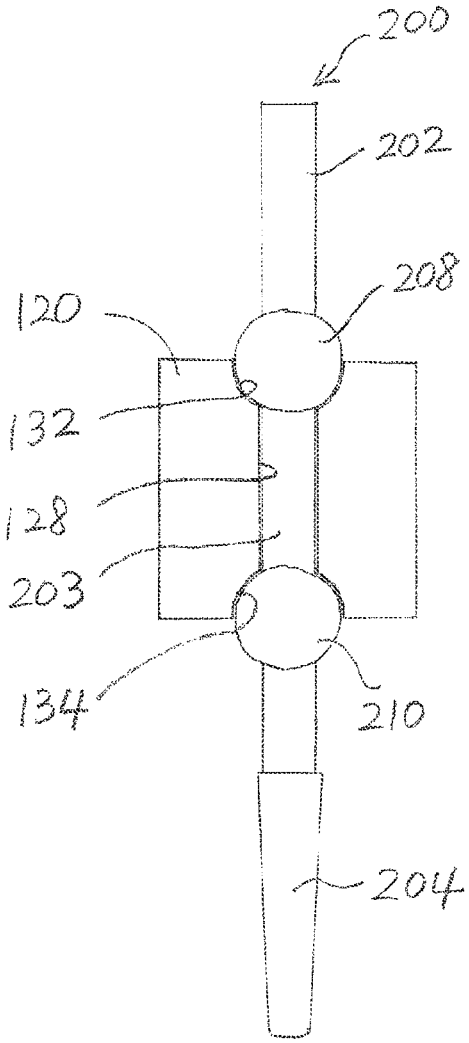
FIG. 36C is a cross-sectional views of a tool guide way and a burr in accordance with one embodiment.
Figure 36D:
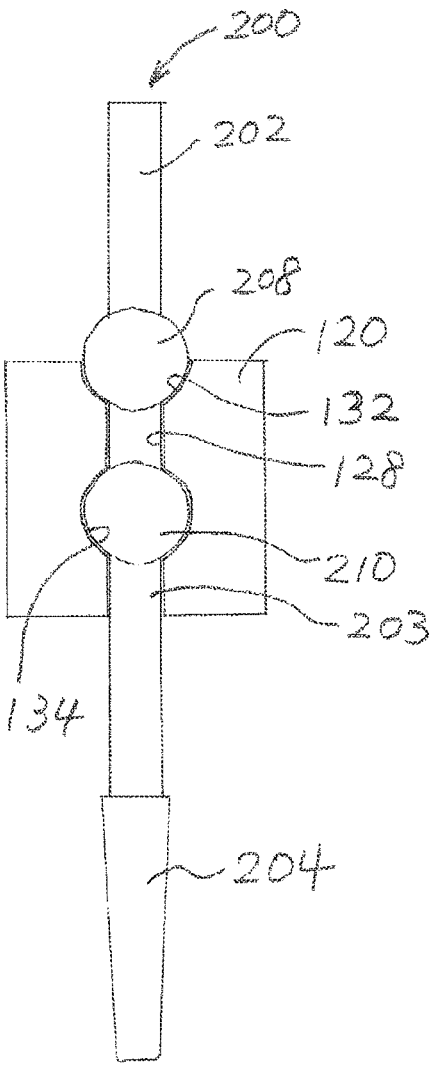
FIG. 36D is a cross-sectional views of a tool guide way and a burr in accordance with one embodiment.
Figure 37A:
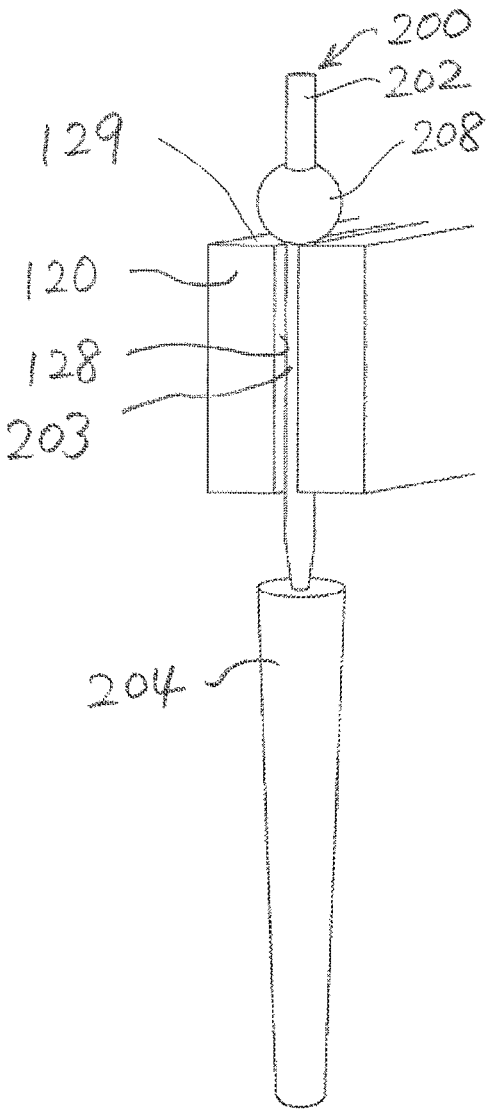
FIGS. 37A and 37B are perspective and cross-sectional views of a tool guide way and a burr in accordance with one embodiment, respectively.
Figure 37B:
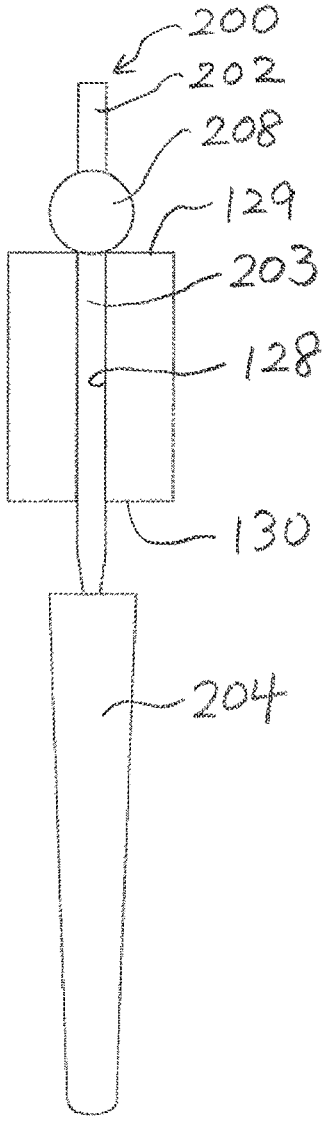

In one embodiment as shown in FIGS. 36A and 36B, the burr 200 includes a sphere-shaped guide projection. The top support surface 129 of a tool guide way 120 includes a groove. As the burr 200 moves along the tool guide way 120, a portion of the sphere-shaped guide projection fits within and moves along the groove formed on the top support surface 129 of the tool guide way 120. In another embodiment as shown in FIG. 36C, the burr 200 includes two sphere-shaped guide projections 208, 210. The top support surface 129 and bottom support surface 130 of a tool guide way 120 each includes a groove. Each guide projection 208, 210 fits within and moves along each respective groove. On the other hand, in one embodiment as shown in FIGS. 37A and 37B, a guide projection 207 moves while in contact with the top support surface 129 of the tool guide way 120 as the burr 200 moves along the tool guide way 120.

Figure 38A:
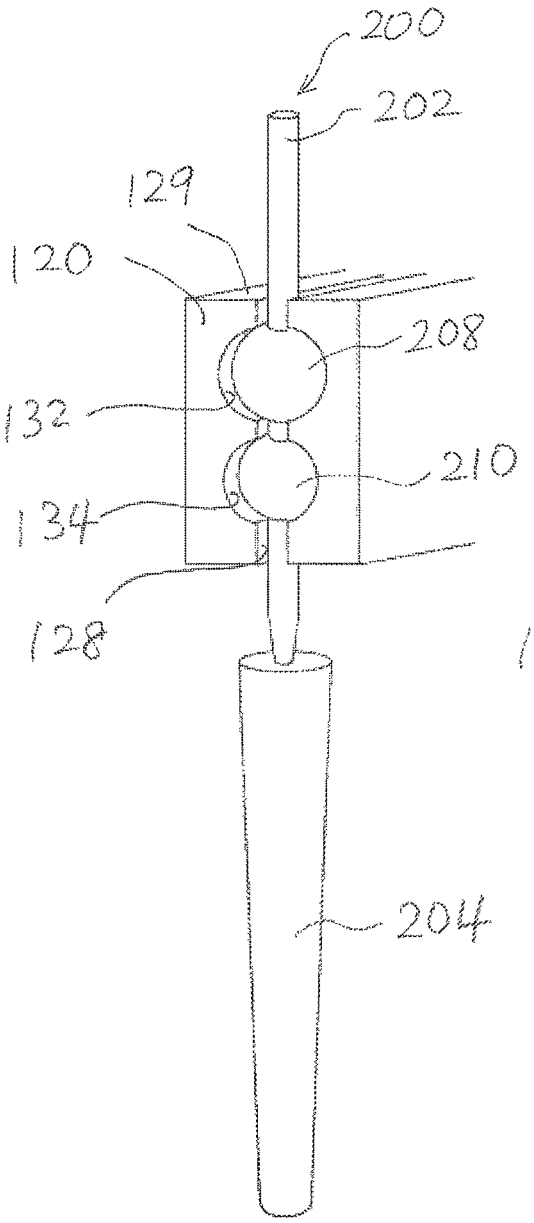
FIGS. 38A and 38B are perspective and cross-sectional views of a tool guide way and a burr in accordance with one embodiment, respectively.
Figure 38B:
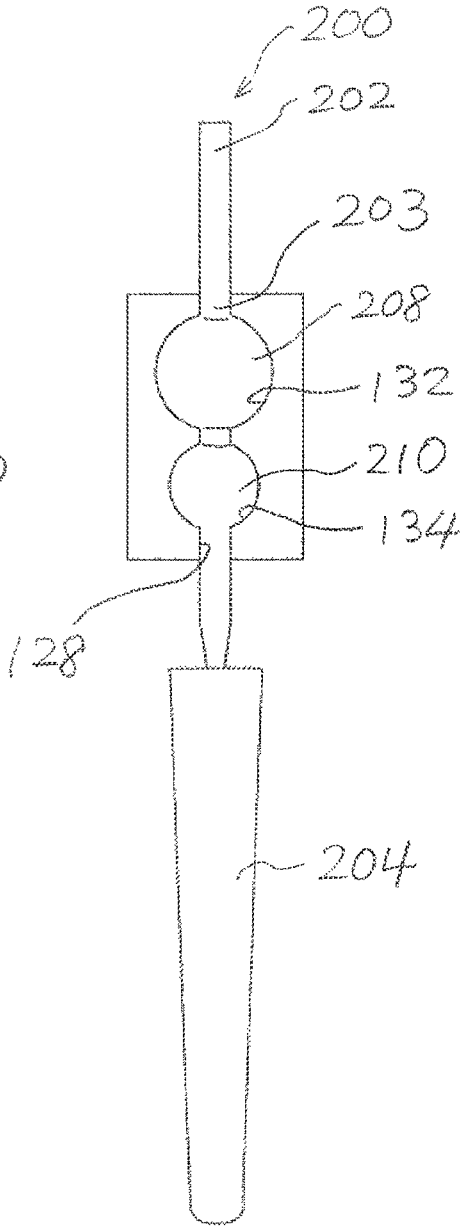
Figure 39A:
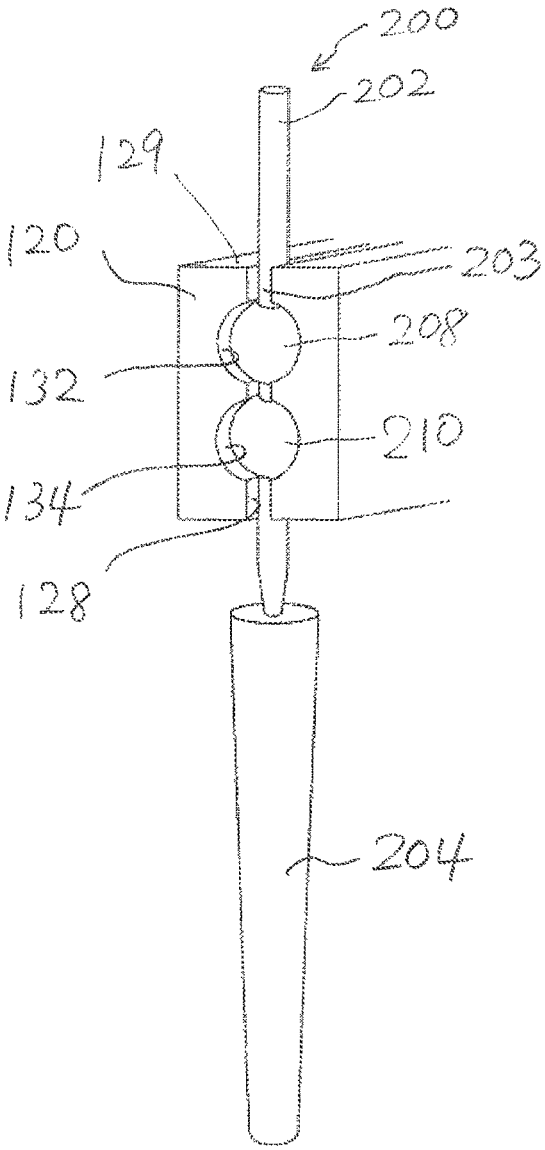
FIGS. 39A and 39B are perspective and cross-sectional views of a tool guide way and a burr in accordance with one embodiment, respectively.
Figure 39B:
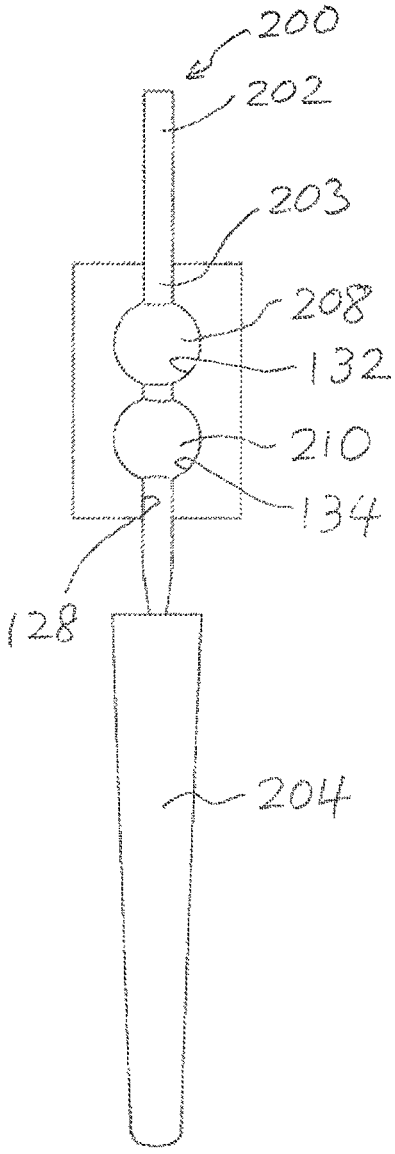

In one embodiment as shown in FIGS. 38A and 38B, the burr 200 includes two sphere-shaped guide projections 208, 210 of different sizes. Side guide surfaces 128 of a tool guide way 120 include grooves 132, 134 that accommodate each guide projection 208, 210. As the burr 200 moves along the tool guide way 120, the two guide projections 208, 210 fit within and move along each groove 132, 134. In one embodiment as shown in FIGS. 39A and 3913, the burr 200 includes two sphere-shaped guide projections 208, 210 of the same size, and as the burr 200 moves along the tool guide way 120, the two guide projections 208, 210 fit within and move along each groove 132, 134.

In one embodiment as illustrated in FIGS. 88A and 88B, the burr 200 includes two sphere-shaped guide projections 208, 210, wherein one is located above the other. Guide surfaces 128 on a side of a tool guide way 120 include rectangular grooves 132, 134. The guide projections fit within and move along such grooves 132, 134. In such an embodiment, the contact area between the grooves 132, 134 and the guide projections 208, 210 may be smaller than that of embodiments illustrated in FIGS. 38 and 39. Accordingly, friction is reduced, allowing for the burr to spin and move smoothly. In addition to being rectangular, the shape of the groove may also be of other polygons, such as triangular, trapezoidal, or pentagonal.

Flow of Cooling Fluid

Cooling fluid, such as water, is generally provided to cool the burr 200 and teeth during cutting. The flow of such cooling fluid is used not only to cool the teeth and the burr 200, but is also used to remove cut tooth pieces and particles from the burr.

In one embodiment as shown in FIG. 43, the preparation guide device 100 includes holes 170 to allow for such cooling fluids to flow through. In one embodiment, such hole(s) 170 is located below the survey line. In other embodiments, as illustrated in FIGS. 11, 13, and 89, a sidewall 10 may extend only to the survey line or include a blocked-out portion 118 to allow cooling fluid to flow through.

Single Preparation Guide Device for Cutting both Occlusal and Side Surfaces

In cases where an abutment tooth's occlusal and side surfaces both need to be cut, for example, for a crown or crown and bridge prosthesis, a single preparation guide device may include tool guide ways that allow cutting of both occlusal and side surfaces. In such cases, the preparation guide device may move relative to the teeth while cutting occlusal surfaces as the side surfaces are being cut. Then, precise cutting cannot be performed on the occlusal surfaces due to movement of the preparation guide device. This is especially the case when the preparation guide device is placed directly on an abutment tooth or when the abutment tooth is not sufficiently supported by adjacent teeth. In addition, a tool guide way for occlusal surface may be damaged while cutting the side surfaces. Even if side surfaces are cut after cutting an occlusal surface, a tool guide way necessary for cutting, the side surfaces may already be damaged.

One embodiment of the invention addresses the aforementioned problems via strategic positioning of guide slots. A preparation guide device 100 as shown in FIGS. 44-54 illustrates such an embodiment. For example, a tool guide way 120 for cutting side surfaces may be located on the inside of a tool guide way 120 for cutting an occlusal surface or, in other words, closer to the teeth when viewed from above the occlusal surface. Then, the tool guide ways 120 for guiding burrs 200 to cut occlusal and side surfaces do not cross each other. In such an embodiment, the side surfaces are cut first, and then the occlusal surface.

In contrast, a tool guide way 120 for cutting side surfaces may be located above a tool guide way 120 extending from lingual and buccal directions for cutting, an occlusal surface or, in other words, farther away from the teeth when viewed from the side of a side surface. Then, the tool guide ways 120 for guiding burrs 200 to cut the occlusal and side surfaces do not cross each other. In such an embodiment, the occlusal surface is cut first, and then the side surfaces.

The order of cutting different surfaces may vary depending on whether the occlusal or side surfaces support the preparation guide device more strongly. For example, if the side surfaces provide stronger support, then it is advantageous to cut the occlusal surface first and then the side surfaces. However, if the occlusal surface provides stronger support, then it is advantageous to cut the side surfaces first and then the occlusal surface.

Other embodiments of the invention, as shown in FIGS. 80-85, use two preparation guide devices 1002, 1004 when cutting teeth for crown prosthesis. Such embodiments are discussed in more detail below.

Embodiments as Shown in FIGS. 44-54

According to embodiments as shown in FIGS. 44-54B, both occlusal and side surfaces of an abutment tooth 70 can be cut effectively using a single preparation guide device 100. In the illustrated embodiments, the tool guide way 120 for cutting side surfaces and the tool guide way 120 for cutting occlusal surfaces are configured not to conflict with each other while cutting teeth 2. This configuration prevents the tool guide ways 120 from being damaged while cutting.

FIGS. 44-55B show a preparation guide device 100 used for cutting teeth in order to install a crown and bridge prosthesis 50. The preparation guide device 100 has a tool guide way 120 for guiding the burr 200 to cut an occlusal surface and a tool guide way 120 for guiding the burr 200 to cut side surfaces. The tool guide ways 120, as explained in the embodiment above, include guide slots located between two guide surfaces 128 facing each other. The neck 203 of the burr 200 fits within the guide slot of the tool guide way 120, allowing the burr 200 to move along the tool guide way 120.

The preparation guide device 100 illustrated above can be installed once in the patient's mouth and allow cutting of both occlusal and side surfaces before being removed.

In the illustrated embodiments, the tool guide way 120 for side surfaces has a burr entrance that cuts across the sidewall near the adjacent tooth 72 of an abutment tooth 70. The tool guide way 120 for occlusal surfaces has two distinct tool guide ways per abutment tooth 70. More specifically, for each abutment tooth 70, separate tool guide ways exist for cutting a portion of the occlusal surface closer to the cheek and for cutting a portion of the occlusal surface closer to the tongue. The occlusal tool guide ways 210 each have a burr entrance 125 located on the top wall 116 of the preparation guide device 100.

Cutting Occlusal Surfaces before Cutting Side Surfaces

In cases of cutting occlusal surfaces before side surfaces, a preparation guide device 120 is configured such that a tool guide way 120 for cutting side surfaces is not damaged by a burr 200 while cuffing an occlusal surface. Due to such structure, the burr 200 remains fully supported while cutting side surfaces after cutting occlusal surfaces. More specifically, as shown in FIGS. 48B, 50B, and 51B, a tool guide way 120 for cutting side surfaces cm be located farther from the teeth than the projected path of the cutting head 204 of the burr 200 for cutting occlusal surfaces. In other words, in FIGS. 48B, 50B, and 51B, a tool guide way 120 for cutting side surfaces is located higher and away from the tooth. Such structure prevents the tool guide way 120 for side surfaces from being damaged by the burr 200 while cutting occlusal surfaces. In cases where a connector 1166 is placed across the guide slot of the guide way for side surfaces, the corrector 1166 can be installed at an appropriate location such that it is not cut during the cutting of occlusal surfaces (see FIG. 48B).

A preparation guide devices 100 used for cutting occlusal surfaces before side surfaces may also be purposefully designed to damage the tool guide way 120 for occlusal surfaces while cutting side surfaces. This is because the cutting of occlusal surfaces is already complete by the time side surfaces are cut and the tool guide way 120 for occlusal surfaces is no longer necessary. Such design allows for partially narrower preparation guide devices 100, allowing the guide devices 100 to meet necessary size restrictions. When using a preparation guide device 100 of such configuration, the user (dental practitioner) must be instructed to cut the occlusal surfaces before cutting the side surfaces.

Cutting Side Surfaces before Occlusal Surfaces

In cases of cutting side surfaces before occlusal surfaces, a preparation guide device 120 is structured such that a tool guide way 120 for cutting occlusal surfaces is not damaged by a burr 200 while cutting side surfaces. Due to such configuration, the burr 200 remains fully supported while cutting occlusal surfaces after cutting side surfaces. More specifically, a tool guide way 120 for occlusal surfaces can be located farther from the teeth than the projected path of the cutting head 204 of the burr 200 for cutting side surfaces. Such structure prevents the tool guide way 120 for occlusal surfaces from being damaged by the burr 200 while cutting side surfaces.

A preparation guide devices 100 used for cutting side surfaces before occlusal surfaces may also be purposefully designed to damage the tool guide way 120 for side surfaces while cutting occlusal surfaces. This is because the cutting of side surfaces is completed by the time occlusal surfaces are cut, and thus the tool guide way 120 for side surfaces is no longer necessary. Such configuration allows for partially narrower preparation guide devices 100, allowing the guide devices 100 to meet certain restrictive limitations in size. When using a preparation guide device 100 of such design, however, the user (dental practitioner) must be instructed to cut the side surfaces before cutting the occlusal surfaces.

Checking the installation Status of a Preparation Guide Device

Figure 49:
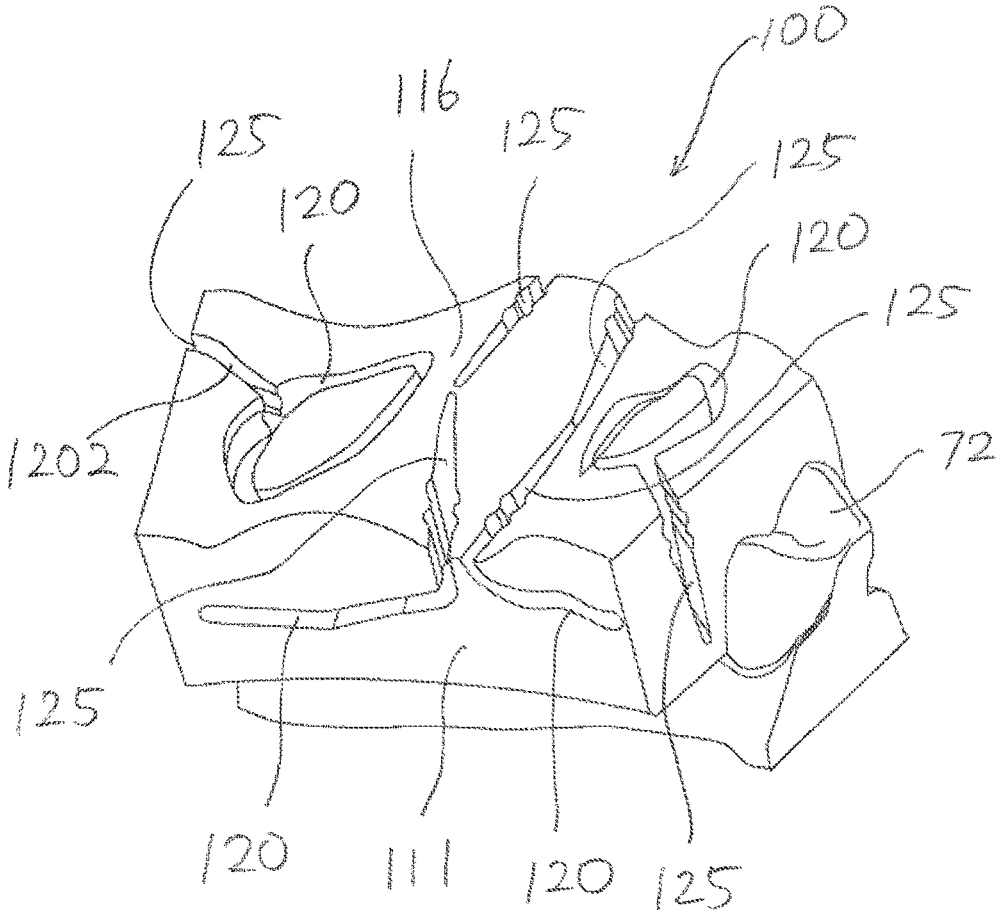
FIG. 49 is a perspective view of the preparation guide device shown in FIG. 44 as mounted on teeth.
Figures 52, 52A, 52B, 52C, 52D:
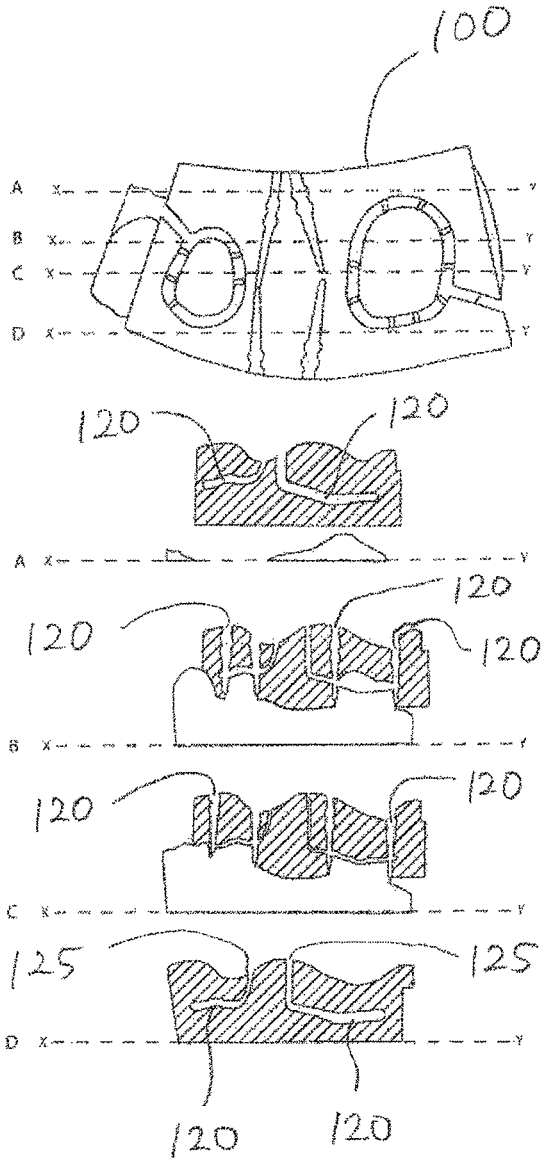
FIG. 52 is a plan view of the preparation guide device shown in FIG. 44 as mounted on teeth.
FIG. 52A is a cross-sectional view taken along a line AX-Y shown in FIG. 52.
FIG. 52B is a cross-sectional view taken along a line BX-Y shown in FIG. 52.
FIG. 52C is a cross-sectional view taken along a line CX-Y shown in FIG. 52.
FIG. 52D is a cross-sectional view taken along a line DX-Y shown in FIG. 52.
Figure 53:
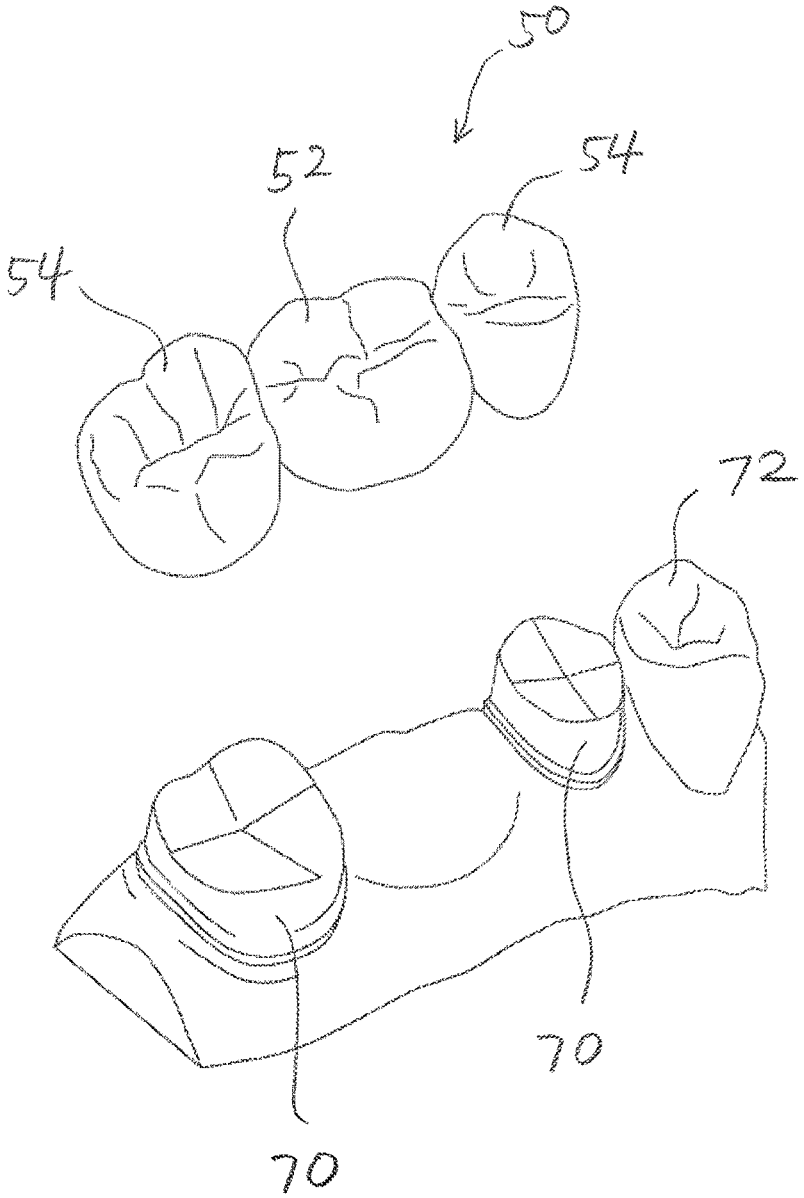
FIG. 53 is a perspective view of prepared teeth and a prosthesis in accordance with one embodiment.
Figure 54:
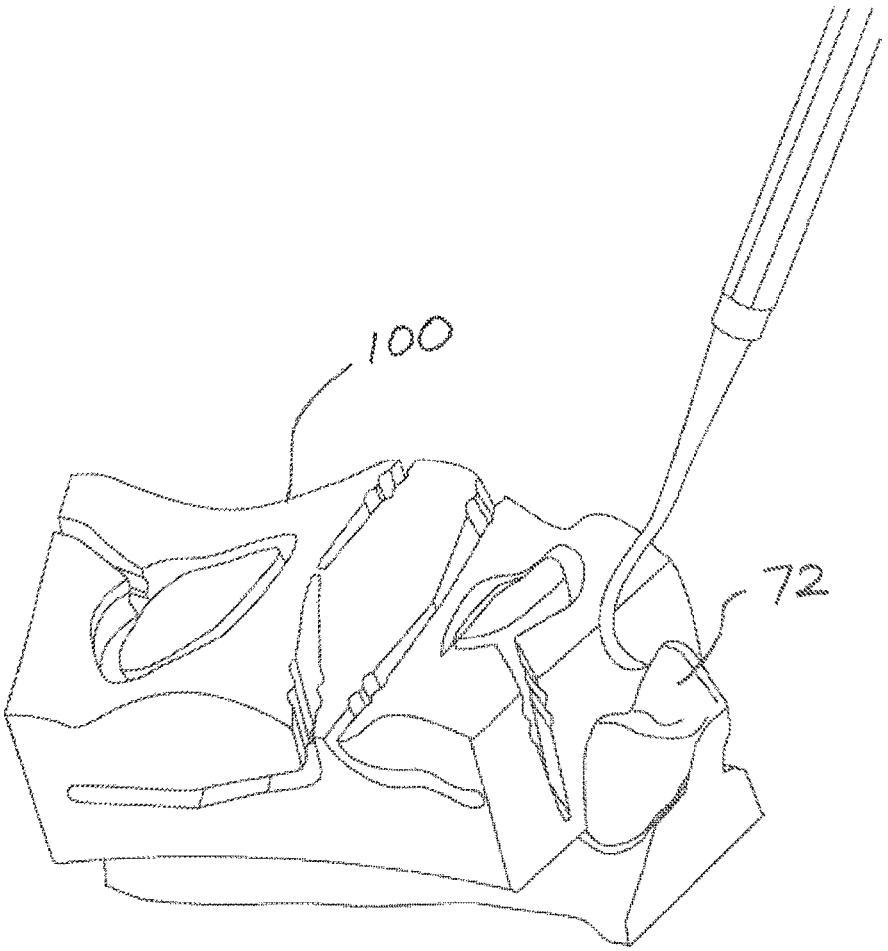
FIG. 54 is a perspective view of a preparation guide device mounted on a teeth in accordance with one embodiment.

As shown in FIGS. 49 and 54, whether a preparation guide device has been properly engaged on the patient may be checked. The installation status of the preparation guide device can be checked either by observation, as shown in FIG. 49, or via use of a probe 250, as shown in FIG. 54.

Figure 56:
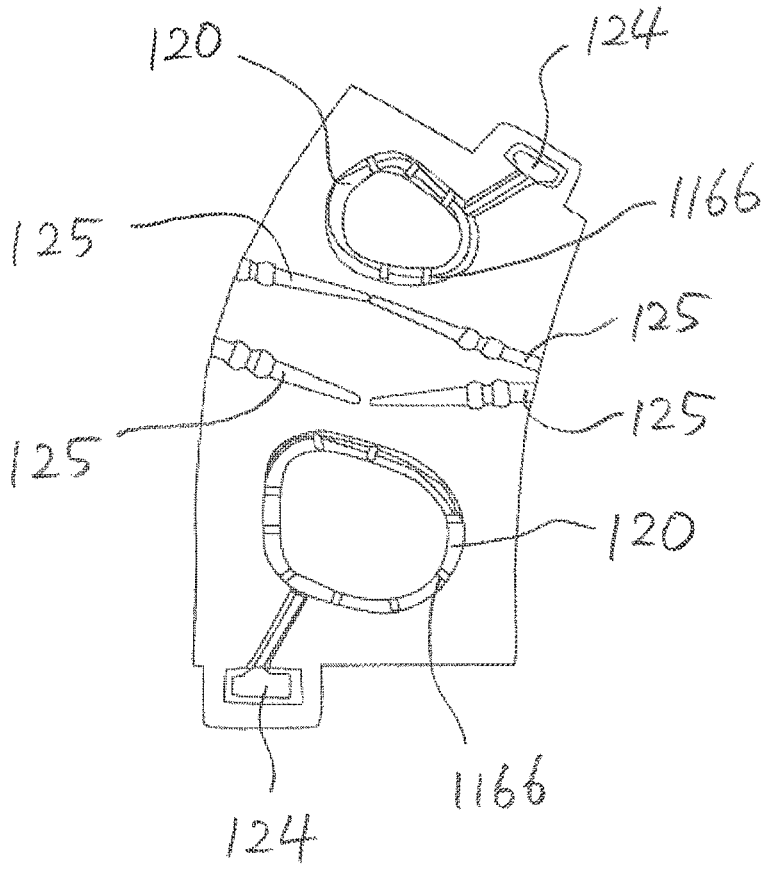
FIG. 56 is a plan view of a preparation guide device in accordance with one embodiment.
Figure 57:
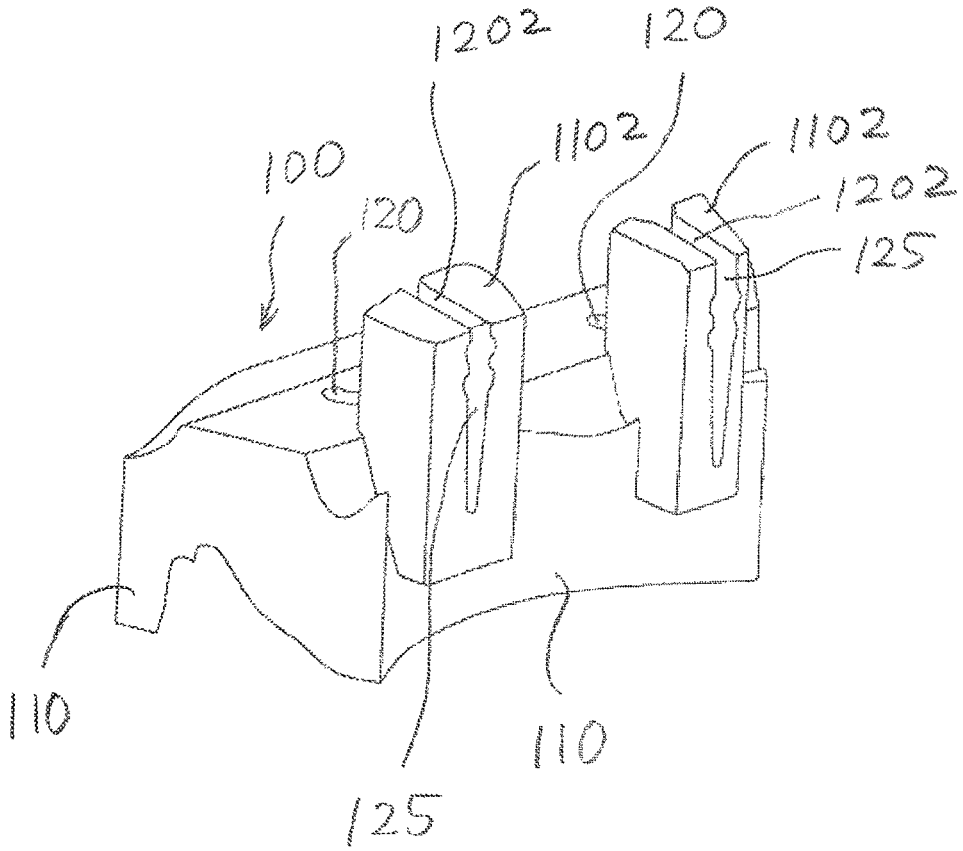
FIG. 57 is a perspective view of a preparation guide device in accordance with one embodiment.
Figure 58:
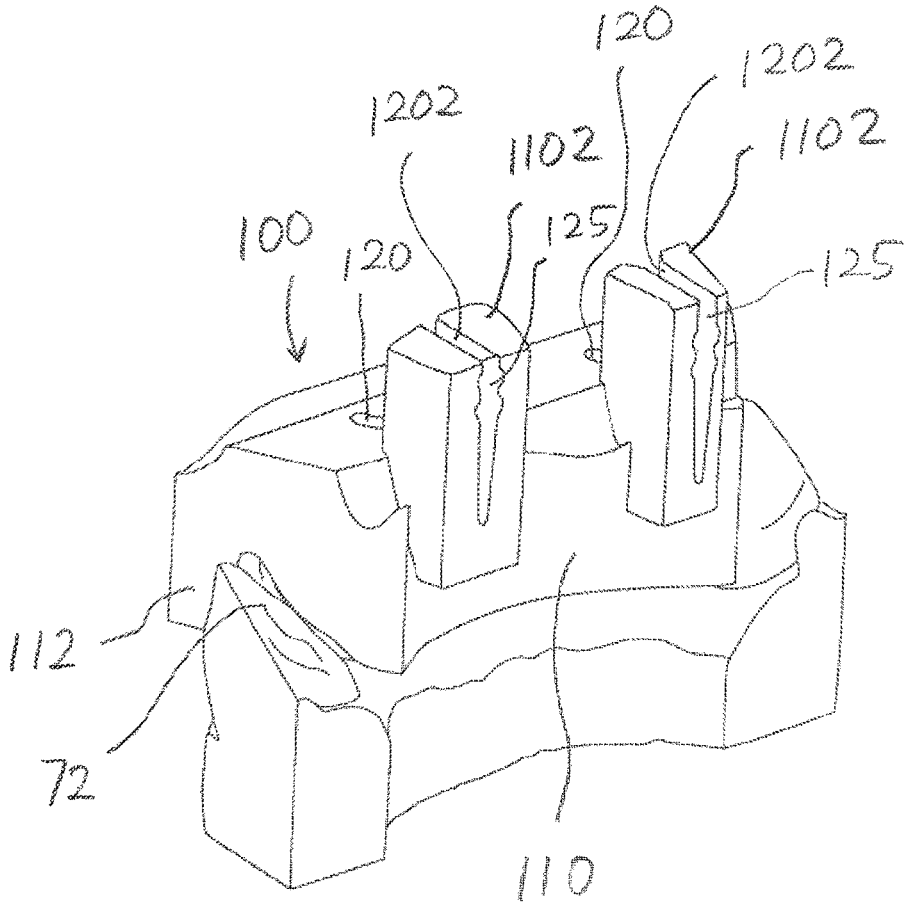
FIG. 58 is a perspective view of the preparation guide shown in FIG. 57 as mounted on teeth.
Figure 59:
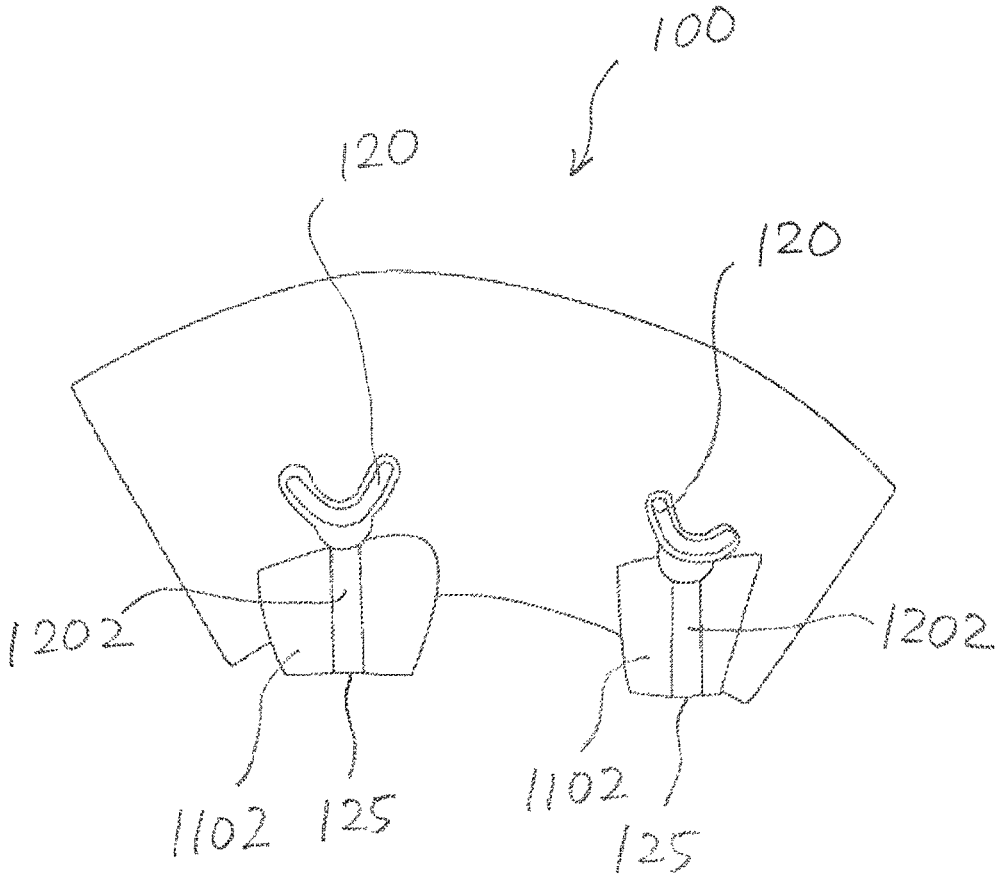
FIG. 59 is a plan view of the preparation guide device shown in FIG. 57.
Figure 61:
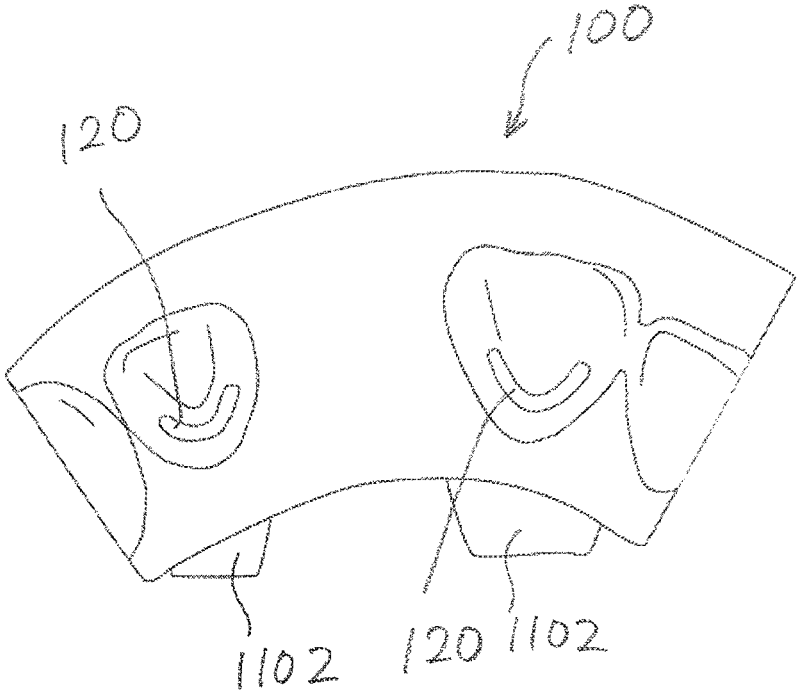
FIG. 61 is a bottom view of the preparation guide device shown in FIG. 57.
Figure 62:
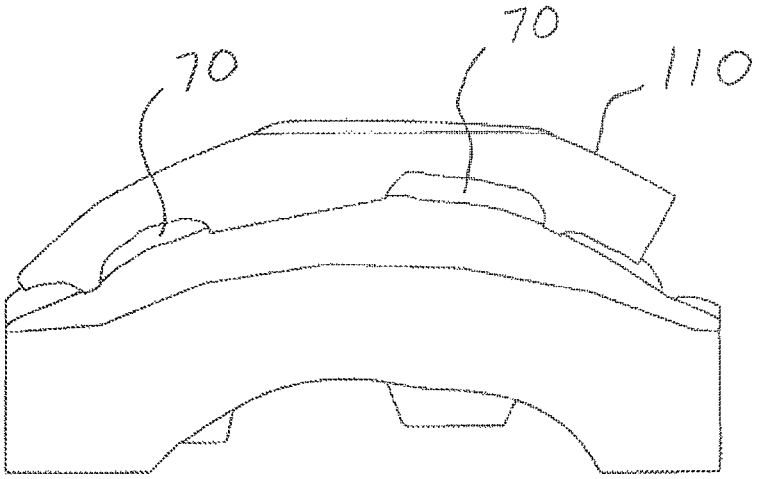
FIG. 62 is a bottom view of a teeth model and the preparation guide device shown in FIG. 57.

Embodiment as Shown in FIG. 56

According to one embodiment as shown in FIG. 56, a burr entrance for entering a tool guide way of the preparation guide device 100 for cutting side surfaces is located on the top wall in the form of a hole. As described above, such entrance structure does not have an opening in the sidewall, allowing the preparation guide device 100 to retain stability over teeth.

Embodiments as Shown in FIGS. 57-65

Figure 63:
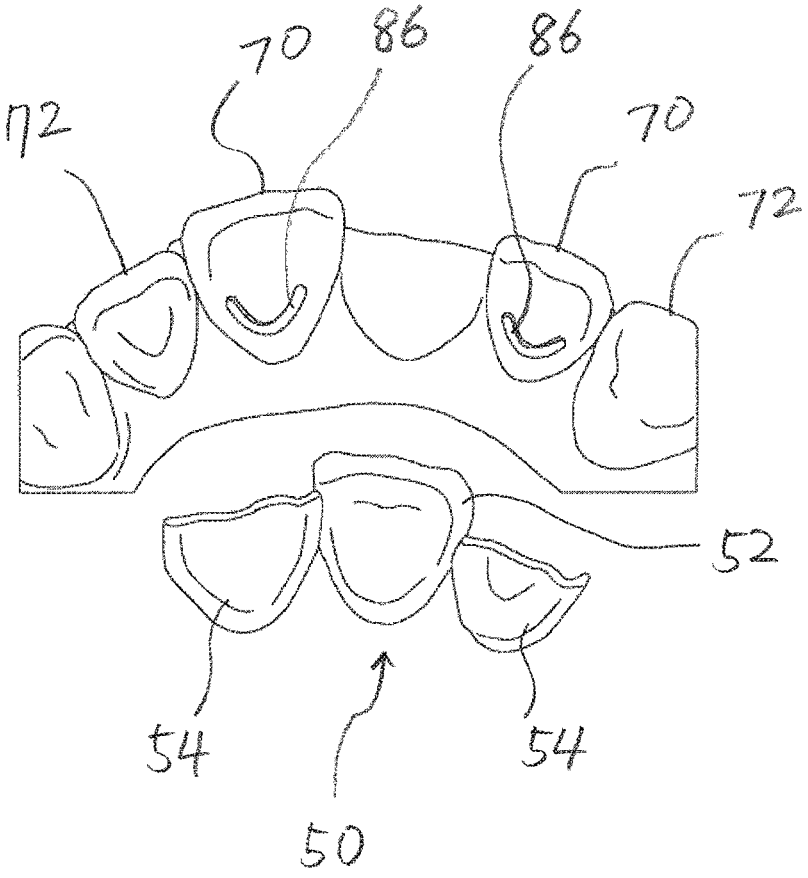
FIG. 63 is a perspective view of prepared anterior teeth and a prosthesis to he installed on the prepared anterior teeth in accordance with one embodiment.
Figure 64:
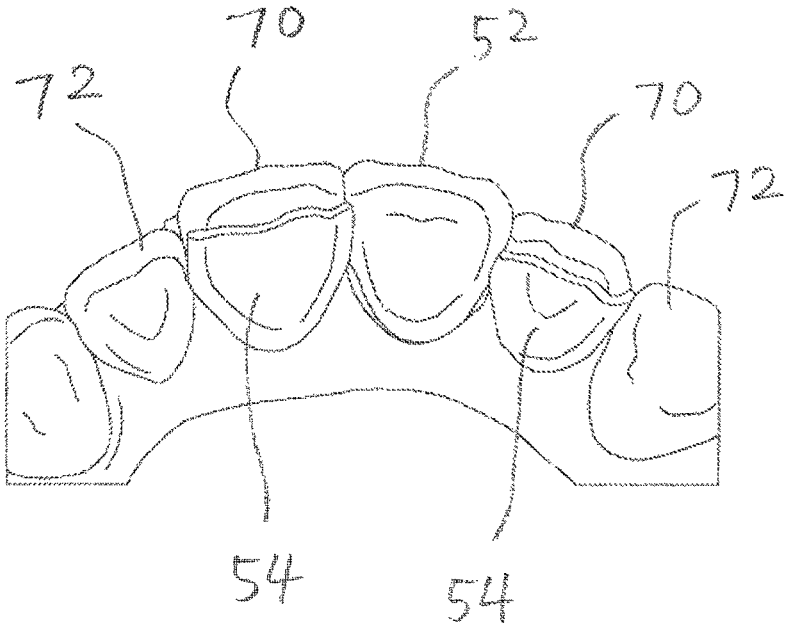
FIG. 64 is a perspective view of prepared anterior teeth and the prosthesis shown in FIG. 63 as installed on the prepared anterior teeth.
Figure 65:
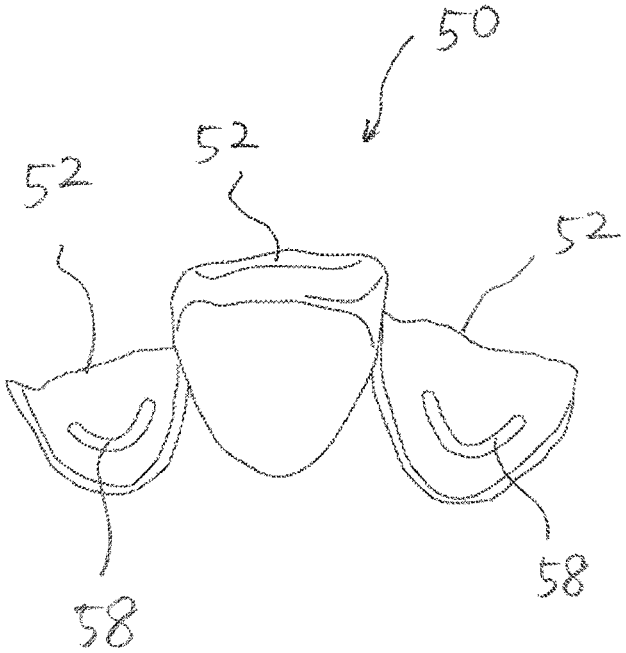
FIG. 65 is a perspective view of the prosthesis shown in FIG. 63.

In one embodiment, as shown in FIGS. 63-65, the prosthesis 50 includes fixing portions 54 to be engaged on abutment teeth 70 on both sides of a missing tooth and an artificial tooth 52 located between the two fixing portions 54. As shown in FIG. 65, the two fixing portions 54 each comprise fixing projections 58 that can be inserted into and fixed within arc-shaped or horseshoe-shaped prosthesis fixing grooves 86 formed on each anterior abutment tooth 70 along the cingulum. In one embodiment of the invention, the fixing portion 54 is made of metallic materials, such as gold, gold alloy, titanium, or titanium alloy, and an artificial tooth 52 is made of an appropriate material for artificial teeth, such as gold or zirconia, In other embodiments, the fixing projection can be made of ceramic material, such as zirconia, and not of metallic material.

In one embodiment, fixing projections are formed on the prosthesis and grooves are formed on the teeth in order to fix the prosthesis. In order to obtain sufficient retention force when fixing the fixing projections and the grooves, the grooves must be precisely prepared. More specifically, the three-dimensional shape and size of fixing projections 58 formed on the fixing portions 54 of the prosthesis 50 must be precisely complementary to the three-dimensional shape and size of the prosthesis fixing grooves 86 formed on an abutment tooth. When viewed along the intended axis of insertion of the prosthesis 50, all cut surfaces that form the sidewalls of the prosthesis fixing grooves 86 must be consistent with or substantially consistent with the intended axis of insertion. Similarly, when viewed from the intended axis of insertion of the prosthesis 50, all cut surfaces that form the sidewalls of a fixing projection [56 ] *58* must be consistent with or substantially consistent with the intended axis of insertion. Also, when a fixing projection [56] *58* is inserted into and fixed upon a prosthesis fixing groove 86 in the prosthesis's axis of insertion, a gap between the sidewall of the fixing projection and the sidewall of the prosthesis fixing groove, on average, is less than about 60μ, about 80μ, about 100μ, about 120μ, about 140μ, about 160μ, about 180μ, or about 200μ. Such conditions are difficult to achieve without using a preparation guide device and depending solely on a dental practitioner's hand movement.

As illustrated in FIGS. 57-62, the preparation guide device 100 of one embodiment allows cutting of anterior lingual surfaces along the cingulum such that the prosthesis can be fixed on two anterior teeth. The preparation guide device 100 includes a tool guide way 120 having an arc shape to guide a burr. In one embodiment, prosthesis fixing grooves 86 on the lingual surfaces 70 of anterior teeth are formed along the cingulum by engaging a preparation guide device 100 and cutting teeth as the burr moves along a tool guide way 120.

The interior walls of prosthesis fixing grooves 86 thus formed have no undercut with respect to the prosthesis's intended axis of insertion. As shown in FIG. 23E, in one embodiment, the side surfaces 80 of such prosthesis fixing grooves 86 have sloped surfaces 80 that are consistent with or are slightly angled compared to the prosthesis axis of insertion 76. The angle formed between such sloped interior surfaces 80 and a line parallel to the prosthesis's axis of insertion, α,ranges from about 0° to about 3°. In one embodiment of the invention, the angle can be about 0.3°, about 0.4°, about 0.5°, about 0.6°, about 0.7°, about 0.8°, about 0.9°, about 1°, about 1.1°, about 1.2°, about 1.3°, about 1.4°, about 1.5°, about 1.7°, about 1.9°, about 2°, about 2.3°, about 2.7°, about 3°, about 3.5°, or about 4°. In other embodiments, the angle can be within the range of two of the aforementioned numbers. The grooves formed on two teeth have the same axis of insertion.

Figure 23A:
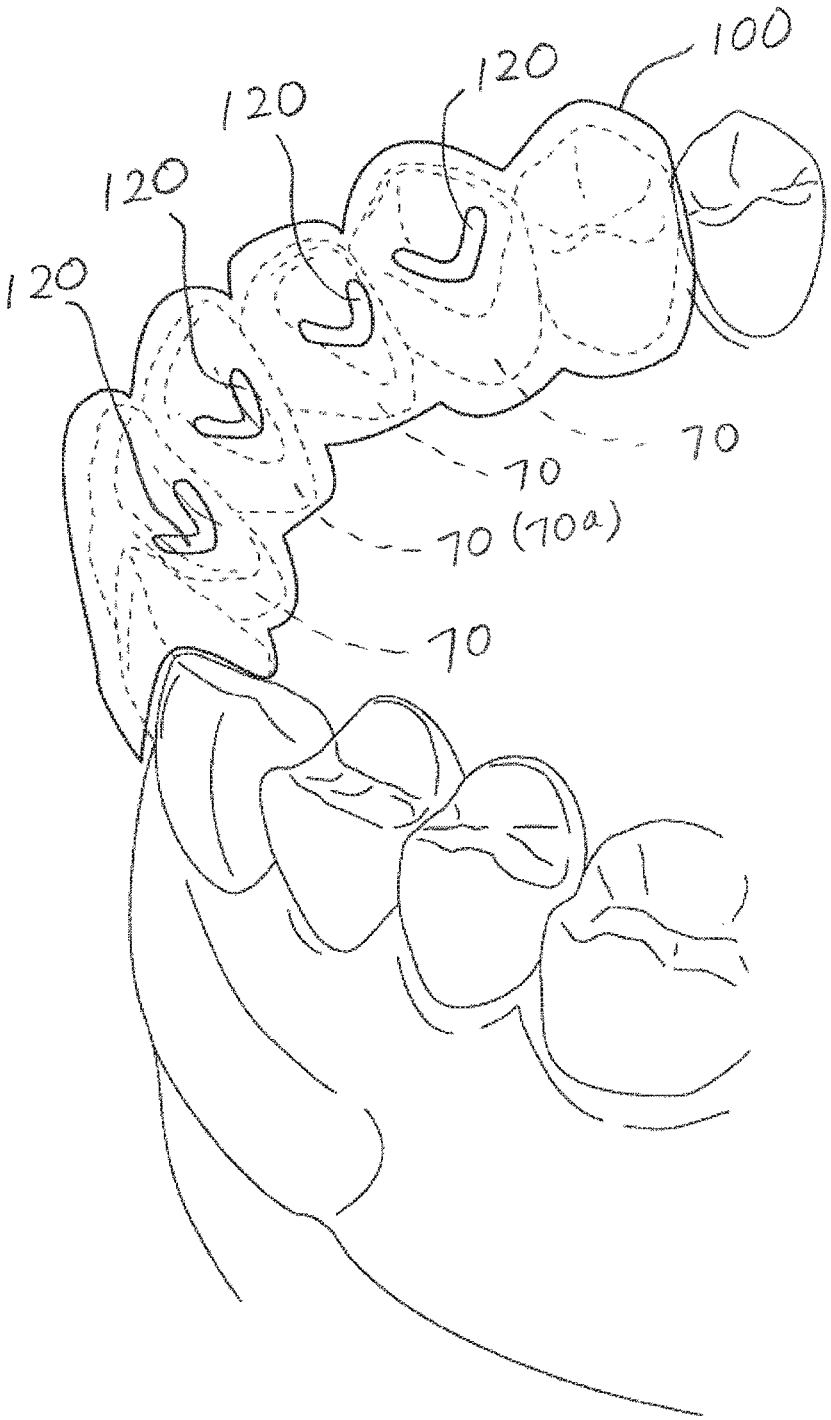
FIG. 23A is a perspective view of a preparation guide device in accordance with one embodiment as mounted on teeth.
Figure 23B:
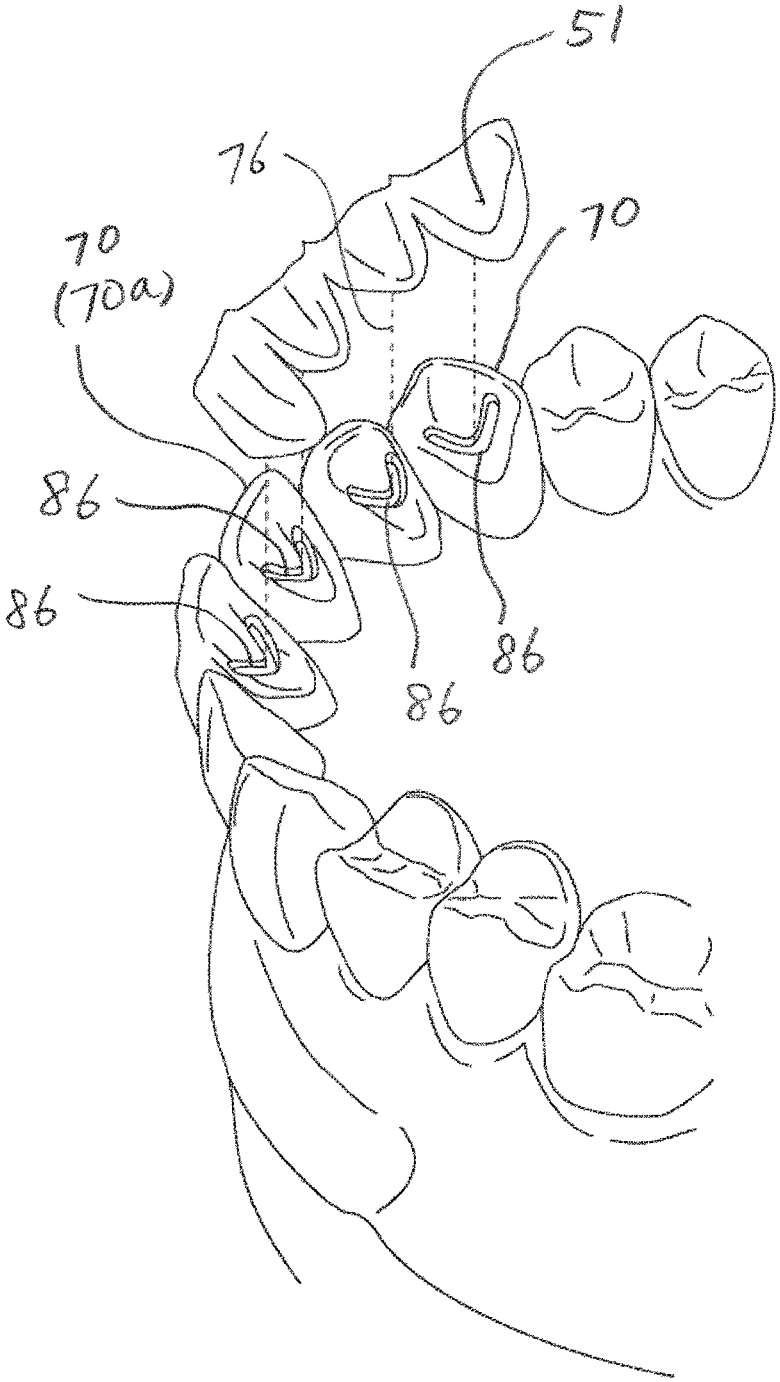
FIG. 23B is a perspective view of prepared teeth and a splint prosthesis to be installed on the prepared teeth in accordance with one embodiment.
Figure 23C:
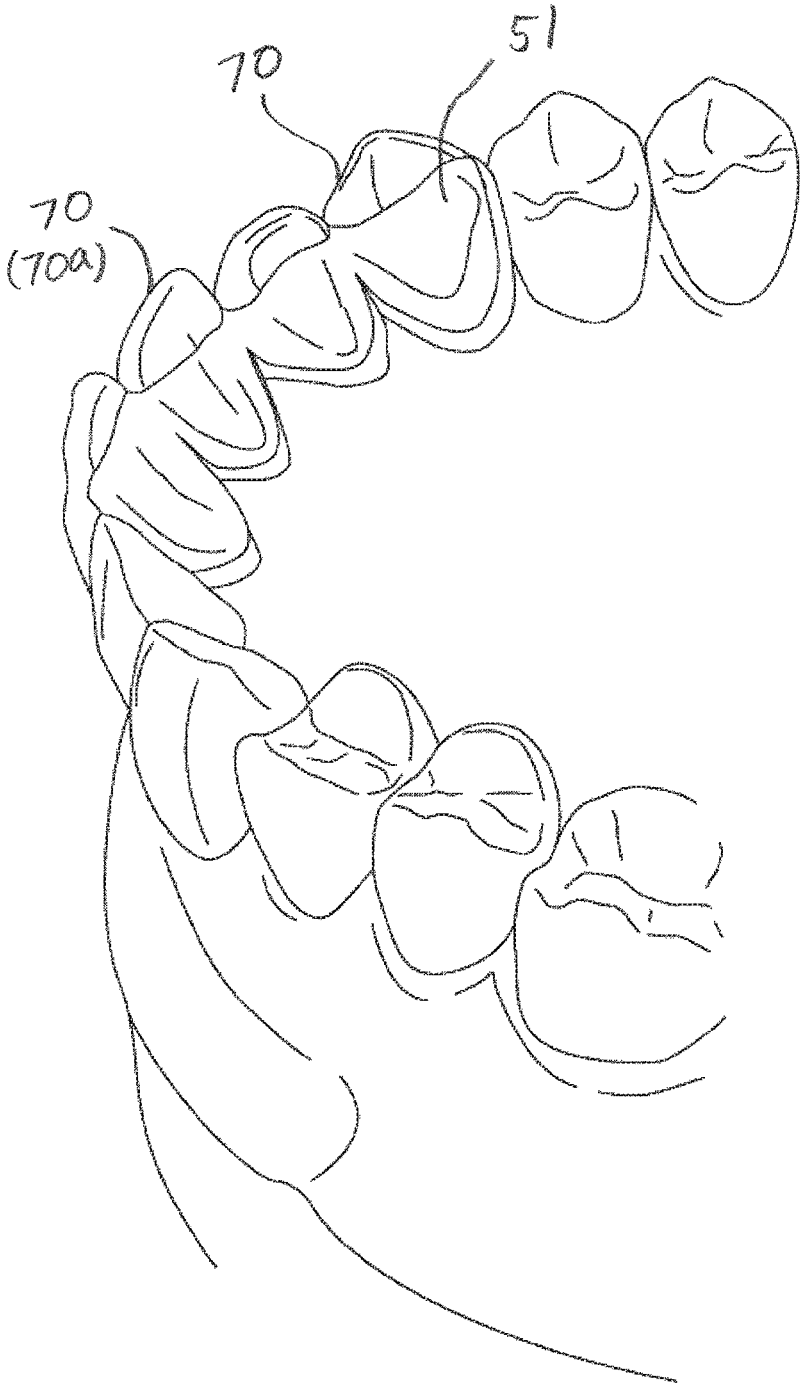
FIG. 23C is a perspective view of the prepared teeth an the splint prosthesis shown in FIG. 23B as installed on the prepare teeth.
Figure 23D:
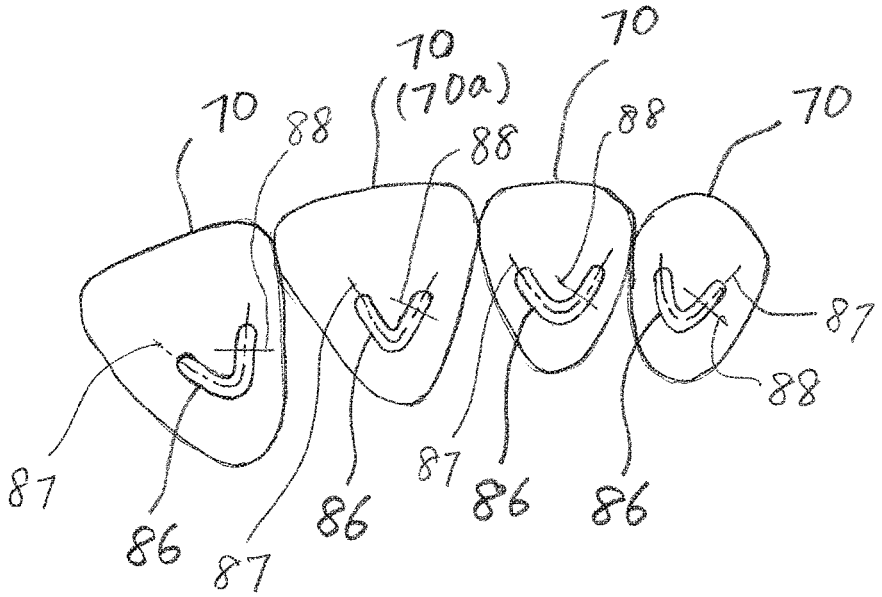
FIG. 23D is a plan view of teeth viewed along an axis of prosthesis insertion.
Figure 23E:
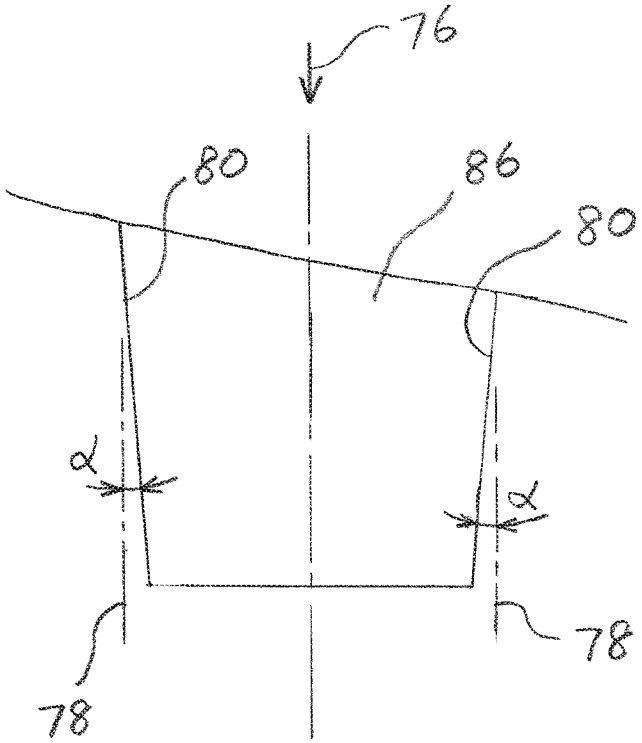
FIG. 23E is a cross-sectional view of a groove shown in FIG. 23D.
Figure 23F:
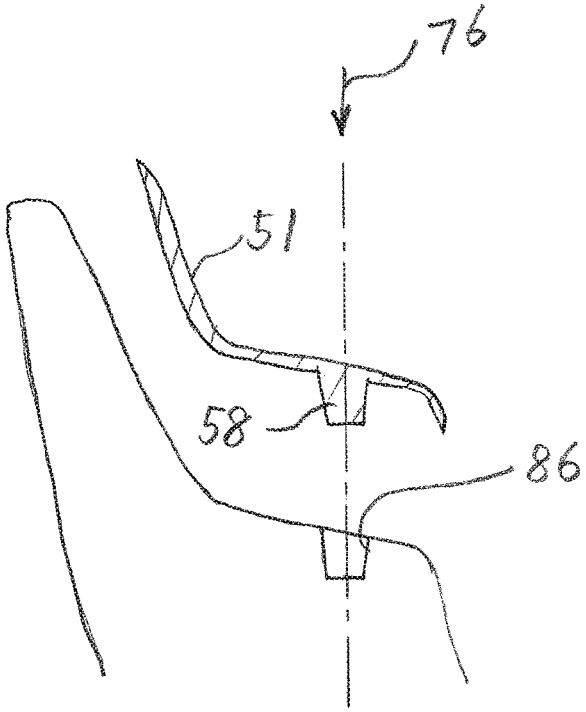
FIG. 23F is a cross-sectional view of a prepared tooth and a prosthesis to be installed on the prepared tooth.
Figure 23G:
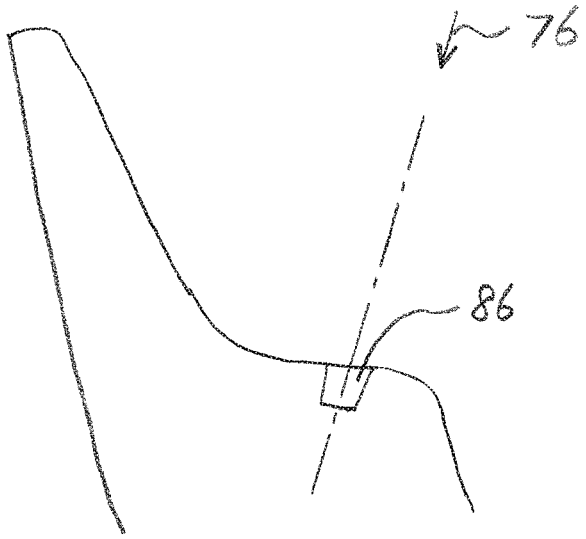
FIG. 23G is a cross-sectional view of a tooth having an inclined prospective axis of prosthesis insertion in accordance with one embodiment.

As shown in FIGS. 23F and 65, fixing projections 58 of the prosthesis are formed such that they can be inserted and fixed within the prosthesis fixing grooves 86. Thus, the projections 58 on both sides of an artificial tooth protrude in the same direction as the axis of insertion of the prosthesis. In one embodiment, the side surfaces of the projection 58 also have the same or slightly larger sloped angle compared to that of the side surfaces of the prosthesis fixing grooves 86. In one embodiment, the configurations and structures of such fixing projections, prosthesis fixing grooves, and prosthesis axis of insertion are the same as described below for an embodiment as shown in FIG. 23B.

Each tool guide way 120 of the preparation guide device 100 includes a projected structure 1102 that extends and protrudes up from a lingual sidewall 110. The projected structure 1102 includes a non-cutting access way 1202 in the tool guide way 120, which extends to a tool entrance 125 located on the lingual side of the projected structure 1102. Thus, unlike in an embodiment where an entrance is located on a sidewall 110, notches are not formed on the sidewalls 110 of the preparation guide device 100 of the embodiment, allowing the preparation guide device 100 to be firmly engaged. Such configuration with a tool entrance located on the projected structure that extends up from a sidewall can also be applied to preparation guide devices for posterior teeth as well as for anterior teeth.

Figure 78:
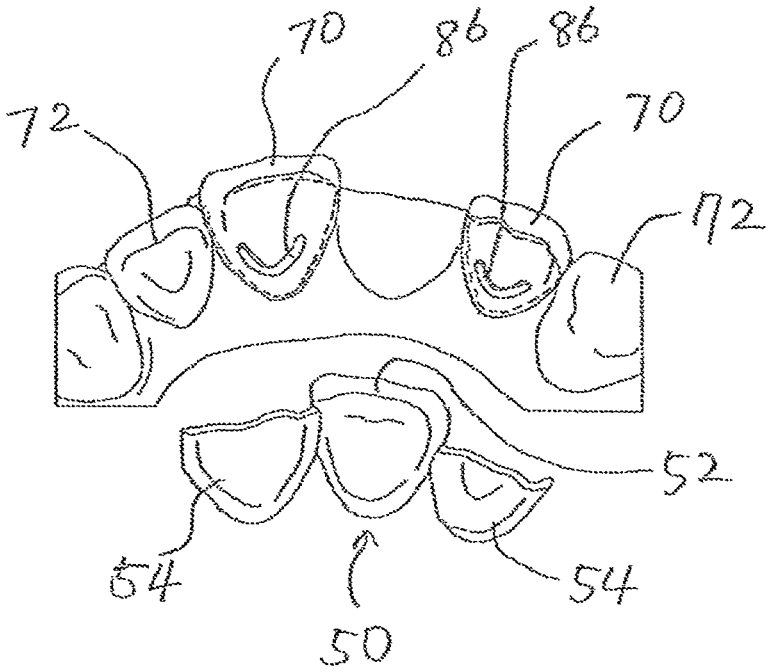
FIG. 78 is a perspective view of prepared anterior teeth and a prosthesis to be installed on the prepared anterior teeth in accordance with one embodiment.
Figure 80:
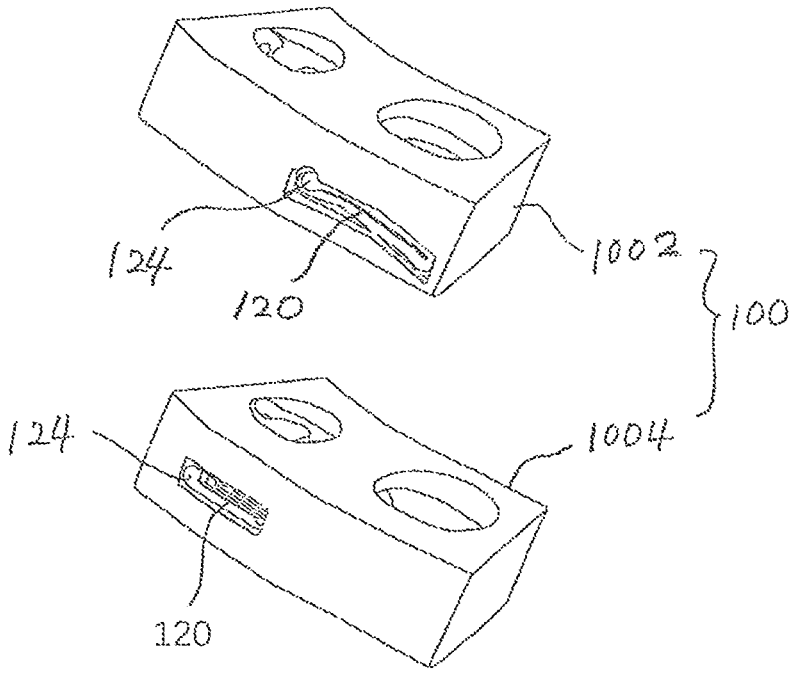
FIG. 80 is a perspective view of a pair of preparation guide devices in accordance with one embodiment.

Embodiment as Shown in FIGS. 76-78

As shown, in FIGS. 76-78, the preparation guide device 100 according to one embodiment includes tool guide ways 120 that guide burrs to cut two anterior teeth along the cingulum. Such preparation guide device differs from the embodiments shown in FIGS. 57-65 in that a tool hole 124 is configured to allow the burr 200 to be inserted top down and in that it provides an open portion 118 on the bottom of a sidewall 110. Other basic configurations of the embodiment are similar to those of other embodiments, as shown in FIGS. 57-65.

Preparation Guide Device Set for Cutting Teeth

Either one or two preparation guide devices can be used to cut teeth for crown bridge prosthesis. In an embodiment where two preparation guide devices are used to cut a single tooth, one of the preparation guide devices is configured to engage a tooth before any cutting is performed. The other preparation guide device is configured to engage a tooth after cutting some portions so as to allow cutting of portions that remain uncut after the first cutting process. Thus, the first preparation guide device is used to cut portions or the entirety of proximal, occlusal, buccal or lingual surfaces of a tooth. Then, the second preparation guide device is used to cut remaining portions that require additional cutting after the cutting process using the first preparation guide device is completed.

Use of two preparation guide devices is advantageous for maintaining the position of the preparation guide device while cutting teeth. This is so for the first preparation guide device because the remaining uncut portions of teeth continue to provide retention force to maintain the preparation guide device in place. The second preparation guide device can continue to obtain retention force from portions that remain uncut and will not be cut during the whole process. In addition, it is less likely that a tool guide way of the preparation guide device for cutting side surfaces and a tool guide way for cutting occlusal surfaces cross each other, thus preventing the preparation guide device from becoming relatively large or complicated. Therefore, it is possible to cut teeth without having any conflict between guide slots for cutting side surfaces (buccal, lingual, and proximal surfaces to be more specific) and guide slots for cutting occlusal surfaces. In one embodiment, the preparation guide device with a tool guide way mainly for cutting lingual surfaces of a tooth includes a tool guide way for cutting occlusal surfaces on the cheek side of that tooth (see FIG. 82). In addition, another preparation guide device with a tool guide way mainly for cutting lingual surface of a tooth includes a tool guide way for cutting occlusal surfaces on the tongue side of that tooth (see FIG. 84).

Embodiment as Shown in FIGS. 80-85

FIGS. 80-85 show a pair of preparation guide devices according to one embodiment of the invention to cut teeth in preparation for engaging a crown and bridge prosthesis 50. The first preparation guide device [100] *1002*, as illustrated in FIGS. 80A, 81, and 82, is configured to cut a molar's occlusal surface on the buccal side and side surfaces on the lingual side and a premolar's occlusal surface on the lingual side and side surfaces on the buccal side from uncut conditions. The second preparation guide device [100] *1004*, as shown in FIG. 80B, is configured to cut those portions that remain after cutting using the first preparation guide device [100] *1002*. These remaining portions are a molar's occlusal surface on the lingual side and side surfaces on the buccal side and a premolar's occlusal surface on the buccal side and side surfaces on the lingual side. Referring to FIGS. 81B and 81C, the first preparation guide device [100] *1002* is first engaged to cut an abutment tooth and is then removed. Subsequently, as shown in FIGS. 83B and 83C, the second preparation guide device [100] *1004* is engaged to cut the abutment tooth 70. The cutting process is completed once the second preparation guide device is removed, as shown in FIG. 85. The Crown and bridge prosthesis 50 is subsequently engaged.

Embodiment as Shown in FIGS. 93-104

A pair of preparation guide devices according to one embodiment, as shown in FIGS. 93-104, is configured for cutting teeth in preparation for engaging a crown prosthesis. The first preparation guide device 1002 of the pair, as shown in FIG. 93, is for culling a posterior tooth's buccal surface and occlusal surface on the lingual side. An installation supporting portion 102 of the first preparation guide device 1002 includes a mouthpiece-type shape so as to occupy only a small amount of space within the mouth.

In order to provide a tool guide way 120 for cutting the buccal surface, a projecting structure 150 extends from the top of the installation support portion 102. The interior of such projecting structure 150 includes a tool guide way 120, and the tool guide way 120 includes a tool hole 124. A projecting wall 152 surrounds the tool guide way 120 and the tool hole 124. In addition, to provide a tool guide way 120 for cutting the occlusal surface on the lingual side, a projecting structure 160 extends from the side of the installation fixing portion 102. The interior of such projecting structure 160 includes a tool guide way 120, and the tool guide way 120 includes a tool hole 124. A projecting wall 162 surrounds the tool guide way 120 and the tool hole 124.

Meanwhile, the second preparation guide 1004 for cutting posterior tooth's lingual surface and occlusal surface on the buccal side also includes a mouthpiece-type shape. Similar to the first preparation guide device 1002, the second preparation guide device 1004 includes a first projecting structure 150 that extends from the top to provide a tool guide way 120 for cutting the lingual surface and a second projecting structure 160 that extends from the side to provide a tool guide way 120 for culling then occlusal surface on the buccal side. The interior of these projecting structures 150, 160 include tool guide ways 120 and tool holes 124. Structures of the tool guide ways 120 and tool holes 124 of the preparation guide devices 1002, 1004 can include any of the structures as described in embodiments above or below.

Embodiment as Shown in FIGS. 86-87

Referring to FIG. 86, the preparation guide device 100 according to one embodiment of the invention is for cutting labial surfaces of anterior teeth in preparation for engaging an aesthetic prosthesis 50, such as laminates. Burrs shown in FIG. 87 can be used in combination with a preparation guide device illustrated in FIG. 86 to cut anterior teeth in preparation for engaging a laminate prosthesis 50.

Using a Preparation Guide Device for Restoration of Alveolar Bones or other Dental Procedures Embodiments mentioned above mainly use a preparation guide device for dental procedures to restore lost portions of teeth, such as in combination with bridge prosthesis. The invention, however, is not limited to such uses. In an embodiment of the invention, a preparation guide device can be used not only to cut teeth but also to attach materials to support an alveolar bone when the alveolar bone is damaged or broken. In an embodiment, after cutting an alveolar bone, material to support the alveolar bone can be inserted to stabilize a broken portion or to restore a damaged portion. In some embodiments, a preparation guide device can be used to recover a damaged alveolar bone in preparation for implants.

In some embodiments, procedures for cutting an alveolar bone using a preparation guide device is different from using the same for cutting teeth in that a support portion of a preparation guide device comes into contact with an alveolar bone to prevent the preparation guide device from moving. In some embodiments, other aspects of the two procedures are substantially similar. Similar to embodiments where a preparation guide device is used to cut teeth, in embodiments for cutting an alveolar bone, teeth present near the alveolar bone to be cut, if any, can further supply retention force.

In an embodiment of the invention, an alveolar bone can be cut in various forms by moving a burr along a tool guide way of a preparation guide device, and implants of various forms, such as a mesh, bar or net, can be inserted as needed. Although implant procedures generally comprise drilling a hole in an alveolar bone in a top-down direction, an embodiment of the invention allows for cutting portions of alveolar bones in various forms as needed while moving a burr along a cutting guide way of a preparation guide device. Thus, in some embodiments, alveolar bones can he cut in horizontal or curved directions, among others.

In addition, in some embodiments, methods of producing a prosthesis designed for minimally invasive cutting can be applied to produce laminates for aesthetic purposes and splints to stabilize teeth as well. Also, in some embodiments, crown bridges and crown and bridge prosthesis designed for minimally invasive cutting can also be produced using a preparation guide device. Furthermore, in other embodiments, prosthesis to prevent food particles from becoming stuck in between teeth that require only minimally invasive cutting can be produced. For such purposes, it is important to cut a minimally invasive amount while securing sufficient retention force by grouping a number of teeth where food particles are easily stuck when determining the appropriate axis of insertion of the prosthesis. Large amounts of cutting may be required if the axis of insertion is not ideal.

Various forms of prosthesis may be produced using a preparation guide device of embodiments of the invention. In some embodiments, a prosthesis can be produced before cutting of teeth using a preparation guide device because the prospective cut shape of teeth is predictable.

Furthermore, in sonic embodiments, a preparation guide device may be used to insert a pillar comprising both a crown bridge, either inlay or onlay, and endodontic treatment on a tooth. Also, in some embodiments, a preparation guide device may be used to cut remains of a damaged tooth that is not pleasing for aesthetic reasons or is important for stabilization purposes for further dental procedures, In other words, in some embodiments, traditional prosthesis, including splints, laminates, and crown bridges, all remain as viable options in combination with use of a preparation guide device.

Additionally, according to an embodiment of the invention, a prosthesis with sufficient retention force may be produced, by cutting minimally invasive amounts of teeth in a shape of a scratch, hole, or groove such that the direction of cutting corresponds to the prosthesis's axis of insertion. In some embodiments, factors that allow for minimally invasive cutting while obtaining sufficient retention force or aesthetic value can easily be determined. In some embodiments, such factors can include, among others, preferable amounts and portions of a tooth to be cut and a prosthesis's axis of insertion.

Splint Prosthesis

When an alveolar bone is damaged, teeth that are supported, by the damaged portion of the alveolar bone begin to shake. If a shaking tooth is neglected, the alveolar bone is damaged further and the shaking tooth eventually fails out. In an embodiment, to prevent such results, a shaking tooth and its adjacent teeth may be connected via a prosthesis to stabilize the shaking tooth. Such prosthesis that connects a shaking tooth and its adjacent teeth is called a splint prosthesis. In an embodiment, if a shaking tooth is fixed via a splint prosthesis, the alveolar bone located below the shaking tooth can be stabilized. In such embodiments, a stabilized alveolar bone strongly supports the tooth to prevent it from shaking. In addition, in such embodiments where a splint prosthesis fixes a shaking tooth, damage to the alveolar bone can be delayed, and the alveolar bone can regenerate in some cases as well.

To install a splint prosthesis according to an embodiment of the invention, damage to the alveolar bone is first diagnosed and teeth to engage the splint prosthesis are determined. In some embodiments, a splint prosthesis is engaged on two or more adjacent teeth. In some embodiments, a rough configuration of the splint prosthesis is determined once the teeth to engage the splint prosthesis are determined. A splint prosthesis according to an embodiment has a structure that can very strongly unite the teeth it is engaged upon without requiring a crown structure. Thus, in some embodiments, such a splint prosthesis does not include any crown structure that requires cutting of whole occlusal surfaces and/or side surfaces. On the other hand, according an embodiment, appropriate occlusal or side surfaces of teeth to engage a splint prosthesis is cut using a preparation guide device. in some embodiments, a splint prosthesis includes structures that tightly fit with the shape of such cut portions so that it is strongly fixed and bonded.

Splint Prosthesis for Anterior Teeth

Referring to FIGS. 23A, 23B, and 23C, in an embodiment, a splint prosthesis [60] is engaged to fix a shaking tooth 70 a with its adjacent teeth. In order to do so, a preparation guide device 100 of an embodiment is engaged on a shaking tooth 70 a and its adjacent teeth 70. In some embodiments, the preparation guide device 100 includes a tool guide way 120 per tooth. In some embodiments, such tool guide ways 120 generally have an arrow-shaped guide channel. In some embodiments, arrow-shaped prosthesis fixing grooves 86 are formed on each tooth, as illustrated in FIGS. 23B and 23D, as a burr moves along the guide channels of a tool guide way 120.

FIG. 23D illustrates an embodiment where prosthesis fixing grooves 86 are formed on teeth as viewed from the prosthesis's axis of insertion 76. Referring to FIG. 23F, a splint prosthesis 51 of an embodiment has a single body structure which includes one fixing projection 58 per tooth. In some embodiments, such fixing projections protrude and extend in the prosthesis's axis of insertion. In an embodiment, these fixing projections 58 are inserted into their respective prosthesis fixing grooves 86 and are cemented such that the splint prosthesis 51 is fixed on teeth (see FIG. 23C). As such, in an embodiment, the shaking tooth 70a becomes connected to its adjacent teeth, substantially reducing the shaking which in turn can allow the supporting alveolar bone to regenerate.

In an embodiment as shown in FIGS. 23B, 23D, and 23F, four fixing projections 58 protrude and extend in the prosthesis's axis of insertion 76. FIG. 23D illustrates each prosthesis fixing groove's 86 centerlines 87 that depict a burr's axis of rotation (see 201 of [FIG. 92] *FIGS. 92A-92B*) as it proceeds along a tool guide way 120. FIG. 23E is a cross-sectional view of a prosthesis fixing groove 86 of an embodiment cut along a line 88 perpendicular to the centerline 87 at any given point thereof. In such embodiment, it can be seen that all four prosthesis fixing grooves 86 are sloped inwards along the prosthesis's axis of insertion 76.

In an embodiment as shown in FIG. 23E, no undercut in the prosthesis's axis of insertion 76 exists on the interior of prosthesis fixing grooves 86. In an embodiment, a sidewall 80 of a prosthesis fixing groove is sloped in the prosthesis's axis of insertion. The angle $\alpha$ between such sidewall 80 and a line 78 parallel to the prosthesis's axis of insertion 76 ranges from about 0.3° to about 3°. In an embodiment of the invention, the angle $\alpha$ is about 0.4°, about 0.5°, about 0.6°, about 0.7°, about 0.8°, about 0.9°, about 1°, about 1.1°, about 1.2°, about 1.3°, about 1.4°, about 1.5°, about 1.7°, about 1.9°, about 2°, about 2.3°, about 2.7°, about 3°, about 3.5°, or about 4°. In other embodiments, the angle $\alpha$ can be within a range of any of the two aforementioned numbers. In some embodiments, prosthesis fixing grooves with a relatively large sloped angle can be easier to insert a fixing projection into but can have less retention force compared to those with a relatively small sloped angle.

In an embodiment, all four prosthesis fixing grooves 86 as shown in FIG. 23B can be cut with a single burr. In some embodiments, when a single burr cuts all four prosthesis fixing grooves 86 so that the angles of the side surfaces of each groove are all equal. In contrast, in other embodiments, each prosthesis fixing groove 86 can be cut with different burrs as well.

As shown in FIG. 23, other embodiments can cut teeth according to a prosthesis axis of insertion that is different from that shown in FIG. 23F.

Splint Prosthesis for Posterior Teeth

FIGS. 18A, 18B, 18C, and 116-123 show various splint prostheses for posterior teeth. In the embodiments illustrated in FIGS. 18A, 18B, and 18C, portions of lingual and proximal surfaces are cut, and a splint prosthesis 51 is engaged. In the illustrated embodiments, the splint prosthesis 51 is engaged to fix a shaking tooth 70a to its adjacent teeth while not damaging the contact points between the two teeth.

In the embodiments as shown in FIGS. 116-118, the preparation guide device 100 includes tool guide ways 120 for cutting the lingual, distal, and buccal surfaces of a first molar 70a, the lingual, mesial, and buccal surfaces of a second molar, and the lingual surfaces of a premolar. In the embodiments shown, the tool guide ways 120 are all connected such that the burr 200 is inserted top-down in a tool hole 124 and moved along the tool guide ways 120 for cutting. Although the contact point between two molars is cut in this embodiment, retention force of the prosthesis is stronger than that of the embodiment illustrated in FIG. 18 because the splint prosthesis 51 is engaged using both the lingual and buccal surfaces (which face each other) of each molar.

In the embodiments illustrated in FIGS. 119-121, the preparation guide device 100 includes tool guide ways 120 for cutting the lingual, distal, and buccal surfaces of a second molar, the lingual and buccal surfaces of a shaking first molar, and the lingual surfaces of a premolar. In the embodiments shown, the tool guide ways 120 are all connected such that the burr 200 is inserted in a tool hole 124 located near the premolar and is moved along the tool guide ways 120 for cutting. In this embodiment, the splint prosthesis 51 can be engaged without damaging the contact points between two adjacent teeth. In addition, retention force of the prosthesis is stronger than that of the embodiment illustrated in FIG. 18 because the splint prosthesis 51 is engaged using both the lingual and buccal surfaces of each molar, which face each other.

In one embodiment, as shown in FIGS. 122-123, cutting occurs on the lingual, mesial, and buccal surfaces of a second molar, a portion of the lingual and proximal surfaces of a shaking first molar, and portions of the lingual and proximal surfaces of two premolars. In the illustrated embodiment, buccal surfaces of the two premolars and the first molar are not cut. In order to increase the retention force of the splint prosthesis, the prosthesis is inserted between the first molar's mesial surface and the second premolar's distal surface that face each other. The prosthesis is further configured to use a second molar's lingual and buccal surfaces. Thus, although the contact points between a second premolar and a first molar and between the two molars can be damaged according to this embodiment, the prosthesis can obtain sufficient retention force.

As such, multiple posterior teeth can also be connected using a splint prosthesis, and cutting methods for engaging a posterior splint prosthesis can use a preparation guide device according to the various embodiments described above.

Dental Procedure Using a Preparation Guide Device

In an embodiment, a dental procedure using the preparation guide device includes the steps of deciding which dental procedures to perform, gathering 3-D shape data about the teeth, selecting a final prospective shape with a prosthesis installed, designing the prospective shape of teeth after cutting, designing or selecting the burr, designing the preparation guide device, manufacturing the prosthesis, manufacturing the tool, manufacturing the preparation guide device, cutting the teeth, and installing the prosthesis.

Deciding on Dental Procedure and Collecting Data about Patient's Teeth

Referring to FIG. 105, when a patient visits a dental clinic, the dental practitioner examines the patient and decides on the dental procedure to be performed (S100). In an embodiment of the present invention, the dentist decides on a dental procedure that includes installing a prosthesis in the patient's mouth. At this time, the dental practitioner roughly considers the general configuration of the desired prosthesis. The specifics of the prosthesis are not designed at this point. For example, if a dentist decides to use a bridge prosthesis, the dentist can then decide how many and which teeth to use as abutments.

In an embodiment, then, 3-D data of the patient's teeth shape and/or mouth shape is gathered (S200). In some embodiments, collection of a patient's teeth data can occur before the dental practitioner diagnoses the patient or decides on a dental procedure. The collection of patient teeth data can occur in various places using various methods. In one embodiment, the dental practitioner obtains data of the patient's mouth shape using an impression. The dental practitioner or the dental lab forms a model of the mouth shape, including the teeth, using the acquired impression. In an embodiment, the shape of this model is scanned and digitalized using a 3-D scanner. In some embodiments, the scanning and/or manufacturing of the model takes place at the dentist's office. In other embodiments, the scanning and/or manufacturing takes place somewhere other than at the dentist's office, such as a lab. In such embodiments, the dental practitioner sends the impression to a dental lab or other location that performs the scanning and/or manufacturing. In such embodiments, the dental lab or other location creates a model based on the impression and digitalizes the data. Alternatively, in other embodiments, the dental practitioner can use an intra oral scanner to directly scan the oral shape and generate data, and send the data to the dental lab.

In other embodiments, collection of teeth data cart occur at a dental lab or another place other than the dentist's office. Images can be generated from the data collected in this way and sent to the dental practitioner, and the dental practitioner can determine the dental procedure based on these images.

Selecting Prospective Teeth Shape after Prosthesis Installation

In an embodiment, once a dental procedure is determined, data of the original teeth shape is processed to generate data about the prospective teeth shape after installation of the prosthesis and to generate a corresponding image. In one embodiment, data and image of the prospective shape are generated for various types of prosthesis. The generated images are sent to the patient. In some embodiments, the one or more images of prospective shapes of one or more teeth after installation of a dental prosthesis can be delivered to the patient via email, text message, mail, courier service, hand-delivery, video conference, in-person meeting with the patient or an agent thereof, posting on an Internet website, or any appropriate communication means currently existing or to be developed in the future. In an embodiment, the patient checks the images and chooses one of the suggested prospective shapes. The selected prospective shape becomes the final teeth shape after the installation of the prosthesis.

Designing Prospective Teeth Shape

In some embodiments, either prior to or after deciding the prospective shape of teeth after installation of prosthesis, post-cutting shapes are modeled and designed for each tooth using the CAD/CAM system (S300). In an embodiment, during the modeling process, the 3-D images of the teeth to be cut are tilted in multiple directions, and one orientation is selected out of the various options. In an embodiment, based on this orientation, the surface of the teeth to be cut and the axis of insertion or orientation of the prosthesis are later decided. In an embodiment, the basic structure of the desired prosthesis or corresponding, teeth cutting conditions or parameters, based on the selected orientation, are inputted into the computer program. In an embodiment, the program allows for designing the prospective teeth shape on the computer and displays the completed image on the screen. As illustrated in FIGS. 106-109, in some embodiments, the 3-D data about the prospective shape of teeth after cutting can be rendered ahead of time and displayed on the monitor as an image. In an embodiment, the portion to be cut and the amount to be cut are determined based on the prospective teeth shape.

Deciding the Axis of Insertion of Prosthesis

According to one embodiment, a dental practitioner selects the axis of insertion of the prosthesis which provides sufficient space for fixing the prosthesis while reducing the amount of teeth cut. More specifically, in some embodiments, the CAD/CAM computer program allows tilting of 3-D images of patient teeth in various directions. In some embodiments, the program can further display the portion of the teeth to be cut for each tilting direction based on preselected parameters. In one embodiment, such parameters can include the angle between the orientation and cut surface (see angle $\alpha$ in FIGS. 92B and 92C) and the location of the lower portion to be cut (e.g., the boundary between gum and teeth). In such embodiments, if one tilts the 3-D image in a certain direction and transposes a line with an angle of $\alpha$ (including 0 degrees) in reference to that direction on top of that orientation so that the line meets at a point on the boundary of the gum and teeth, such line will show the side surfaces of teeth that will be cut. If this process is repeated for all points on the boundary of gum and teeth, the amount of teeth cut (volume cut in 3D or depth cut in 2-D) when a particular orientation is selected can be displayed on the screen. Furthermore, by repeating this process for different orientations of the 3-D image, one can see how much of the teeth will be cut depending on the axis of insertion. Based on this, an axis of insertion can be determined so to obtain a prosthesis with a desired configuration while reducing the amount of teeth cut.

Designing Prosthesis

In an embodiment, once the prospective teeth shape after installing a prosthesis is determined, the prosthesis is designed based on such prospective shape (S700). As in the embodiment shown in the flowchart of FIG. 105, designing the prosthesis and deciding the prospective teeth shape can occur at the same time, but the present invention is not limited as such, In other embodiments, the prospective teeth shape can be determined prior to designing the prosthesis, and vice versa. Moreover, in another embodiment, the prosthesis shape and the prospective teeth shape can be decided at the same time by reviewing how the shape of one affects the shape of the other. For example, in an embodiment, this can be done by varying the prosthesis shape in view of the accompanying retention force and seeing the corresponding prospective teeth shape.

Designing Burr and Guide Device

In an embodiment, after the prospective teeth shape is designed, the burr is designed based on the prospective teeth shape. In designing the burr according to an embodiment, factors to consider include the diameter of the cutting head and the distance between the terminal end of the cutting head and the guide projections (S400). In some embodiments, the design of the burr can also involve using the CAD/CAM system. Although a burr is designed in the foregoing embodiment, in other embodiments, several burrs can be manufactured or designed beforehand and selected appropriately in view of the teeth to be cut.

In an embodiment, after designing the prospective teeth shape and deciding on a burr, the travel path for the burr is determined using the CAD/CAM system (S500). As in the illustrated embodiments, the design of the path can occur at the same as the design of the tool by showing how they affect one another. In an embodiment, after the path is decided, a preparation guide device that has a tool guide way in the shape of the path is designed (S600). As shown in FIGS. 100-115, in an embodiment, the design of the preparation guide device can be reviewed as a graphic image. According to an embodiment, the installation portion of the preparation guide device is designed using factors such as abutment teeth data, adjacent teeth data, and gum data. In some embodiments, the number and shape of the burr entrance and the number and shape of the cooling water are also designed.

In the above embodiments, the burr is designed first, and the preparation guide device is designed subsequently, but the design of the burr and the preparation guide device can occur at the same time by considering how they affect each other.

Manufacturing Prosthesis, Guide Device, and Burr

In an embodiment, the prosthesis is manufactured according to the design of the prosthesis (S800), and the preparation guide device is manufactured according to the design of the preparation guide device (S620). In an embodiment, the burr is produced according to the design of the burr (S640).

Sending Prosthesis, Guide Device, and Burr

In an embodiment, once the prosthesis, guide device, and burr are manufactured, they are sent to the location where the dental procedure will he performed (S900). In one embodiment, the prosthesis, guide device, and burr are sent as a kit in a single box or in a single container. An embodiment can include an indication in an appropriate location on each of the three items to show that the items are for the same patient. In some embodiments, such indication can be the patient's name or identification information. In other embodiments, markings can be placed on the packaging if it is difficult to include the indication on the product itself in some embodiments where one patient requires multiple guide devices, indications can note for which tooth/teeth the preparation guide device and burr will be used. Moreover, in some embodiments where two or more guide devices are needed for a single tooth, an indication can denote the order in which the preparation guide devices should be used.

Cutting, Teeth and Installing Prosthesis

In some embodiments, when the patient visits the dentist's office, cutting is performed by installing the preparation guide device inside the mouth and installing the burr on the hand piece (S1000). Once the cutting is completed, the prepared prosthesis is installed immediately on the cut teeth in some embodiments. In some embodiments, cementing procedures can be used to engage the teeth if necessary.

Using CAD/CAM System

The preparation guide device according to an embodiment of the present invention can be designed and manufactured using a CAD/CAM system that employs computer design/manufacturing. In some embodiments, if a CAD/CAM system is used to manufacture prosthesis, precision can be achieved, costs can be reduced, and the production time can be shortened. In some embodiments, for example, a dental lab can manufacture a preparation guide device using data received about the teeth to be cut or the teeth to be used as abutments or using digitalized data of an impression.

More specifically, in some embodiments, numbers regarding the retention force needed by a prosthesis are obtained from a database in view various external forces such as chewing force and oral environment. Then, an insertion path for the prosthesis that can meet the required retention force with the minimum amount of cutting can be determined. Accordingly, in an embodiment, the shape, amount, and portion to be cut are determined to provide the desired retention force. A preparation guide device is then designed in the CAD system by analyzing such data. A preparation guide device thus prepared can then allow for optimal cutting of teeth. In some embodiments, it is also possible to make various prostheses with minimally invasive cutting. In some embodiments, Depending on the oral environment, well-known studies cart be used, to determine how much retention force is needed by the abutment teeth depending on the oral environment in order for a prosthesis to be fixed. In other words, some embodiments may employ existing studies that have analyzed how well a prosthesis withstands various types of forces exerted on the teeth, including bite force, tensile force, shear force, and rotational force. In some embodiments, dental practitioners can also accumulate data to use for their own dental procedures.

In an embodiment, a CAD/CAM system can be used to calculate the surface area of a tooth to be used as abutment to determine the percentage that needs to be cut. Also, in some embodiments, an optimal location that can provide maximum retention force with minimal invasive cutting can be determined. In some embodiments, whether the retention force is sufficient can be determine at this time. In some embodiments, data for calculating the retention force can be inputted into a computer for simulation. In other embodiments, the CAD/CAM system can be used to determine the optimal portion and shape for cutting for aesthetic prosthesis.

Examples of Designing Guide Device Using CAD/CAM System

Figure 127:
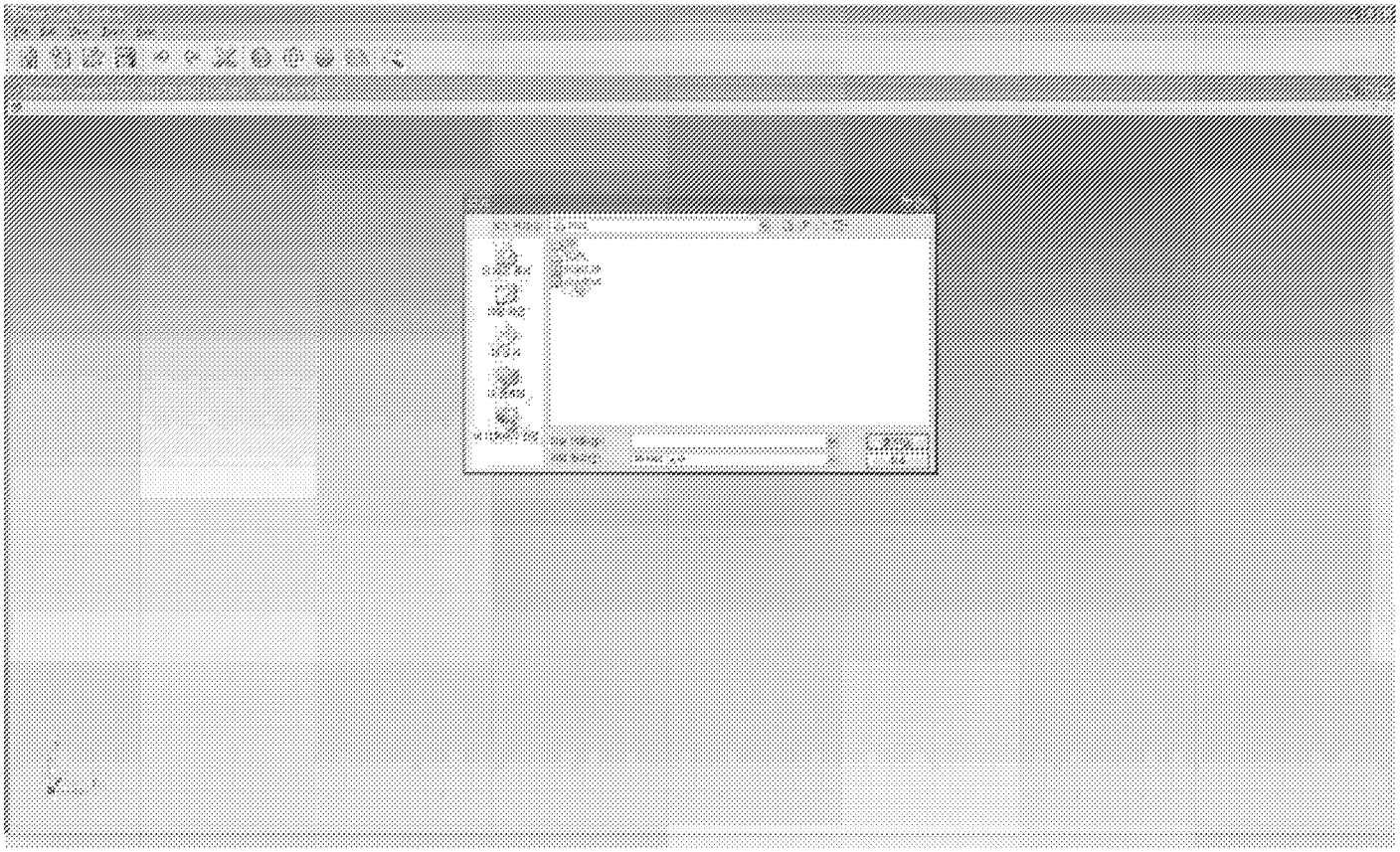
Figure 128:
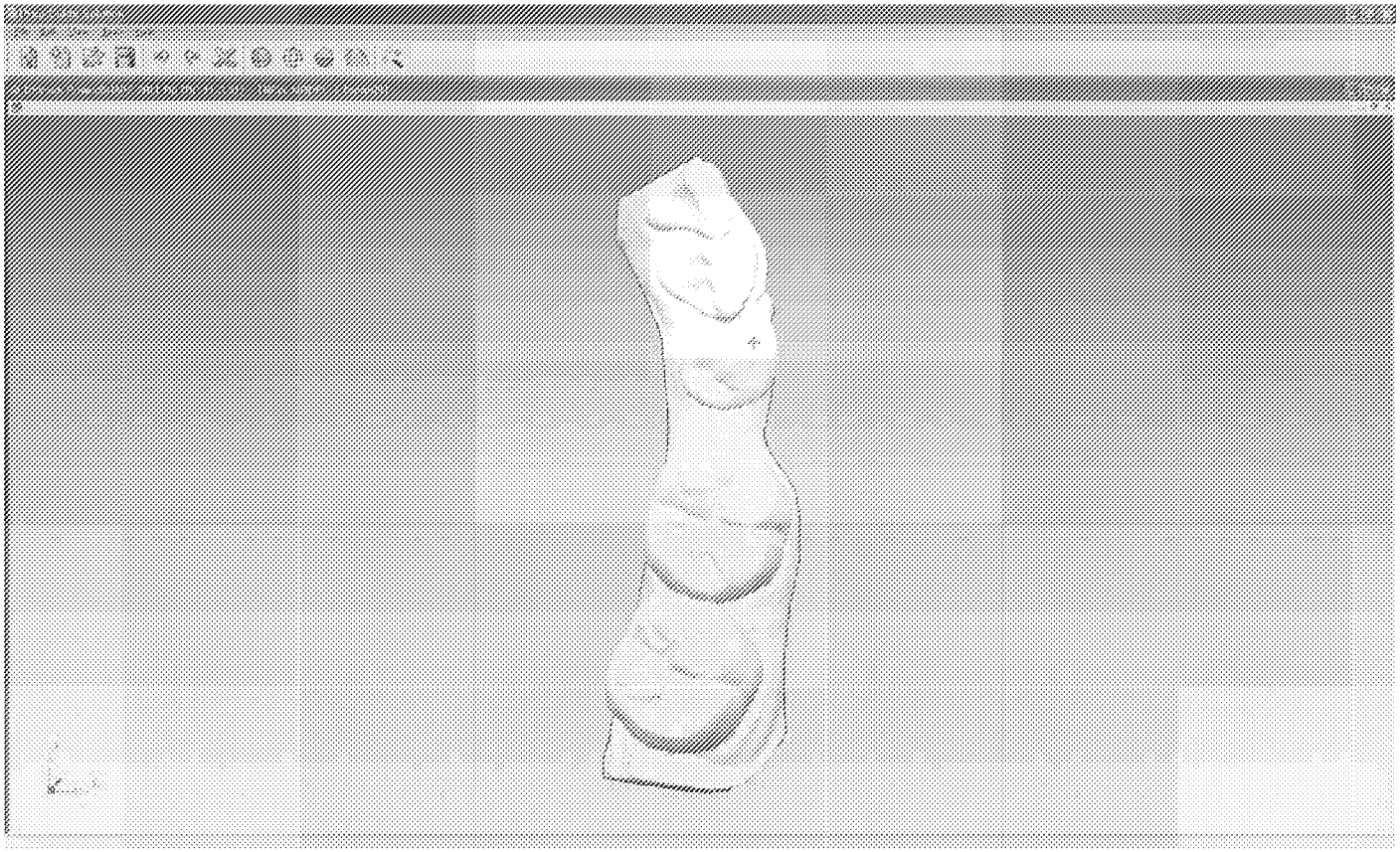
Figure 129:
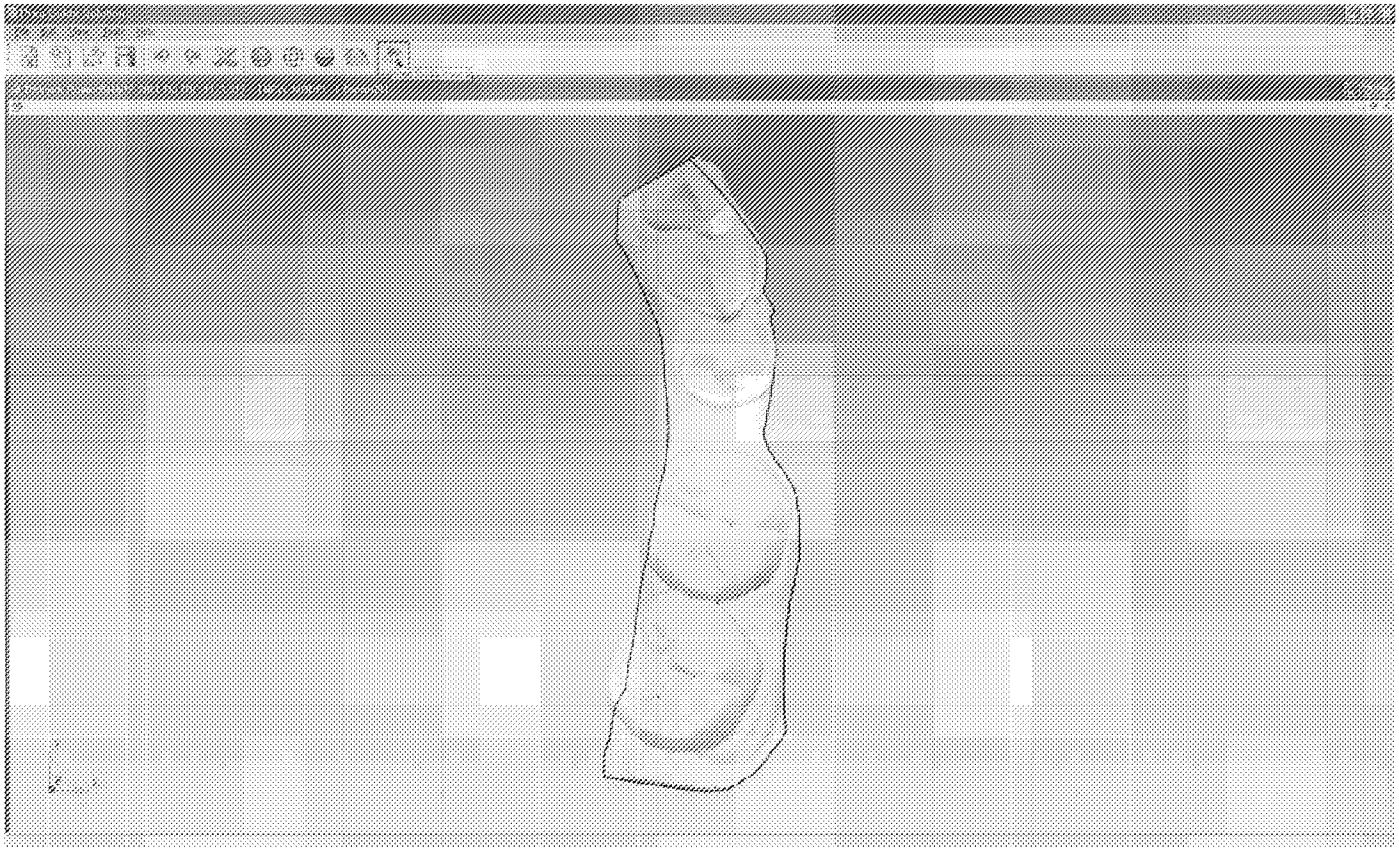
Figure 130:
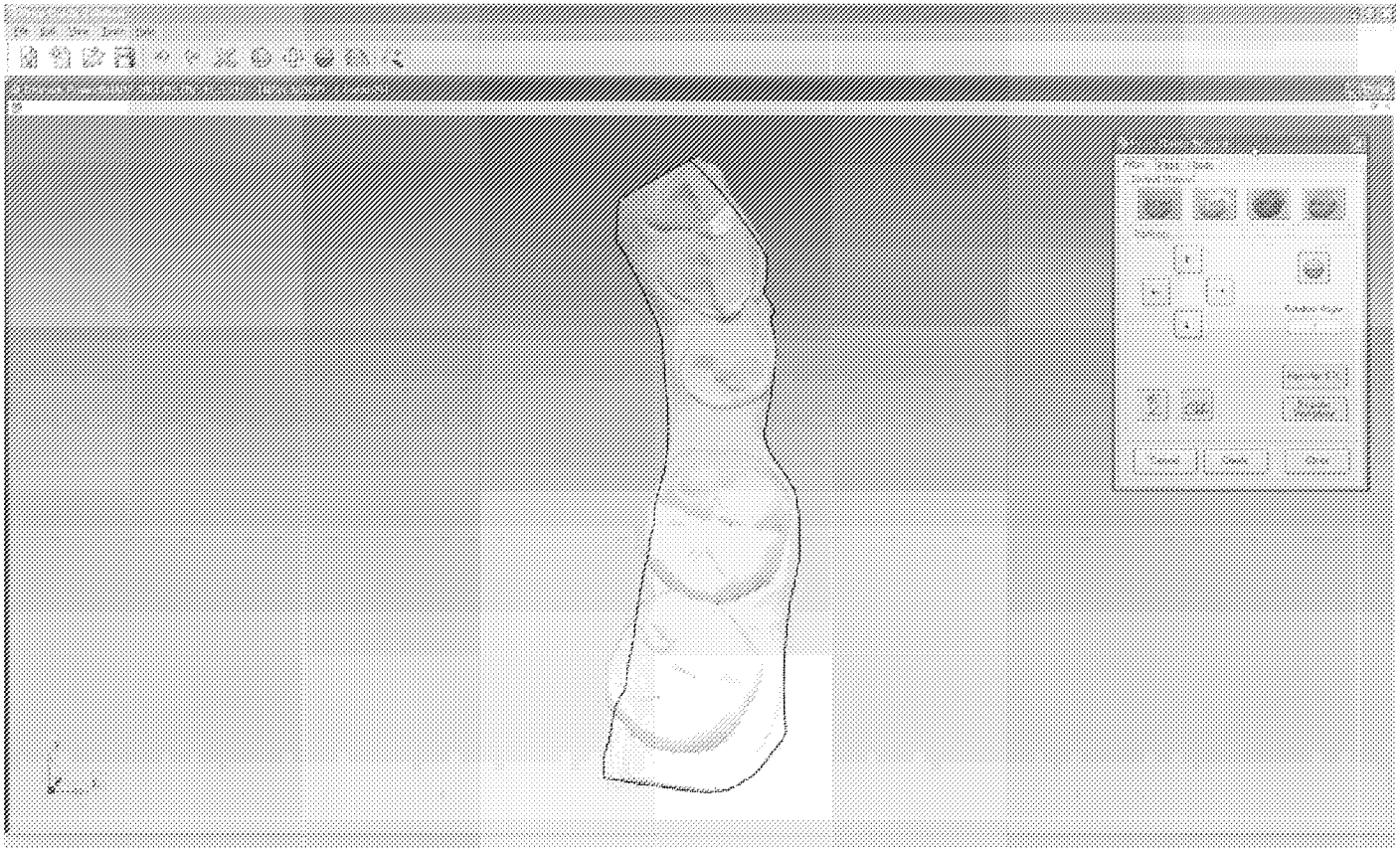

FIGS. 127-172 illustrate screen shots which show steps of designing a preparation guide device by processing 3-D (three dimensional) data of a tooth using a CAD/CAM computer system in an embodiment. in an embodiment as shown in FIG. 127, a user selects a set of data of teeth among those listed on a screen. The selected data set is then processed. Then, in an embodiment as shown in FIG. 128, the computer system displays an image of a model for a patient's tooth and gum portions corresponding to the selected data set by processing the selected 3-D data set for the selected patient's teeth. In an embodiment, while the selected teeth image is being displayed as shown in FIG. 129, the user clicks a "Prep Guide Wizard" icon, for designing a preparation guide device. Subsequently, in an embodiment as shown in FIG. 130, the computer system displays a menu window with design tools.

Figure 131:
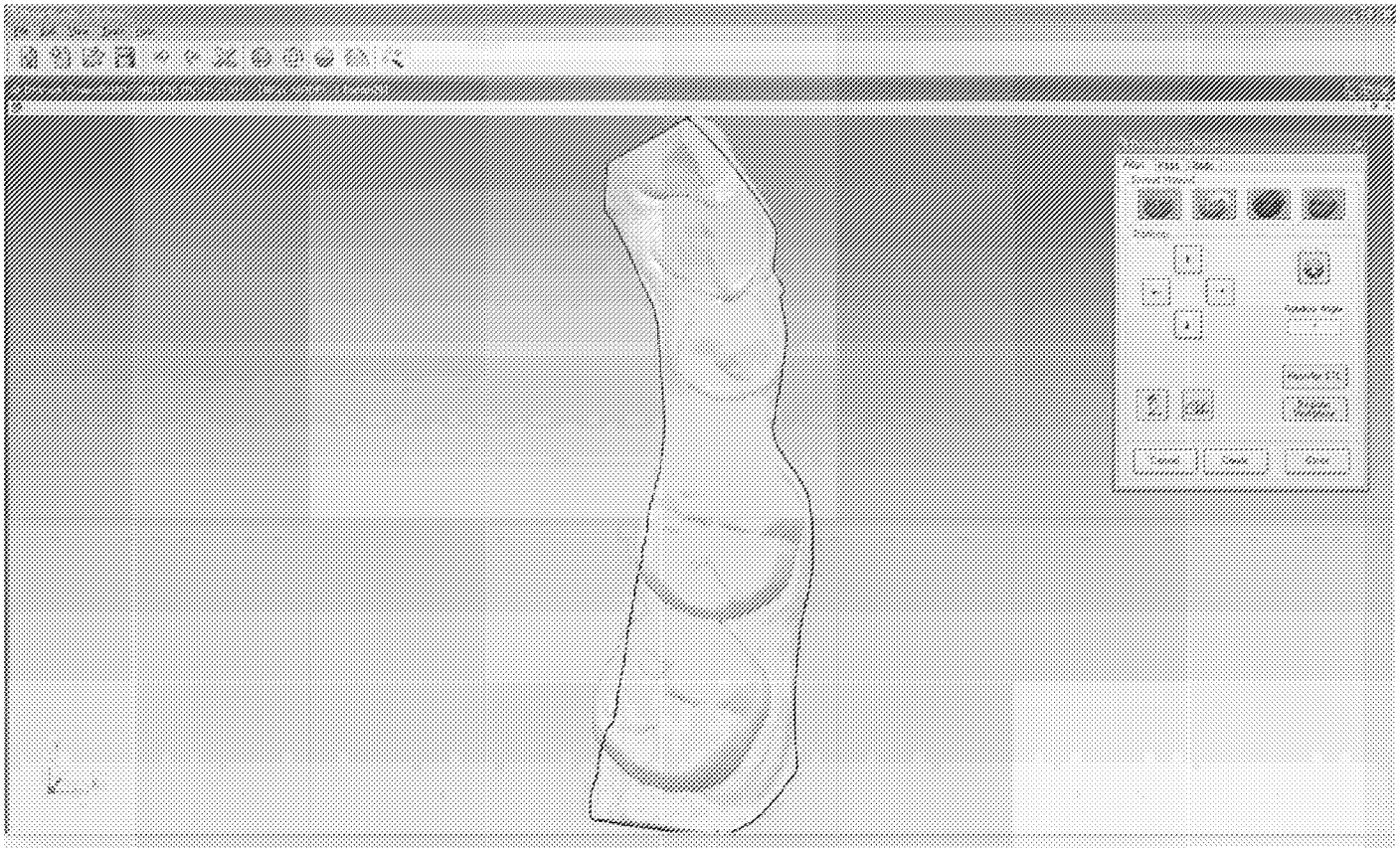
Figure 132:
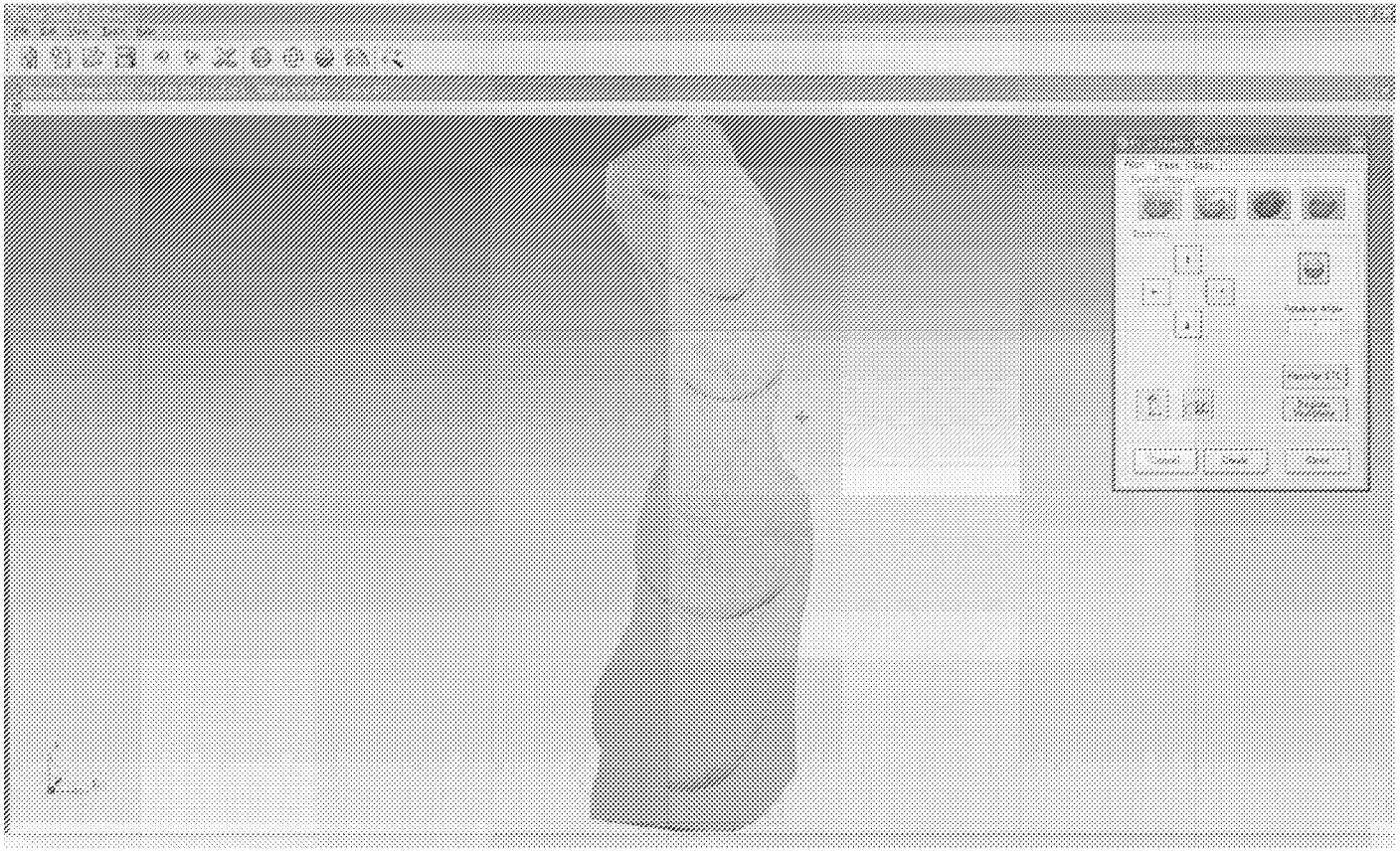

In an embodiment as shown in FIG. 131, the user clicks an "Align" tab within the menu window for determining the axis of prosthesis insertion. Then, in an embodiment as shown in FIG. 132, the computer system provides an interactive screen image of the selected teeth so that the user can see different views of the teeth with different view angles. In an embodiment, the user can change the viewing angle by dragging a curser with a mouse or by using arrow keys. In response, the computer system of an embodiment interactively displays a view of the selected teeth corresponding to the selected viewing angle. In an embodiment, when the user stops the dragging and selects a view of the selected teeth that is currently displayed, the viewing angle of the image is recognized a candidate for a prospective axis of prosthesis insertion.

Figure 133:
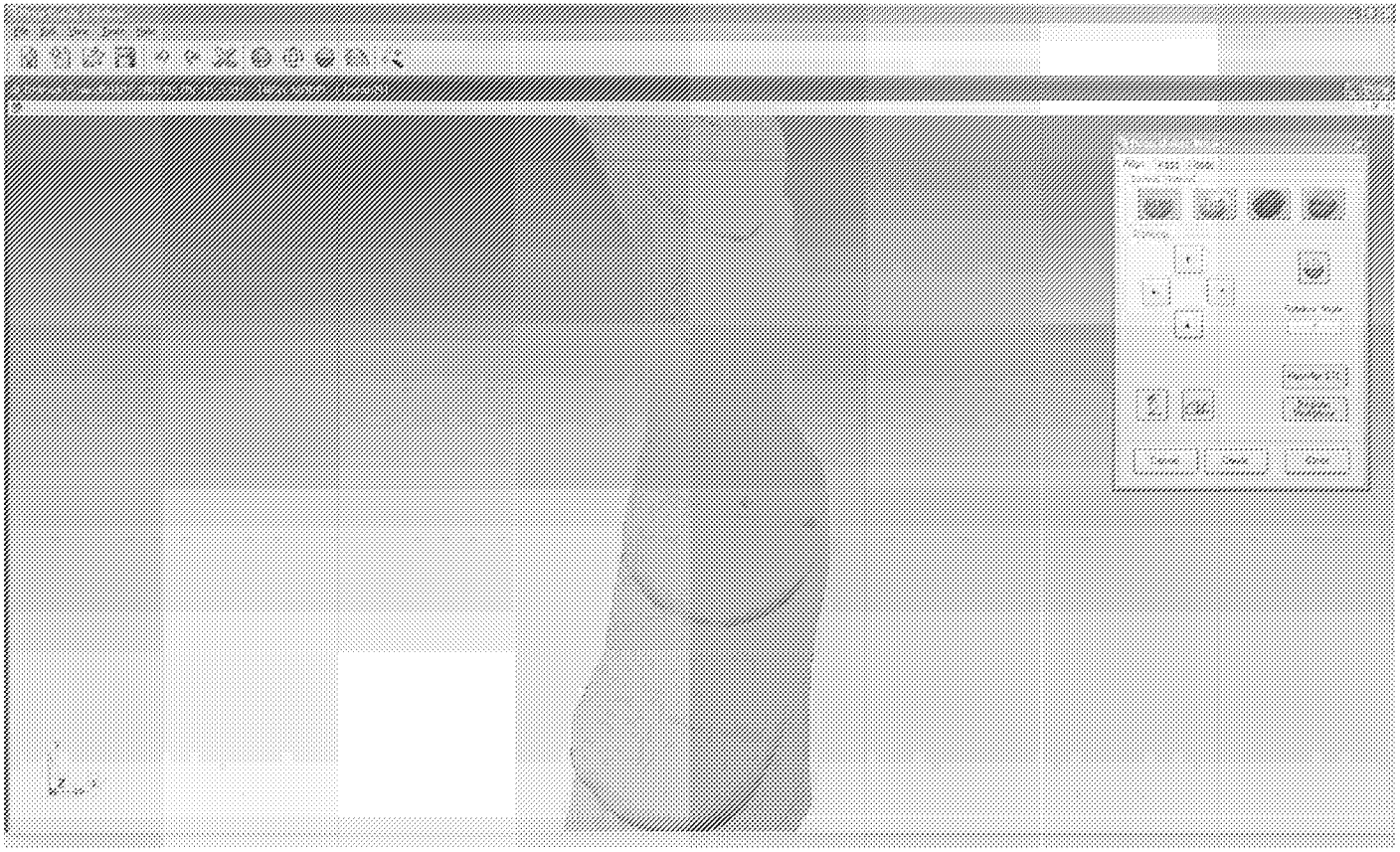
Figure 134:
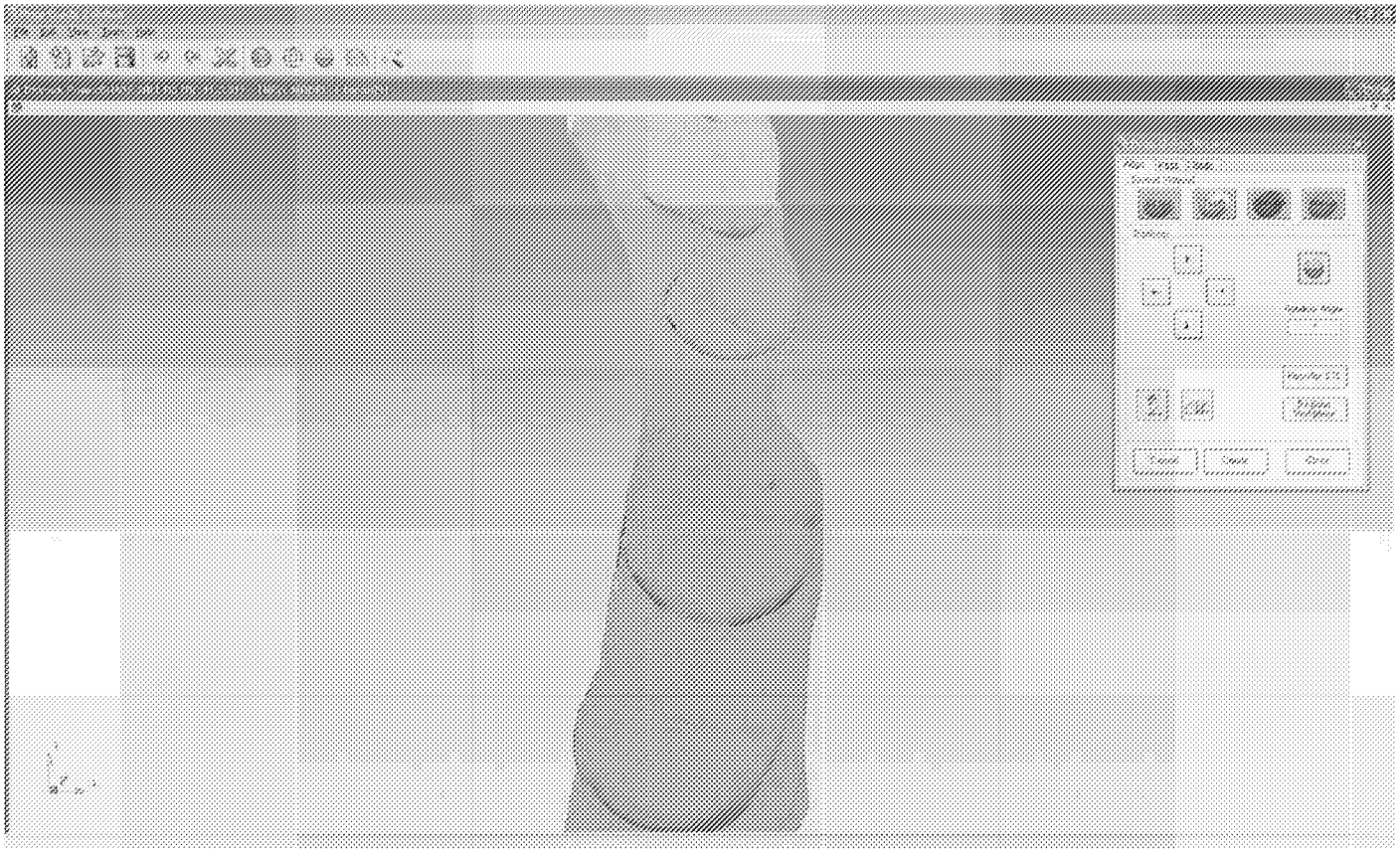
Figure 135:
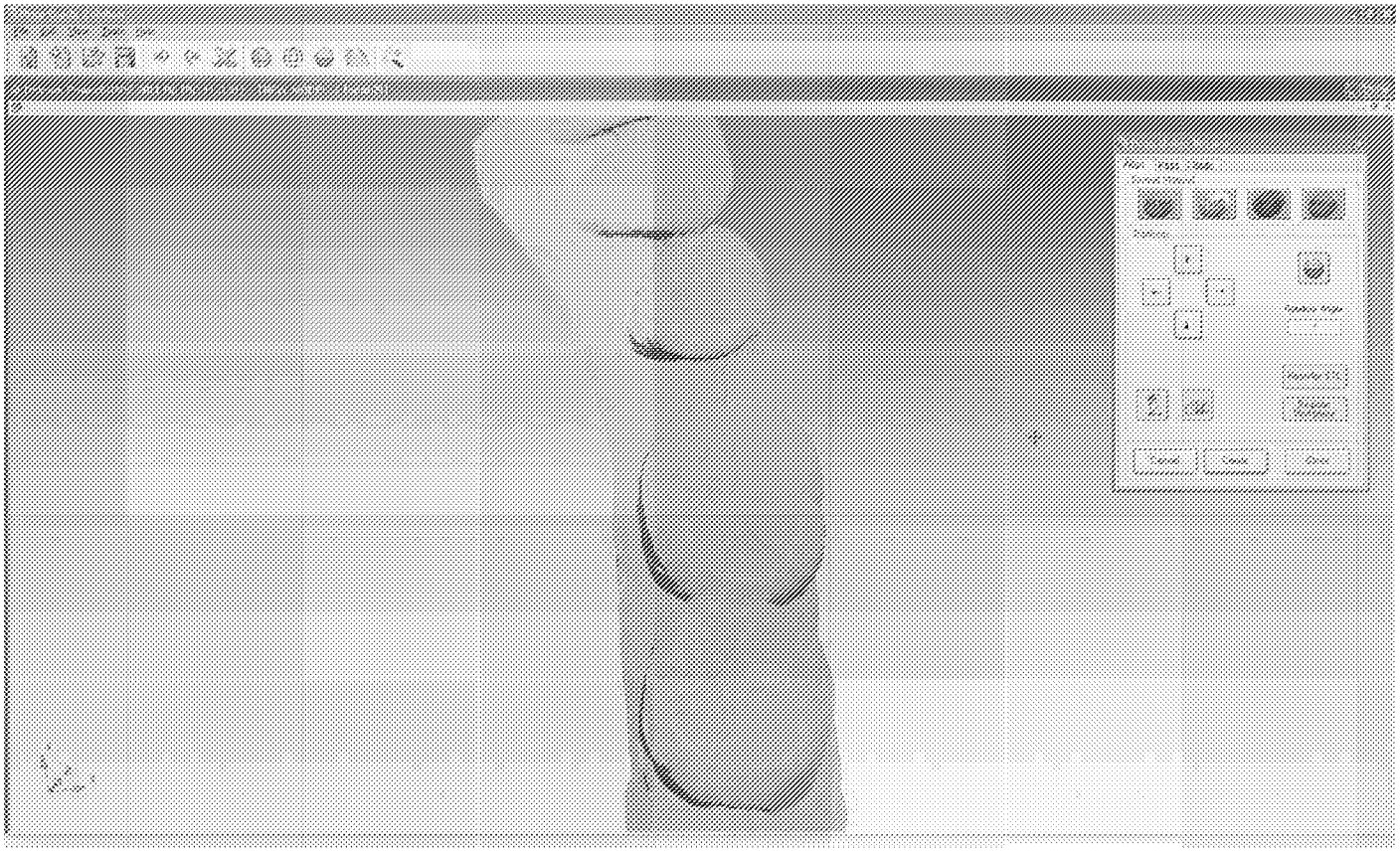
Figure 136:
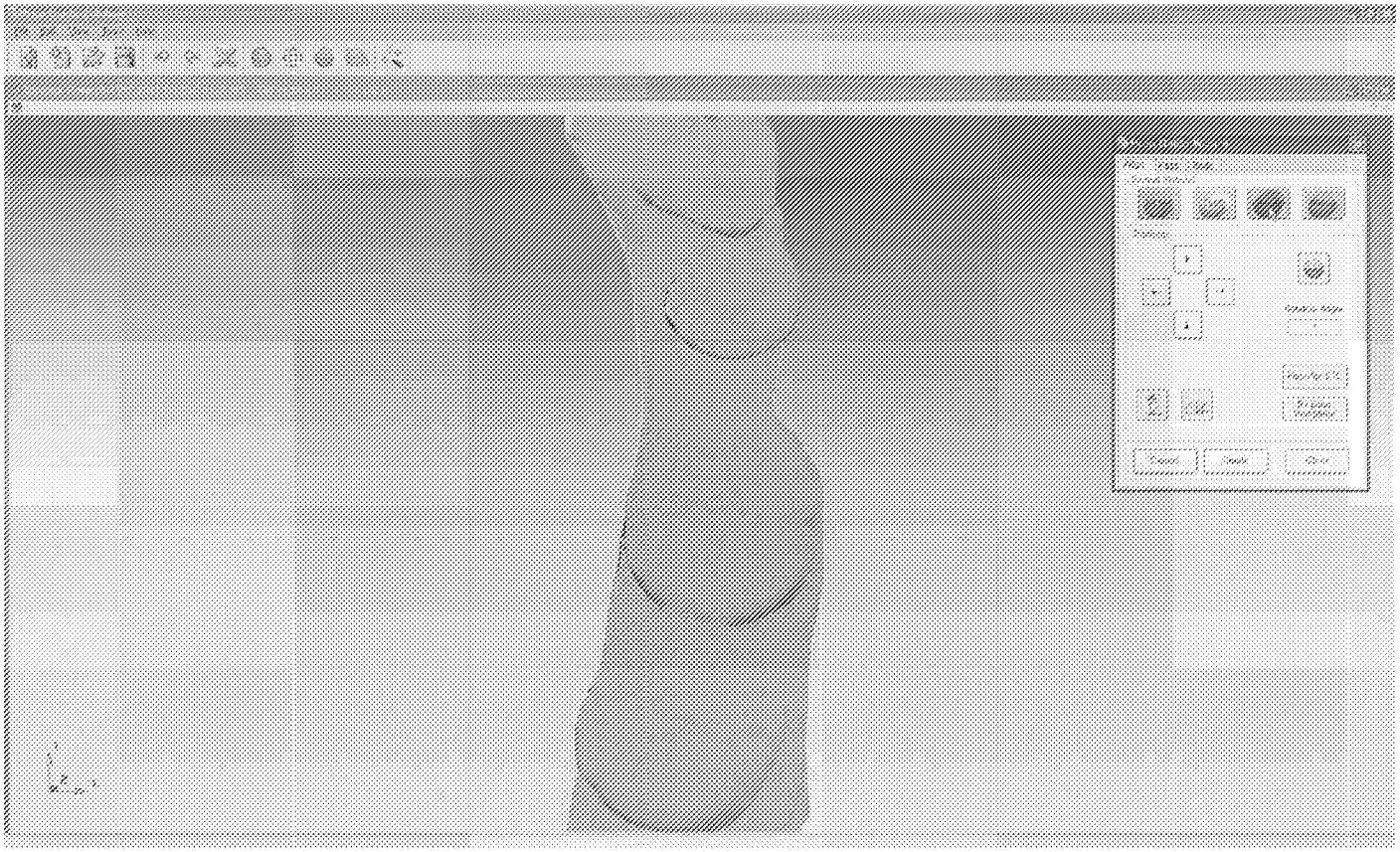
Figure 137:
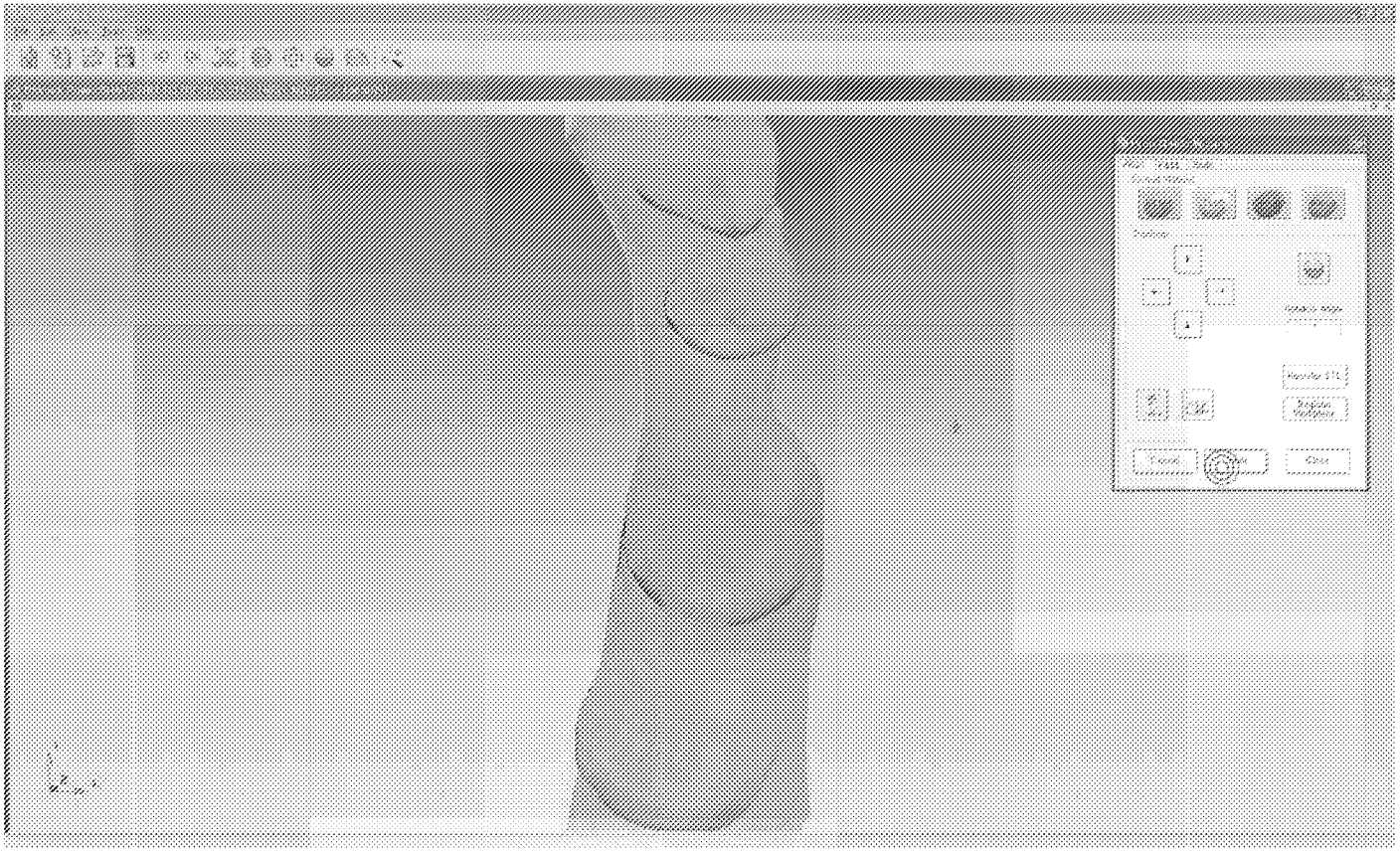
Figure 138:
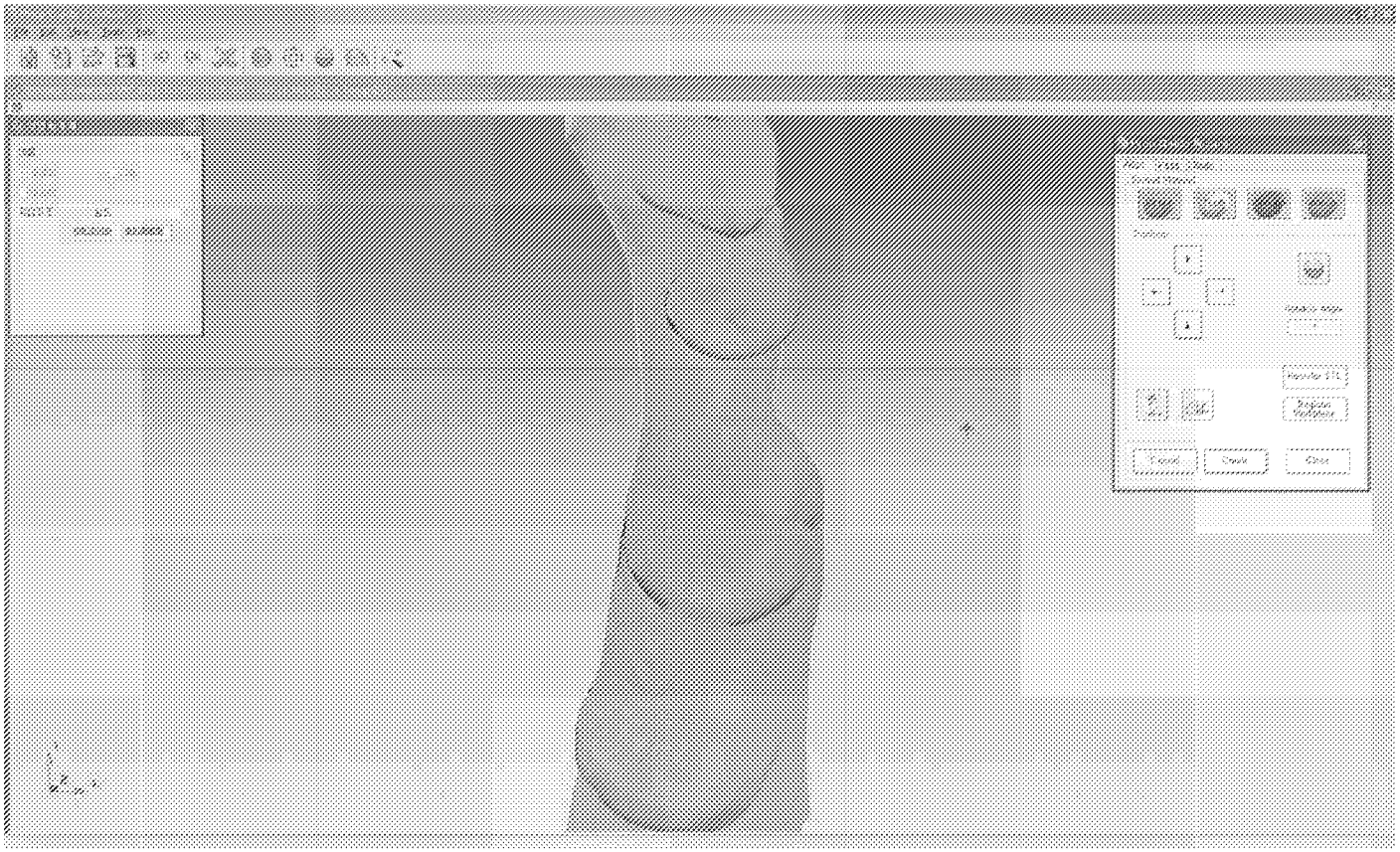

In an embodiment, with respect to each candidate of the prospective axis of prosthesis insertion, the computer system processes the 3-D data to identify undercut portions and displays the undercut portions using different colors and/or brightness. Examples of the foregoing processes are shown in FIGS. 133, 134 and 135. The area of the undercut portions and the depth from the ridge of the survey line to the undercut portion can vary according to the selection of the axis of prosthesis insertion. Because the cutting portions are generally located between the undercut portions and the occlusal surface, the area and thickness of the cutting portions can vary according to the locations and/or depth of the undercut portions. In an embodiment, when the user selects another candidate for the prospective axis of prosthesis insertion, the computer system shows the corresponding teeth image, processes the 3-D data, identifies undercut portions, computes the area, locations and thickness of prospective cutting portions, and stores the resulting data. In an embodiment, the user can check such images and resulting data, and select one among the candidates as the prospective axis of prosthesis insertion as shown in FIG. 136. Then, in an embodiment as shown in FIGS. 137 and 138, the computer system generates or retrieves data for the selected axis of prosthesis insertion and displays the corresponding tooth image.

Figure 139:
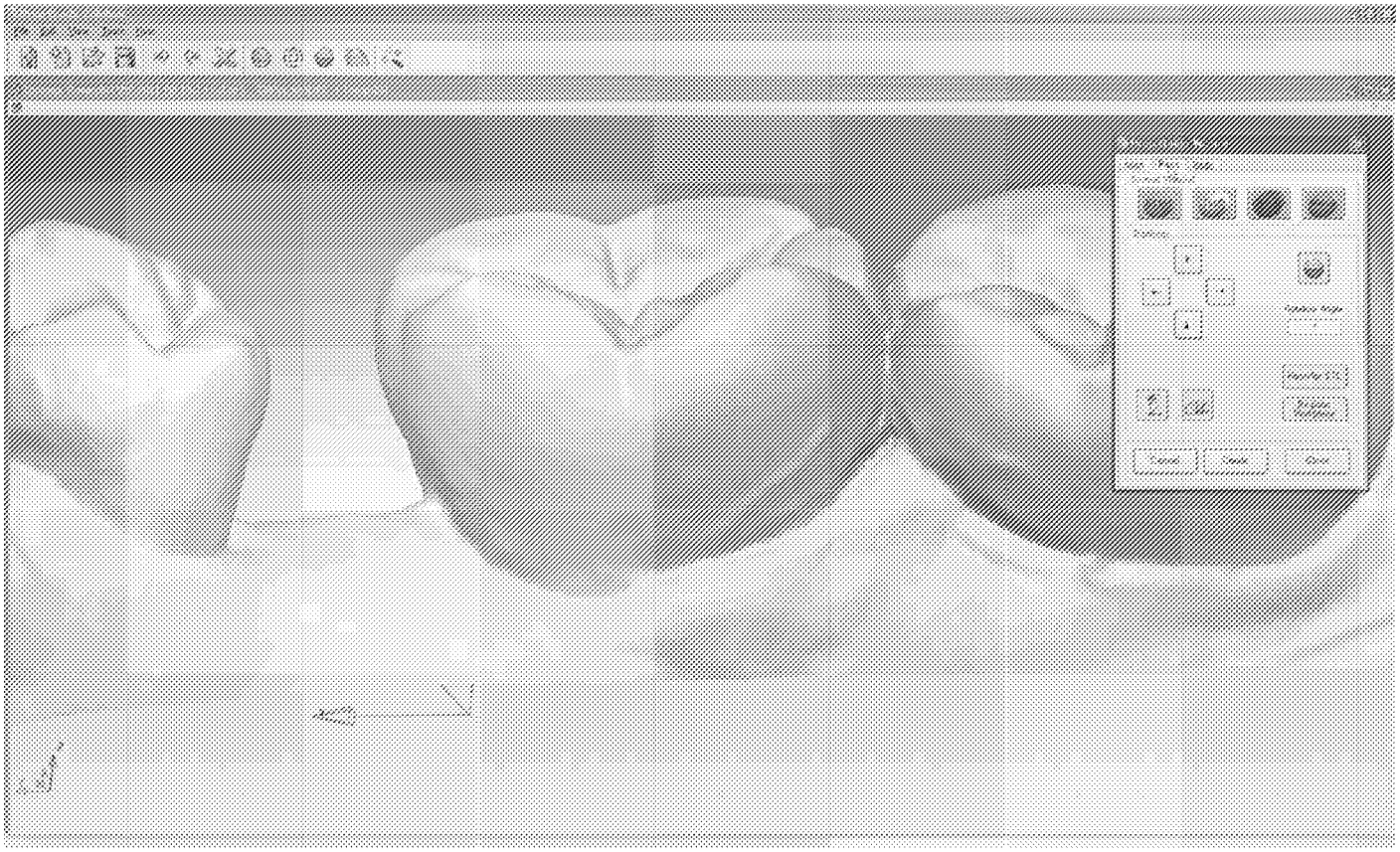
Figure 140:
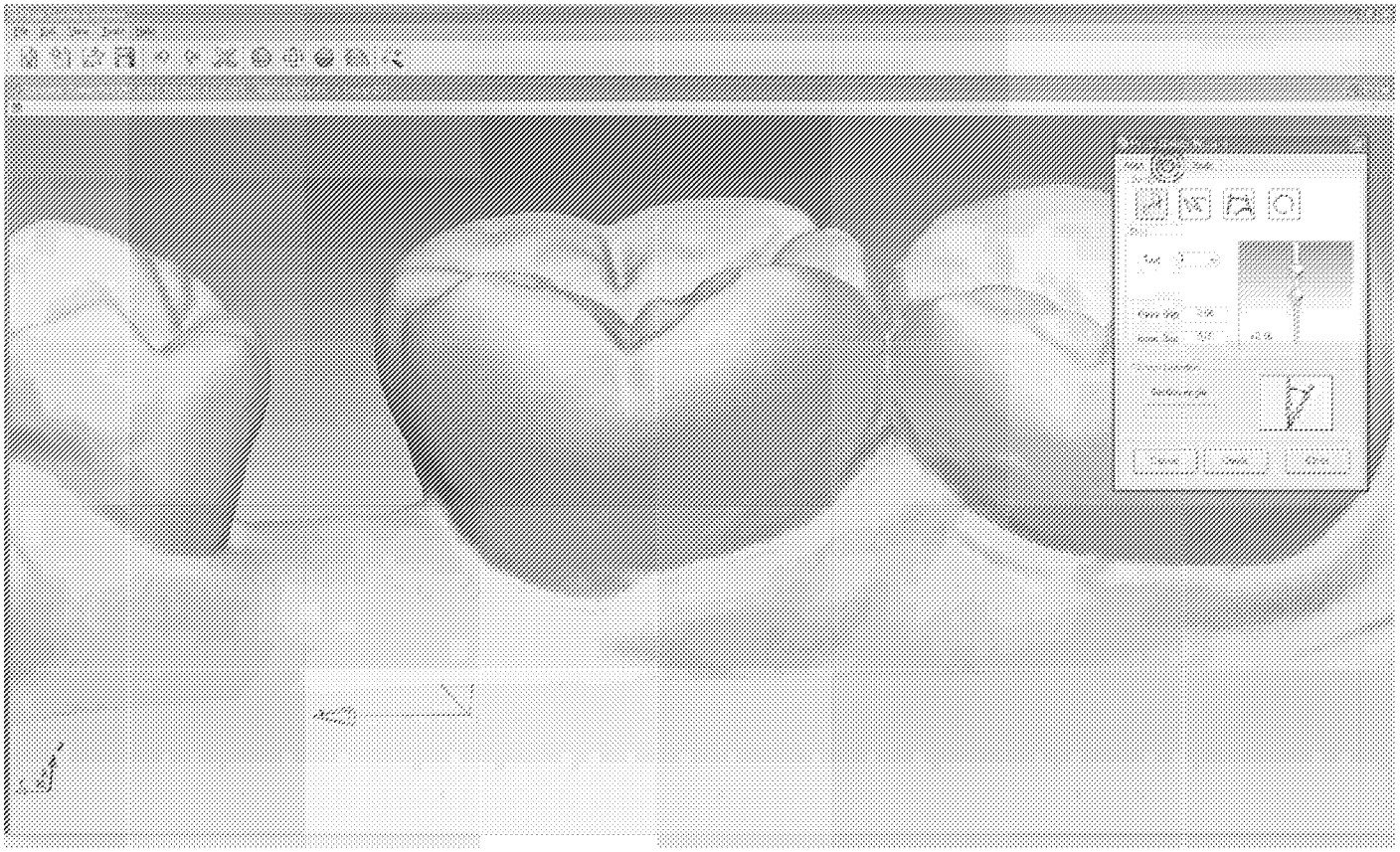

In an embodiment as shown in FIG. 139, the user can click a "Pass" tab in the menu window for determining a cutting margin line and select a cutting tool as shown in FIG. 140. In some embodiments, the diameter of the cutting tool, a distance between the end of the cutting head and the guide bump, the slope of the tapered portion of the cutting head, and other features of the cutting tool can be parameters to be used in the subsequent steps.

Figure 144:
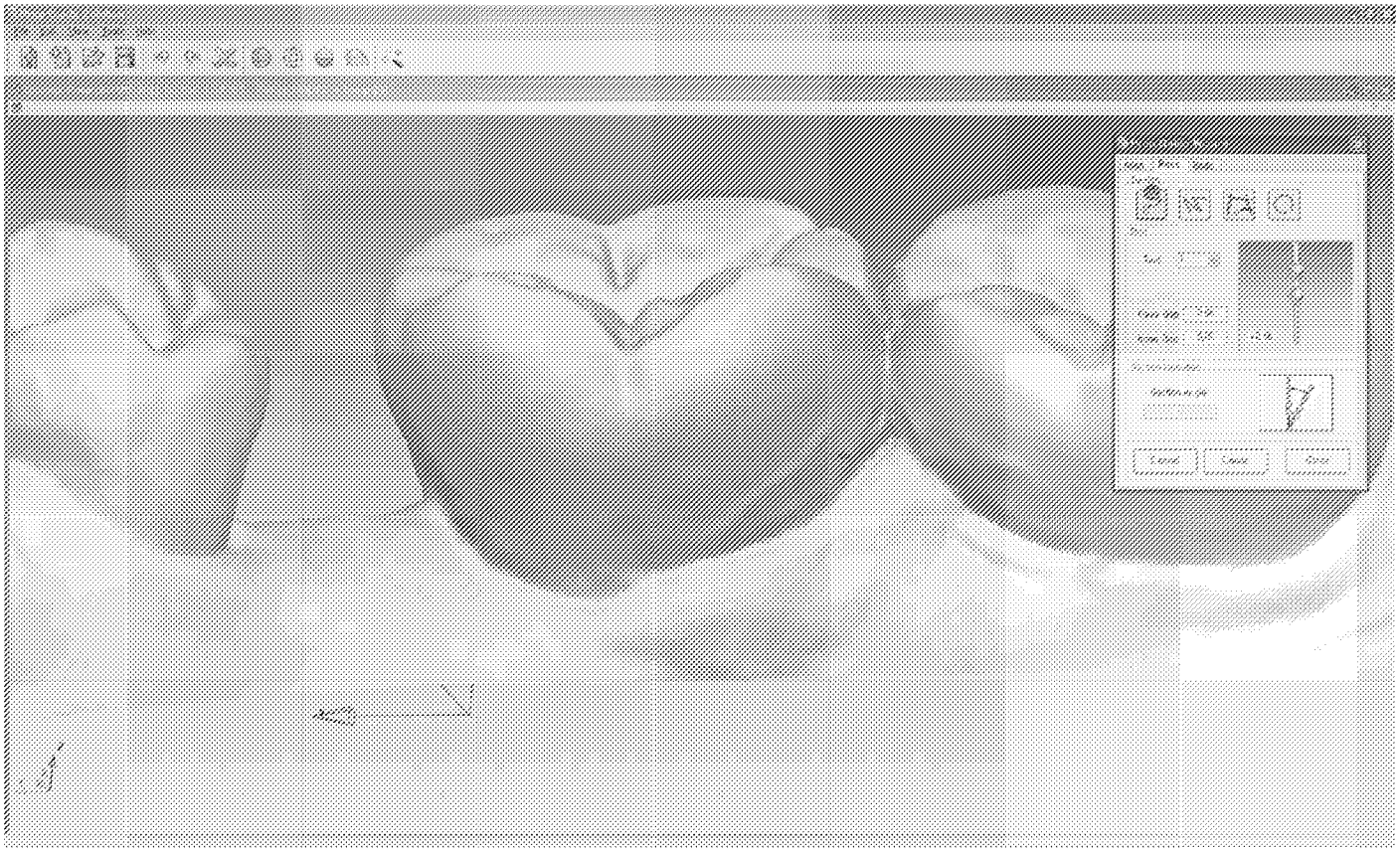
Figure 142:
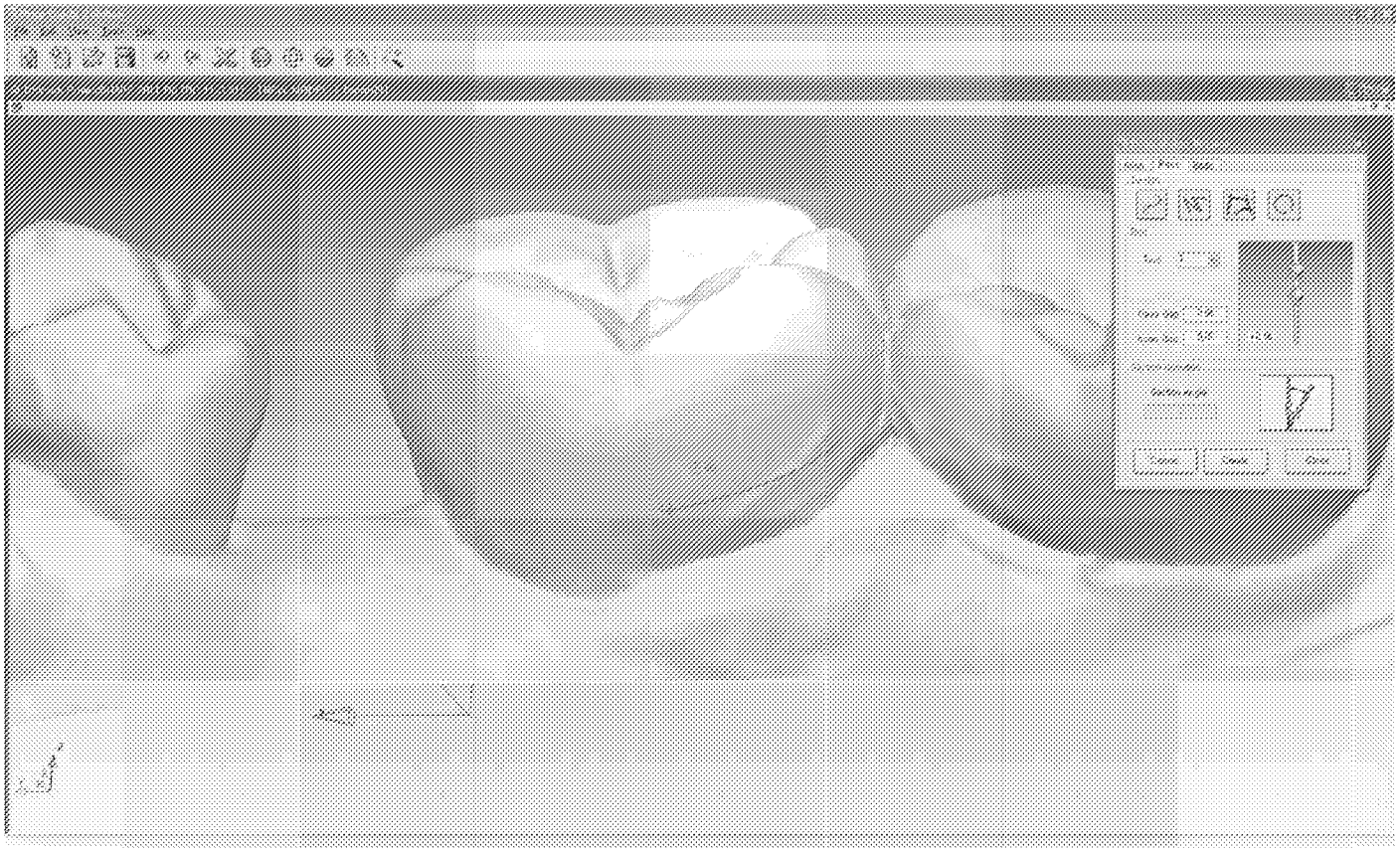
Figure 143:
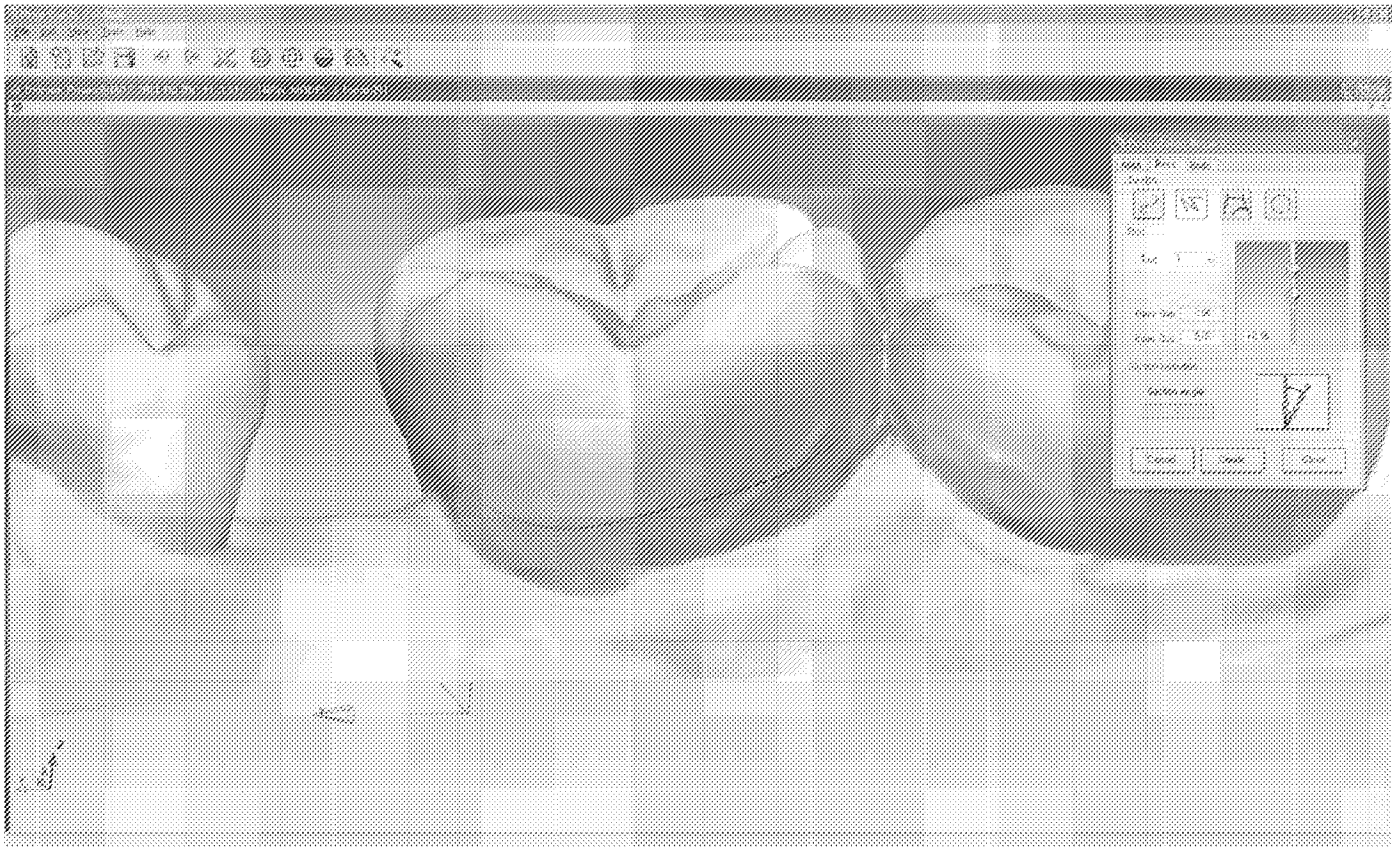
Figure 144:
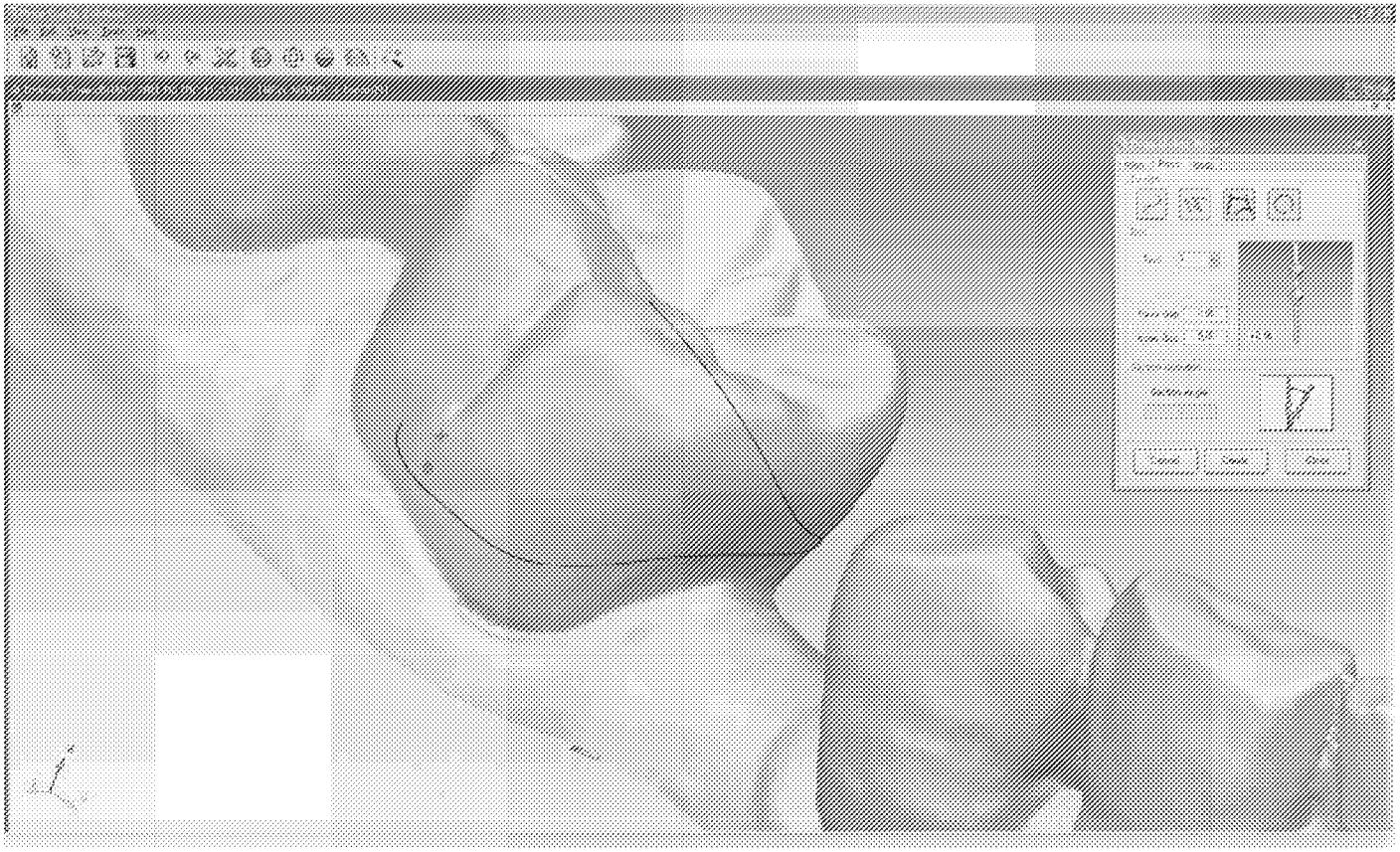
Figure 145:
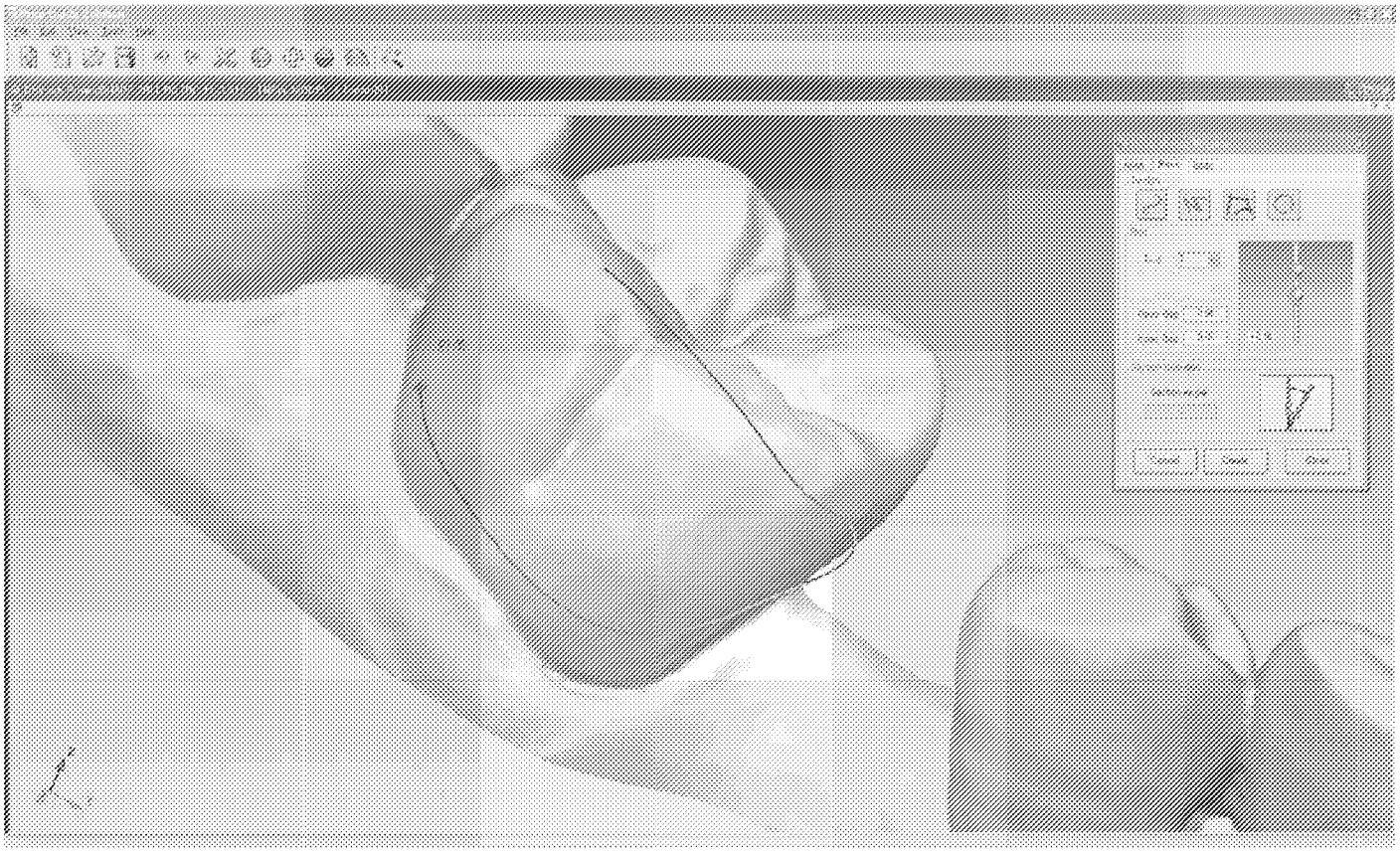
Figure 146:
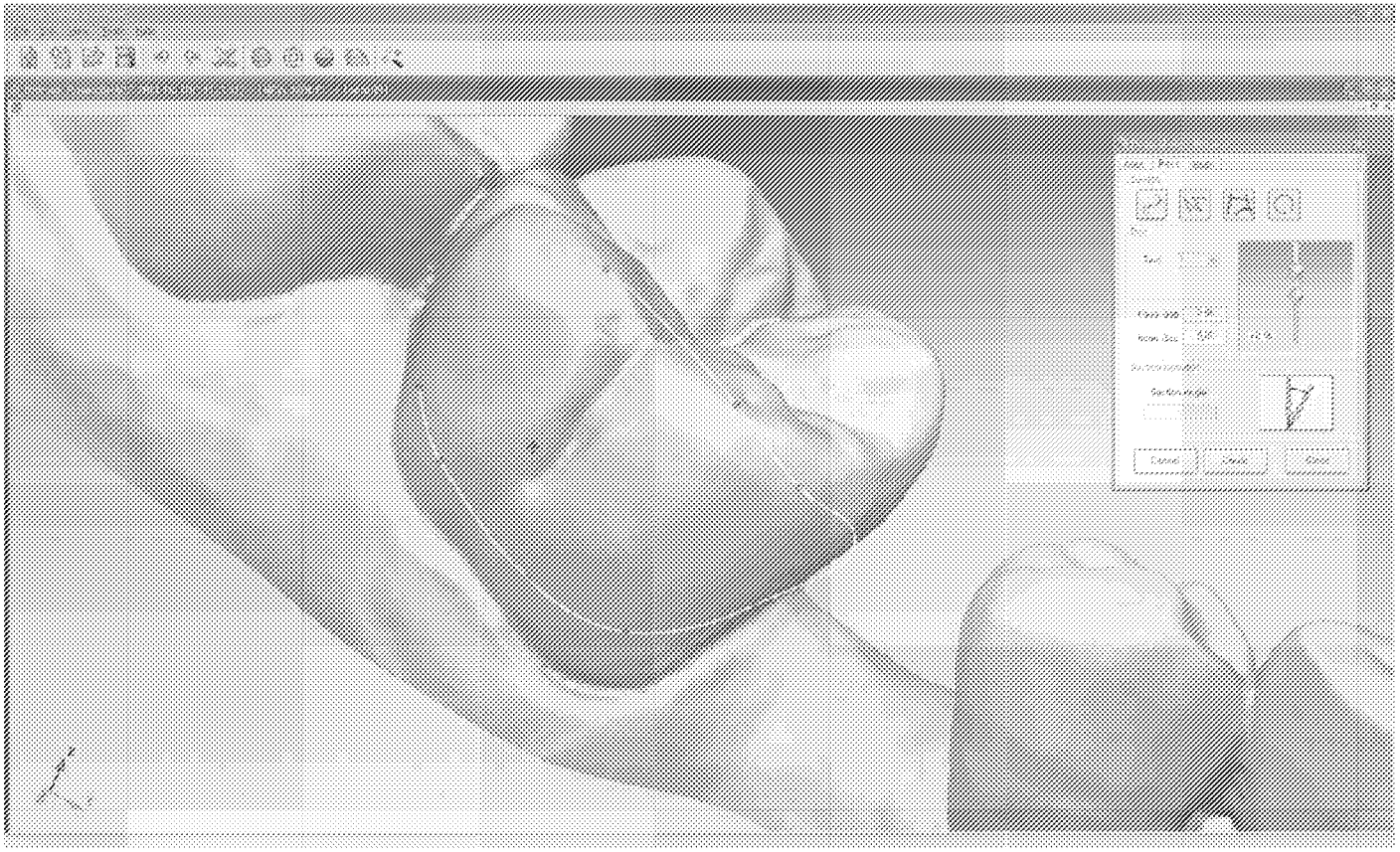
Figure 147:
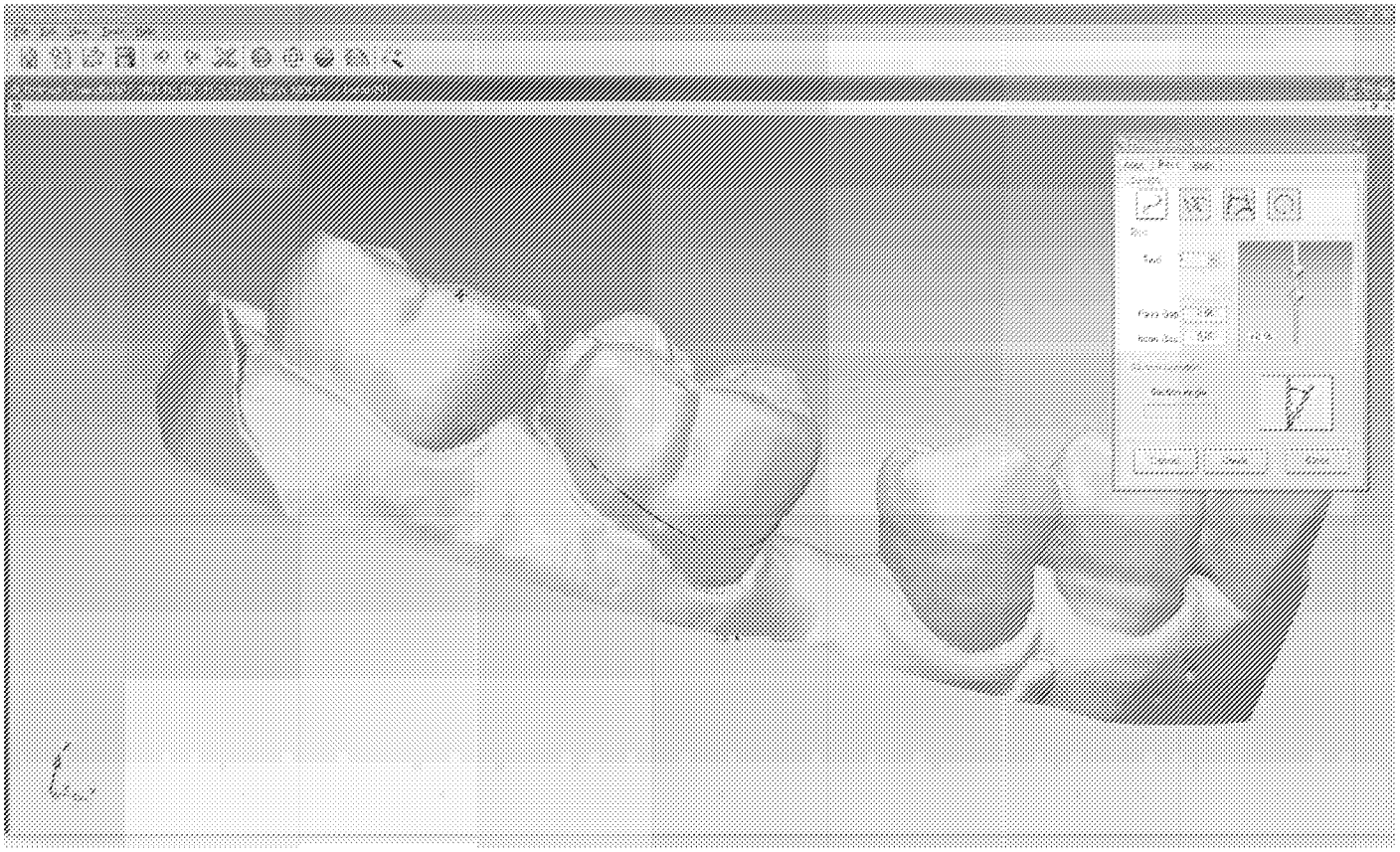
Figure 148:
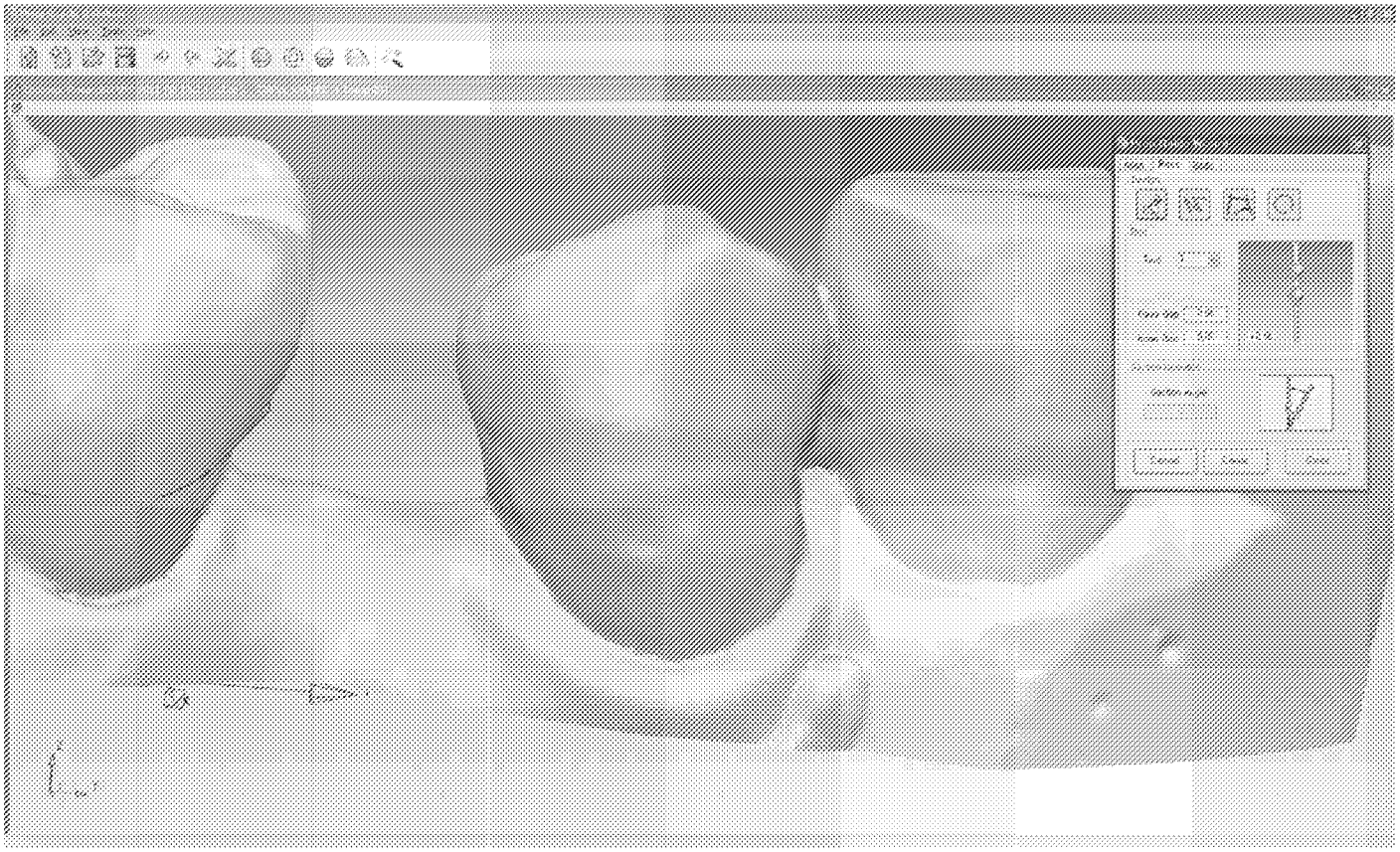
Figure 149:
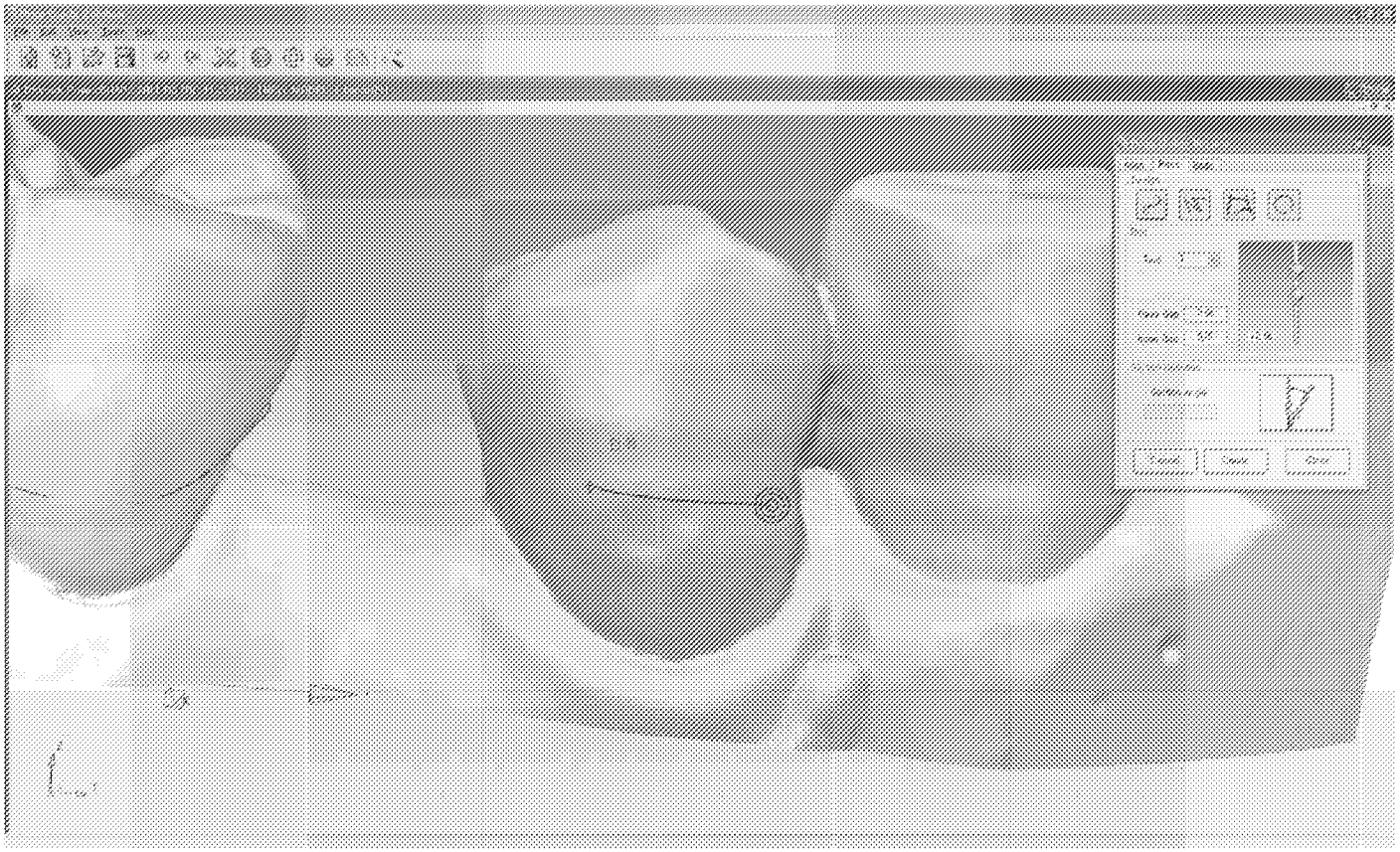
Figure 150:
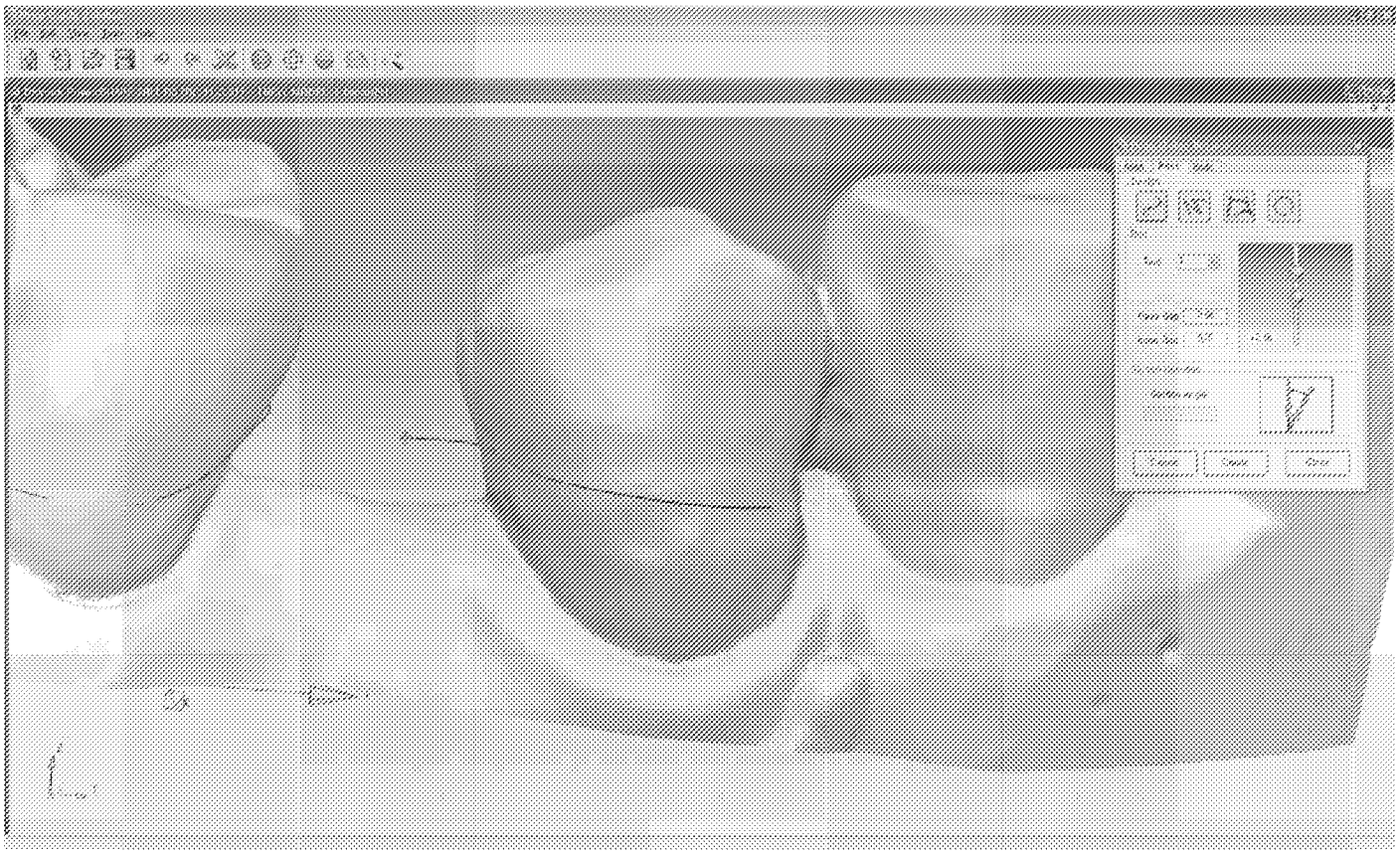
Figure 151:
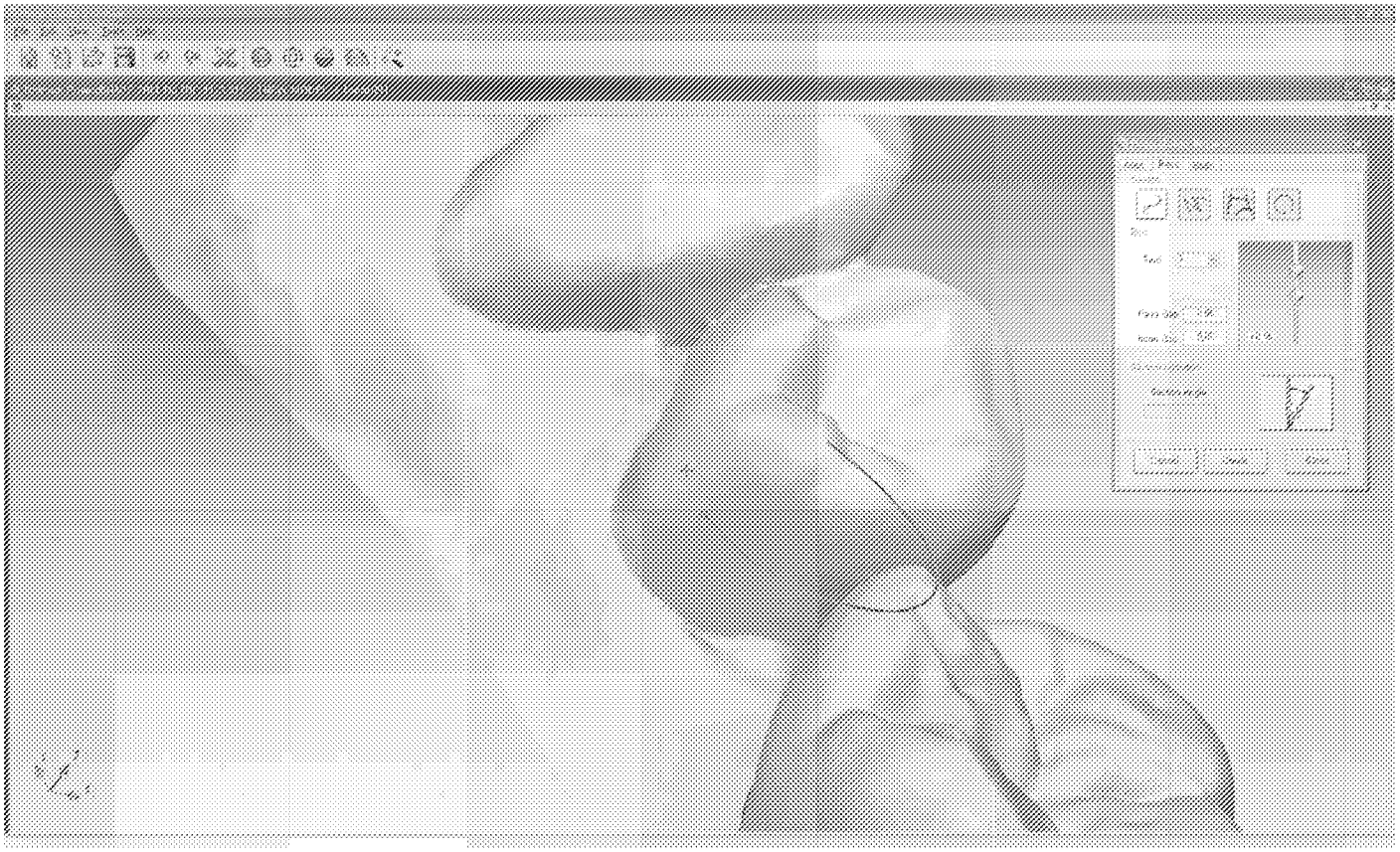
Figure 152:
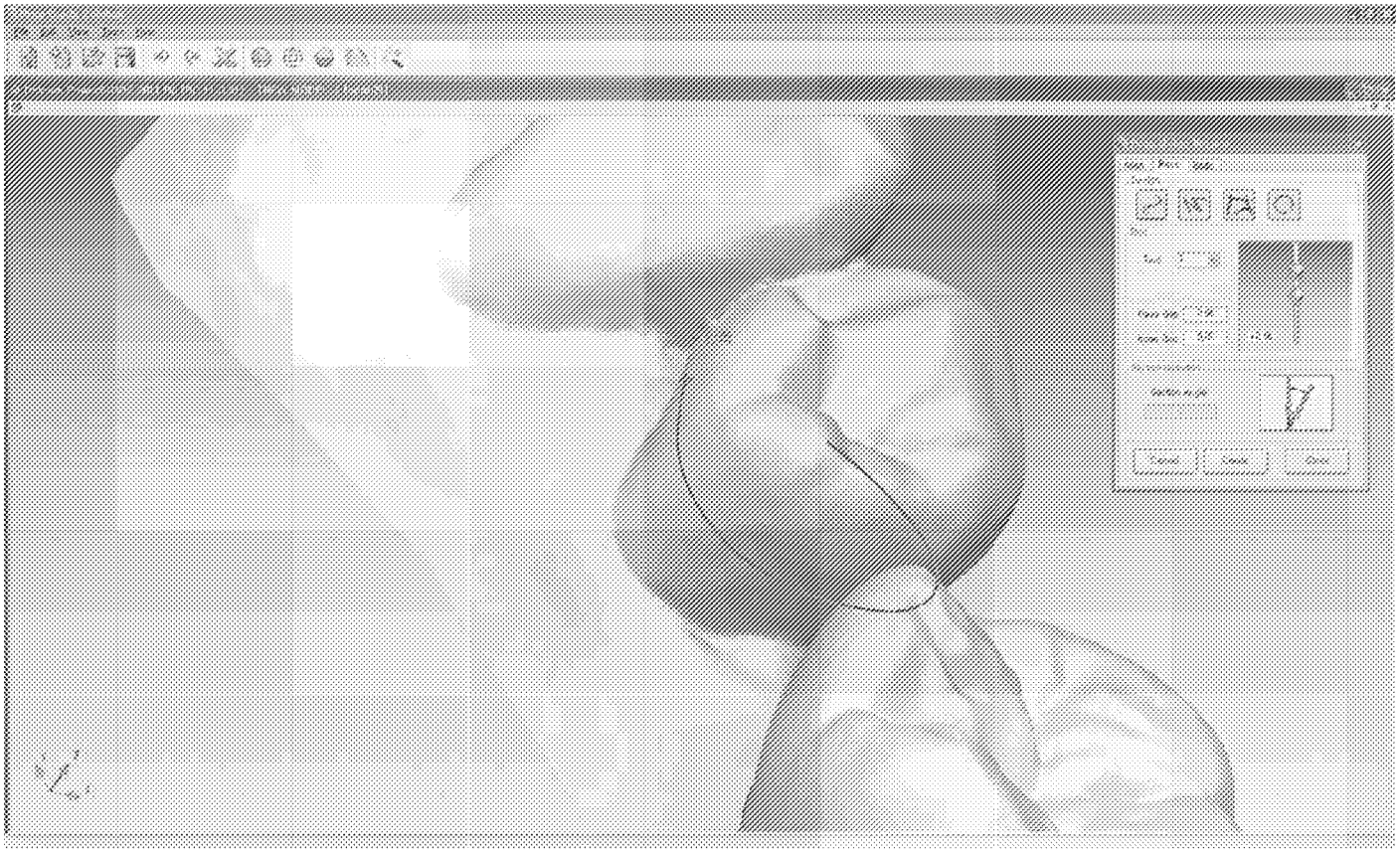
Figure 153:
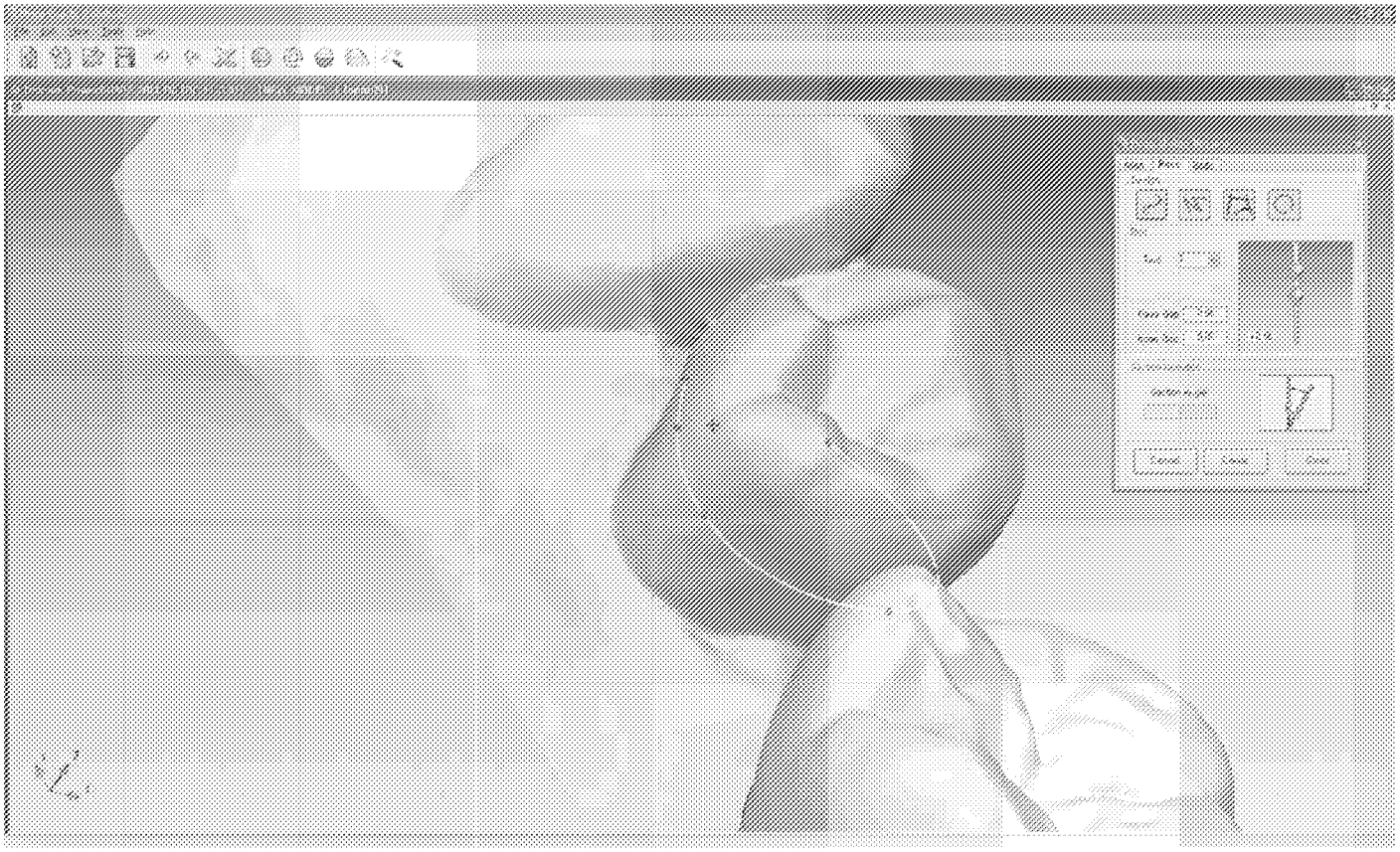

In an embodiment, the user determines the cutting margin line that a terminal end of the cutting tool will follow. First, in an embodiment as shown in FIG. 141, the user selects one location on the lingual surface of, for example, the first molar as a starting point. And then, in an embodiment as shown in FIG. 142, the user selects a subsequent location on the lingual surface of the first molar as a second point, and the computer system processes the 3-D data to determine the cutting margin line between the starting point and the second point. In one embodiment, the foregoing work can be done by dragging and pointing a curser with a pointing device, such as a mouse. In an embodiment, the computer system then stores data regarding the [staring] *starting* point and the second point, computes the margin line connecting the [staring] *starting* and second points, and displays the line on the screen. Subsequently, in an embodiment as shown in FIGS. 143, 144 and 145, the user determines other portions of the cutting margin line on the lingual surface and the portions of the cutting margin line on the mesial and buccal surfaces. In an embodiment as shown in FIG. 145, the user selects a location on the buccal surface as an end point to complete designing the cutting margin line. FIG. 146 shows the cutting margin line of the first molar in an embodiment.

Figure 154:
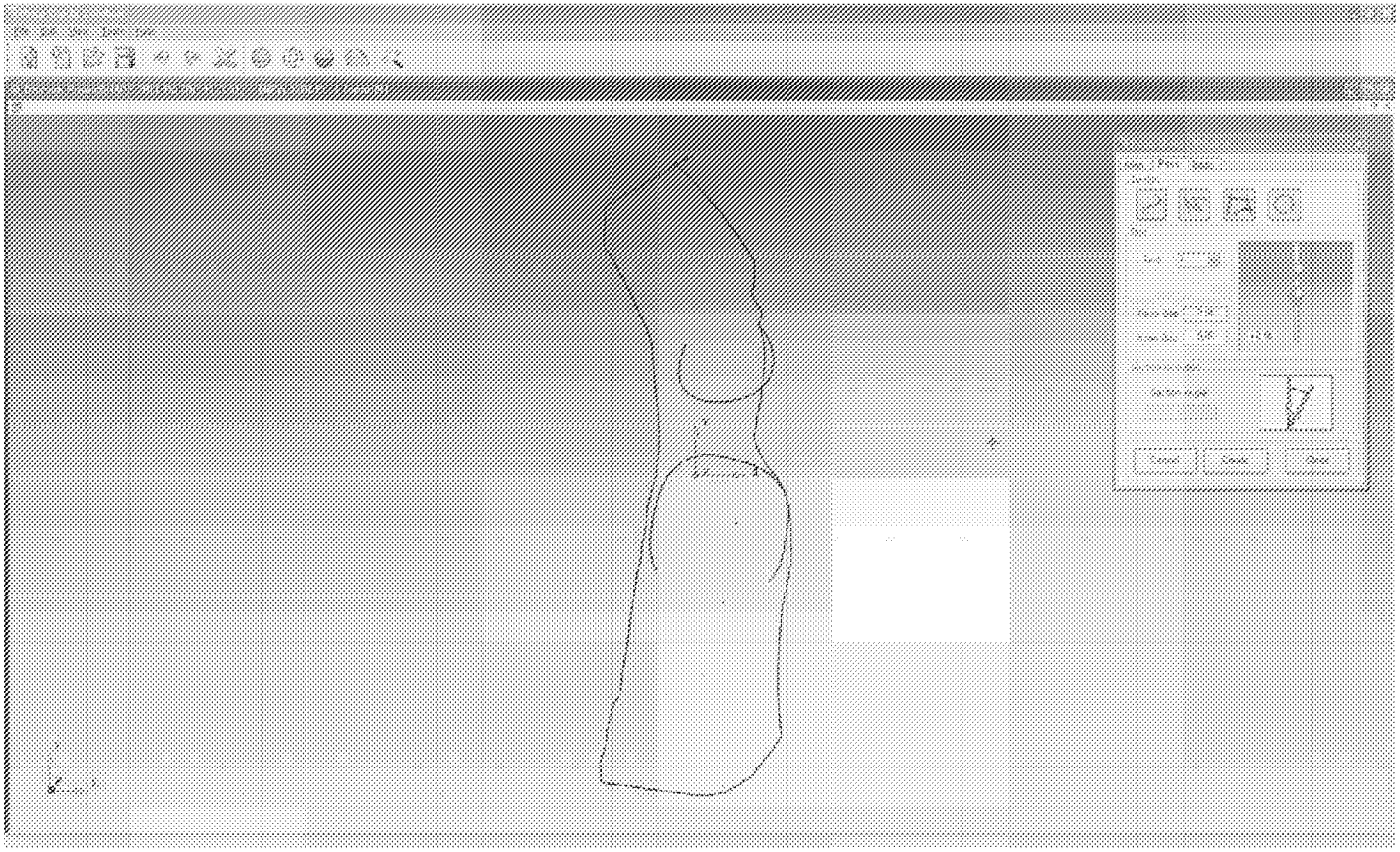

In an embodiment, the user subsequently changes the viewing angle of the tooth image and determines the cutting margin line of the first premolar as shown in FIGS. 147-153. In an embodiment, once determination of the cutting margin line is completed, as shown in FIG. 154, the computer system removes the tooth image from the screen and displays only the cutting margin lines and border lines of the tooth model.

In the foregoing embodiments, the user determines the axis of prosthesis insertion and the cutting margin line. In an alternative embodiment, the computer system automatically computes and determines the axis of prosthesis insertion and the cutting margin line using a pre-prepared algorithm, and displays the results to the user. In such embodiment, upon receipt of the user's approval, the computer designs the preparation guide device. If the user rejects the axis and line selected by the computer in such embodiment, the computer system chooses another axis of prosthesis insertion and cutting margin line and provides them to the user.

In the foregoing embodiments, the locations, thickness and other factors of the cutting potions are determined according to the determined cutting margin line. In alternative embodiments, the user provides a maximum cutting depth or thickness, and then, the computer system determines the locations of the cutting portions and the cutting margin lines using a pre-prepared algorithm. In other embodiments, the user can select the locations and areas of the cutting portions. In one embodiment, the user selects at least one of the buccal, mesial, lingual and distal surfaces as a surface to be cut, and then, the computer system determines the cutting margin lines using a pre-installed algorithm. In some embodiments, the computer system may require only one parameter among the aforementioned parameters from the user or may require two or more parameters.

Figure 155:
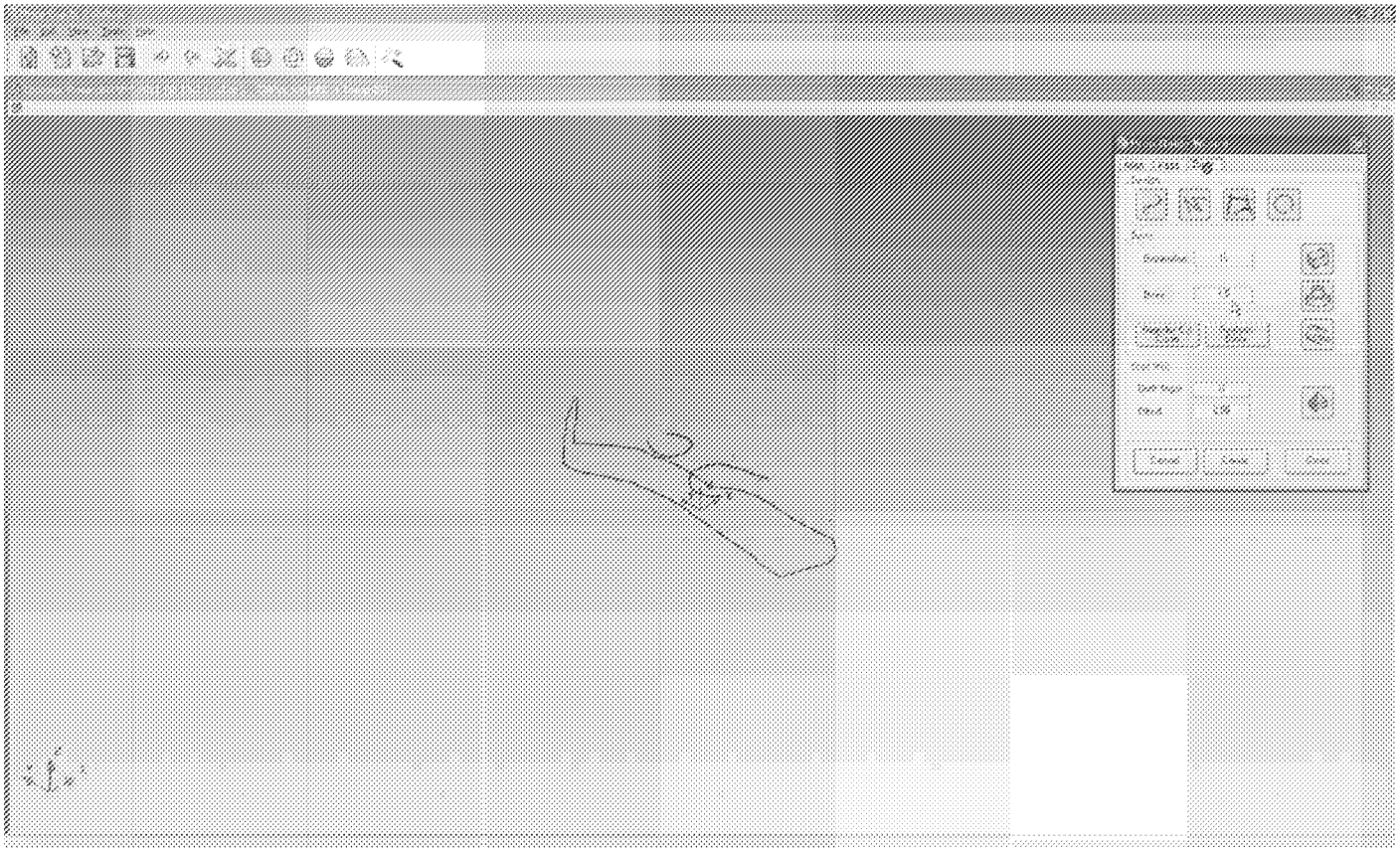
Figure 156:
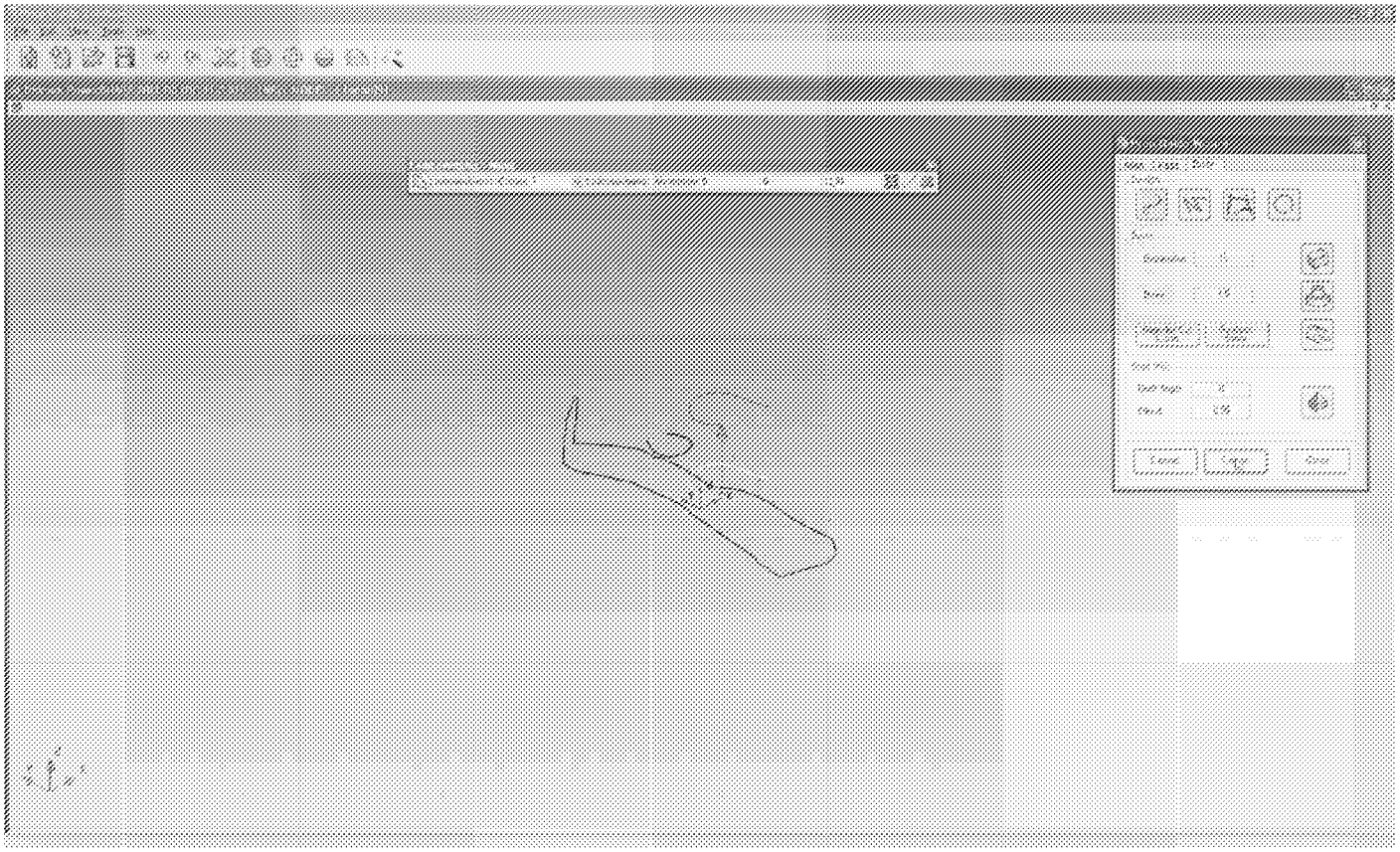
Figure 157:
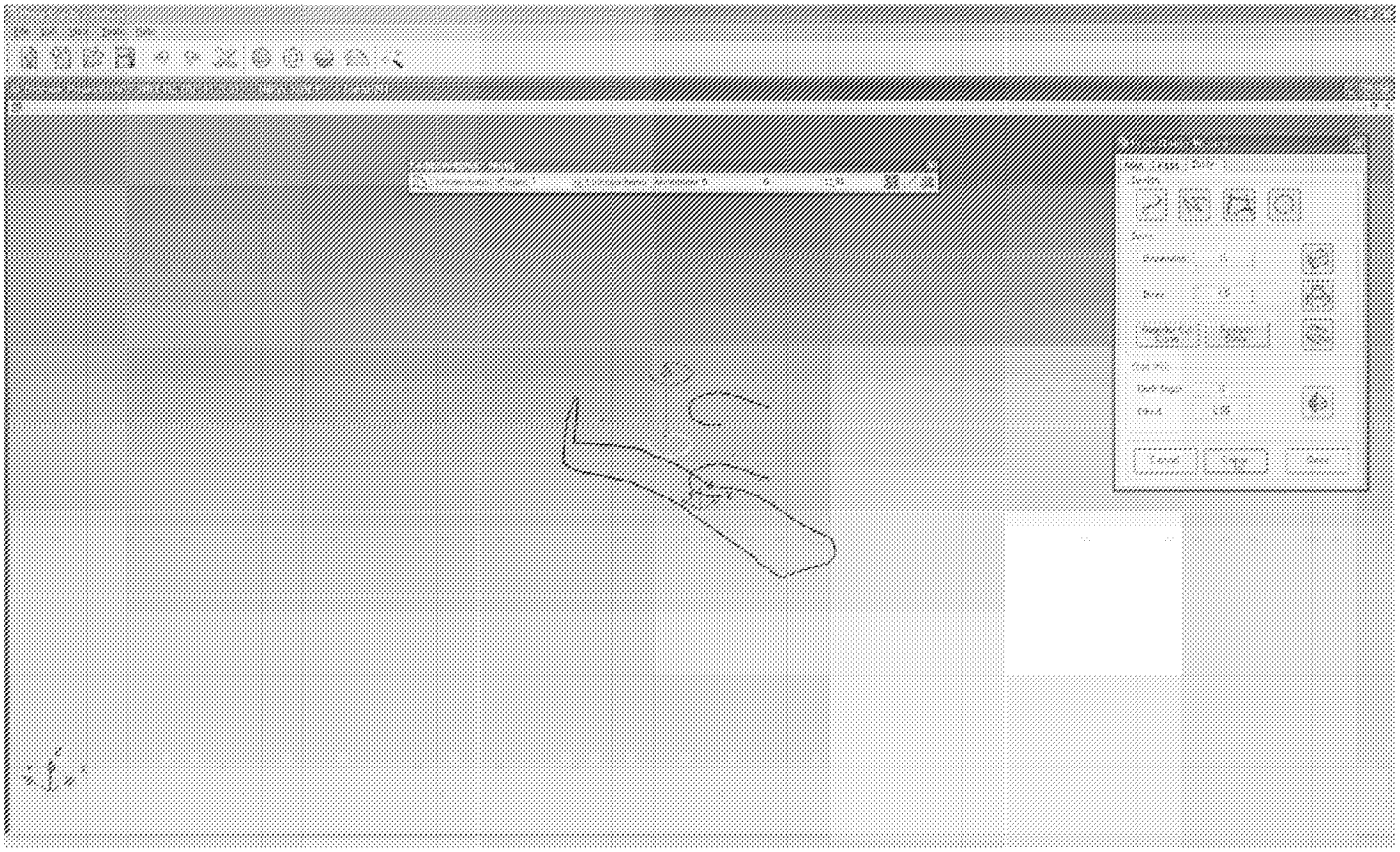
Figure 158:
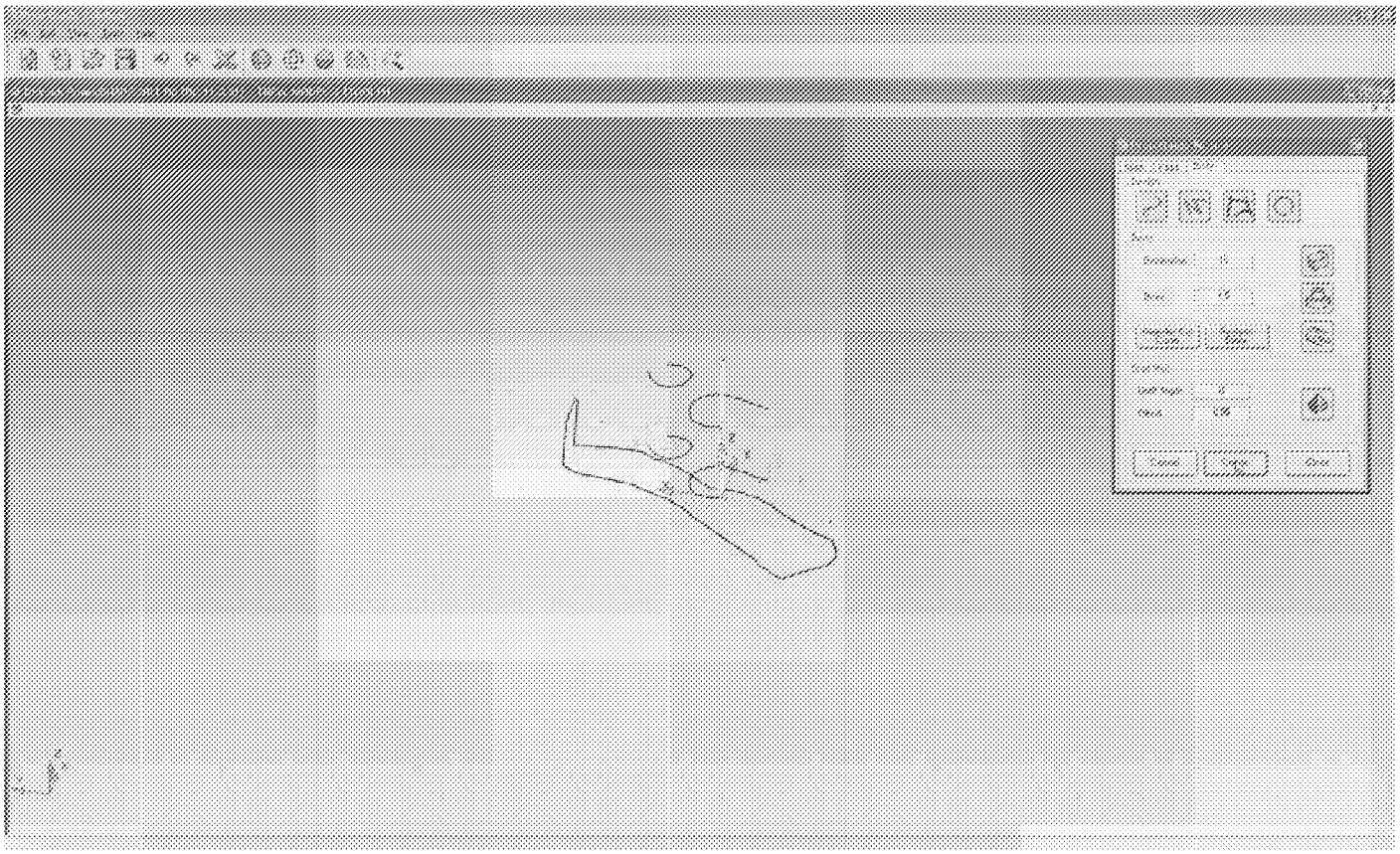
Figure 159:
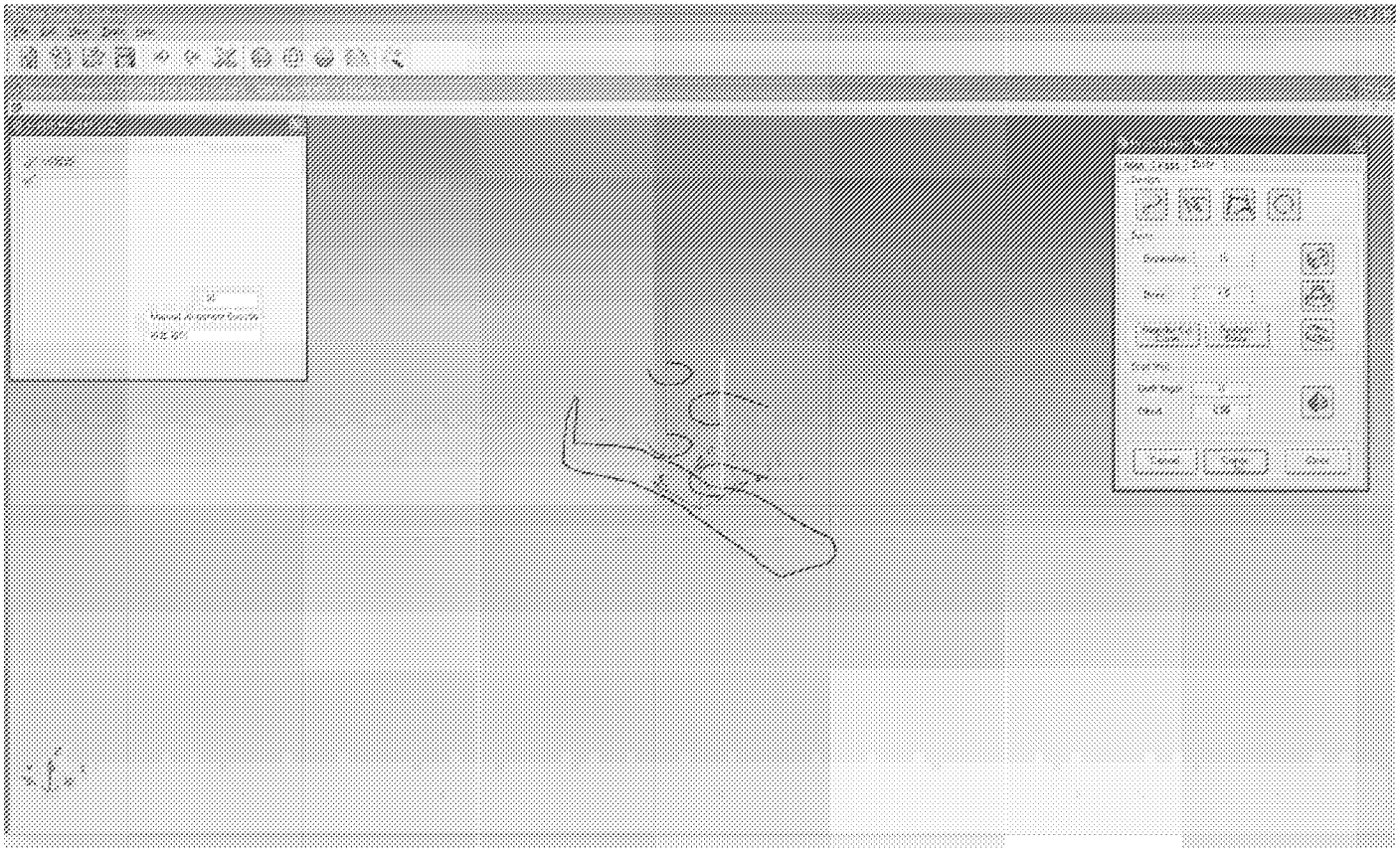
Figure 160:
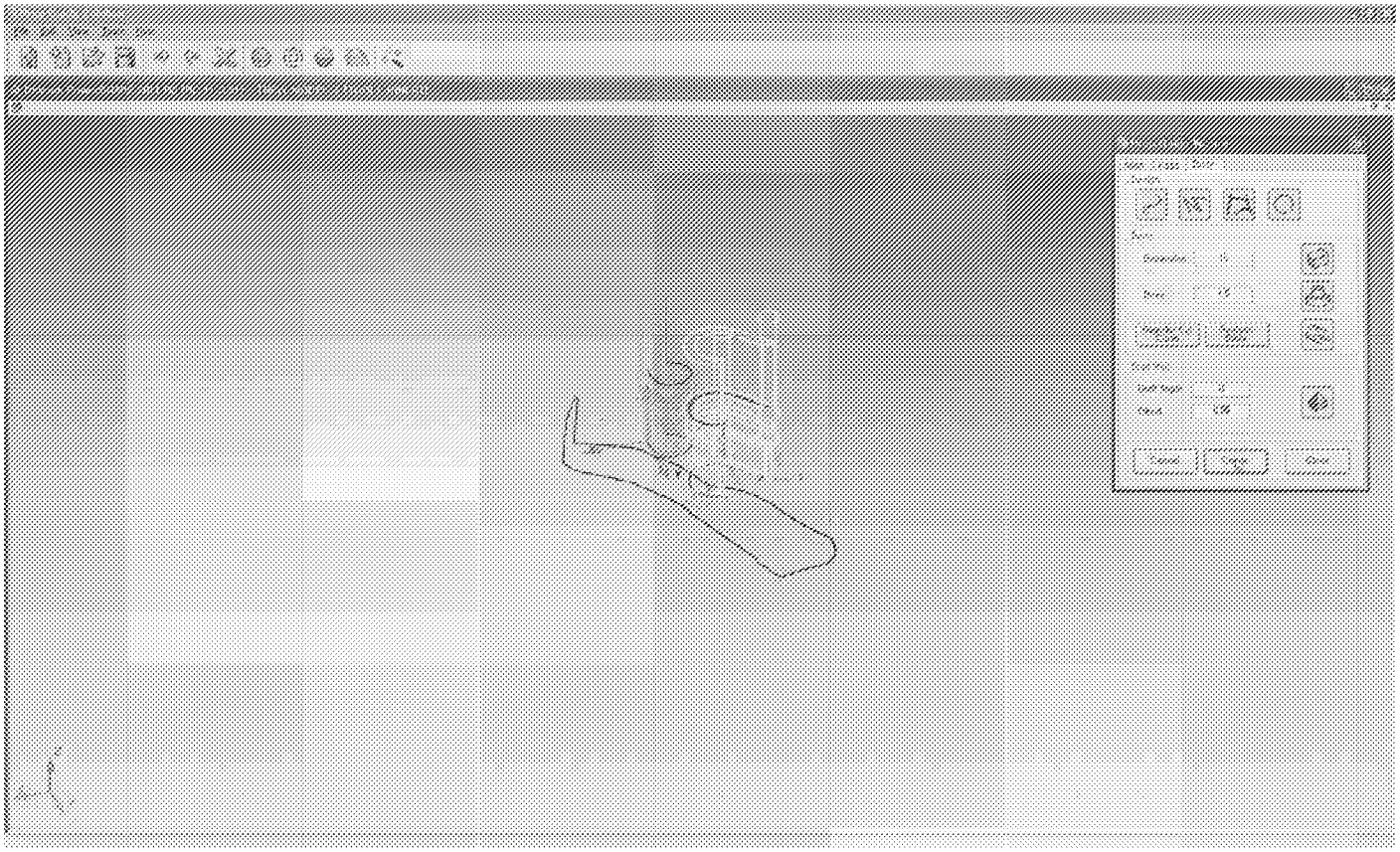
Figure 161:
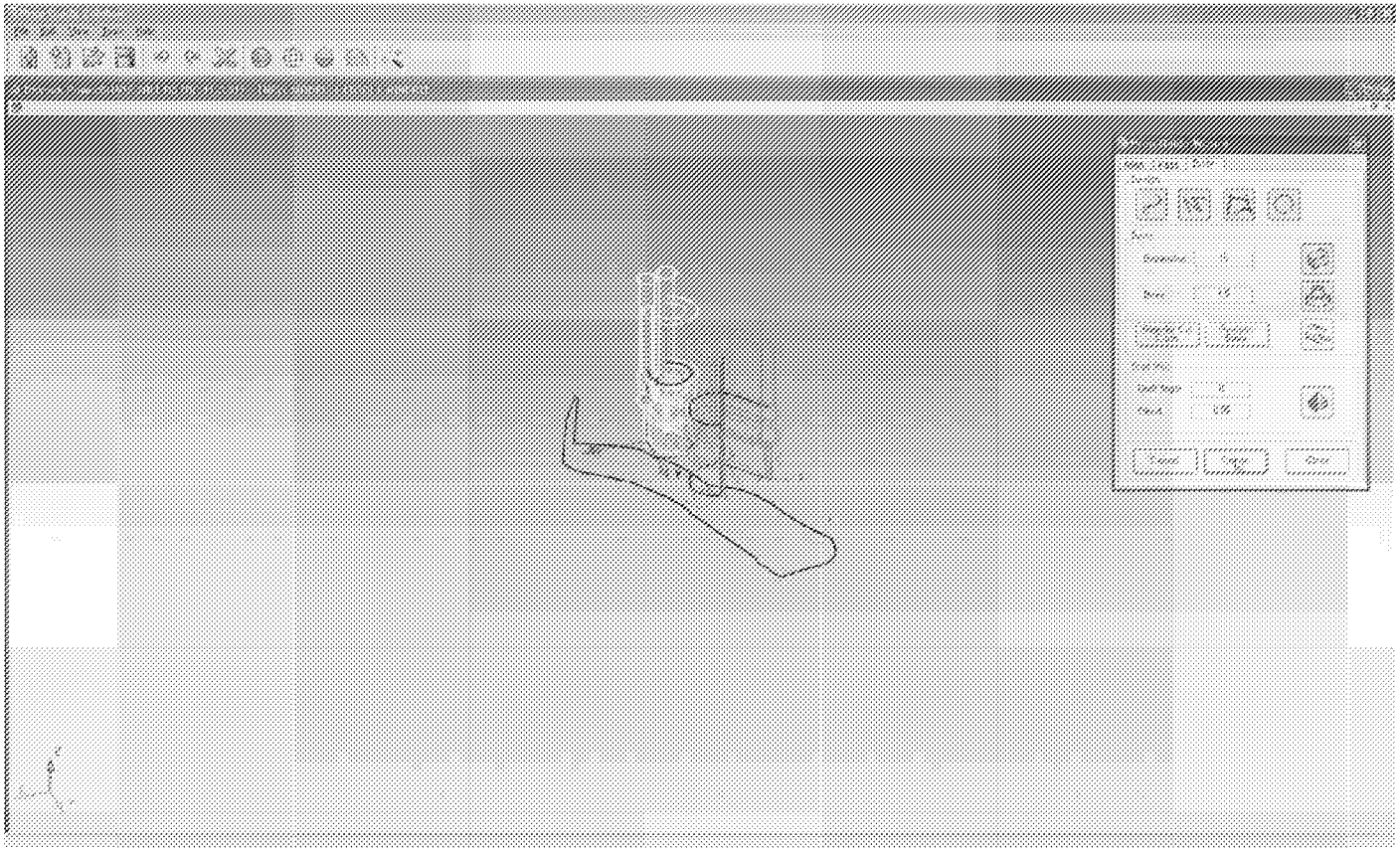
Figure 162:
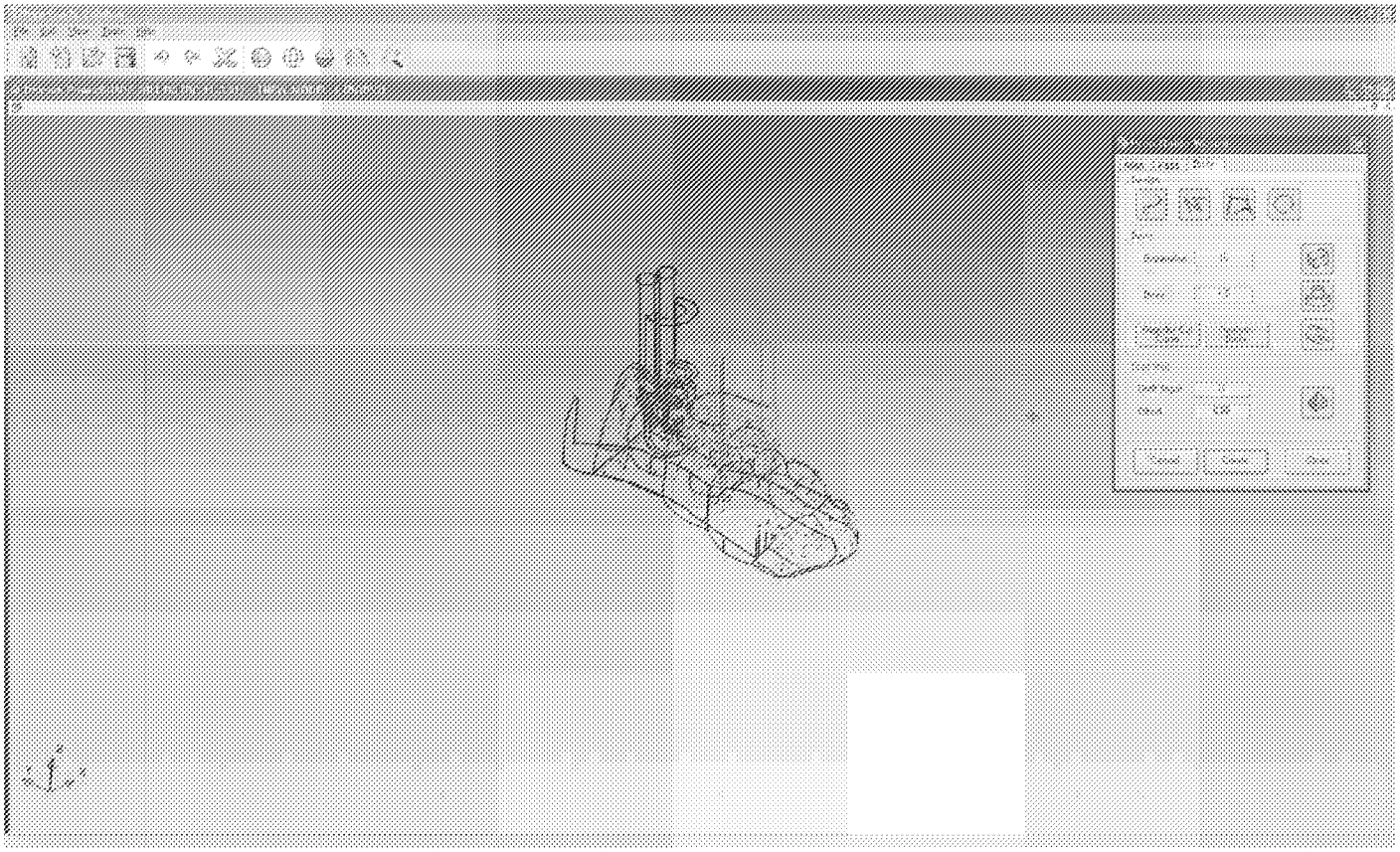
Figure 163:
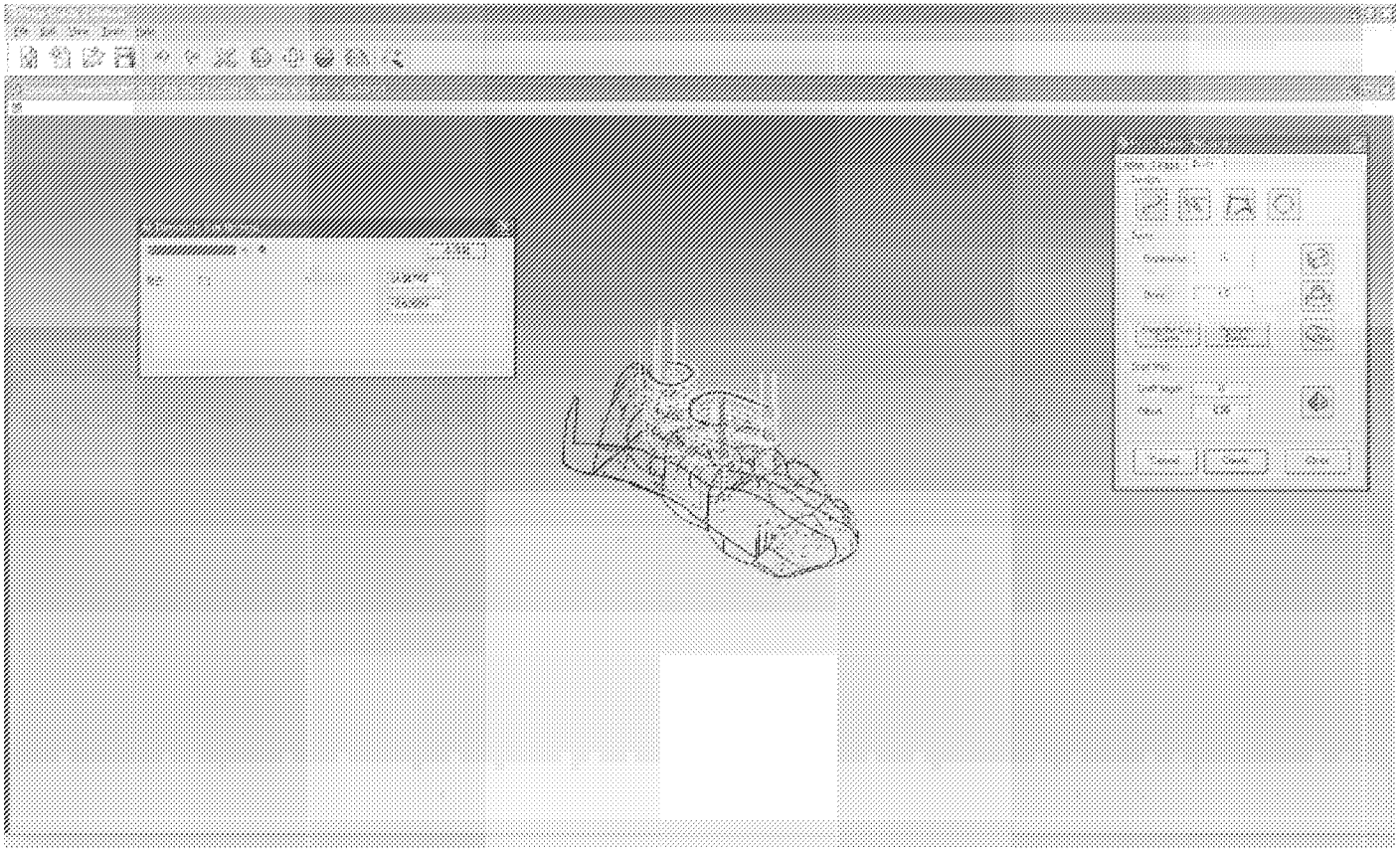
Figure 164:
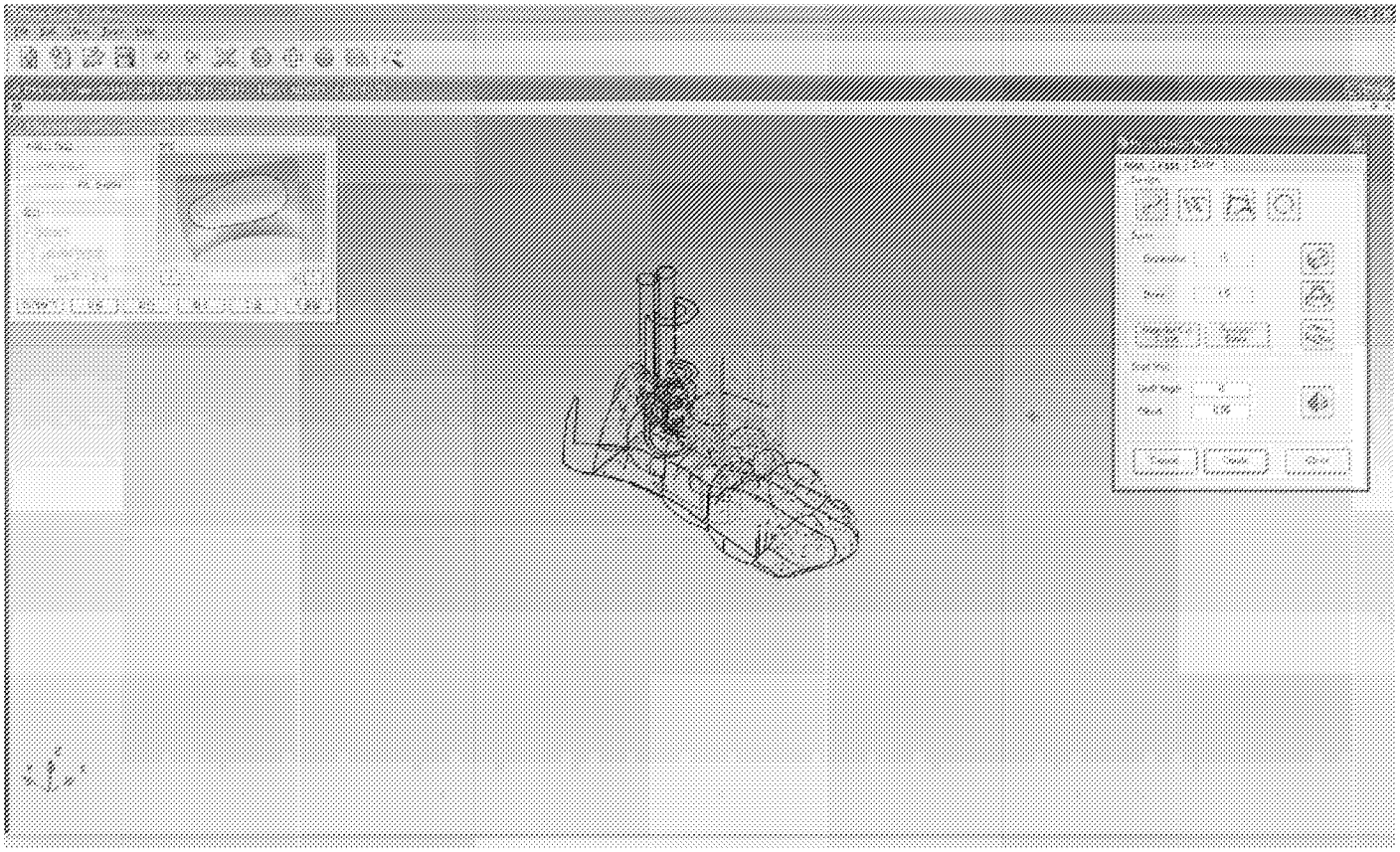
Figure 165:
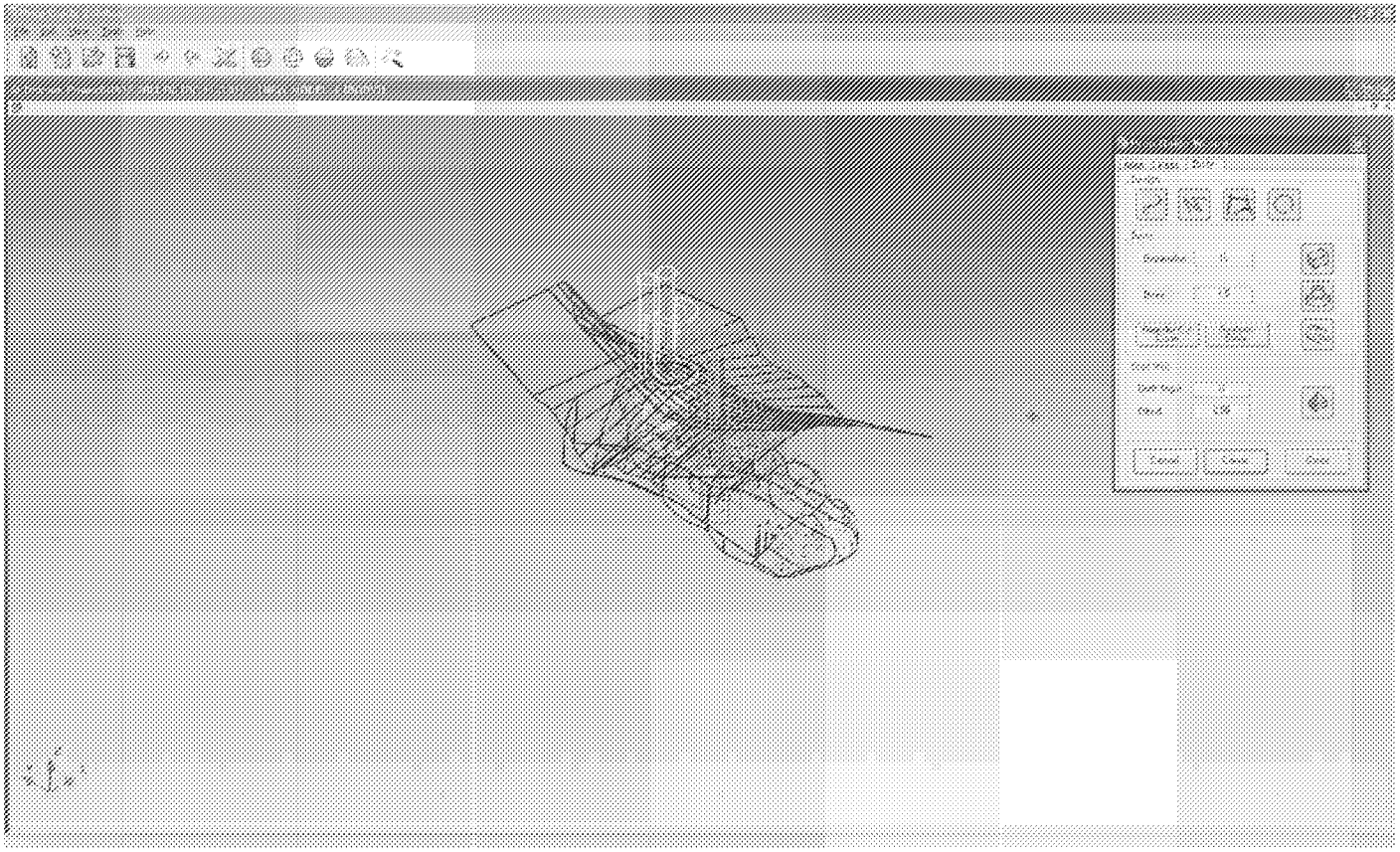
Figure 166:
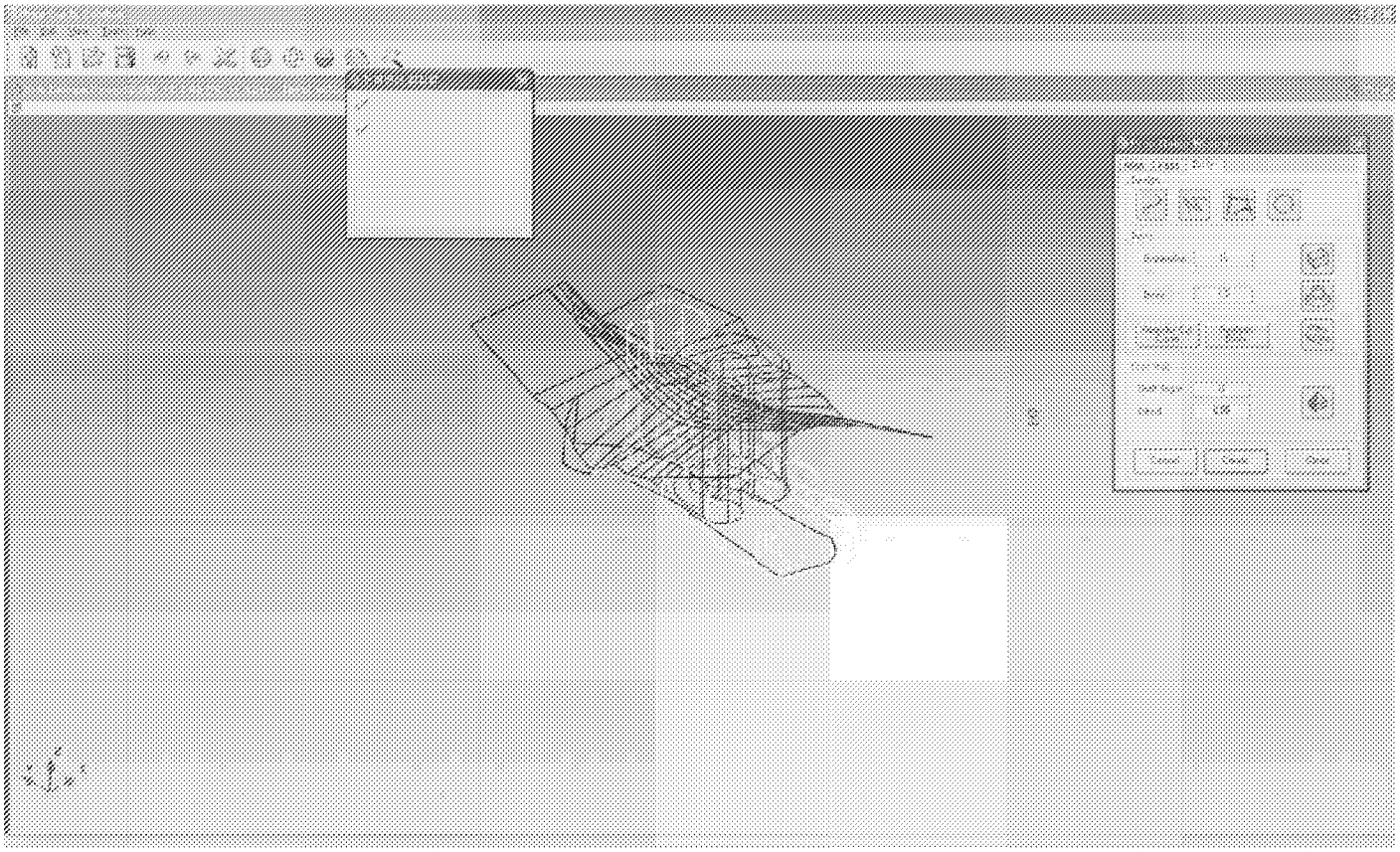
Figure 167:
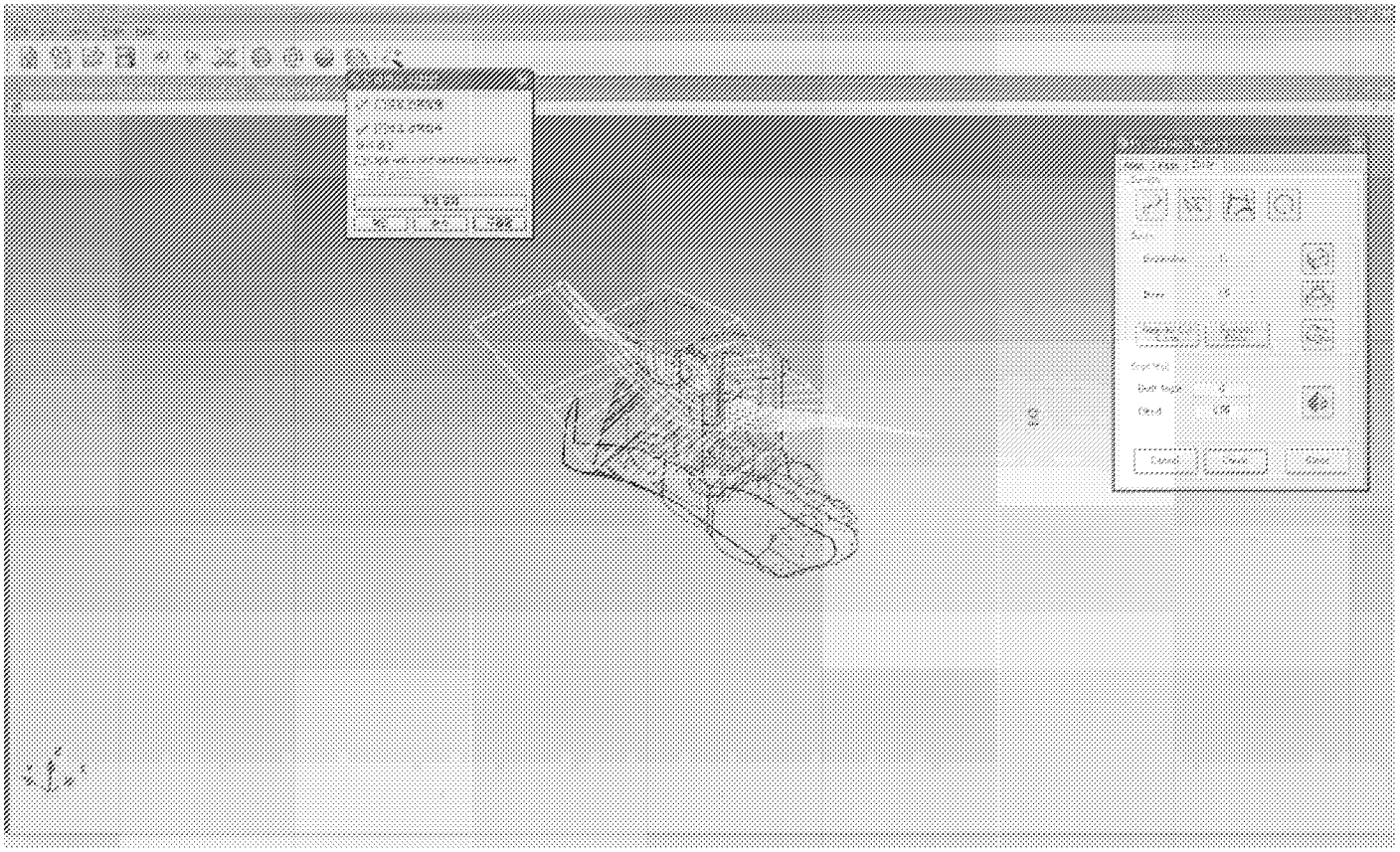
Figure 168:
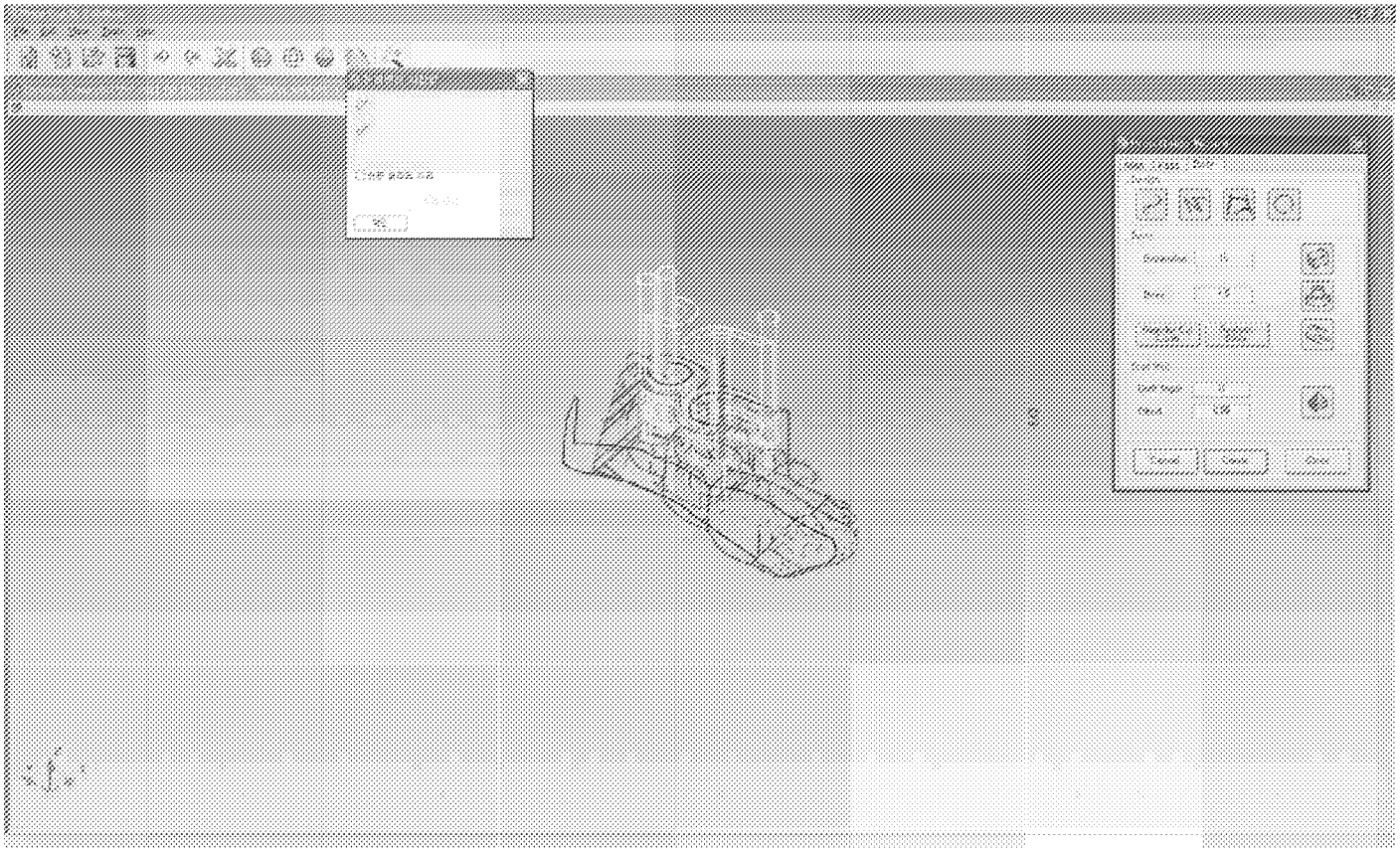
Figure 169:
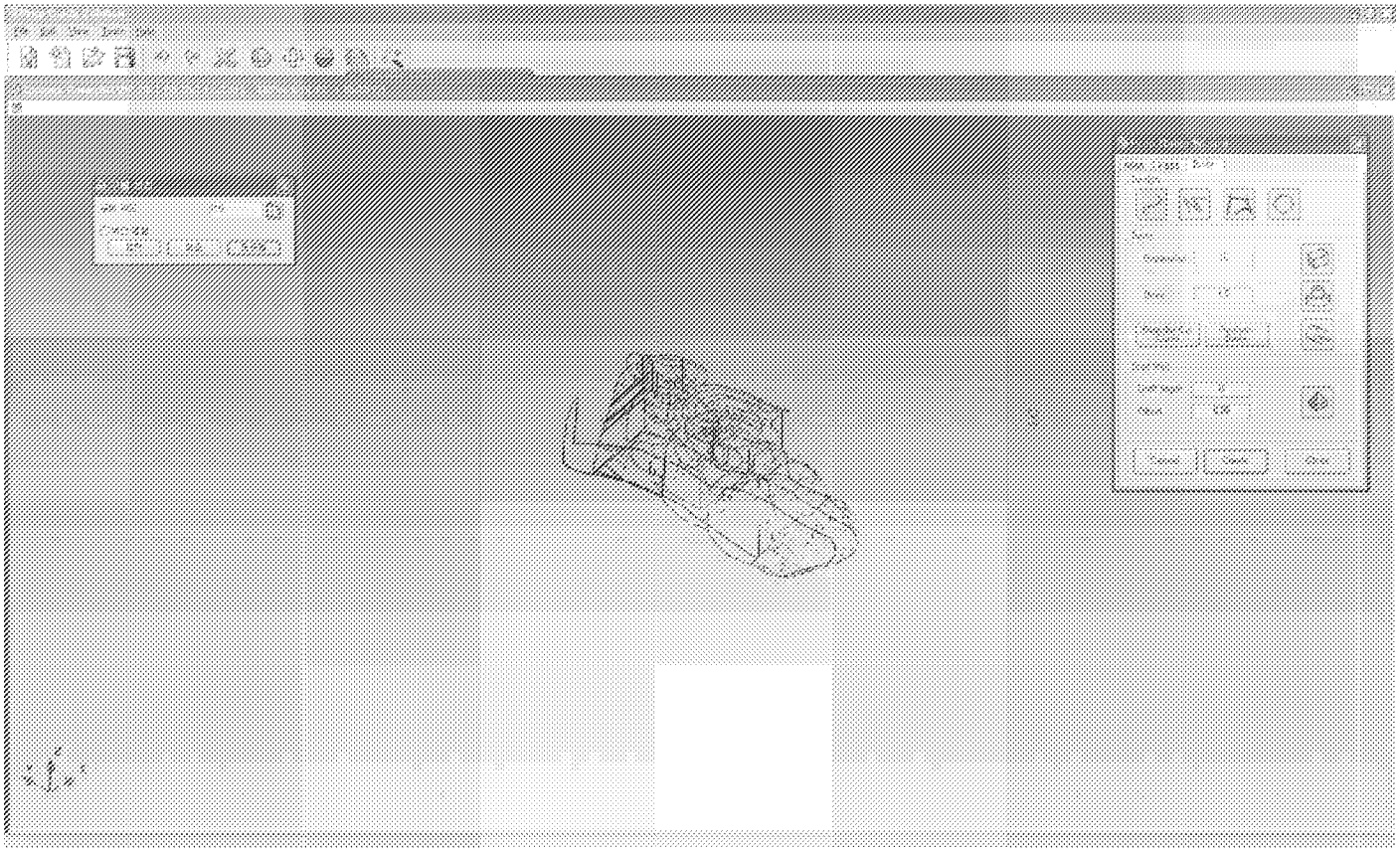
Figure 170:
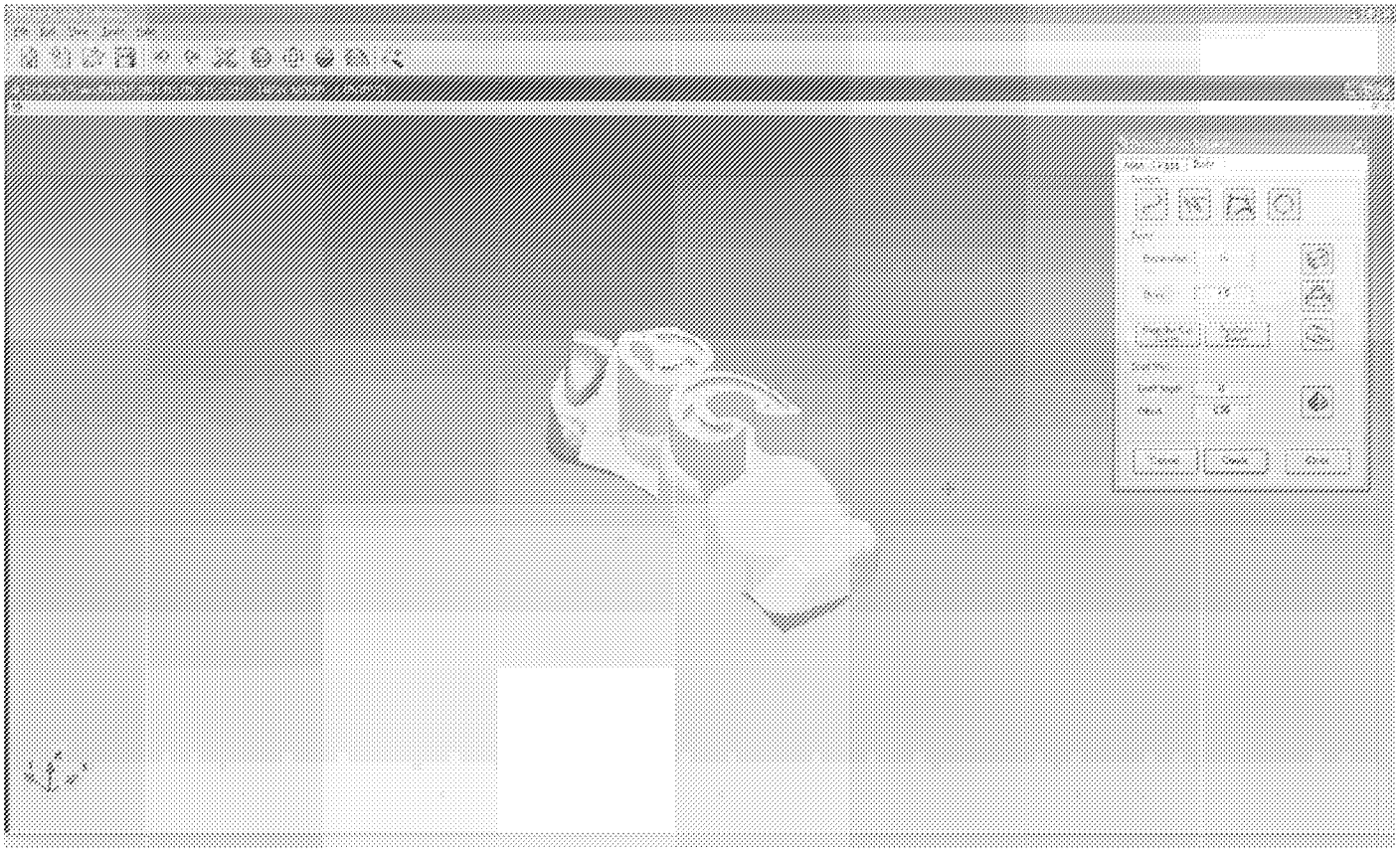
Figure 171:
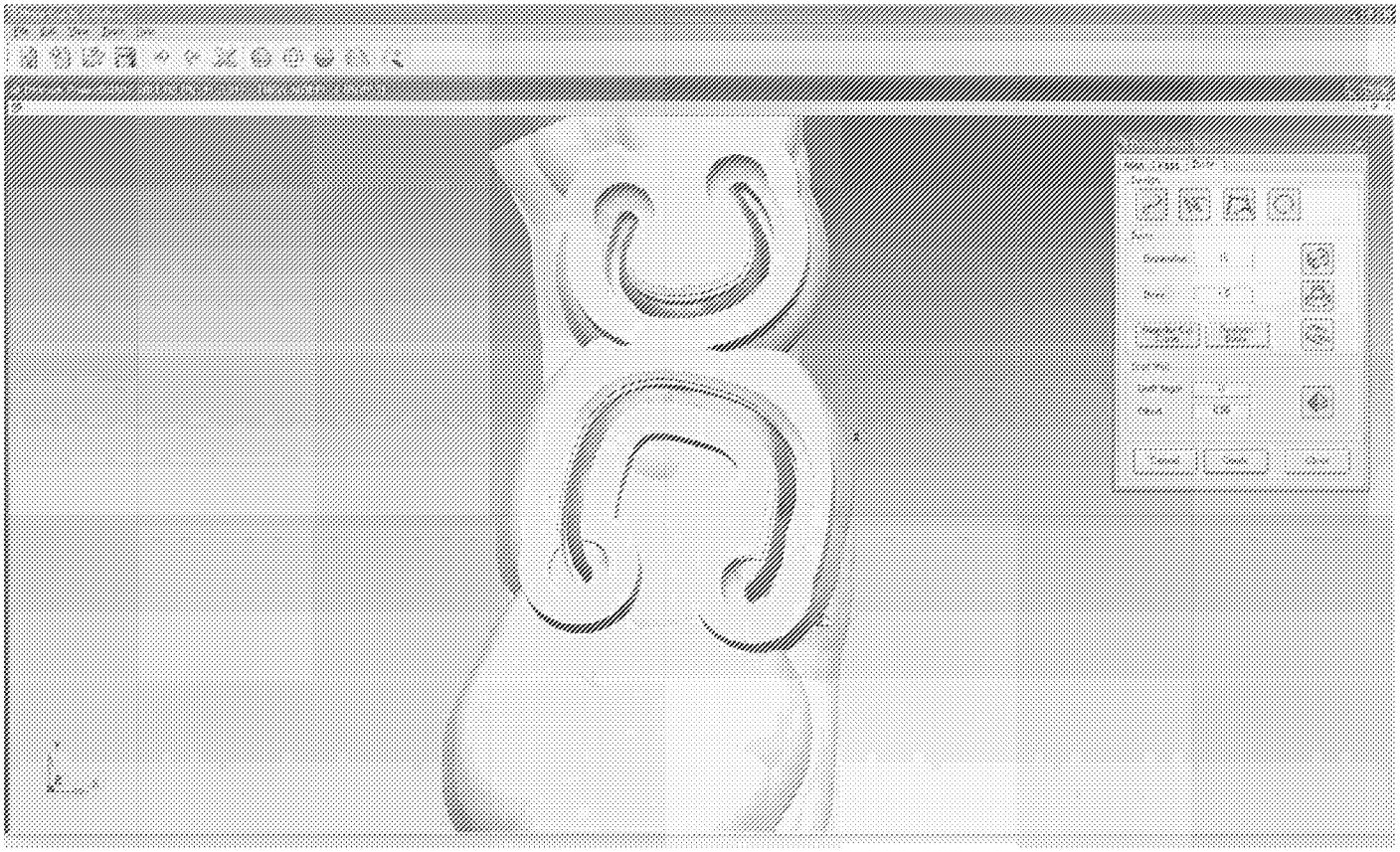
Figure 172:
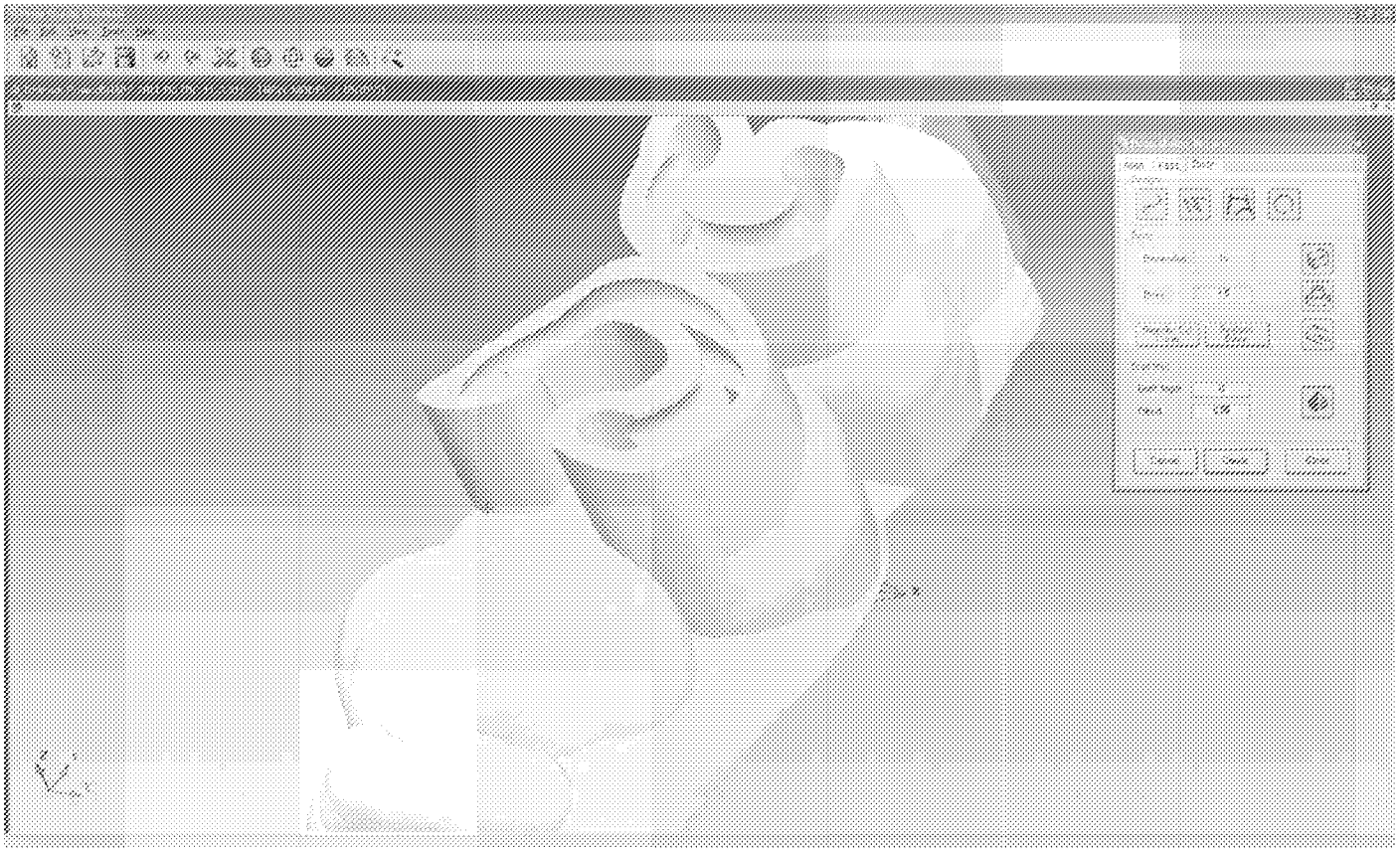

In an embodiment, once the cutting margin lines are determined, as shown in FIG. 155, the user clicks a "Body" tab in the menu window for designing the body of the preparation guide device. Subsequently, in an embodiment as shown in FIGS. 156 and 157, the computer system generates two lines, each of which is parallel to one of the two cutting margin lines. Along the two generated lines, in an embodiment as shown in FIG. 158-161, the computer system computes and displays a pathway of the cutting tool. In particular, pathways of a specific structure of the cutting tool, such as the neck, portion and/or guide projections, are displayed. Then, the tool guide channel is designed. Subsequently, in an embodiment as shown in FIG. 162-169, the computer system generates data for the body structure and tool guide way structures and displays them on the screen. In an embodiment as shown in FIG. 170-172, the computer system completes the design of the preparation guide device and displays it as a solid model on the screen.

No Need for Temporary Crown Prosthesis

According to an embodiment of the present invention, it is not necessary to install a temporary tooth where a tooth has been cut, as is done currently in procedures without using a preparation guide device. This reduces the amount of time and manufacturing costs required for such dental procedures.

No Need for Anesthesia

Currently existing dental procedures that require cutting a large amount of teeth, such as a crown prosthesis for example, generally involve removing all of the enamel layer and exposing the dentin layer. If the exposed dentin is further cut, the pulp layer inside can stimulate the nerve, and the patient can experience sharp pains. Therefore, anesthesia is generally required for such procedures. According to embodiments of the present invention, however, precise cutting is possible while cutting only an optimal and minimal amount. Especially in embodiments where minimal cutting technology is employed by using a preparation guide device to cut only the enamel layer, the dentin layer remains unexposed. Accordingly, the patient will experience almost no pain and such dental procedures can be performed without anesthesia. In such embodiments, the patient does not experience pain after the procedure for the same reason.

What is claimed is:

[1. A dental preparation guide apparatus in a single body, the single body apparatus comprising a lingual sidewall, a buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, mid the occlusal surface faces the occlusal wall, the apparatus further comprising a guide channel formed in the single body and shaped to receive a cutting tool and guide the cutting tool to travel along a trajectory;

the guide channel comprising two opposing channel surfaces that are substantially parallel to each other and extend along the trajectory such that the cutting tool is constrained by the two opposing surfaces while traveling along the trajectory, the guide channel further comprising at least one anti-tilting configuration formed into at least one of the two channel surfaces and configured to engage with the cutting tool for preventing or reducing tilting of the cutting tool in a plane parallel to a direction of movement of the cutting tool at a given point of the trajectory while the cutting tool travels along the trajectory;

wherein the guide channel comprises a buccal section, a lingual section, and an interconnecting section interconnecting the buccal and lingual sections, which are connected to provide the guide channel as a single integrated, channel that allows the cutting tool to travel through the buccal, interconnecting and lingual sections of the guide channel without having to remove the cutting tool therefrom; and wherein when viewing in a direction toward the occlusal wall, the buccal section extends generally along the buccal sidewall, and the lingual section extends generally along the lingual sidewall.]

[2. The apparatus of claim 1, wherein the buccal section is configured to cause a portion of the cutting tool to enter into a buccal area of the interior space between the buccal sidewall and the tooth such that the portion of the cutting tool cuts at least part of the buccal surface while traveling, in the buccal section;

wherein the lingual section is configured to cause the portion of the cutting tool to enter into a lingual area of the interior space between the lingual sidewall and the tooth such that the portion of the cutting tool cut at least part of the lingual surface while traveling in the lingual section; and wherein the interconnecting section is configured to cause the portion of the cutting tool to enter into an abutting area of the interior space between the tooth and an immediately neighboring tooth such that the portion of the cutting tool cut at least part of the mesial or distal surface while traveling in the interconnecting section.]

[3. The apparatus of claim 1, wherein when viewing in the direction toward the occlusal wall, a tangential line of the buccal section at a point thereof is parallel to a tangential line of the lingual section at a point thereof, wherein the at least one anti-titling configuration comprises a first engagement structure and a second engagement structure extending, along the trajectory and substantially parallel to each other, the first and second engagement structures being configured to engage respectively with first and second counterpart structures of the cutting tool, wherein engagement of the first and second engagement structures respectively with the first and second counterpart structures is to prevent or reduce tilting of the cutting tool in the plane parallel to the movement direction and further to prevent disengagement of the cutting tool from the guide channel while traveling along the trajectory except where a port of entry or discharge of the cutting tool is provided.]

[4. The apparatus of claim 3, Wherein the guide channel further comprises a second interconnecting section that further interconnects the buccal and lingual sections to provide the guide channel in the form of a closed loop when viewing in the direction toward the occlusal wall.]

[5. The apparatus of claim 3, wherein the guide channel further comprises another section extending front either the buccal section or the lingual section, wherein when viewing in the direction toward the occlusal wall, a tangential line of the other section at a point thereof is parallel to a tangential line of the interconnecting section at a point thereof.]

[6. The apparatus of claim 3, wherein the guide channel further comprises another section extending front either the buccal section or the lingual section, wherein when viewing in the direction toward the occlusal wall, a tangential line of the other section at a point thereof is parallel to a tangential line of the interconnecting section at a point thereof, wherein the other section does not interconnect between the buccal and lingual sections, which makes the guide channel in the form of an open loop.]

[7. The apparatus of claim 3, wherein the guide channel is configured to allow a proximal portion of the cutting tool pass through the occlusal wall while allowing a distal portion of the cutting tool extends into the interior, wherein each of the first and second counterpart structures is in a spherical shape as part of the cutting tool, and wherein each of the first and second engagement structures is a channel portion of the guide channel to accommodate traveling of the spherical shape therethrough.]

[8. A method of providing a dental restoration kit, the method comprising:

providing a first 3D image data representing one or more teeth of a patient before a desired preparation of the one or more teeth for installing a desired dental prosthesis;

before the desired preparation and before making the desired dental prosthesis, determining an axis of insertion along which the desired dental prosthesis should approach the one or more teeth for engaging the desired dental prosthesis with the one or more teeth after the desired preparation, wherein the axis of insertion is determined relative to the one or more teeth;

generating a second 3D image data representing the one or more teeth after the desired preparation;

producing the dental preparation guide apparatus of claim 3 based on the first 3D image data and the second 3D image data, wherein the interior space of the dental preparation guide apparatus is configured to receive the one or more teeth for engagement therewith, wherein the guide channel of the dental preparation guide apparatus is configured to guide the cutting tool comprising a burr for cutting at least part of the one or more teeth for the desired preparation; and producing the desired prosthesis based on the first 3D image data arid the second 3D image data.]

[9. The method of claim 8, wherein determining the axis of insertion comprises:

processing the first 3D image data to orient a 3D image of the one or more teeth in multiple directions;

providing information of undercuts in multiple directions of orientation of the 3D image; and choosing a direction of orientation of the 3D image as the axis of insertion based on the information of the undercuts.]

[10. The method of claim 8, wherein generating the second 3D image data comprises processing the first 3D image data with the input of an area of cutting and depth of cutting, wherein the single body apparatus further comprises a port configured to allow the burr to enter into or discharged from the guide channel, wherein the port is located in a portion of the single body that corresponds to another tooth received by the interior space, wherein the guide channel further comprises a non-cutting access way interconnecting between the port and one of the buccal section, the interconnecting section and the lingual section, wherein the non-cutting access way does not cause the burr to cut the other tooth received by the interior space.]

[11. The method of claim 8, wherein generating the second 3D image data comprises processing the first 3D image data with the input of one or more selected from the group consisting of an orientation of the burr, a diameter of the burr, a length of the burr, tapered shape information of the burr, a position of the burr relative to the one or more teeth, a distance between a rotational axis of the burr and an exterior surface of the one or more teeth, and a level of the burr relative to the one or more teeth, wherein each of the first and second counterpart structures is in a spherical shape as part of the burr, and wherein each of the first and second engagement structures is a channel portion of the guide channel to accommodate traveling of the spherical shape therethrough.]

[12. The method of claim 8 wherein producing the desired prosthesis comprises:

generating a fourth 3D image data of the desired prosthesis; and making the desired prosthesis using the fourth 3D image data.]

[13. The method of claim 8, further comprising providing the burr, wherein at least one of the first and second counter-part structures is in a spherical shape as part of the burr, and wherein at least one of the first and second engagement structures is a channel portion of the guide channel to accommodate traveling of the spherical shape therethrough.]

[14. A method of making devices for dental procedure, comprising:

providing a first 3D image data representing one or more teeth of a patient before a desired preparation of the one or more teeth for installing a desired dental prosthesis;

before the desired preparation, generating a first image illustrating a first prospective shape of the one or more teeth that would exist after installation of a first dental prosthesis;

before the desired preparation, providing the first image for the patient's review of the first image;

subsequent to the patient's approval of the first image and before the desired preparation, causing to make the first dental prosthesis based on the first image; and subsequent to the patient's approval of the image, making the dental preparation guide apparatus of claim 3 based on the first 3D image data, wherein the interior space of the dental preparation guide apparatus is configured to fit at least part of the one or more teeth, wherein the guide channel of the dental preparation guide apparatus is configured to guide the cutting tool comprising a burr to travel along the trajectory to cut the one or more teeth for fitting the first dental prosthesis without the need of additional substantial cutting of the one or more teeth.]

[15. The method of claim 14, further comprising:

before the desired preparation, generating a second 3D image data representing a prospective, prepared shape of the one or more teeth that would exist after the desired preparation thereof, wherein the single body apparatus further comprises a port configured to allow the burr to enter into or discharged from the guide channel, wherein the port is located in a portion of the single body that corresponds to another tooth received by the interior space, wherein the guide channel further comprises a non-cutting access way interconnecting between the port and one of the buccal section, the interconnecting section and the lingual section, wherein the non-cutting access way does not cause the burr to cut the other tooth received by the interior space.]

[16. The method of claim 14, further comprising:

before the desired preparation, generating a second image illustrating a second prospective shape of the one or more teeth that would exist after installation of a second dental prosthesis;

before the desired preparation, providing a plurality of images comprising the first and second images for the patient's review; and receiving the patient's approval of the first image rather than the second image, wherein the first and second prospective shapes differ in at least one selected from the group consisting of length, width, surface curvature, embrasure and shading.]

[17. The method of claim 14, further comprising:

subsequent to providing the first image and prior to the patient's approval, receiving the patient's request to modify the first image;

changing the first prospective shape based on the patient's request to modify the first image; and providing art modified first image illustrating the changed first prospective shape for the patient's approval.]

[18. A method of dental procedure, comprising:

making a first dental prosthesis and a preparation guide device in accordance with the method of claim 14, wherein at least one of the first and second counterpart structures is in a spherical shape as part of the burr, and wherein at least one of the first and second engagement structures is a channel portion of the guide channel to accommodate traveling of the spherical shape therethrough; and providing the first dental prosthesis and the preparation guide device to a dental practitioner for preparing the one or more teeth and installing the first dental prosthesis onto the one or more teeth after preparation.]

[19. The method of claim 18, further comprising: providing the burr along with the first dental prosthesis and the dental preparation guide apparatus, wherein the dental preparation guide apparatus further comprises a guide groove formed along the at least one guide channel, wherein the burr comprises an elongated body with a bump between two ends thereof, wherein the elongated body is configured to fit in the at least one guide channel of the preparation guide device and the bump is configured to fit the guide groove such that the guide channel and the guide groove in combination position and orient the burr relative to the one or more teeth in a predetermined manner.]

[20. The apparatus of claim 1, wherein the interior space defined by the lingual sidewall, the buccal sidewall and the occlusal wall is configured to receive one or more additional teeth, wherein the single body apparatus further comprises a port configured to allow the cutting tool to enter into or discharged from the guide channel, wherein the port is located in a portion of the single body that corresponds to one of the one or more additional teeth, wherein the guide channel further comprises a non-cutting access way interconnecting between the port and one of the buccal section, the interconnecting section and the lingual section, wherein the non-cutting access way does not cause the cutting tool to cut the tooth or one or more additional teeth.]

[21. A method of preparing a tooth for dental restoration, the method comprising:

providing the apparatus of claim 1 for preparation of a tooth comprising a buccal surface, a lingual surface, a mesial surface, a distal surface and an occlusal surface;

engaging the apparatus with the tooth such that the tooth is received in the interior space and such that the lingual surface faces the lingual sidewall, the buccal surface faces the buccal sidewall, and the occlusal surface faces the occlusal wall;

inserting the cutting tool comprising a burr into the guide channel via an insertion hole;

traveling the burr along the trajectory of the guide channel comprising the buccal section, lingual section and inter-connecting section, by which the burr cuts side surface of the tooth comprising at least part of the lingual surface, at least part of the buccal surface and at least part of the mesial or distal surface; and wherein during traveling of the burr along the trajectory, the burr is not removed from the wide channel until completion of the cutting side surfaces of the tooth.]

[22. The method of claim 21, wherein when viewing in the direction toward the occlusal wall, a tangential line of the buccal section at a point thereof is parallel to a tangential line of the lingual section at a point thereof, wherein the at least one anti-titling configuration comprises a first engagement structure and a second engagement structure extending along the trajectory and substantially parallel to each other, the first and second engagement structures being configured to engage respectively with first and second counterpart structures of the cutting tool, wherein engagement of the first and second engagement structures respectively with the first and second counterpart structures is to prevent or reduce tilting of the cutting tool in the plane parallel to the movement direction and further to prevent disengagement of the cutting tool from the guide channel while traveling along the trajectory except where a port of entry or discharge of the cutting tool is provided.]

[23. The apparatus of claim 1, wherein the cutting tool comprises an inserting structure connected to a dentist's handpiece, in which the inserting structure is inserted between the two surfaces, wherein the inserting structure comprises at least one counterpart structure configured to engage with the at least one anti-tilting feature of the guide channel.]

[24. A system for dental preparation, comprising:

the apparatus of claim 1;

a dental handpiece comprising an inserting structure, wherein the inserting structure and a burr constitutes a cutting tool to be received by the guide channel of the apparatus; and the inserting structure comprising at least one counterpart structure configured to engage with the at least one anti-tilting configuration of the guide channel such that the inserting structure is constrained by the at least one anti-tilting configuration of the guide channel rather than the burr.]

[25. The apparatus of claim 1, wherein the cutting tool comprises a burr and an inserting structure that are connected to a dentist's handpiece, wherein the inserting structure is inserted between and constrained by the two channel surfaces of the guide channel, wherein the inserting structure comprises at least one counterpart structure configured to engage with the at least one anti-tilting configuration of the guide channel.]

[26. The apparatus of claim 1, wherein when the cutting tool is received by the guide channel, the inserting structure is constrained by the guide channel whereas the burr is not directly constrained by the guide channel.]

[27. A dental preparation guide apparatus in a single body, the single body apparatus comprising a lingual sidewall, buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive two or more teeth comprising a first tooth and a second tooth, wherein the lingual sidewall comprises a first lingual sidewall and a second lingual sidewall, the buccal sidewall comprises a first buccal sidewall and a second buccal sidewall, the occlusal wall comprises a first occlusal wall and a second occlusal wall;

wherein the first: lingual sidewall and the first buccal sidewall oppose each other and are configured to sandwich the first tooth when the first and second teeth are received in the interior space;

wherein the second lingual sidewall and the second buccal sidewall oppose each other and are configured to sandwich the second tooth when the first and second teeth are received in the interior space;

wherein the first occlusal wall interconnecting between the first lingual sidewall and the first buccal sidewall and is configured to overlap the first tooth when the first and second teeth are received in the interior space;

wherein the second occlusal wall interconnecting between the second lingual sidewall and the second buccal sidewall and is configured to overlap the second tooth when the first and second teeth are received in the interior space;

wherein the apparatus further comprises a first guide channel formed in the single body and shaped to receive a cutting tool and guide the cutting tool along a first trajectory, the first guide channel comprising a first engagement structure configured to engage with a first counterpart structure of the cutting tool and further configured to prevent disengagement of the cutting tool from the first guide channel while traveling along the first trajectory; and wherein the single body comprises a second guide channel formed in the second occlusal wall and shaped to receive the cutting tool or another cutting tool to guide the same along the second guide channel.]

[28. The apparatus of claim 27, wherein the first and second teeth are adjacent with each other with no tooth therebetween and with no missing tooth therebetween, wherein the first guide channel and the second guide channel are connected together and form a single connected channel such that the cutting tool received in the first guide channel can travel to the second guide channel without having to be removed from the first guide channel.]

[29. The apparatus of claim 27, wherein the first and second teeth are immediately next to each other with no tooth therebetween and with no missing tooth therebetween, wherein the first guide channel and the second guide channel are separate from each other and a portion of the single piece body blocks between the first and second channels such that the cutting tool received in the first guide channel must be removed from the first guide channel in order to be received in the second guide channel, wherein the first guide channel comprises a second engagement structure configured to engage with a second counterpart structure of the cutting tool, wherein engagement of the first and second engagement structures respectively with the first and second counterpart structures is to prevent or reduce tilting of the cutting tool is the plane parallel to the movement direction while traveling along the first trajectory.]

[30. The apparatus of claim 27, wherein a missing tooth exists between the first and second teeth, wherein the lingual sidewall further comprises a third lingual sidewall located between the first lingual sidewall and the second lingual sidewall;

wherein the buccal sidewall further comprises a third buccal sidewall located between the first buccal sidewall and the second buccal sidewall;

wherein the occlusal wall further comprises a third occlusal wall located between the first occlusal wall and the second occlusal wall;

wherein the third lingual sidewall, the third buccal sidewall and the third occlusal wall at least partially surrounds a space of the missing tooth when the first and second teeth are received in the interior space; and wherein the first guide channel comprises a second engagement structure configured to engage with a second counterpart structure of the cutting tool, wherein engagement of the first and second engagement structures respectively with the first and second counterpart structures is to prevent or reduce tilting of the cutting tool in the plane parallel to the movement direction while traveling along the first trajectory.]

[31. The apparatus of claim 30, wherein the single body comprises a third guide channel formed in the third occlusal wall and shaped to receive the cutting tool or another cutting, tool to guide the same along the third guide channel, wherein the first guide channel and the second guide channel are connected together via the third guide channel and form a single connected channel such that the cutting tool received in the first guide channel can travel to the second guide channel without having to be removed from the first guide channel.]

[32. The apparatus of claim 30, wherein the single body does not comprise a guide channel in the third occlusal wall, wherein the first guide channel and the second guide channel are separate from each other and a portion of the third occlusal wall blocks between the first and second channels such that the cutting tool received in the first guide channel must be removed from the first guide channel in order to be received in the second guide channel.]

[33. The apparatus of claim 27, wherein a third tooth exist between the first and second teeth, wherein the lingual sidewall further comprises a third lingual sidewall located between the first lingual sidewall and the second lingual sidewall;

wherein the buccal sidewall further comprises a third buccal sidewall located between the first buccal sidewall and the second buccal sidewall;

wherein the occlusal wall further comprises a third occlusal wall located between the first occlusal wall and the second occlusal wall;

wherein the third lingual sidewall, the third buccal sidewall and the third occlusal wall at least partially surrounds the third tooth when the first, second and third teeth are received in the interior space; and wherein the first guide channel comprises a second engagement structure configured to engage with a second counterpart structure of the cutting tool, wherein engagement of the first and second engagement structures respectively with the first and second counterpart structures is to prevent or reduce tilting of the cutting tool in the plane parallel to the movement direction while traveling along the first trajectory.]

[34. The apparatus of claim 33, wherein the single body comprises a third guide channel formed in the third occlusal wall and shaped to receive the cutting tool or another cutting tool to guide the same along the third guide channel, wherein the first guide channel and the second guide channel are connected together via the third guide channel and form a single connected channel such that the cutting tool received in the first guide channel can travel to the second guide channel without having to be removed from the first guide channel.]

[35. The apparatus of claim 27, wherein the first guide channel comprises a first buccal section, a first lingual section, and a first interconnecting section interconnecting the first buccal and first lingual sections to provide the first guide channel as a single integrated channel that allows the cutting tool to travel between the first lingual section and the first buccal section without having to remove the cutting tool therefrom, wherein when viewing in a direction toward the occlusal wall, the first buccal section extends generally along the first buccal sidewall, and the first lingual section extends generally along the first lingual sidewall; and wherein the first guide channel comprises a second engagement structure configured to engage with a second counterpart structure of the cutting tool, wherein engagement of the first and second engagement structures respectively with the first and second counterpart structures is to prevent or reduce tilting of the cutting tool in the plane parallel to the movement direction while traveling along the first trajectory.]

[36. The apparatus of claim 35, wherein the first buccal section is configured to cause a portion of the cutting tool to enter into a buccal area of the interior space between the first buccal sidewall and the first tooth for cutting at least part of a buccal surface of the first tooth while traveling in the first buccal section when the first and second teeth are received in the interior space;

wherein the first lingual section is configured to cause the portion of the cutting tool to enter into a lingual area of the interior space and between the first lingual sidewall and the tooth for cutting at least part of a lingual surface of the first tooth while traveling in the first lingual section when the first and second teeth are received in the interior space; and wherein the first interconnecting section is configured to cause the portion of the cutting tool to enter into the interior space for cutting at least part of a mesial or distal surface of the first tooth while traveling in the first interconnecting section when the first and second teeth are received in the interior space.]

[37. The apparatus of claim 35, wherein when viewing in the direction toward the occlusal wall, a tangential line of the first buccal section at a point thereof is parallel to a tangential line of the first lingual section at a point thereof, wherein each of the first and second counterpart structures is in a spherical shape as part of the cutting tool, and wherein each of the first and second engagement structures is a channel portion of the first guide channel to accommodate traveling of the spherical shape therethrough.]

[38. The apparatus of claim 35, wherein the first guide channel further comprises a second interconnecting section that further interconnects the first buccal section and the first lingual section to provide the first guide channel in the form of a closed loop when viewing in the direction toward the occlusal wall, wherein each of the first and second counterpart structures is in a spherical shape as part of the cutting tool, and wherein each of the first and second engagement structures is a channel portion of the first guide channel to accommodate traveling o I the spherical shape therethrough.]

[39. The apparatus of claim 35, wherein the first guide channel further comprises another section extending from either the first buccal section or the first lingual section, wherein when viewing in the direction toward the occlusal wall, a tangential line of the other section at a point thereof is parallel to a tangential line of the first interconnecting section at a point thereof, wherein the single body apparatus further comprises a port configured to allow the cutting tool to enter into or discharged from the first guide channel, wherein the port is located in a portion of the single body that corresponds to one of the two or more teeth received by the interior space, wherein the first guide channel further comprises a non-cutting access way interconnecting between the port and one of the buccal section, the interconnecting section and the lingual section, wherein the non-cutting access way does not cause the cutting tool to cut the two or more teeth.]

[40. The apparatus of claim 35, wherein the first guide channel further comprises another section extending from either the first buccal section or the first lingual section, wherein when viewing in the direction toward the occlusal wall, a tangential fine of the other section at a point thereof is parallel to a tangential line of the first interconnecting section at a point thereof, wherein the other section does not interconnect between the first buccal section and the first lingual section to make the guide channel in the form of an open loop, wherein the single body apparatus further comprises a port configured to allow the cutting tool to enter into or discharged from the first guide channel, wherein the port is located in a portion of the single body that corresponds to one of the two or more teeth received by the interior space, wherein the first guide channel further comprises a non-cutting access way interconnecting between the port and one of the buccal section, the interconnecting section and the lingual section, wherein the non-cutting access way does not cause the cutting tool to cut the two or more teeth.]

[41. The apparatus of claim 27, wherein the first guide channel comprises two substantially parallel and opposing surfaces formed in the single body, wherein the two surfaces are configured to receive the cutting tool therebetween and to constrain the cutting tool while traveling along the trajectory.]

[42. The apparatus of claim 41, wherein the cutting tool comprises an inserting structure connected to a dentist's handpiece, in which the inserting structure is inserted between the two surfaces and constrained by the two surfaces while the cutting tool is traveling along the trajectory.]

[43. A system for dental preparation, comprising:

the apparatus of claim 41;

a dental handpiece with an inserting structure connected to the dental handpiece; and wherein the inserting structure is configured to be inserted between and constrained by the two surfaces of the first guide channel.]

[44. A method of dental procedure, comprising:

providing a dental prosthesis for installing onto one or more teeth of a patient, the one or more teeth comprising a first tooth comprising an occlusal surface, a buccal side, a lingual side, a distal side and a mesial side;

providing a preparation guide device in a single piece far use in preparing the one or more teeth of the patient for installing the dental prosthesis, wherein the preparation guide device is custom-made to fit at least part of the one or more teeth and comprises at least one guide channel configured to guide a cutting tool, wherein the at least one guide channel comprises a first single channel that the cutting tool can travel along a first trajectory thereof, the first single channel comprising a first engagement structure and a second engagement structure extending along the first trajectory and substantially parallel to each other;

mounting the preparation guide device over the one or more teeth such that the preparation guide device fit the at least part of the one or more teeth;

providing the cutting tool comprising a burr, the cutting tool further comprising a first counterpart structure and a second counterpart structure;

engaging the cutting tool with the first single channel such that the first and second counterpart structures of the burr engage respectively with the first and second engagement structures of the first single channel;

moving the burr along the first trajectory to cut the first tooth on three or four of the buccal, lingual, distal and mesial sides without having to remove the burr from the preparation guide device, which completes preparation of the first tooth for installing the dental prosthesis onto the first tooth without the need of an additional preparation guide for preparing the first tooth and without the need of an additional substantial cutting of the first tooth, wherein engagement of the first and second engagement structures with the first and second counterpart structures prevents or reduces tilting of the burr in a plane parallel to a direction of movement of the bur at a given point of the first trajectory and further prevents disengagement of the burr from the first single channel while the burr is traveling along the trajectory except where a disengagement configuration is provided; and installing the dental prosthesis onto the first tooth so as to surround the three or four of the buccal, lingual, distal and mesial sides of the first tooth.]

[45. The method of claim 44, wherein cutting of the three or four sides leaves at least a portion of the four sides uncut, wherein the uncut portion comprises a contact point of the first tooth that contacts a neighboring tooth, wherein at least one of the first and second counterpart structures is in a spherical shape as part of the cutting tool, and wherein at least one of the first and second engagement structures is a channel portion of the first single channel to accommodate traveling of the spherical shape therethrough.]

[46. The method of claim 44, wherein the first single channel is configured to cut the four of the buccal, lingual, distal and mesial sides, wherein cutting of the four sides entirely encircles the first tooth when viewing in a direction toward the occlusal surface, wherein the dental prosthesis comprises a ring structure contacting the four sides of the first tooth that are cut using the first single channel, wherein at least one of the first and second counterpart structures is in a spherical shape as part of the cutting tool, and wherein at least one of the first and second engagement structures is a channel portion of the first single channel to accommodate traveling of the spherical shape therethrough.]

[47. The method of claim 44, wherein the first single channel is configured to cut the four of the buccal, lingual, distal and mesial sides, wherein cutting of the four sides does not entirely encircle the first tooth and leaves at least part of one of the four sides uncut when viewing in a direction toward the occlusal surface, wherein the dental prosthesis comprises a C-shaped structure contacting the four sides of the first tooth that are cut using the first single channel, wherein the single piece device further comprises a port configured to allow the burr to enter into or discharged from the single channel, wherein the port is located in a portion of the single piece device that corresponds to one of the one or more teeth, wherein the single channel further comprises a non-cutting access way interconnecting between the port and one of the buccal section, the interconnecting section and the lingual section, wherein the non-cutting access way does not cause the burr to cut the one or more teeth.]

[48. The method of claim 44, wherein the one or more teeth comprise a first tooth and a second tooth, wherein cutting the one or more teeth comprises cutting the first tooth and then cutting the second tooth, wherein the preparation guide device is not disconnected from the one or more teeth between cutting the first tooth and cutting the second tooth, and wherein the first single channel is further configured to cut the second tooth in addition to cutting the first tooth without having to remove the burr from the first single channel, wherein the single piece device further comprises a port configured to allow the burr to enter into or discharged from the single channel, wherein the port is :located in a portion of the single piece device that corresponds to one of the one or more teeth, wherein the single channel further comprises a non-cutting access way interconnecting between the port and one of the buccal section, the interconnecting section and the lingual section, wherein the non-cutting access way does not cause the burr to cut the one or more teeth.]

[49. The method of claim 44, wherein the one or more teeth comprise a first tooth and a second tooth, wherein cutting the one or more teeth comprises cutting the first tooth and then cutting the second tooth, wherein the preparation guide device is not disconnected from the one or more teeth between cutting the first tooth and cutting the second tooth, and wherein the at least one channel comprises a second single channel that is distinct from the first single channel and configured to cut the second tooth.]

[50. The method of claim 44, wherein providing the dental prosthesis comprises receiving the dental prosthesis from a third party or making the dental prosthesis in-house, wherein providing the preparation guide device comprises receiving the preparation guide device from a third party or making the preparation guide device in-house.]

[51. The method of claim 44, further comprising:

causing to provide a 3D image data representing the one or more teeth of the patient before preparation sufficient to install the dental prosthesis, wherein causing to provide the 3D image data comprises at least one selected from the group consisting of:

scanning of the patient's oral features using a 3D scanning device;

taking an impression of the patient's oral features;

producing a 3D model of the patient's oral features from the impression; and scanning the 3D model using a 3D scanning device.]

[52. The method of claim 44, wherein the first single channel comprises two substantially parallel and opposing surfaces formed in the single piece such that the cutting tool is constrained by the two opposing surfaces while traveling along the first trajectory.]

[53. The method of claim 52, wherein the burr is engaged with the first single channel via an inserting structure connected to a dentist's handpiece, in which the inserting structure is inserted between the two surfaces and constrained by the two opposing surfaces while traveling along the first trajectory. ]

[54. A dental preparation guide apparatus in a single body, the single body apparatus comprising a lingual sidewall, a buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, and the occlusal surface faces the occlusal wall, wherein the single body comprising a first guide channel formed in the occlusal wall and shaped to engage with a first cutting tool to guide the first cutting tool to travel along a first trajectory;

wherein when viewing in a direction toward the occlusal wall, the first guide channel comprising a section that extends generally along at least part of the buccal sidewall;

wherein the single body comprising a second guide channel formed in at least one of the buccal and lingual sidewalls and shaped to engage with the first cutting tool or a second cutting tool to guide the same to travel along a second trajectory; and wherein when viewing in a direction toward the buccal sidewall, the second guide channel extends generally along at least part of the occlusal wall.]

[55. The apparatus of claim 54, wherein the occlusal wall comprises an interior surface facing, the occlusal surface of the tooth when the tooth is received in the interior space, wherein the second guide channel extends generally along the interior surface of the occlusal wall when viewing in the direction toward the buccal sidewall; and wherein the buccal side wall comprises an interior surface facing the buccal surface of the tooth when the tooth is received in the interior space, wherein the first guide channel extends generally along the interior surface of the buccal wall when viewing in the direction toward the occlusal wall.]

[56. The apparatus of claim 54, wherein the first guide channel further comprises another section, which is configured to have the first cutting tool pass through the occlusal wall such that the first cutting tool extends into the interior space, and further such that the first cutting tool cuts one of the mesial and distal surfaces when the first cutting tool travels in the other section.]

[57. A method of preparing a tooth for dental restoration, the method comprising:

providing the apparatus of claim 54 for preparation of a tooth comprising a buccal surface, a lingual surface, a mesial surface, a distal surface and an occlusal surface;

engaging the apparatus with the tooth such that the tooth is received in the interior space and such that the lingual surface faces the lingual sidewall, the buccal surface faces the buccal sidewall, and the occlusal surface faces the occlusal wall;

inserting the first cutting tool comprising a burr into the first guide channel of the apparatus, whereby a cutting portion of the burr enters into the interior space and between the buccal sidewall and the tooth;

cutting at least part of the buccal surface of the tooth while traveling the burr along the first guide channel;

inserting the first cutting tool or a second cutting tool comprising a burr into the second guide channel, whereby a cutting portion of the burr of the first or second cutting tool enters into the interior space and between the occlusal wall and the tooth, wherein inserting the into the second guide channel can occur either before or after cutting the buccal surface; and cutting at least part of the buccal surface of the tooth while traveling the burr of the first or second cutting tool along the second guide channel.]

[58. The apparatus of claim 54, wherein the first guide channel comprises two substantially parallel and opposing surfaces formed in the single body such that the first cutting tool is constrained by the two opposing surfaces while traveling along the first trajectory.]

[59. The apparatus of claim 58, wherein the first cutting tool is to be engaged with the first guide channel via an inserting structure connected to a dentist's handpiece, in which the inserting structure is inserted between the two surfaces and constrained by the two surfaces while the first cutting tool is traveling along the trajectory.]

[60. A system for dental preparation, comprising:

apparatus of claim 58;

a dental handpiece with an inserting structure connected to the dental handpiece; and wherein the inserting structure is configured to be inserted between the two surfaces of the first guide channel and constrained by the two surfaces while the first cutting tool is traveling along the first trajectory.]

[61. A dental preparation guide apparatus in a single body, the single body apparatus comprising a lingual sidewall, buccal sidewall opposing the lingual sidewall, and an occlusal wall interconnecting the lingual and buccal sidewalls to form the single body, wherein the lingual sidewall, the buccal sidewall and the occlusal wall in combination define an interior space in which to receive a tooth comprising a buccal surface, a lingual surface, a mesial surface, a distal surface and an occlusal surface such that the lingual surface faces the lingual sidewall, the buccal surface faces the buccal sidewall, and the occlusal surface faces the occlusal wall, wherein the single body comprises a guide channel formed through at least one of the lingual and buccal sidewalls and shaped to engage with a cutting tool to guide the cutting tool along a trajectory, the guide channel comprising two opposing channel surfaces that are substantially parallel to each other and extending along the trajectory such that the cutting tool is constrained by the two opposing surfaces while traveling along the trajectory; and wherein the guide channel is configured to cause a portion of the cutting tool to enter into the interior space and to be inserted between the occlusal wall and the tooth such that the portion of the cutting tool cuts at least part of the occlusal surface while traveling in the guide channel.]

[62. The apparatus of claim 61, wherein the guide channel comprises a port configured to permit the entry of the cutting tool into the guide channel, wherein the port of the guide channel is formed through the occlusal wall such that the cutting tool enters into the guide channel formed in the at least one of the lingual and buccal sidewalls via the port through the occlusal wall, wherein the guide channel comprises an anti-tilting configuration formed into at least one of the two channel surfaces and configured to engage with the cutting tool for preventing or reducing tilting of the cutting tool in a plane parallel to a direction of movement of the cutting tool at a given point of the trajectory while the cutting tool travels along the trajectory.]

[63. The apparatus of claim 62, wherein the cutting tool is to be engaged with the guide channel via an inserting structure connected to a dentist's handpiece, in which the inserting structure is inserted between the two surfaces, wherein the inserting structure comprises a counterpart structure configured to engage with the anti-tilting configuration of the guide channel such that the inserting structure is further constrained by the guide channel rather than the cutting tool.]

[64. A method of preparing a tooth for dental restoration, the method comprising:

providing the apparatus of claim 62 far preparation of a tooth comprising a buccal surface, a lingual surface, a mesial surface, a distal surface and an occlusal surface, wherein the anti-titling configuration comprises a first engagement structure and a second engagement structure extending along the trajectory and substantially parallel to each other, the first and second engagement structures being configured to engage respectively with first and second counterpart structures of the cutting tool, wherein engagement of the first and second engagement structures respectively with the first and second counterpart structures is to prevent or reduce tilting of the cutting tool in the plane parallel to the movement direction and further to prevent disengagement of the cutting tool from the guide channel while traveling along the trajectory except where a port of entry or discharge of the cutting tool is provided;

integrating the apparatus with the tooth such that the tooth is received in the interior space and such that the lingual surface faces the lingual sidewall, the buccal surface faces the buccal sidewall, and the occlusal surface faces the occlusal wall;

engaging the guide channel of the apparatus with the cutting tool comprising a burr, whereby a cutting portion of the burr enters into the interior space and between the occlusal wall and the tooth; and traveling the burr along the guide channel while running the burr, thereby cutting at least part of the occlusal surface of the tooth.]

*65. A dental preparation apparatus, comprising:*

*a single body including a buccal wall and an occlusal wall, wherein the buccal wall and the occlusal wall define an interior space configured to receive a plurality of teeth such that the occlusal wall overlays occlusal surfaces of the plurality of teeth; and*

*at least one guide channel formed in the single body and configured to receive a cutting assembly and to guide the cutting assembly along a tool path for cutting one of the plurality of teeth positioned in the interior space, the at least one guide channel includes a first engagement structure configured to engage the cutting assembly to keep the cutting assembly in the at least one guide channel while the cutting assembly moves along the tool path,*

*wherein the first engagement structure defines a first guide groove and a second guide groove opposing the first guide groove, wherein the first and second guide grooves are configured to receive a guide projection of the cutting assembly and allow rotation of a cutting tool of the cutting assembly, and the guide projection has a spherical shape.*

*66. The dental preparation apparatus of claim 65, wherein the at least one guide channel includes a first guide channel and a second guide channel spaced apart from one another, wherein a portion of the single body is between the first guide channel and the second guide channel, and wherein when the cutting assembly is in the first guide channel, the cutting assembly must be removed from the first guide channel to be placed in the second guide channel.*

*67. The dental preparation apparatus of claim 65, wherein the first engagement structure extends along the at least one guide channel and is configured to slidably contact a complementary engagement feature of the cutting assembly to keep the cutting assembly in the at least one guide channel.*

*68. The dental preparation apparatus of claim 65, wherein the cutting assembly includes a rotatable burr and a handpiece holding the rotatable burr, wherein the first engagement structure includes a slot configured engage a portion of the handpiece while the rotatable burr is positioned in the interior space.*

*69. The dental preparation apparatus of claim 65, wherein the cutting assembly includes a burr and is configured to contact the at least one guide channel to prevent contact between the burr and the dental preparation apparatus while the cutting assembly moves along the tool path.*

*70. The dental preparation apparatus of claim 65, wherein the tool path is a veneer tool path extending along an occlusal region or buccal region of the interior space.*

*71. A dental preparation apparatus, comprising:*

*a unitary body including a buccal wall and an occlusal wall, wherein the buccal wall and the occlusal wall together define an interior space configured to receive a plurality of teeth; and*

*at least one guide channel formed in the unitary body and configured to receive a cutting assembly and to guide the cutting assembly along the interior space to cut one of the plurality of teeth at least partially covered by the unitary body, wherein a section of the at least one guide channel is configured to prevent the cutting assembly from being pulled out of the at least one guide channel.*

*72. The dental preparation apparatus of claim 71, wherein the at least one guide channel includes a first guide channel and a second guide channel spaced apart from one another, wherein a portion of the unitary body is between the first guide channel and the second guide channel such that the cutting assembly, when in the first guide channel, must be removed from the first guide channel to be placed in the second guide channel.*

*73. A dental preparation guide apparatus comprising:*

*a single body including a buccal sidewall and an occlusal wall connected to the buccal sidewall to form the single body, wherein the buccal sidewall and the occlusal wall in combination define an interior space configured to receive a tooth; and*

*a guide channel formed in the single body and shaped to receive a cutting assembly and guide the cutting assembly to travel along a trajectory, the guide channel comprising two opposing channel surfaces that extend along the trajectory such that the cutting assembly is constrained by the two opposing channel surfaces while the cutting assembly moves along the trajectory, the guide channel is configured to engage with the cutting assembly for inhibiting tilting of the cutting assembly in a plane parallel to a movement direction of the cutting assembly at a given point of the trajectory while the cutting assembly travels along the trajectory.*

*74. The dental preparation guide apparatus of claim 73, wherein the single body is configured to permit at least part of the cutting assembly to enter into a buccal area of the interior space between the buccal sidewall and the tooth such that the cutting assembly cuts at least part of a buccal surface of the tooth while traveling in a buccal section of the guide channel; and*

*wherein the single body is configured to permit at least part of the cutting assembly to enter into an abutting area of the interior space between the tooth and an immediately neighboring tooth such that the cutting assembly cuts at least part of the mesial or distal surface of the tooth while traveling in the single body.*

*75. The dental preparation guide apparatus of claim 73, further comprising a first engagement structure and a second engagement structure extending along the trajectory and substantially parallel to each other, the first and second engagement structures being configured to engage respectively with first and second counterpart structures of the cutting assembly, wherein engagement of the first and second engagement structures respectively with the first and second counterpart structures is to prevent disengagement of the cutting assembly from a section of the guide channel while traveling along the trajectory.*

*76. The dental preparation guide apparatus of claim 73, wherein the guide channel is configured to allow a proximal portion of the cutting assembly to pass through the occlusal wall while allowing a distal portion of the cutting assembly to extend into the interior space, wherein each of first and second counterpart structures of the cutting assembly is in a spherical shape as part of the cutting tool, and wherein each of the first and second engagement structures is configured to accommodate traveling of the spherical shape therethrough.*

* * * * *